(12) United States Patent
Bao et al.

(10) Patent No.: US 6,303,593 B1
(45) Date of Patent: Oct. 16, 2001

(54) 3-THIENYL AND 3-FURANYL PYRROLIDINE MODULATORS OF CHEMOKINE RECEPTOR ACTIVITY

(75) Inventors: Jianming Bao, Scotch Plains, NJ (US); Christopher Forbes, Philadelphia, PA (US); Shouwu Miao; William H. Parsons, both of Edison, NJ (US); Kathleen Rupprecht, Cranford, NJ (US); Frank Kayser, San Francisco, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/516,621

(22) Filed: Mar. 1, 2000

Related U.S. Application Data

(60) Provisional application No. 60/122,586, filed on Mar. 2, 1999.

(51) Int. Cl.[7] .......................... A61K 31/395; A61K 31/44; C07D 451/00; C07D 401/00; C07D 405/00
(52) U.S. Cl. .......................... 514/210; 514/213; 514/255; 514/278; 514/291; 514/297; 514/318; 514/319; 514/326; 514/327; 514/331; 514/442; 540/594; 540/602; 544/372; 546/17; 546/18; 546/192; 546/195; 546/196; 546/198; 546/201; 546/202; 546/205; 546/207; 546/208; 546/209; 546/465; 546/517; 546/518; 546/527
(58) Field of Search .................. 546/18, 17, 213, 546/214, 201, 202, 198, 208, 209, 192, 195, 196, 205, 207; 514/318, 319, 327, 331, 291, 797, 210, 213, 255, 278, 326, 422; 544/372; 540/594, 602; 548/465, 517, 518, 527

(56) References Cited

U.S. PATENT DOCUMENTS 5,998,444 * 12/1999 Russell .................................. 514/331

* cited by examiner

Primary Examiner—Alan L. Rotman
Assistant Examiner—Raymond Covington
(74) Attorney, Agent, or Firm—J. Eric Thies; David L. Rose

(57) ABSTRACT

The present invention is directed to pyrrolidine compounds of the formula I:

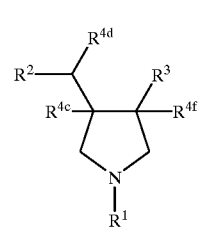

(wherein $R^1$, $R^2$, $R^3$, $R^{4c}$, $R^{4d}$, and $R^{4f}$ are defined herein) which are useful as modulators of chemokine receptor activity. In particular, these compounds are useful as modulators of the chemokine receptors CCR-3 and/or CCR-5.

20 Claims, No Drawings

3-THIENYL AND 3-FURANYL PYRROLIDINE MODULATORS OF CHEMOKINE RECEPTOR ACTIVITY

This application claims benefit of Provisional Application Ser. No. 60/122,586 filed Mar. 2, 1999.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183(1991) and Murphy, *Rev. Immun.*, 12, 593–633 (1994)). There are two classes of chemokines, C-X-C (α) and C-C (β), depending on whether the first two cysteines are separated by a single amino acid (C-X-C) or are adjacent (C-C). The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR-4") [MIP-1α, RANTES, MCP-1] (Power, et al., *J. Biol. Chem.*, 270, 19495–19500 (1995)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). An antagonist of the CCR3 receptor, Met-chemokine beta 7, has been proposed to be useful in ameliorating leukocyte infiltration associated with allergic inflammation (Nibbs, et al., *J. Immunol.*, 164, 1488–1497 (2000)). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the β-chemokines RANTES. MIP-1α and MIP-1β (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that β-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1α and MIP-1β (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+T cells have been characterized as the β-chemokines RANTES, MIP-1α and MIP-1β.

SUMMARY OF THE INVENTION

The present invention is directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to compounds of formula I:

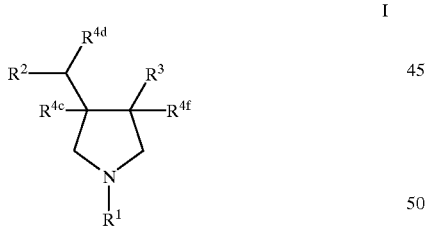

wherein:
$R^1$ is —X—$R^8$, wherein X is selected from the group consisting of:
(1) —$CH_2$—,
(2) —CO—,
(3) —$CH_2CH_2$—,
(4) —$CH_2CH_2CH_2$—, and
(5) —$CH(C_{1-6}$ alkyl)—,
and wherein $R^8$ is a selected from:
phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:

(a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —$NH(C_{1-6}$ alkyl), —$N(C_{1-6}$ alkyl)($C_{1-6}$ alkyl), or trifluoromethyl,
(B) naphthyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH($C_{1-6}$ alkyl), —N($C_{1-6}$ alkyl)($C_{1-6}$ alkyl), or trifluoromethyl,
(C) heterocycle, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH($C_{1-6}$ alkyl), —N($C_{1-6}$ alkyl)($C_{1-6}$ alkyl), or trifluoromethyl,
(D) hydroxy,
(E) —O($C_{1-6}$ alkyl),
(F) —$CO_2(C_{1-6}$ alkyl),
(G) —S(O)$_n$—($C_{1-6}$ alkyl), wherein n is an integer selected from 0, 1 and 2,
(H) halogen,
(I) —$NH_2$,
(J) —NH($C_{1-6}$ alkyl), and
(K) —N($C_{1-6}$ alkyl)($C_{1-6}$ alkyl),
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9CO$—$NR^9R^{10}$,
(ix) —S(O)$_2$—$NR^9R^{10}$, wherein n is an integer selected from 0, 1 and 2,
(x) —$NR^9S(O)_2$—$R^{10}$,
(xi) —$NR^9S(O)_2$—$NR^9R^{10}$,
(xii) —S(O)$_n$—$R^9$,
(xiii) —$CF_3$,
(xiv) —$CHF_2$,
(xv) —$CH_2F$,
(xvi) —O—$R^9$,
(xvii) —O($C_{1-6}$ alkyl)—O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(b) —O—$C_{1-6}$alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9CO$—$NR^9R^{10}$,
(ix) —$S(O)_2$—$NR^9R^{10}$,
(x) —$NR^9S(O)_2$—$R^{10}$,
(xi) —$NR^9S(O)_2$—$NR^9R_{10}$,
(xii) —$S(O)_n$—$R^9$,
(xiii) —$CF_3$,
(xiv) —$CHF_2$,
(xv) —$CH_2F$,
(xvii) —O—$R^9$,
(xvii) —$O(C_{1-6}$ alkyl)—O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(c) —$NO_2$,
(d) hydroxy,
(e) halogen,
(f) —$NR^9R^{10}$,
(g) —$NR^9$—$COR^{10}$,
(h) —$NR^9$—$CO_2R^{10}$,
(i) —CO—$NR^9R^{10}$,
(j) —OCO—$NR^9R^{10}$,
(k) —$NR^9CO$—$NR^9R^{10}$,
(l) —$S(O)_2$—$NR^9R^{10}$,
(m) —$NR^9S(O)_2$—$R^{10}$,
(n) —$NR^9S(O)_2$—$NR^9R^{10}$,
(o) —$S(O)_n$—$R^9$,
(p) —$CF_3$,
(q) —$CHF_2$,
(r) —$CH_2F$,
(s) —OCO—$R^9$,
(t) —$OCO_2$—$R^9$, and
(u) —CO—$R^9$, $R^2$ is selected from the group consisting of:

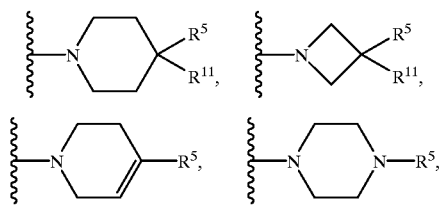

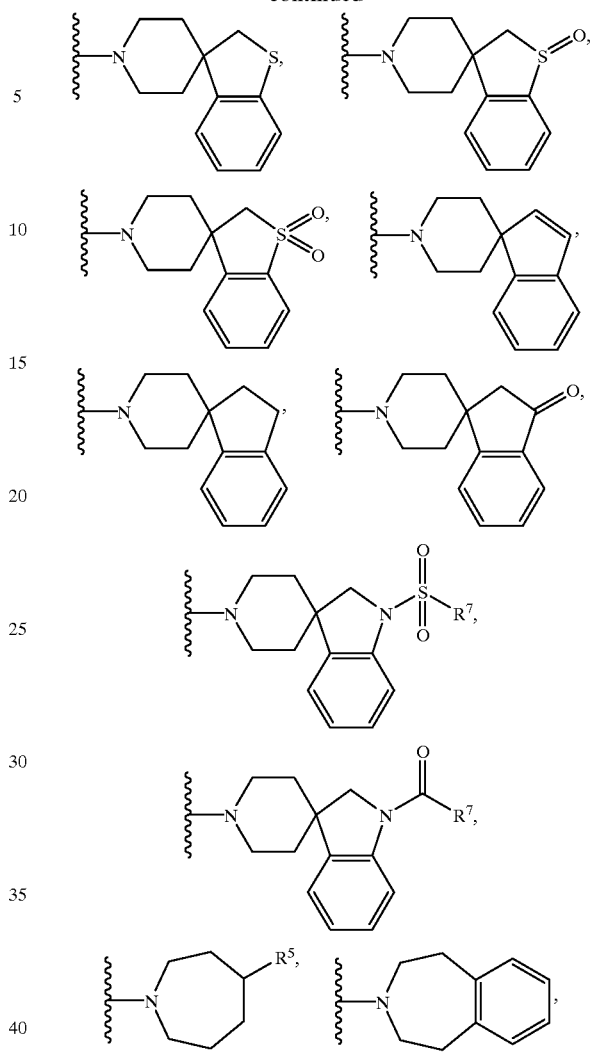

wherein $R^5$ is a selected from:
(1) —$NR^6CO$—O—$R^7$, wherein $R^6$ is hydrogen, $C_{1-6}$ alkyl or $C_{1-6}$ alkyl-$C_{5-6}$ cycloalkyl, and $R^7$ is $C_{1-6}$ alkyl, $C_{5-6}$ cycloalkyl, benzyl or phenyl, wherein the alkyl, cycloalkyl, benzyl or phenyl is unsubstituted or substituted with halogen, $C_{1-3}$alkyl, $C_{1-3}$alkoxy or trifluoromethyl,
(2) phenyl, which is unsubstituted or substituted with halogen, hydroxy, $C_{1-6}$alkyl, $C_{1-6}$alkoxy, —$CO_2(C_{1-6}$ alkyl), —$NH_2$, —$NHR^9$, —$NR^9R^{10}$, or trifluoromethyl,
(3) -pyridyl,
(4) -thienyl,
(5) —$C_{1-6}$alkyl-phenyl, —$C_{1-6}$alkyl-naphthyl, —$C_{1-6}$alkyl-indenyl, —$C_{1-6}$alkyl-indanyl, and —$C_{1-6}$alkyl-heterocycle, wherein the phenyl, naphthyl, indenyl, indanyl, or heterocycle is unsubsituted or substituted with: halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl; and wherein the —$C_{1-6}$alkyl is optionally substituted with oxo, hydroxy, $C_{1-6}$alkoxy, acetoxy, or halogen,
(6) —O—$C_{1-6}$alkyl-phenyl, —O—$C_{1-6}$alkyl-naphthyl, —O—$C_{1-6}$alkyl-indenyl, —O—-$C_{1-6}$alkyl-indanyl, and —O—$C_{1-6}$alkyl-heterocycle, wherein the phenyl, naphthyl, indenyl, indanyl, or heterocycle is unsubsituted or substituted with: halogen, hydroxy, $C_{1-6}$alkyl, $C_{1-6}$alkoxy, —$CO_2(C_{1-6}$ alkyl), —$NH_2$, —$NHR^9$, —$NR^9R^{10}$, or trifluoromethyl, (7) —$C_{1-4}$alkyl—O—$C_{1-4}$alkyl-phenyl, wherein the phenyl is unsubsituted or substituted with halogen, hydroxy, $C_{1-6}$alkyl, $C_{1-6}$alkoxy, —$CO_2(C_{1-6}$ alkyl), —$NH_2$, —$NHR^9$, —$NR^9R^{10}$, or trifluoromethyl, and (8) —$C_{1-4}$alkyl—$S(O)_n$—$C_{1-4}$alkyl-phenyl, wherein the phenyl is unsubstituted or substituted with halogen, hydroxy, $C_{1-6}$alkyl, —$C_{1-6}$alkoxy, —$CO_2(C_{1-6}$ alkyl), —$NH_2$, —$NHR^9$, —$NR^9R^{10}$, or trifluoromethyl;

and wherein $R^{11}$ is a selected from:
(1) -hydrogen,
(2) —OH,
(3) —$C_{1-6}$alkyl, and
(4) -halogen;

$R^3$ is thienyl or furanyl, which may be unsubstituted or substituted, where the substituents are independently selected from:

(1) $C_{1-6}$ alkyl, which is unsubstituted or substituted, wherein the substituents are independently selected from:
(a) hydroxy,
(b) halogen,
(c) —$NR^9R^{10}$,
(d) —$NR^9$—$COR^{10}$,
(e) —$NR^9$—$CO_2R^{10}$,
(f) —$CF_3$,
(g) —$CHF_2$,
(h) —$CH_2F$,
(i) —O—$R^9$, and
(j) phenyl, (2) —O—$C_{1-6}$alkyl, unsubstituted or substituted with a substituent which is independently selected from:
(a) hydroxy,
(b) halogen,
(c) —$NR^9R^{10}$,
(d) —$NR^9$—$COR^{10}$,
(e) —$NR^9$—$CO_2R^{10}$,
(f) —$CF_3$,
(g) —$CHF_2$,
(h) —$CH_2F$,
(i) —O—$R^9$, and
(j) phenyl, (3) hydroxy,
(4) halogen,
(5) —$CF_3$,
(6) —$CHF_2$,
(7) —$CH_2F$,
(8) —O—$R^9$, and
(9) —O($C_{1-6}$ alkyl)—O—$R^9$;

$R^{4c}$, $R^{4d}$, and $R^{4f}$ are independently selected from the group consisting of:
(1) hydrogen, and
(2) $C_{1-6}$ alkyl and pharmaceutically acceptable salts thereof and individual diastereomers thereof.

Preferred compounds of the present invention include those of formula Ia:

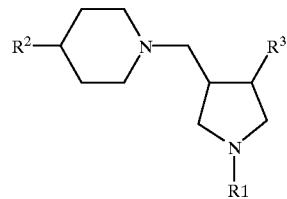

wherein:
$R^1$, $R^2$ and $R^3$ are defined herein;
and pharmaceutically acceptable salts and individual diastereomers thereof.

Preferred compounds of the present invention include those of formula Ib:

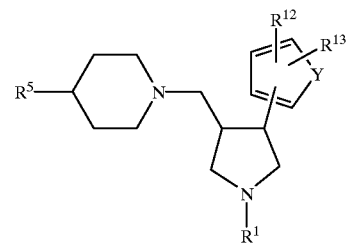

wherein:
$R^1$ is —X—$R^8$, wherein X is selected from the group consisting of:
(1) —$CH_2$—,
(2) —CO—, and
(3) —$CH_2CH_2$—, and wherein $R^8$ is a selected from:
phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:

(a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —$NH(C_{1-6}$ alkyl), —$N(C_{1-6}$ alkyl)($C_{1-6}$ alkyl), or trifluoromethyl,
(B) naphthyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —$NH(C_{1-6}$ alkyl), —$N(C_{1-6}$ alkyl)($C_{1-6}$ alkyl), or trifluoromethyl,
(C) heterocycle, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH ($C_{1-6}$ alkyl), —N($C_{1-6}$ alkyl)($C_{1-6}$ alkyl), or trifluoromethyl,
(D) hydroxy,
(E) —O($C_{1-6}$ alkyl),
(F) —$CO_2$($C_{1-6}$ alkyl),
(G) —S(O)$_n$—($C_{1-6}$ alkyl), wherein n is an integer selected from 0, 1 and 2,
(H) halogen,
(I) —$NH_2$,
(J) —NH($C_{1-6}$ alkyl), and
(K) —N($C_{1-6}$ alkyl)($C_{1-6}$ alkyl),
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9$CO—$NR^9R^{10}$,
(ix) —S(O)$_2$—$NR^9R^{10}$, wherein n is an integer selected from 0, 1 and 2,
(x) —$NR^9$S(O)$_2$—$R^{10}$,
(xi) —$NR^9$S(O)$_2$—$NR^9R^{10}$,
(xii) —S(O)$_n$—$R^9$,
(xiii) —$CF_3$,
(xiv) —$CHF_2$,
(xv) —$CH_2$F,
(xvi) —O—$R^9$,
(xvii) —O($C_{1-6}$ alkyl)—O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(b) —O—$C_{1-6}$alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9$CO—$NR^9R^{10}$,
(ix) —S(O)$_2$—$NR^9R^{10}$,
(x) —$NR^9$S(O)$_2$—$R^{10}$,
(xi) —$NR^9$S(O)$_2$—$NR^9R^{10}$,
(xii) —S(O)$_n$—$R^9$,
(xiii) —$CF_3$,
(xiv) —$CHF_2$,
(xv) —$CH_2$F,
(xvii) —O—$R^9$,
(xvii) —O($C_{1-6}$ alkyl)—O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(c) —$NO_2$,
(d) hydroxy,
(e) halogen,
(f) —$NR^9R^{10}$,
(g) —$NR^9$—$COR^{10}$,
(h) —$NR^9$—$CO_2R^{10}$,
(i) —CO—$NR^9R^{10}$,
(j) —OCO—$NR^9R^{10}$,
(k) —$NR^9$CO—$NR^9R^{10}$,
(l) —S(O)$_2$—$NR^9R^{10}$,
(m) —$NR^9$S(O)$_2$—$R^{10}$,
(n) —$NR^9$S(O)$_2$—$NR^9R^{10}$,
(o) —S(O)$_n$—$R^9$,
(p) —$CF_3$,
(q) —$CHF_2$,
(r) —$CH_2$F,
(s) —OCO—$R^9$,
(t) —$OCO_2$—$R^9$, and
(u) —CO—$R^9$;
$R^5$ is a selected from:
(1) —$NR^6$CO—O—$R^7$, wherein $R^6$ is hydrogen, $C_{1-6}$ alkyl or $C_{1-6}$ alkyl-$C_{5-6}$ cycloalkyl, and $R^7$ is $C_{1-6}$ alkyl, $C_{5-6}$ cycloalkyl, benzyl or phenyl, wherein the alkyl, cycloalkyl, benzyl or phenyl is unsubstituted or substituted with halogen, $C_{1-3}$alkyl, $C_{1-3}$alkoxy or trfluoromethyl,
(2) phenyl, which is unsubstituted or substituted with halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl,
(3) -pyridyl,
(4) -thienyl,
(5) —$C_{1-6}$alkyl-phenyl, —$C_{1-6}$alkyl-naphthyl, —$C_{1-6}$alkyl-indenyl, —$C_{1-6}$alkyl-indanyl, and —$C_{1-6}$alkyl-heterocycle, wherein the phenyl, naphthyl, indenyl, indanyl, or heterocycle is unsubstituted or substituted with: halogen, hydroxy, $C_{1-6}$alkyl, $C_{1-6}$alkoxy, —$CO_2$ ($C_{1-6}$ alkyl), —$NH_2$, —$NHR^9$, —$NR^9R^{10}$, or trifluoromethyl; and wherein the —$C_{1-6}$alkyl is optionally substituted with oxo, hydroxy, $C_{1-6}$alkoxy, acetoxy, or halogen,
(6) —O—$C_{1-6}$alkyl-phenyl, —O—$C_{1-6}$alkyl-naphthyl, —O—$C_{1-6}$alkyl-indenyl, —O—$C_{1-6}$alkyl-indanyl, and —O—$C_{1-6}$alkyl-heterocycle, wherein the phenyl, naphthyl, indenyl, indanyl, or heterocycle is unsubsituted or substituted with: halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl,
(7) —$C_{1-4}$alkyl-O—$C_{1-4}$alkyl-phenyl, wherein the phenyl is unsubstituted or substituted with halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl, and
(8) —$C_{1-4}$alkyl-S(O)$_n$—$C_{1-4}$alkyl-phenyl, wherein the phenyl is unsubstituted or substituted with halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl;
$R^{12}$ and $R^{13}$ are independently selected from:
(1) hydrogen, (2) $C_{1-6}$ alkyl, which is unsubstituted or substituted, wherein the substituents are independently selected from:
   (a) hydroxy,
   (b) halogen,
   (c) —$NR^9R^{10}$,
   (d) —$NR^9$—$COR^{10}$,
   (e) —$NR^9$—$CO_2R^{10}$,
   (f) —$CF_3$,
   (g) —$CHF_2$,
   (h) —$CH_2F$,
   (i) —O—$R^9$, and
   (j) phenyl,
(3) —O—$C_{1-6}$alkyl, unsubstituted or substituted with a substituent which is independently selected from:
   (a) hydroxy,
   (b) halogen,
   (c) —$NR^9R^{10}$,
   (d) —$NR^9$—$COR^{10}$,
   (e) —$NR^9$—$CO_2R^{10}$,
   (f) —$CF_3$,
   (g) —$CHF_2$,
   (h) —$CH_2F$,
   (i) —O—$R^9$, and
   (j) phenyl,
(4) hydroxy,
(5) halogen,
(6) —$CF_3$,
(7) —$CHF_2$,
(8) —$CH_2F$,
(9) —O—$R^9$, and
(10) —O($C_{1-6}$ alkyl)—O—$R^9$,
Y is —S— or —O—;

and pharmaceutically acceptable salts thereof and individual diastereomers thereof.

More preferred compounds of the present invention include those of formula Ic:

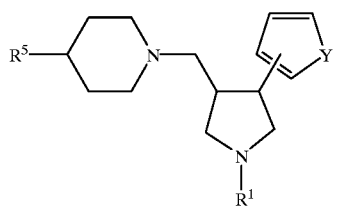

Ic wherein:

$R^1$, $R^5$ and Y are defined herein;

and pharmaceutically acceptable salts and individual diastereomers thereof.

Highly preferred compounds of the present invention include those of formula Id:

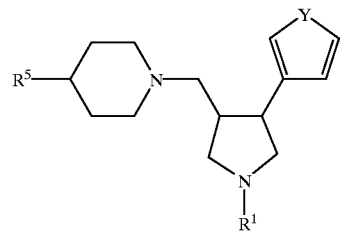

Id wherein $R^1$, $R^5$ and Y are defined herein;
and pharmaceutically acceptable salts and individual diastereomers thereof.

Highly preferred compounds of the present invention further include those of formula Id:

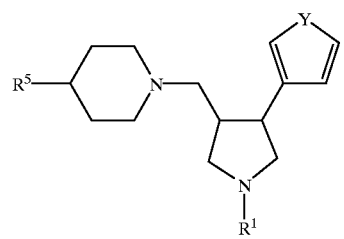

Id

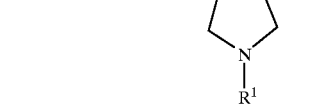

wherein
$R^1$ is —X—$R^8$, wherein X is selected from the group consisting of:
   (1) —$CH_2$—, and
   (2) —CO—,
and wherein $R^8$ is a selected from:
phenyl, naphthyl, indenyl, indanyl, indolyl, quinolyl, isoquinolyl, benzofuranyl, dihydrobenzofuranyl, methylenedioxybenzoyl, benzopyrazolyl, and benzotriazolyl, which may be unsubstituted or substituted, where the substituents are independently selected from:
   (a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
      (i) hydroxy,
      (ii) halogen,
      (iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
         (A) phenyl, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH($C_{1-6}$ alkyl), —N($C_{1-6}$ alkyl)($C_{1-6}$ alkyl), or trifluoromethyl,
         (B) naphthyl, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH($C_{1-6}$ alkyl), —N($C_{1-6}$ alkyl)($C_{1-6}$ alkyl), or trifluoromethyl,
         (C) heterocycle, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH($C_{1-6}$ alkyl), —N($C_{1-6}$ alkyl)($C_{1-6}$ alkyl), or trifluoromethyl,
- (D) hydroxy,
- (E) —O($C_{1-6}$ alkyl),
- (F) —$CO_2(C_{1-6}$ alkyl),
- (G) —S(O)$_n$—($C_{1-6}$ alkyl), wherein n is an integer selected from 0, 1 and 2,
- (H) halogen,
- (I) —$NH_2$,
- (J) —NH($C_{1-6}$ alkyl), and
- (K) —N($C_{1-6}$ alkyl)($C_{1-6}$ alkyl),
- (iv) —$NR^9$—$COR^{10}$,
- (v) —$NR^9$—$CO2R^{10}$,
- (vi) —CO—$NR^9R^{10}$,
- (vii) —OCO—$NR^9R^{10}$,
- (viii) —$NR^9CO$—$NR^9R^{10}$,
- (ix) —$S(O)_2$—$NR^9R^{10}$, wherein n is an integer selected from 0, 1 and 2,
- (x) —$NR^9S(O)_2$—$R^{10}$,
- (xi) —$NR^9S(O)_2$—$NR^9R^{10}$,
- (xii) —$S(O)_n$—$R^9$,
- (xiii) —$CF_3$,
- (xiv) —$CHF_2$,
- (xv) —$CH_2F$,
- (xvi) —O—$R^9$,
- (xvii) —O($C_{1-6}$ alkyl)—O—$R^9$,
- (xviii) phenyl,
- (xix) naphthyl,
- (xx) indenyl,
- (xxi) indanyl,
- (xxii) heterocycle,
- (xxiii) —CO-phenyl,
- (xxiv) —CO-naphthyl,
- (xxv) —CO-indenyl,
- (xxvi) —CO-indanyl,
- (xxvii) —CO-heterocycle,
- (xxviii) —OCO—$R^9$,
- (xxix) —$OCO_2$—$R^9$, and
- (xxx) —CO—$R^9$,
- (b) —O—$C_{1-6}$alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
- (i) hydroxy,
- (ii) halogen,
- (iii) —$NR^9R^{10}$,
- (iv) —$NR^9$—$COR^{10}$,
- (v) —$NR^9$—$CO_2R^{10}$,
- (vi) —CO—$NR^9R^{10}$,
- (vii) —OCO—$NR^9R^{10}$,
- (viii) —$NR^9CO$—$NR^9R^{10}$,
- (ix) —$S(O)_2$—$NR^9R^{10}$,
- (x) —$NR^9S(O)_2$—$R^{10}$,
- (xi) —$NR^9S(O)_2$—$NR^9R^{10}$,
- (xii) —$S(O)_n$—$R^9$,
- (xiii) —$CF_3$,
- (xiv) —$CHF_2$,
- (xv) —$CH_2F$,
- (xvii) —O—$R^9$,
- (xvii) —O($C_{1-6}$ alkyl)—O—$R^9$,
- (xviii) phenyl,
- (xix) naphthyl,
- (xx) indenyl,
- (xxi) indanyl,
- (xxii) heterocycle,
- (xxiii) —CO-phenyl,
- (xxiv) —CO-naphthyl,
- (xxv) —CO-indenyl,
- (xxvi) —CO-indanyl,
- (xxvii) —CO-heterocycle,
- (xxviii) —OCO—$R^9$,
- (xxix) —$OCO_2$—$R^9$, and
- (xxx) —CO—$R^9$,
- (c) —$NO_2$,
- (d) hydroxy,
- (e) halogen,
- (f) —$NR^9R^{10}$,
- (g) —$NR^9$—$COR^{10}$,
- (h) —$NR^9$—$CO_2R^{10}$,
- (i) —CO—$NR^9R^{10}$,
- (j) —OCO—$NR^9R^{10}$,
- (k) —$NR^9CO$—$NR^9R^{10}$,
- (l) —$S(O)_2$—$NR^9R^{10}$,
- (m) —$NR^9S(O)_2$—$R^{10}$,
- (n) —$NR^9S(O)_2$—$NR^9R^{10}$,
- (o) —$S(O)_n$—$R^9$,
- (p) —$CF_3$,
- (q) —$CHF_2$,
- (r) —$CH_2F$,
- (s) —OCO—$R^9$,
- (t) —$OCO_2$—$R^9$, and
- (u) —CO—$R^9$;

wherein $R^5$ is a selected from:
- (1) phenyl, which is unsubstituted or substituted with halogen, hydroxy, $C_{1-6}$alkyl, $C_{1-6}$alkoxy, —$CO_2(C_{1-6}$ alkyl), —$NH_2$, —$NHR^9$, —$NR^9R^{10}$, or trifluoromethyl,
- (2) —$C_{1-6}$alkyl-phenyl, —$C_{1-6}$alkyl-naphthyl, —$C_{1-6}$alkyl-indenyl, —$C_{1-6}$alkyl-indanyl, and —$C_{1-6}$alkyl-heterocycle, wherein the phenyl, naphthyl, indenyl, indanyl, or heterocycle is unsubsituted or substituted with: halogen, hydroxy, $C_{1-6}$alkyl, $C_{1-6}$alkoxy, —$CO_2(C_{1-6}$ alkyl), —$NH_2$, —$NHR^9$, —$NR^9R^{10}$, or trifluoromethyl; and wherein the —$C_{1-6}$alkyl is optionally substituted with oxo, hydroxy, $C_{1-6}$alkoxy, acetoxy, or halogen,
- (3) —O—$C_{1-6}$alkyl-phenyl, —O—$C_{1-6}$alkyl-naphthyl, —O—$C_{1-6}$alkyl-indenyl, —O—$C_{1-6}$alkyl-indanyl, and —O—$C_{1-6}$alkyl-heterocycle, wherein the phenyl, naphthyl, indenyl, indanyl, or heterocycle is unsubsituted or substituted with: halogen, hydroxy, $C_{1-6}$alkyl, $C_{1-6}$alkoxy, —$CO_2(C_{1-6}$ alkyl), —$NH_2$, —$NHR^9$, —$NR^9R^{10}$, or trifluoromethyl,
- (4) —$C_{1-4}$alkyl-O—$C_{1-4}$alkyl-phenyl, wherein the phenyl is unsubsituted or substituted with halogen, hydroxy, $C_{1-6}$alkyl, $C_{1-6}$alkoxy, —$CO_2(C_{1-6}$ alkyl), —$NH_2$, —$NHR^9$, —$NR^9R^{10}$, or trifluoromethyl, and
- (5) —$C_{1-4}$alkyl-$S(O)_n$—$C_{1-4}$alkyl-phenyl, wherein the phenyl is unsubsituted or substituted with halogen, hydroxy, $C_{1-6}$alkyl, $C_{1-6}$alkoxy, —$CO_2(C_{1-6}$ alkyl), —$NH_2$, —$NHR^9$, —$NR^9R^{10}$, or trifluoromethyl;

Y is —S— or —O—;

and pharmaceutically acceptable salts and individual diastereomers thereof.

In the present invention it is preferred that $R^1$ is —X—$R^8$, wherein X is selected from the group consisting of:
- (1) —$CH_2$—, and
- (2) —CO—, and wherein $R^8$ is a selected from:
phenyl, naphthyl, biphenyl, indenyl, indanyl, and heterocycle, which may be unsubstituted or substituted, where the substituents arc independently selected from:

(a) $C_{1-6}$ alkyl, $C_{2-6}$ alkenyl, $C_{2-6}$ alkynyl, wherein the alkyl, alkenyl, or alkynyl is unsubstituted or substituted, wherein the substituents arc independently selected from:
  (i) hydroxy,
  (ii) halogen,
  (iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
    (A) phenyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —$NH(C_{1-6}$ alkyl), —$N(C_{1-6}$ alkyl)($C_{1-6}$ alkyl), or trifluoromethyl,
    (B) naphthyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —$NH(C_{1-6}$ alkyl), —$N(C_{1-6}$ alkyl)($C_{1-6}$ alkyl), or trifluoromethyl,
    (C) heterocycle, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —$NH(C_{1-6}$ alkyl), —$N(C_{1-6}$ alkyl)($C_{1-6}$ alkyl), or trifluoromethyl,
    (D) hydroxy,
    (E) —$O(C_{1-6}$ alkyl),
    (F) —$CO_2(C_{1-6}$ alkyl),
    (G) —$S(O)_n$—($C_{1-6}$ alkyl), wherein n is an integer selected from 0, 1 and 2,
    (H) halogen,
    (I) —$NH_2$,
    (J) —$NH(C_{1-6}$ alkyl), and
    (K) —$N(C_{1-6}$ alkyl)($C_{1-6}$ alkyl),
  (iv) —$NR^9$—$COR^{10}$,
  (v) —$NR^9$—$CO_2R^{10}$,
  (vi) —$CO$—$NR^9R^{10}$,
  (vii) —$OCO$—$NR^9R^{10}$,
  (viii) —$NR^9CO$—$NR^9R^{10}$,
  (ix) —$S(O)_2$—$NR^9R^{10}$, wherein n is an integer selected from 0, 1 and 2,
  (x) —$NR^9S(O)_2$—$R^{10}$,
  (xi) —$NR^9S(O)_2$—$NR^9R^{10}$,
  (xii) —$S(O)_n$—$R^9$,
  (xiii) —$CF_3$,
  (xiv) —$CHF_2$,
  (xv) —$CH_2F$,
  (xvi) —$O$—$R^9$,
  (xvii) —$O(C_{1-6}$ alkyl)—$O$—$R^9$,
  (xviii) phenyl,
  (xix) naphthyl,
  (xx) indenyl,
  (xxi) indanyl,
  (xxii) heterocycle,
  (xxiii) —CO-phenyl,
  (xxiv) —CO-naphthyl,
  (xxv) —CO-indenyl,
  (xxvi) —CO-indanyl,
  (xxvii) —CO-heterocycle,
  (xxviii) —$OCO$—$R^9$,
  (xxix) —$OCO_2$—$R^9$, and
  (xxx) —$CO$—$R^9$,
(b) —$O$—$C_{1-6}$alkyl, —$O$—$C_{2-6}$ alkenyl, —$O$—$C_{2-6}$ alkynyl, wherein the alkyl, alkenyl, or alkynyl is unsubstituted or substituted, wherein the substituents are independently selected from:
  (i) hydroxy,
  (ii) halogen,
  (iii) —$NR^9R^{10}$,
  (iv) —$NR^9$—$COR^{10}$,
  (v) —$NR^9$—$CO_2R^{10}$,
  (vi) —$CO$—$NR^9R^{10}$,
  (vii) —$OCO$—$NR^9R^{10}$,
  (viii) —$NR^9CO$—$NR^9R^{10}$,
  (ix) —$S(O)_2$—$NR^9R^{10}$,
  (x) —$NR^9S(O)_2$—$R^{10}$,
  (xi) —$NR^9S(O)_2$—$NR^9R^{10}$,
  (xii) —$S(O)_n$—$R^9$,
  (xiii) —$CF_3$,
  (xiv) —$CHF_2$,
  (xv) —$CH_2F$,
  (xvii) —$O$—$R^9$,
  (xvii) —$O(C_{1-6}$ alkyl)—$O$—$R^9$,
  (xviii) phenyl,
  (xix) naphthyl,
  (xx) indenyl,
  (xxi) indanyl,
  (xxii) heterocycle,
  (xxiii) —CO-phenyl,
  (xxiv) —CO-naphthyl,
  (xxv) —CO-indenyl,
  (xxvi) —CO-indanyl,
  (xxvii) —CO-heterocycle,
  (xxviii) —$OCO$—$R^9$,
  (xxix) —$OCO_2$—$R^9$, and
  (xxx) —$CO$—$R^9$,
(c) —$NO_2$,
(d) hydroxy,
(e) halogen,
(f) —$NR^9R^{10}$,
(g) —$NR^9$—$COR^{10}$,
(h) —$NR^9$—$CO_2R^{10}$,
(i) —$CO$—$NR^9R^{10}$,
(j) —$OCO$—$NR^9R^{10}$,
(k) —$NR^9CO$—$NR^9R^{10}$,
(l) —$S(O)_2$—$NR^9R^{10}$,
(m) —$NR^9S(O)_2$—$R^{10}$,
(n) —$NR^9S(O)_2$—$NR^9R^{10}$,
(o) —$S(O)_n$—$R^9$,
(p) —$CF_3$,
(q) —$CHF_2$,
(r) —$CH_2F$,
(s) —$OCO$—$R^9$,
(t) —$OCO_2$—$R^9$, and
(u) —$CO$—$R^9$.

invention it is even more preferred that $R^1$ is —X—$R^8$, wherein X is selected from the group consisting of:
(1) —$CH_2$—, and
(2) —CO—,
and wherein $R^8$ is a selected from:
phenyl, naphthyl, indenyl, indanyl, indolyl, quinolyl, isoquinolyl, benzofuranyl, dihydrobenzofuranyl, methylenedioxybenzoyl, benzopyrazolyl, and benzotriazolyl, which may be unsubstituted or substituted, where the substituents are independently selected from:
  (a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
    (i) hydroxy, (ii) halogen,
(iii) —NR$^9$R$^{10}$, wherein R$^9$ and R$^{10}$ are independently selected from hydrogen, C$_{1-6}$ alkyl, C$_{2-6}$ alkenyl. and C$_{2-6}$ alkynyl, wherein the alkyl, alkenyl, or alkynyl is unsubstituted or substituted, wherein the substituents are independently selected from:
  (A) phenyl, unsubstituted or substituted, wherein the substituents are independently selected from: halogen, hydroxy, C$_{1-6}$alkyl C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
  (B) naphthyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
  (C) heterocycle, unsubstituted or substituted, wherein the substituents are independently selected from: halogen, hydroxy, C$_{1-6}$alkyl, C$_{1-6}$alkoxy, —CO$_2$(C$_{1-6}$alkyl), —NH$_2$, —NH(C$_{1-6}$alkyl), —N(C$_{1-6}$ alkyl)(C$_{1-6}$ alkyl), or trifluoromethyl,
  (D) hydroxy,
  (E) —O(C$_{1-6}$ alkyl),
  (F) —CO$_2$(C$_{1-6}$ alkyl),
  (G) —S(O)$_n$—(C$_{1-6}$ alkyl), wherein n is an integer selected from 0, 1 and 2,
  (H) halogen,
  (I) —NH$_2$,
  (J) —NH(C$_{1-6}$ alkyl) and
  (K) —N(C$_{1-6}$ alkyl)(C$_6$ alkyl),
(v) —NR$^9$—COR$^{10}$,
(vi) —NR$^9$—CO$_2$R$^{10}$,
(vii) —CO—NR$^9$R$^{10}$,
(viii) —OCO—NR$^9$R$^{10}$,
(ix) —NR$^9$CO—NR$^9$R$^{10}$,
(x) —S(O)$_2$—NR$^9$R$^{10}$, wherein n is an integer selected from 0, 1 and 2,
(xi) —NR$^9$S(O)$_2$—R$^{10}$,
(xii) —NR$^9$S(O)$_2$—NR$^9$R$^{10}$,
(xiii) —S(O)$_n$—R$^9$,
(xiv) —CF$_3$,
(xv) —CHF$_2$,
(xvi) —CH$_2$F,
(xvii) —O—R$^9$,
(xviii) —O(C$_{1-6}$ alkyl)—O—R$^9$,
(xix) phenyl,
(xx) naphthyl,
(xxi) indenyl,
(xxii) indanyl,
(xxiii) heterocycle,
(xxiv) —CO-phenyl,
(xxv) —CO-naphthyl,
(xxvi) —CO-indenyl,
(xxvii) —CO-indanyl,
(xxviii) —CO-heterocycle,
(xxix) —OCO—R$^9$,
(xxx) —OCO$_2$—R$^9$, and
(xxxi) —CO—R$^9$,
(b) —O—C$_{1-6}$alkyl, —O—C$_{2-6}$ alkenyl, —O—C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$,
(iv) —NR$^9$—COR$^{10}$,
(v) —NR$^9$—CO$_2$R$^{10}$,
(vi) —CO—NR$^9$R$^{10}$,
(vii) —OCO—NR$^9$R$^{10}$,
(viii) —NR$^9$CO—NR$^9$R$^{10}$,
(ix) —S(O)$_2$—NR$^9$R$^{10}$,
(x) —NR$^9$S(O)$_2$—R$^{10}$,
(xi) —NR$^9$S(O)$_2$—NR$^9$R$^{10}$,
(xii) —S(O)$_n$—R$^9$,
(xiii) —CF$_3$,
(xiv) —CHF$_2$,
(xv) —CH$_2$F,
(xvi) —O—R$^9$,
(xvii) —O(C$_{1-6}$ alkyl)—O—R$^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—R$^9$,
(xxix) —OCO$_2$—R$^9$, and
(xxx) —CO—R$^9$,
(c) —NO$_2$,
(d) hydroxy,
(e) halogen,
(f) —NR$^9$R$^{10}$,
(g) —NR$^9$—COR$^{10}$,
(h) —NR$^9$—CO$_2$R$^{10}$,
(i) —CO—NR$^9$R$^{10}$,
(j) —OCO—NR$^9$R$^{10}$,
(k) —NR$^9$CO—NR$^9$R$^{10}$,
(l) —S(O)$_2$—NR$^9$R$^{10}$,
(m) —NR$^9$S(O)$_2$—R$^{10}$,
(n) —NR$^9$S(O)$_2$—NR$^9$R$^{10}$,
(o) —S(O)$_n$—R$^9$,
(p) —CF$_3$,
(q) —CHF$_2$,
(r) —CH$_2$F,
(s) —OCO—R$^9$,
(t) —OCO$_2$—R$^9$, and
(u) —CO—R$^9$.

In the present invention it is highly preferred that R$^1$ is selected from the group consisting of:
(1) —CH$_2$-phenyl,
(2) —CO-phenyl,
(3) —CH$_2$-(2,4-dichlorophenyl),
(4) —CO-(2,4-dichlorophenyl)
(5) —CH$_2$-(2-naphthyl),
(6) —CO-(1-naphthyl),
(7) —CH$_2$-indolyl, and
(8) —CO-indolyl.

In the present invention it is most preferred that R$^1$ is selected from the group consisting of:
(1) —CH$_2$-phenyl,
(2) —CO-phenyl,
(3) —CH$_2$-(2,4-dichlorophenyl),
(4) —CH$_2$-(7-indolyl), and
(5) —CO-(7-indolyl).

In the present invention it is preferred that $R^2$ is:

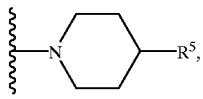

herein $R^5$ is selected from:
(1) phenyl, which is unsubstituted or substituted with halogen, hydroxy, $C_{1-6}$alkyl, $C_{1-6}$alkoxy, or trifluoromethyl,
(2) —$C_{1-6}$alkyl-phenyl, wherein the phenyl is unsubsituted or substituted with: halogen, hydroxy, $C_{1-6}$alkyl, $C_{1-6}$alkoxy, or trifluoromethyl; and wherein the —$C_{1-6}$ alkyl is optionally substituted with oxo, hydroxy, $C_{1-6}$alkoxy, acetoxy, or halogen,
(3) —O-$C_{1-6}$alkyl-phenyl, wherein the phenyl is unsubsituted or substituted with halogen, hydroxy, $C_{1-6}$alkyl, $C_{1-6}$alkoxy, or trifluoromethyl,
(4) —$C_{1-4}$alkyl—O—$C_{1-4}$alkyl-phenyl, wherein the phenyl is unsubsituted or substituted with halogen, hydroxy, $C_{1-6}$alkyl, $C_{1-6}$alkoxy, or trifluoromethyl, and
(5) —$C_{1-4}$alkyl—S(O)$_n$-$C_{1-4}$alkyl-phenyl, wherein n is an integer selected from 0, 1 and 2, and wherein the phenyl is unsubsituted or substituted with halogen, hydroxy, $C_{1-6}$alkyl, $C_{1-6}$alkoxy, or trifluoromethyl.

In the present invention it is more preferred that $R^2$ is:

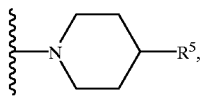

wherein $R^5$ is a selected from:
(1) phenyl, which is unsubstituted or substituted with halogen, hydroxy, $C_{1-6}$alkyl, $C_{1-6}$alkoxy, or trifluoromethyl,
(2) —$C_{2-4}$alkyl-phenyl, wherein the phenyl is unsubsituted or substituted with chloro, fluoro, trifluoromethyl, methyl or ethyl and wherein the —$C_{2-4}$ alkyl is optionally substituted with oxo, hydroxy, halogen, or methoxy,
(3) —$C_{1-3}$alkyl—O—$C_{1-3}$alkyl-phenyl, wherein the phenyl is unsubsituted or substituted with chloro, fluoro, trifluoromethyl, methyl or ethyl, and
(4) —$C_{1-3}$alkyl—S(O)$_n$—$C_{1-3}$alkyl-phenyl, wherein the phenyl is unsubsituted or substituted with chloro, fluoro, trifluoromethyl, methyl or ethyl.

In the present invention it is still more preferred that $R^2$ is:

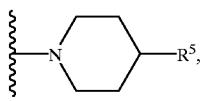

wherein $R^5$ is a selected from:
(1) phenyl, which is unsubstituted to substituted with halogen, hydroxy, $C_{1-6}$alkyl, $C_{1-6}$alkoxy, or trifluoromethyl,
(2) —$C_{3-4}$alkyl-phenyl, wherein the phenyl is unsubsituted or substituted with chloro, fluoro or methyl, and wherein the —$C_{3-4}$alkyl is optionally substituted with oxo, hydroxy, or methoxy,
(3) —$C_{1-3}$alkyl—O—$C_{1-3}$alkyl-phenyl, wherein the phenyl is unsubsituted or substituted with chloro, fluoro or methyl, and
(4) —$C_{1-3}$alkyl—S(O)$_n$—$C_{1-3}$alkyl-phenyl, wherein the phenyl is unsubsituted or substituted with chloro, fluoro or methyl.

In the present invention it is highly preferred that $R^2$ is:

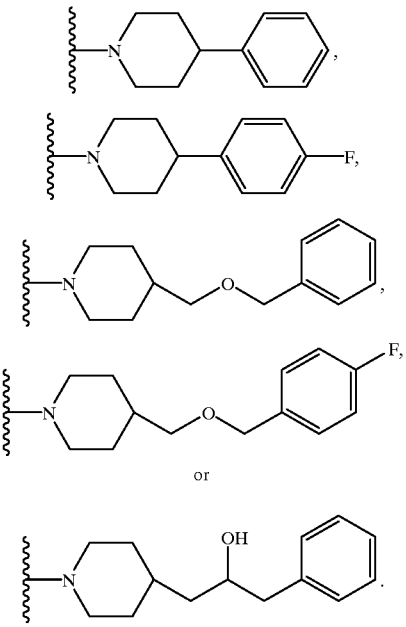

In the present invention it is preferred that $R^3$ is thienyl or furanyl, which may be unsubstituted or substituted, where the substituents are independently selected from:
(1) $C_{1-6}$alkyl, which is unsubstituted or substituted, wherein the substituents are independently selected from:
  (a) hydroxy,
  (b) halogen,
  (c) —$NH_2$,
  (d) —$NHR^9$,
  (e) —$NR^9R^{10}$, wherein $R^9$ and $R^{10}$ are independently selected from $C_{1-6}$alkyl, wherein the alkyl is unsubstituted or substituted, wherein the substituents are independently selected from:
    (A) halogen,
    (B) phenyl, and
    (C) —$CO_2(C_{1-6}$alkyl),
  (f) —$NR^9$—$COR^{10}$,
  (g) —$NR^9$—$CO_2R^{10}$,
  (h) —$CF_3$,
  (i) —$CHF_2$,
  (j) —$C_2F$,
  (k) —O—$R^9$, and
  (l) phenyl,
(2) —O—$C_{1-6}$alkyl, unsubstituted or substituted with a substituent which is independently selected from:
  (a) hydroxy,
  (b) halogen,
  (c) —$NH_2$,
  (d) —$NHR^9$,
  (e) —$NR^9R^{10}$,
  (f) —$NR^9$—$COR^{10}$,
  (g) —$NR^9$—$CO_2R^{10}$, (h) —CF$_3$,
(i) —CHF$_2$,
(j) —CH$_2$F,
(k) —O—R$^9$, and
(l) phenyl,
(3) hydroxy,
(4) halogen,
(5) —CF$_3$,
(6) —CHF$_2$,
(7) —CH$_2$F,
(8) —O—R$^9$, and
(9) —O(C$_{1-6}$alkyl)—O—R$^9$.

In the present invention it is more preferred that R$^3$ is thienyl or furanyl, which may be unsubstituted or substituted, where the substituents are independently selected from:

C$_{1-6}$alkyl, which is unsubstituted or substituted, wherein the substituents are independently selected from:
(a) hydroxy,
(b) —O(C$_{1-6}$alkyl), and
(c) —CO$_2$(C$_{1-6}$alkyl).

In the present invention it is highly preferred that R$^3$ is unsubstituted thienyl or furanyl.

In the present invention it is most preferred that R$^3$ be 3-thienyl. The compounds wherein R$^3$ is 3-thienyl have unexpected properties with respect to compounds wherein R$^3$ is 2-thienyl In the present invention it is preferred that R$^{4c}$, R$^{4d}$, and R$^{4h}$ are independently selected from the group consisting of:
(1) hydrogen, and
(2) C$_{1-6}$alkyl.

In the present invention it is more preferred that R$^{4c}$, R$^{4d}$, and R$^{4h}$ are each hydrogen and that R$^4$d is selected from the group consisting of hydrogen, and —CH$_3$ In the present invention it is most preferred that R$^{4c}$, R$^{4d}$, and R$^{4h}$ are each hydrogen.

The compounds of the instant invention have at least two asymmetric centers at the ring junction of the substitutents bearing R$^2$ and R$^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the most preferred compounds of this invention are of the trans orientation, i.e. as depicted:

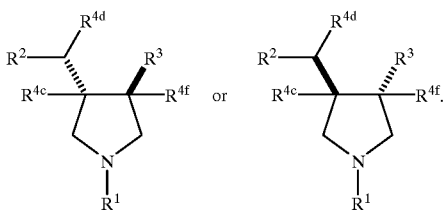

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetnic center of known absolute configuration.

As appreciated by those of skill in the art, halo or halogen as used herein are intended to include chloro, fluoro, bromo and iodo. Similarly, C$_{1-8}$, as in C$_{1-8}$alkyl is defined to identify the group as having 1, 2, 3, 4, 5, 6, 7 or 8 carbons in a linear or branched arrangement, such that C$_{1-8}$alkyl specifically includes methyl, ethyl, propyl, butyl, pentyl, hexyl, heptyl and octyl. The term "heterocycle" as used herein is intended to include the following groups: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, Exemplifying the invention is the use of the compounds disclosed in the Examples and herein.

Specific compounds within the present invention include a compounds which selected from the group consisting of:

1-Benzyl-3-(RS)-(4-phenylpipenidinylmethyl)-4-(RS)-(3-thienyl)-pyrrolidine;
3-(SR)-(4-Phenylpiperidinylmethyl)-4-(RS)-(3-thienyl) pyrrolidine,
1-(1-Naphthylmethyl)-3-(RS)-(4-phenylpiperidinylmethyl)-4-(RS)-(3-thienyl)pyrrolidine;
1-(2-Naphthylmethyl)-3-(RS)-(4-phenylpiperidinylmethyl)-4-(RS)-(3-thienyl)pyrrolidine;
1-Benzyl-3-(RS)-(4-(4-fluorophenyl)piperidinylmethyl)-4-(RS)-(3-thienyl)pyrrolidine;
3-(SR)-(4-(4-Fluorophenyl)piperidinylmethyl)-4-(RS)-(3-thienyl)-pyrrolidine;
1-(2,3-Dichlorophenyl)methyl-3-(RS)-(4-(4-fluorophenyl) piperidinyl-methyl)-4-(RS)-(3-thienyl)pyrrolidine;
1-(1-Naphthylmethyl)-3-(RS)-(4-(4-fluorophenyl) piperidinylmethyl)-4-(RS)-(3-thienyl)pyrrolidine;
1-(2-Naphthylmethyl)-3-(RS)-(4-(4-fluorophenyl) pipridinylmethyl)-4-(RS)-(3-thienyl)pyrrolidine;
1-(4-Chlorobenzyl)-3-(RS)-(4-(4-fluorophenyl) piperidinylmethyl)-4-(RS)-(3-thienyl)pyrrolidine;
1-(3,4-Difluorobenzoyl)-3-(RS)-(4-phenylpiperidinylmethyl)-4-(RS)-(3-thienyl)pyrrolidine;
1-(7-Indolylcarbonyl)-3-(RS)-(4-phenylpiperidinylmethyl)-4-(RS)-(3-thienyl)pyrrolidine;
5-Benzoyl-3-(RS)-(4-phenylpiperidinylmethyl)-4-(RS)-(3-thienyl)pyrrolidine;
1-(1-Naphthoyl)-3-(RS)-(4-phenylpiperidinylmethyl)-4-(RS)-(3-thienyl)pyrrolidine,
1-(2,3-Dichlorobenzoyl)-3-(RS)-(4-phenylpiperidinylmethyl)-4-(RS)-(3-thienyl)pyrrolidine;
1-(3,4-Dichlorobenzoyl)-3-(RS)-(4-phenylpiperidinylmethyl)-4-(RS)-(3-thienyl)pyrrolidine;
1-(2,3-Dimethylbenzoyl)-3-(RS)-(4-phenylpiperidinylmethyl)-4-(RS)-(3-thienyl)pyrrolidine;

1-(6-Methoxy-1-naphthoyl)-3-(RS)-(4-phenylpiperidinylmethyl)-4-(RS)-(3-thienyl)pyrrolidine;
1-(4-Bromo-1-naphthoyl)-3-(RS)-(4-phenylpiperidinylmethyl)-4-(RS)-(3-thienyl)pyrrolidine;
1-(8-Bromo-1-naphthoyl)-3-(RS)-(4-phenylpiperidinylmethyl)-4-(RS)-(3-thienyl)pyrrolidine;
1-(4-Fluoro-1-naphthoyl)-3-(RS)-(4-phenylpiperidinylmethyl)-4-(RS)-(3-thienyl)pyrrolidine;
1-(8-Quinolinecarbonyl)-3-(RS)-(4-phenylpiperidinylmethyl)-4-(RS)-(3-thienyl)pyrrolidine;
1-(4-Quinolinylcarbonyl)-3-(RS)-(4-phenylpiperidinylmethyl)-4-(RS)-(3-thienyl)pyrrolidine;
1-(2,3-Difluorobenzoyl)-3-(RS)-(4-phenylpiperidinylmethyl)-4-(RS)-(3-thienyl)pyrrolidine,
1-(2,3,4-Trifluorobenzoyl)-3-(RS)-(4-phenylpiperidinylmethyl)-4-(RS)-(3-thienyl)pyrrolidine;
1-(2,3,4,5,6-Pentafluorobenzoyl)-3-(RS)-(4-phenylpiperidinylmethyl)-4-(RS)-(3-thienyl)pyrrolidine;
1-(3-Fluoro-4-trifluoromethylbenzoyl)-3-(RS)-(4-phenylpiperidinyl-methyl)-4-(RS)-(3-thienyl)pyrrolidine;
1-(4-Chlorobenzoyl)-3-(RS)-(4-phenylpiperidinylmethyl)-4-(RS)-(3-thienyl)pyrrolidine;
1-(3-Chlorobenzoyl)-3-(RS)-(4-phenylpiperidinylmethyl)-4-(RS)-(3-thienyl)pyrrolidine;
1-(4-Methoxybenzoyl)-3-(RS)-(4-phenylpiperidinylmethyl)-4-(RS)-(3-thienyl)pyrrolidine;
1-(4-Methylbenzoyl)-3-(RS)-(4-phenylpiperidinylmethyl)-4-(RS)-(3-thienyl)pyrrolidine;
1-(2-Amino-3-methoxybenzoyl)-3-(RS)-(4-(4-fluorophenyl)piperidinyl-methyl)-4-(RS)-(3-thienyl)pyrrolidine;
1-(2-Acetoxy-3-methylbenzoyl)-3-(RS)-(4-(4-fluorophenyl)piperidinyl-methyl)-4-(RS)-(3-thienyl)pyrrolidine;
Acetyl-3-(RS)-(4-(4-fluorophenyl)piperidinylmethyl)-4-(RS)-(3thienyl)pyrrolidine;
1-(2-Trifluoroacetylaminobenzoyl)-3-(RS)-(4-(4-fluorophenyl)-piperidinylmethyl)-4-(RS)-(3-thienyl)pyrrolidine;
1-(2-Difluoromethoxybenzoyl)-3-(RS)-(4-(4-fluorophenyl)piperidinyl-methyl)-4-(RS)-(3-thienyl)pyrrolidine;
1-(2-Amino-3-methylbenzoyl)-3-(RS)-(4-(4-fluorophenyl)piperidinyl-methyl)-4-(RS)-(3-thienyl)pyrrolidine;
1-(2-Methyl-3-fluorobenzoyl)-3-(RS)-(4-(4-fluorophenyl)piperidinyl-methyl)-4-(RS)-(3-thienyl)pyrrolidine;
1-(2-Methyl-3-aminobenzoyl)-3-(RS)-(4-(4-fluorophenyl)piperidinyl-methyl)-4-(RS)-(3-thienyl)pyrrolidine;
1-(2,3-Dihydroxybenzoyl)-3-(RS)-(4-(4-fluorophenyl)piperidinylmethyl)-4-(RS)-(3-thienyl)pyrrolidine;
1-(7-Indolecarbonyl)-3-(RS)-(4-(4-fluorophenyl)piperidinylmethyl)-4-(RS)-(3-thienyl)pyrrolidine;
1-(2-Chloro-3-pyridylcarbonyl)-3-(RS)-(4-(4-fluorophenyl)piperidinyl-methyl)-4-(RS)-(3-thienyl)pyrrolidine;
1-(2,3-Difluorobenzoyl)-3-(RS)-(4-(4-fluorophenyl)piperidinylmethyl)-4-(RS)-(3-thienyl)pyrrolidine;
1-(3,4-Difluorobenzoyl)-3-(RS)-(4-(4-fluorophenyl)piperidinylmethyl)-4-(RS)-(3-thienyl)pyrrolidine;
1-(2,4-Difluorobenzoyl)-3-(RS)-(4-(4-fluorophenyl)piperidinylmethyl)-4-(RS)-(3-thienyl)pyrrolidine;
1-(8-Quinolinylcarbonyl)-3-(RS)-(4-(4-fluorophenyl)piperidinylmethyl)-4-(RS)-(3-thienyl)pyrrolidine;
1-(4-Pyrazolylcarbonyl)-3-(RS)-(4-(4-fluorophenyl)piperidinylmethyl)-4-(RS)-(3-thienyl)pyrrolidine;
1-(5-Methyl-2-thienylcarbonyl)-3-(RS)-(4-(4-fluorophenyl)piperidinyl-methyl)-4-(RS)-(3-thienyl)pyrrolidine:
1-(3-Methyl-2-thienylcarbonyl)-3-(RS)-(4-(4-fluorophenyl)piperidinyl-methyl)-4-(RS)-(3-thienyl)pyrrolidine;
1-(4-Chlorobenzoyl)-3-(RS)-(4-(4-fluorophenyl)piperidinylmethyl)-4-(RS)-(3-thienyl)pyrrolidine;
1-Methoxycarbonyl-3-(RS)-(4-(4-fluorophenyl)piperidinylmethyl)-4-(RS)-(3-thienyl)pyrrolidine,
1-Isopropyloxycarbonyl-3-(RS)-(4-(4-fluorophenyl)piperidinylmethyl)-4-(RS)-(3-thienyl)pyrrolidine;
1-Benzoyl-3-(RS)-(4-(4-fluorophenyl)piperidinylmethyl)-4-(RS)-(3-thienyl)pyrrolidine;
1-(5-Chloro-2-thienylcarbonyl)-3-(RS)-(4-(4-fluorophenyl)piperidinylmethyl)-4-(RS)-(3-thienyl)pyrrolidine;
1-(4-Methylbenzoyl)-3-(RS)-(4-(4-fluorophenyl)piperidinylmethyl)-4-(RS)-(3-thienyl)pyrrolidine;
1-(4,5-Dichloro-3-thiazolylcarbonyl)-3-(RS)-(4-(4-fluorophenyl)piperidinylmethyl)-4-(RS)-(3-thienyl)pyrrolidine;
1-(4-Methyl-5-thiadizolylcarbonyl)-3-(RS)-(4-(4-fluorophenyl)piperidinylmethyl)-4-(RS)-(3-thienyl)pyrrolidine;
1-(4-Methyl-5-thiadizolylcarbonyl)-3-(RS)-(4-(4-fluorophenyl)piperidinylmethyl)-4-(RS)-(3-thienyl)pyrrolidine;
1-(3-Methyl-2-furanylcarbonyl)-3-(RS)-(4-(4-fluorophenyl)piperidinylmethyl)-4-(RS)-(3-thienyl)pyrrolidine;
1-(5-Methylthio-2-thienylcarhonyl)-3-(RS)-(4-(4-fluorophenyl)piperidinylmethyl)-4-(RS)-(3-thienyl)pyrrolidine;
1-(2,3-Dibromo-5-thienylcarbonyl)-3-(RS)-(4-(4-fluorophenyl)piperidinylmethyl)-4-(RS)-(3-thienyl)pyrrolidine;
1-(2,4-Dimethyl-5-thiazolylcabonyl)-3-(RS)-(4-(4-fluorophenyl)piperidinylmethyl)-4-(RS)-(3-thienyl)pyrrolidine;
1-(2-Bromo-3-methylbenzoyl)-3-(RS)-(4-(4-fluorophenyl)piperidinylmethyl)-4-(RS)-(3-thienyl)pyrrolidine;
1-(5-Isoxazolylcarbonyl)-3-(RS)-(4-(4-fluorophenyl)piperidinylmethyl)-4-(RS)-(3-thienyl)pyrrolidine;
1-(2-Thienylcarbonyl)-3-(RS)-(4-(4-fluorophenyl)piperidinylmethyl)-4-(RS)-(3-thienyl)pyrrolidine;
1-(3-Thienylcarbonyl)-3-(RS)-(4-(4-fluorophenyl)piperidinylmethyl)-4-(RS)-(3-thienyl)pyrrolidine;
1-(2-Nitro-4-thienylcarbonyl)-3-(RS)-(4-(4-fluorophenyl)piperidinylmethyl)-4-(RS)-(3-thienyl)pyrrolidine;
1-(2-(2-pyridyl)-4-thienylcarbonyl)-3-(RS)-(4-(4-fluorophenyl)piperidinylmethyl)-4-(RS)-(3-thienyl)pyrrolidine;
1-(4-Methoxybenzoyl)-3-(RS)-(4-(4-fluorophenyl)piperidinylmethyl)-4-(RS)-(3-thienyl)pyrrolidine;
1-(3-Chlorobenzoyl)-3-(RS)-(4-(4-fluorophenyl)piperidinylmethyl)-4-(RS)-(3-thienyl)pyrrolidine;
1-(2,3-Dimethylbenzoyl)-3-(RS)-(4-(4-fluorophenyl)piperidinylmethyl)-4-(RS)-(3-thienyl)pyrrolidine;
1-(3,4-Dimethylbenzoyl)-3-(RS)-(4-(4-fluorophenyl)piperidinylmethyl)-4-(RS)-(3-thienyl)pyrrolidine;
1-(4-Nitrobenzoyl)-3-(RS)-(4-(4-fluorophenyl)piperidinylmethyl)-4-(RS)-(3-thienyl)pyrrolidine;
1-(2-Phenylbenzoyl)-3-(RS)-(4-(4-fluorophenyl)piperidinylmethyl)-4-(RS)-(3-thienyl)pyrrolidine,
1-(2,3-Dimethyl-7-indolylcarbonyl)-3-(RS)-(4-(4-fluorophenyl)piperidinylmethyl)-4-(RS)-(3-thienyl)pyrrolidine;
1-(7-Benzo-2,3-dihydrofuranylcarbonyl)-3-(RS)-(4-(4-fluorophenyl)-piperdinylmethyl)-4-(RS)-(3-thienyl)pyrrolidine;
1-(1-Naphthoyl)-3-(RS)-(4-(4-fluorophenyl)piperidinylmethyl)-4-(RS)-(3-thienyl)pyrrolidine;
1-(2-Benzoylbenzoyl)-3-(RS)-(4-(4-fluorophenyl)piperidinylmethyl)-4-(RS)-(3-thienyl)pyrrolidine, 1-(1-Methyl-7-indolylcarbonyl)-3-(RS)-(4-(4-fluorophenyl) piperidinylmethyl)-4-(RS)-(3-thienyl)pyrrolidine;

1-(1,2-Dimethyl-7-indolylcarbonyl)-3-(RS)-(4-(4-fluorophenyl)piperidinylmethyl)-4-(RS)-(3-thienyl) pyrrolidine;

1-(2,3-Methylenedioxybenzoyl)-3-(RS)-(4-(4-fluorophenyl)piperidinylmethyl)-4-(RS)-(3-thienyl) pyrrolidine;

1-(2,3-Difluoromethylenedioxybenzoyl)-3-(RS)-(4-(4-fluorophenyl) piperidinylmethyl)-4-(RS)-(3-thienyl) pyrrolidine;

1-(([1,2,3,4]Tetrazolo[1,5a]pyridinoyl)-3-(RS)-(4-(4-fluorophenyl) piperidinylmethyl)-4-(RS)-(3-thienyl) pyrrolidine, 1-(2-Indolecarbonyl)-3-(RS)-(4-(4-flurophenyl) piperidinylmethyl)-4-(RS)-(3-thienyl)pyrrolidine;

1-(4-Indolecarbonyl)-3-(RS)-(4-(4-fluorophenyl) piperidinylmethyl)-4-(RS)-(3-thienyl)pyrrolidine;

1-(1-Indolecarbonyl)-3-(RS)-(4-(4-fluorophenyl) piperidinylmethyl)-4-(RS)-(3-thienyl)pyrrolidine;

1-(3-Indoleacteyl)-3-(RS)-(4-(4-fluorophenyl) piperidinylmethyl)-4-(RS)-(3-thienyl)pyrrolidine;

1-(1-Naphthoyl)-3-(SR)-formyl-4-(RS)-(3-thienyl) pyrrolidine;

1-(1-Naphthoyl)-3-(RS)-(4-(4-trifluoromethylphenyl) piperidinylmethyl)-4-(RS)-(3-thienyl)pyrrolidine;

1-(1-Naphthoyl)-3-(RS)-(4-(4-chlorophenyl) piperidinylmethyl)-4-(RS)-(3-thienyl)pyrrolidine;

1-(1-Naphthoyl)-3-(RS)-(4-(3,4-difluorophenyl) piperidinylmethyl)-4-(RS)-(3-thienyl)pyrrolidine;

1-(1-Naphthoyl)-3-(RS)-(4-(3,4,5-trifluorophenyl) piperidinylmethyl)-4-(RS)-(3-thienyl)pyrrolidine;

1-(1-Naphthoyl)-3-(RS)-(4-(4-methylphenyl) piperidinylmethyl)-4-(RS)-(3-thienyl)pyrrolidine;

1-(1-Naphthoyl)-3-(RS)-(4-(4-methoxyphenyl) piperidinylmethyl)-4-(RS)-(3-thienyl)pyrrolidine;

1-(1-Naphthoyl)-3-(RS)-(4-(2-methoxyphenyl) piperdinylmethyl)-4-(RS)-(3-thienyl)pyrrolidine;

1-(1-Naphthoyl)-3-(RS)-(4-(3-trifluoromethylphenyl) piperidinylmethyl)-4-(RS)-(3-thienyl)pyrrolidine;

1-(1-Naphthoyl)-3-(RS)-(4-((4-pyridyl)piperidinylmethyl)-4-(RS)-(3-thienyl)pyrrolidine;

1-(1-Naphthoyl)-3-(RS)-(4-(2-fluorophenyl) piperidinylmethyl)-4-(RS)-(3-thienyl)pyrrolidine;

1-(1-Naphthoyl)-3-(RS)-(4-(2-carbomethoxyphenyl) piperidinylmethyl)-4-(RS)-(3-thienyl)pyrrolidine;

1-(1-Naphthoyl)-3-(RS)-(4-(3-aminophenyl) piperidinylmethyl)-4-(RS)-(3-thienyl)pyrrolidine;

1-(1-Naphthoyl)-3-(RS)-(4-(3-chlorophenyl) piperidinylmethyl)-4-(RS)-(3-thienyl)pyrrolidine;

1-(1-Naphthoyl)-3-(RS)-(4-(2,4-difluorophenyl) piperidinylmethyl)-4-(RS)-(3-thienyl)pyrrolidine;

1-(1-Naphthoyl)-3-(RS)-(4-(3-fluorophenyl) piperidinylmethyl)-4-(RS)-(3-thienyl)pyrrolidine;

1-(1-Naphthoyl)-3-(RS)-(4-(3-thiophenyl) piperidinylmethyl)-4-(RS)-(3-thienyl)pyrrolidine;

1-(1-Naphthoyl)-3-(RS)-(4-(3-pyridyl)piperidinylmethyl)-4-(RS)-(3-thienyl)pyrrolidine;

1-(1-Naphthoyl)-3-(RS)-(spiro[indenyl-3,4'piperidin-1'-yl] methyl)-4-(RS)-(3-thienyl)pyrrolidine;

1-(1-Naphthoyl)-3-(RS)-(spiro[indanyl-3,4'piperidin-1'-yl] methyl)-4-(RS)-(3-thienyl)pyrrolidine;

1-(1-Naphthoyl)-3-(RS)-(spiro[indan-1-one-3,4'piperidin-1'-yl]methyl)-4-(RS)-(3-thienyl)pyrrolidine;

1-(1-Naphthoyl)-3-(RS)-(4-(4-bromophenyl)-piperidnylmethyl)-4-(RS)-(3thienyl)pyrrolidine;

1-(1-Naphthoyl)-3-(RS)-(4-(4-hydroxyphenyl)-piperidinylmethyl)-4-(RS)-(3thienyl)pyrrolidine;

1-(1-Naphthoyl)-3-(RS)-(4-(4-fluorophenyl)-tropanylmethyl)-4-(RS)-(3-thienyl)pyrrolidine;

1-(1-Naphthoyl)-3-(RS)-(4-(2-pyridyl)piperidinylmethyl)-4-(RS)-(3-thienyl)pyrrolidine;

1-(3,4-Dichlorobenzoyl)-3-(RS)-(spiro[indan-1-one-3,4'piperidin-1'-yl]methyl)-4-(RS)-(3-thienyl)pyrrolidine;

1-(2,3-Dichlorobenzoyl)-3-(RS)-(spiro[indan-1-one-3,4'piperidin-1'-yl]methyl)-4-(RS)-(3-thienyl)pyrrolidine;

1-(3,4-Dichlorobenzoyl)-3-(RS)-(spiro[indenyl-3,4'piperidin-1'-yl]methyl)-4-(RS)-(3-thienyl)pyrrolidine;

1-(2,3-Dichlorobenzoyl)-3-(RS)-(spiro[indenyl-3,4'piperidin-1'-yl]methyl)-4-(RS)-(3-thienyl)pyrrolidine;

1-(3,4-Dichlorobenzoyl)-3-(RS)-(spiro[indanyl-3,4'piperidin-1'-yl]methyl)-4-(RS)-(3-thienyl)pyrrolidine;

1-(2,3-Dichlorobenzoyl)-3-(RS)-(spiro[indanyl-3,4'piperidin-1'-yl]methyl)-4-(RS)-(3-thienyl)pyrrolidine;

1-(1-Naphthoyl)-3-(RS)-(4-(4-fluorophenyl)-piperidinyl-1-ethyl)-4-(RS)-(3-thienyl)pyrrolidine;

1-Benzyl-3-(RS)-(4-hydroxy-4-(3-phenylpropyl) piperidinylmethyl)-4-(SR)-(3-thienyl)pyrrolidine;

1-Benzyl-3-(RS)-(4-hydroxy-4-(3-fluorophenyl)propyl) piperidinyl methyl)-4-(SR)-(3-thienyl)pyrrolidine;

1-Benzyl-3-(RS)-(4-hydroxy-4-(3-(4-methoxyphenyl) propyl)piperidinylmethyl)-4-(SR)-(3-thienyl)pyrrolidine;

1-Benzyl-3-(RS)-(4-hydroxy-4-(3-(3-methoxyphenyl) propyl)piperidinylmethyl)-4-(SR)-(3-thienyl)pyrrolidine;

1-Benzyl-3-(RS)-(4-hydroxy-4-(3-(2-methylphenyl)propyl) piperidinylmethyl)-4-(SR)-(3-thienyl)pyrrolidine;

1-Benzyl-3-(RS)-(4-hydroxy-4-(3-(2-fluorophenyl)propyl) piperidinylmethyl)-4-(SR)-(3-thienyl)pyrrolidine;

1-Benzyl-3-(RS)-(4-hydroxy-4-(3-(3-fluorophenyl)propyl) piperidinylmethyl)-4-(SR)-(3-thienyl)pyrrolidine;

1-Benzyl-3-(RS)-(4-hydroxy-4-(3-(2-methoxyphenyl) propyl)piperidinylmethyl)-4-(SR)-(3-thienyl)pyrrolidine;

1-Benzyl-3-(RS)-(4-hydroxy-4-(3-(4-tetrazolylphenyl) propyl)piperidinylmethyl)-4-(SR)-(3-thienyl)pyrrolidine;

1-Benzyl-3-(RS)-(4-hydroxy-4-(3-phenylprop-2-enyl) piperidinylmethyl)-4-(SR)-(3-thienyl)pyrrolidine;

1-Benzyl-3-(RS)-(4-hydroxy-4-(2-methyl-3-phenylpropyl) piperidinyl-methyl)-4-(SR)-(3-thienyl)pyrrolidine;

1-Benzyl-3-(RS)-(4-hydroxy-4-(3-methyl-3-phenylpropyl) piperidinylmethyl)-4-(SR)-(3-thienyl)pyrrolidine;

1-(2-Phenethyl)-3-(RS)-(4-hydroxy-4-(3-phenylpropyl) piperidinylmethyl)-4-(SR)-(3-thienyl)pyrrolidine;

1-(3,4-Dimethylbenzyl)-3-(RS)-(4-hydroxy-4-(3-phenylpropyl)piperidinylmethyl)-4-(SR)-(3-thienyl) pyrrolidine;

1-(3,4-Dichlorobenzyl)-3-(RS)-(4-hydroxy-4-(3-phenylpropyl)piperidinylmethyl)-4-(SR)-(3-thienyl) pyrrolidine;

1-(2,3-Dichlorobenzyl)-3-(RS)-(4-hydroxy-4-(3-phenylpropyl)piperidinylmethyl)-4-(SR)-(3-thienyl) pyrrolidine;

1-(3,5-Dichlorobenzyl)-3-(RS)-(4-hydroxy-4-(3-phenylpropyl)piperidinylmethyl)-4-(SR)-(3-thienyl) pyrrolidine;

1-(4-Chlorobenzyl)-3-(RS)-(4-hydroxy-4-(3-phenylpropyl) piperidinylmethyl)-4-(SR)-(3-thienyl)pyrrolidine;

1-(4-Fluorobenzyl)-3-(RS)-(4-hydroxy-4-(3-phenylpropyl) piperidinylmethyl)-4-(SR)-(3-thienyl)pyrrolidine;

1-(4-Bromobenzyl)-3-(RS)-(4-hydroxy-4-(3-phenylpropyl) piperidinyl-methyl)-4-(SR)-(3-thienyl)pyrrolidine;

1(2-Chlorobenzyl)-3-(RS)-(4-hydroxy-4-(3-phenylpropyl) piperidinylmethyl)-4-(SR)-(3-thienyl)pyrrolidine;

1-(2-Methylbenzyl)-3-(RS)-(4-hydroxy-4-(3-phenylpropyl) piperidinyl-methyl)-4-(SR)-(3-thienyl)pyrrolidine;

1-(3-Chlorobenzyl)-3-(RS)-(4-hydroxy-4-(3-phenylpropyl) piperidinyl-methyl)-4-(SR)-(3-thienyl)pyrrolidine;

1-(4-Nitrobenzyl)-3-(RS)-(4-hydroxy-4-(3-phenylpropyl) piperidinylmethyl)-4-(SR)-(3-thienyl)pyrrolidine;
1-(4-Methoxybenzyl)-3-(RS)-(4-hydroxy-4-(3-phenylpropyl)piperidinylmethyl)-4-(SR)-(3-thienyl) pyrrolidine;
1-(4-Methylbenzyl)-3-(RS)-(4-hydroxy-4-(3-phenylpropyl) piperidinyl-methyl)-4-(SR)-(3-thienyl)pyrrolidine;
1-(4-Trifluoromethylbenzyl)-3-(RS)-(4-hydroxy-4-(3-phenylpropyl)-piperidinylmethyl)-4-(SR)-(3-thienyl) pyrrolidine;
1-(3-Methylbenzyl)-3-(RS)-(4-hydroxy-4-(3-phenylpropyl) piperidinyl-methyl)-4-(SR)-(3-thienyl)pyrrolidine;
1-(2,4-Dichlorobenzyl)-3-(RS)-(4-hydroxy-4-(3-phenylpropyl)piperidinylmethyl)-4-(SR)-(3-thienyl) pyrrolidine;
1-Benzoyl-3-(RS)-(4-hydroxy-4-(3-phenylpropyl) piperidinylmethyl)-4-(SR)-(3-thienyl)pyrrolidine;
1-(4-Fluorobenzoyl)-3-(RS)-(4-hydroxy-4-(3-phenylpropyl)piperidinyl-methyl)-4-(SR)-(3-thienyl) pyrrolidine;
1-(4-Bromobenzoyl)-3-(RS)-(4-hydroxy-4-(3-phenylpropyl)piperidinyl-methyl)-4-(SR)-(3-thienyl) pyrrolidine;
1-(4-Nitrobenzoyl)-3-(RS)-(4-hydroxy-4-(3-phenylpropyl) piperidinyl-methyl)-4-(SR)-(3-thienyl)pyrrolidine;
1-(4-Methoxybenzoyl)-3-(RS)-(4-hydroxy-4-(3-phenylpropyl)piperidinylmethyl)-4-(SR)-(3-thienyl) pyrrolidine;
1-(2,4-Dichlorobenzoyl)-3-(RS)-(4-hydroxy-4-(3-phenylpropyl)piperidinylmethyl)-4-(SR)-(3-thienyl) pyrrolidine;
1-(3-Chlorobenzoyl)-3-(RS)-(4-hydroxy-4-(3-phenylpropyl)piperidinyl-methyl)-4-(SR)-(3-thienyl) pyrrolidine;
1-(4-Chlorobenzoyl)-3-(RS)-(4-hydroxy-4-(3-phenylpropyl)piperidinyl-methyl)-4-(SR)-(3-thienyl) pyrrolidine;
1-(2-Chlorobenzoyl)-3-(RS)-(4-hydroxy-4-(3-phenylpropyl)piperidinyl-methyl)-4-(SR)-(3-thienyl) pyrrolidine;
1-(2-Naphthoyl)-3-(RS)-(4-hydroxy-4-(3-phenylpropyl) piperidinylmethyl)-4-(SR)-(3-thienyl)pyrrolidine;
1-(1-Naphthoyl)-3-(RS)-(4-hydroxy-4-(3-phenylpropyl) piperidinylmethyl)-4-(SR)-(3-thienyl)pyrrolidine;
1-(3,4-Dichlorobenzoyl)-3-(RS)-(4-hydroxy-4-(3-phenylpropyl)piperidinylmethyl)-4-(SR)-(3-thienyl) pyrrolidine;
1-(2,3-Dichlorobenzoyl)-3-(RS)-(4-hydroxy-4-(3-phenylpropyl)piperidinylmethyl)-4-(SR)-(3-thienyl) pyrrolidine;
1-(4-Methylbenzoyl)-3-(RS)-(4-hydroxy-4-(3-phenylpropyl)piperidinylmethyl)-4-(SR)-(3-thienyl) pyrrolidine;
1-(4-Trifluoromethylbenzoyl)-3-(RS)-(4-hydroxy-4-(3-phenylpropyl)-piperidinylmethyl)-4-(SR)-(3-thienyl) pyrrolidine;
1-(4-Chloro-3-methylbenzoyl)-3-(RS)-(4-hydroxy-4-(3-phenylpropyl)-piperidinylmethyl)-4-(SR)-(3-thienyl) pyrrolidine;
1-(1-Naphthoyl)-3-(RS)-(4-hydroxy-4-(3-(4-fluorophenyl)-1-propyl)piperidinylmethyl)-4-(SR)-(3-thienyl) pyrrolidine;
1-(2,3-Dichlorobenzoyl)-3-(RS)-(4-hydroxy-4-(3-(4-fluorophenyl)-1-propyl)piperidinylmethyl)-4-(SR)-(3-thienyl)pyrrolidine;
1-(3,4-Dichlorobenzoyl)-3-(RS)-(4-hydroxy-4-(3-(4-fluorophenyl)-1-propyl)piperidinylmethyl)-4-(SR)-(3-thienyl)pyrrolidine;
1-(1-Naphthoyl)-3-(RS)-(4-hydroxy-4-(3-(2-methylphenyl)-1-propyl)piperidinylmethyl)-4-(SR)-(3-thienyl)pyrrolidine;
1-(2,3-Dichlorobenzoyl)-3-(RS)-(4-hydroxy-4-(3-(2-methylphenyl)-1-propyl)piperidinylmethyl)-4-(SR)-(3-thienyl)pyrrolidine;
1-(3,4-Dichlorobenzoyl)-3-(RS)-(4-hydroxy-4-(3-(2-methylphenyl)-1-propyl)piperidinylmethyl)-4-(SR)-(3-thienyl)pyrrolidine;
1-(1-Naphthoyl)-3-(RS)-(4-hydroxy-4-(3-(2-fluorophenyl)-1-propyl)piperidinylmethyl)-4-(SR)-(3-thienyl) pyrrolidine;
1-(2,3-Dichlorobenzoyl)-3-(RS)-(4-hydroxy-4-(3-(2-fluorophenyl)-1-propyl)piperidinylmethyl)-4-(SR)-(3-thienyl)pyrrolidine;
1-(3,4-Dichlorobenzoyl)-3-(RS)-(4-hydroxy-4-(3-(2-fluorophenyl)-1-propyl)piperidinylmethyl)-4-(SR)-(3-thienyl)pyrrolidine;
1-(1-Naphthoyl)-3-(RS)-(4-hydroxy-4-(3-(3-fluorophenyl) propyl)piperidinylmethyl)-4-(SR)-(3-thienyl)pyrrolidine;
1-(2,3-Dichlorobenzoyl)-3-(RS)-(4-hydroxy-4-(3-(3-fluorophenyl)propyl)piperidinylmethyl)-4-(SR)-(3-thienyl)pyrrolidine;
1-(3,4-Dichlorobenzoyl)-3-(RS)-(4-hydroxy-4-(3-(3-fluorophenyl)-1-propyl)piperidinylmethyl)-4-(SR)-(3-thienyl)pyrrolidine;
1-(1-Naphthoyl)-3-(RS)-(4-hydroxy-4-(3-(4-methoxyphenyl)propyl)piperidinylmethyl)-4-(SR)-(3-thienyl)pyrrolidine;
1-(2,3-Dichlorobenzoyl)-3-(RS)-(4-hydroxy-4-(3-(4-methoxyphenyl)propyl)piperidinylmethyl)-4-(SR)-(3-thienyl)pyrrolidine;
1-(3,4-Dichlorobenzoyl)-3-(RS)-(4-hydroxy-4-(3-(4-methoxyphenyl)propyl)piperidinylmethyl)-4-(SR)-(3-thienyl)pyrrolidine;
1-(1-Naphthoyl)-3-(RS)-(4-hydroxy-4-(3-(3-methoxyphenyl)propyl)piperidinylmethyl)-4-(SR)-(3-thienyl)pyrrolidine;
1-(2,3-Dichlorobenzoyl)-3-(RS)-(4-hydroxy-4-(3-(3-methoxyphenyl)propyl)piperidinylmethyl)-4-(SR)-(3-thienyl)pyrrolidine;
1-(3,4-Dichlorobenzoyl)-3-(RS)-(4-hydroxy-4-(3-(3-methoxyphenyl)propyl)piperidinylmethyl)-4-(SR)-(3-thienyl)pyrrolidine;
1-(3,4-Dichlorobenzoyl)-3-(RS)-(4-hydroxy-4-(3-(2-methoxyphenyl)propyl)piperidinylmethyl)-4-(SR)-(3-thienyl)pyrrolidine;
1-(3,4-Dichlorobenzoyl)-3-(RS)-(4-hydroxy-4-(3-(4-tetrazolylphenyl)propyl)piperidinylmethyl)-4-(SR)-(3-thienyl)pyrrolidine;
1-(3,4-Dichlorobenzoyl)-3-(RS)-(4-hydroxy-4-(3-phenyl-2-propenyl)-piperidinylmethyl)-4-(SR)-(3-thienyl) pyrrolidine;
1-(3,4-Dichlorobenzoyl)-3-(RS)-(4-hydroxy-4-(2-methyl-3-phenylpropyl)-piperidinylmethyl)-4-(SR)-(3-thienyl) pyrrolidine;
1-(3,4-Dichlorobenzoyl)-3-(RS)-(4-hydroxy-4-(3-methyl-3-phenylpropyl)-piperidinylmethyl)-4-(SR)-(3-thienyl) pyrrolidine;
1-Benzyl-3-(RS)-(4-(3-phenylpropyl)piperidinylmethyl)-4-(SR)-(3-thienyl)pyrrolidine;
1-(3,4-Dichlorobenzoyl)-3-(RS)-(4-(3-phenylpropyl) piperidinylmethyl)-4-(SR)-(3-thienyl)pyrrolidine;
1-Benzyl-3-(RS)-(4-(2-(4-fluorophenoxy)ethyl) piperidinylmethyl)-4-(SR)-(3-thienyl)pyrrolidine;
1-(2,4-Dichlorobenzoyl)-3-(RS)-(4-(2-(4-fluorophenoxy) ethyl)piperidinyl-methyl)-4-(SR)-(3-thienyl)pyrrolidine;

1-(3,4-Dichlorobenzoyl)-3-(RS)-(4-(2-(4-fluorophenoxy)ethyl)piperidinylmethyl)-4-(SR)-(3-thienyl)pyrrolidine;
1-Benzyl-3-(RS)-(4-(2-phenoxy)ethyl)piperidinylmethyl)-4-(SR)-(3-thienyl)pyrrolidine;
1-(2,4-Dichlorobenzyl)-3-(RS)-(4-(2-phenoxy)ethyl)piperidinylmethyl)-4-(SR)-(3-thienyl)pyrrolidine;
1-(3,4-Dichlorobenzoyl)-3-(RS)-(4-(2-(4-fluorophenoxy)ethyl)piperidinylmethyl)-4-(SR)-(3-thienyl)pyrrolidine;
1-Benzyl-3-(RS)-(4-(benzyloxymethyl)piperidinylmethyl)-4-(SR)-(3-thienyl)pyrrolidine;
1-(2,4-Dichlorobenzyl)-3-(RS)-(4-(benzyloxymethyl)piperidinylmethyl)-4-(SR)-(3-thienyl)pyrrolidine;
1-(3,4-Dichlorobenzoyl)-3-(RS)-(4-(benzyloxymethyl)piperidinylmethyl)-4-(SR)-(3-thienyl)pyrrolidine;
1-Benzyl-3-(RS)-(4-(4-fluorobenzyloxymethyl)piperidinylmethyl)-4-(SR)-(3-thienyl)pyrrolidine;
1-(2,4-Dichlorobenzyl)-3-(RS)-(4-(4-fluorobenzyloxymethyl)piperidinylmethyl)-4-(SR)-(3-thienyl)pyrrolidine;
1-(3,4-Dichlorobenzoyl)-3-(RS)-(4-(4-fluorobenzyloxymethyl)piperidinylmethyl)-4-(SR)-(3-thienyl)pyrrolidine;
1-(2-Chlorobenzyl)-3-(RS)-(4-(4-fluorobenzyloxymethyl)piperidinylmethyl)-4-(SR)-(3-thienyl)pyrrolidine;
1-(2-Methylbenzyl)-3-(RS)-(4-(4-fluorobenzyloxymethyl)piperidinylmethyl)-4-(SR)-(3-thienyl)pyrrolidine;
1-(3-Chlorobenzyl)-3-(RS)-(4-(4-fluorobenzyloxymethyl)piperidinylmethyl)-4-(SR)-(3-thienyl)pyrrolidine;
1-(3-Methylbenzyl)-3-(RS)-(4-(4-fluorobenzyloxymethyl)piperidinylmethyl)-4-(SR)-(3-thienyl)pyrrolidine;
1-(4-Chlorobenzyl)-3-(RS)-(4-(4-fluorobenzyloxymethyl)piperidinylmethyl)-4-(SR)-(3-thienyl)pyrrolidine;
1-(4-Methylbenzyl)-3-(RS)-(4-(4-fluorobenzyloxymethyl)piperidinylmethyl)-4-(SR)-(3-thienyl)pyrrolidine;
1-(4-Methoxybenzyl)-3-(RS)-(4-(4-fluorobenzyloxymethyl)piperidinylmethyl)-4-(SR)-(3-thienyl)pyrrolidine;
1-(4-Bromobenzyl)-3-(RS)-(4-(4-fluorobenzyloxymethyl)piperidinylmethyl)-4-(SR)-(3-thienyl)pyrrolidine;
1-(3,4-Dichlorobenzyl)-3-(RS)-(4-(4-fluorobenzyloxymethyl)piperidinylmethyl)-4-(SR)-(3-thienyl)pyrrolidine;
1-(3,5-Dichlorobenzyl)-3-(RS)-(4-(4-fluorobenzyloxymethyl)piperidinylmethyl)-4-(SR)-(3-thienyl)pyrrolidine;
1-(2,5-Dichlorobenzyl)-3-(RS)-(4-(4-fluorobenzyloxymethyl)piperidinylmethyl)-4-(SR)-(3-thienyl)pyrrolidine,
1-(2-Naphthyl)-3-(RS)-(4-(4-fluorobenzyloxymethyl)piperidinylmethyl)-4-(SR)-(3-thienyl)pyrrolidine;
1-(1-Naphthylmethyl)-3-(RS)-(4-(4-fluorobenzyloxymethyl)piperidinylmethyl)-4-(SR)-(3-thienyl)pyrrolidine;
1-(1-Naphthoyl)-3-(RS)-(4-(4-fluorobenzyloxymethyl)piperidinylmethyl)-4-(SR)-(3-thienyl)pyrrolidine;
1-Benzoyl-3-(RS)-(4-(4-fluorobenzyloxymethyl)piperidinylmethyl)-4-(SR)-(3-thienyl)pyrrolidine;
1-(4-Chlorobenzoyl)-3-(RS)-(4-(4-fluorobenzyloxymethyl)piperidinylmethyl)-4-(SR)-(3-thienyl)pyrrolidine;
1-(4-Methylbenzoyl)-3-(RS)-(4-(4-fluorobenzyloxymethyl)piperidinylmethyl)-4-(SR)-(3-thienyl)pyrrolidine;
1-(3-Chlorobenzoyl)-3-(RS)-(4-(4-fluorobenzyloxymethyl)piperidinylmethyl)-4-(SR)-(3-thienyl)pyrrolidine;
1-(2,6-Dichlorobenzoyl)-3-(RS)-(4-(4-fluorobenzyloxymethyl)piperidinylmethyl)-4-(SR)-(3-thienyl)pyrrolidine;
1-(2-Chlorobenzoyl)-3-(RS)-(4-(4-fluorobenzyloxymethyl)piperidinylmethyl)-4-(SR)-(3-thienyl)pyrrolidine;
1-(4-Nitrobenzoyl)-3-(RS)-(4-(4-fluorobenzyloxymethyl)piperidinylmethyl)-4-(SR)-(3-thienyl)pyrrolidine;
1-(3,4-Dichlorobenzoyl)-3-(RS)-(4-(2-(phenylmercapto)-1-ethyl)piperidinylmethyl)-4-(SR)-(3-thienyl)pyrrolidine;
1-(2,4-Dichlorobenzyl)-3-(RS)-(4-(2-(phenylmercapto)ethyl)piperidinylmethyl)-4-(SR)-(3-thienyl)pyrrolidine;
1-(3,4-Dichlorobenzoyl)-3-(RS)-(4-(4-(3-phenyl-2-hydroxy-1-propyl)piperidinylmethyl)-4-(SR)-(3-thienyl)pyrrolidine,
1-(2,4-Dichlorobenzyl)-3-(RS)-(4-(3-phenyl-2-hydroxypropyl)piperidinylmethyl)-4-(SR)-(3-thienyl)pyrrolidine;
1-(2,4-Benzyl)-3-(RS)-(4-(3-phenyl-2-hydroxypropyl)piperidinylmethyl)-4-(SR)-(3-thienyl)pyrrolidine;
1-(3,4-Dichlorobenzoyl)-3-(RS)-(4-(4-(3-phenyl-2-acetoxypropyl)piperidinylmethyl)-4-(SR)-(3-thienyl)pyrrolidine;
1-(2,4-Dichlorobenzyl)-3-(RS)-(4-(4-(3-phenyl-2-acetoxypropyl)piperidinylmethyl)-4-(SR)-(3-thienyl)pyrrolidine;
1-(3,4-Dichlorobenzoyl)-3-(RS)-(4-(4-(3-phenyl-3-hydroxypropyl)piperidinylmethyl)-4-(SR)-(3-thienyl)pyrrolidine;
1-(2,4-Dichlorobenzyl)-3-(RS)-(4-(3-phenyl-3-hydroxypropyl)piperidinylmethyl)-4-(SR)-(3-thienyl)pyrrolidine;
1-(3,4-Dichlorobenzoyl)-3-(RS)-(4-(4-(3-phenyl-3-acetoxypropyl)piperidinylmethyl)-4-(SR)-(3-thienyl)pyrrolidine;
1-(2,4-Dichlorobenzyl)-3-(RS)-(4-(3-phenyl-3-acetoxypropyl)piperidinylmethyl)-4-(SR)-(3-thienyl)pyrrolidine;
1-(2,4-Dichlorobenzyl)-3-(RS)-(4-(3-phenyl-3-oxopropyl)piperidinylmethyl)-4-(SR)-(3-thienyl)pyrrolidine;
1-(2,4-Dichlorobenzyl)-3-(RS)-(4-(4-(3-phenyl-3-oxoplopyl)piperidinylmethyl)-4-(SR)-(3-thienyl)pyrrolidine;
1-(2,4-Dichlorobenzyl)-3-(RS)-(4-(3-phenyl-1-hydroxypropyl)piperidinylmethyl)-4-(SR)-(3-thienyl)pyrrolidine;
1-(2,4-Dichlorobenzyl)-3-(RS)-(4-(4-(3-phenyl-1-oxopropyl)piperidinylmethyl)-4-(SR)-(3-thienyl)pyrrolidine;
1-Benzyl-3-(R)-(4-(4-fluorophenyl)piperidinylmethyl)-4-(R)-(3-thienyl)-pyrrolidine;
3-(S)-(4-(4-fluorophenyl)piperidinylmethyl)-4-(R)-(3-thienyl)pyrrolidine;
1-(1-Naphthoyl)-3-(R)-(4-phenylpiperidinylmethyl)-4-(R)-(3-thienyl)pyrrolidine;
1-(Naphth-1-oyl)-3-(S)-(4-phenylpiperidinylmethyl)-4-(S)-(3-thienyl)pyrrolidine;
1-(1-Naphthoyl)-3-(R)-(4-(4-fluorophenyl)piperidinylmethyl)-4-(R)-(3-thienyl)pyrrolidine;
1-(3,4-Dichlorobenzoyl)-3-(R)-(4-(4-fluorophenyl)piperidinylmethyl)-4-(R)-(3-thienyl)pyrrolidine;
1-(2,3-Dichlorobenzyl)-3-(R)-(4-(4-fluorophenyl)piperidinylmethyl)-4-(R)-(3-thienyl)pyrrolidine;
1-(7-Indolecarbonyl)-3-(R)-(4-(4-fluorophenyl)piperidinylmethyl)-4-(R)-(3-thienyl)pyrrolidine;
1-(2,3-Dimethylbenzoyl)-3-(R)-(4-(4-fluorophenyl)piperidinylmethyl)-4-(R)-(3-thienyl)pyrrolidine;
1-(7-2,3-Dihydrobenzofuranylcarbonyl)-3-(R)-(4-(4-fluorophenyl)piperidinylmethyl)-4-(R)-(3-thienyl)pyrrolidine;
1-(7-Benzofuranylcarbonyl)-3-(R)-(4-(4-fluorophenyl)piperidinylmethyl)-4-(R)-(3-thienyl)pyrrolidine;
1-(N-methyl-7-indolecarbonyl)-3-(R)-(4-(4-fluorophenyl)piperidinylmethyl)-4-(R)-(3-thienyl)pyrrolidine;

1-(1-Carbomethoxymethyl-7-indolecarbonyl)-3-(R)-(4-(4-fluorophenyl)piperidinylmethyl)-4-(R)-(3-thienyl)pyrrolidine;
1-(1-t-Butoxycarbonylmethyl-7-indolecarbonyl)-3-(R)-(4-(4-fluorophenyl)piperidinylmethyl)-4-(R)-(3-thienyl)pyrrolidine;
1-(1-Carboxymethyl-7-indolecarbonyl)-3-(R)-(4-(4-fluorophenyl)piperidinylmethyl)-4-(R)-(3-thienyl)pyrrolidine;
1-(1-Carboxamidomethyl-7-indolecarbonyl)-3-(R)-(4-(4-fluorophenyl)piperidinylmethyl)-4-(R)-(3-thienyl)pyrrolidine;
1-(1-(2-Hydroxyethyl)-7-indolecarbonyl)-3-(R)-(4-(4-fluorophenyl)piperidinylmethyl)-4-(R)-(3-thienyl)pyrrolidine;
1-(1-Ethyl-7-indolecarbonyl)-3-(R)-(4-(4-fluorophenyl)piperidinylmethyl)-4-(R)-(3-thienyl)pyrrolidine;
1-(1-Acetyl-7-indolecarbonyl)-3-(R)-(4-(4-fluorophenyl)piperidinylmethyl)-4-(R)-(3-thienyl)pyrrolidine;
1-(1-Methoxycarbonyl-7-indolecarbonyl)-3-(R)-(4-(4-fluorophenyl)piperidinylmethyl)-4-(R)-(3-thienyl)pyrrolidine;
1-(1-Allyl-7-indolecarbonyl)-3-(R)-(4-(4-fluorophenyl)piperidinylmethyl)-4-(R)-(3-thienyl)pyrrolidine;
1-(3-Methylbenzoyl)-3-(R)-(4-(4-fluorophenyl)piperidinylmethyl)-4-(R)-(3-thienyl)pyrrolidine;
1-(3-Methyl-2-phenylbenzoyl)-3-(R)-(4-(4-fluorophenyl)piperidinylmethyl)-4-(R)-(3-thienyl)pyrrolidine;
1-(2-Vinyl-3-methylbenzoyl)-3-(R)-(4-(4-fluorophenyl)piperindinylmethyl)-4-(R)-(3-thienyl)pyrrolidine;
1-(2-Ethyl-3-methylbenzoyl)-3-(R)-(4-(4-fluorophenyl)piperidinylmethyl)-4-(R)-(3-thienyl)pyrrolidine;
1-(7-Benzimidazolecarbonyl)-3-(R)-(4-(4-fluorophenyl)piperidinylmethyl)-4-(R)-(3-thienyl)pyrrolidine;
1-(1-Methyl-4-benzimidazolecarbonyl)-3-(R)-(4-(4-fluorophenyl)piperidinylmethyl)-4-(R)-(3-thienyl)pyrrolidine;
1-(1-Methyl-7-benzimidazolecarbonyl)-3-(R)-(4-(4-fluorophenyl)piperidinylmethyl)-4-(R)-(3-thienyl)pyrrolidine;
1-(1-(Methoxycarbonylmethyl)-4-benzimidazolecarbonyl)-3-(R)-(4-(4-fluorophenyl)piperidinylmethyl)-4-(R)-(3-thienyl)pyrrolidine;
1-(1-(Methoxycarbonylmethyl)-7-benzimidazolecarbonyl)-3-(R)-(4-(4-fluorophenyl)piperidinylmethyl)-4-(R)-(3-thienyl)pyrrolidine;
1-(1-(t-Butoxycarbonylmethyl)-4-benzimidazolecarbonyl)-3-(R)-(4-(4-fluorophenyl)piperidinylmethyl)-4-(R)-(3-thienyl)pyrrolidine;
1-(1-(t-Butoxycarbonylmethyl)-7-benzimidazolecarbonyl)-3-(R)-(4-(4-fluorophenyl)piperidinylmethyl)-4-(R)-(3-thienyl)pyrrolidine;
1-(1-(Carboxymethyl)-4-benzimidazolecarbonyl)-3-(R)-(4-(4-fluorophenyl)piperidinylmethyl)-4-(R)-(3-thienyl)pyrrolidine;
1-(1-(Carboxymethyl)-7-benzimidazolecarbonyl)-3-(R)-(4-(4-fluorophenyl)piperidinylmethyl)-4-(R)-(3-thienyl)pyrrolidine;
1-(1-(2-Hydroxyethyl)-4-benzimidazolecarbonyl)-3-(R)-(4-(4-fluorophenyl)piperidinylmethyl)-4-(R)-(3-thienyl)pyrrolidine;
1-(1-(2-Hydroxyethyl)-4-benzimidazolecarbonyl)-3-(R)-(4-(4-fluorophenyl)piperidinylmethyl)-4-(R)-(3-thienyl)pyrrolidine;
1-(1-Naphthoyl)-3-(RS)-(4-phenylpiperidinylmethyl)-4-(RS)-(3-furanyl)pyrrolidine;
1-(3,4-Dichlorobenzoyl)-3-(RS)-(4-phenylpiperidinylmethyl)-4-(RS)-(3-furanyl)pyrrolidine;
1-(2,3-Dichlorobenzoyl)-3-(RS)-(4-phenylpiperidinylmethyl)-4-(RS)-(3-furanyl)pyrrolidine;
1-(1-Naphthoyl)-3-(RS)-(4-(4-fluorophenyl)piperidinylmethyl)-4-(RS)-(3-furanyl)pyrrolidine;
1-(3,4-Dichlorobenzoyl)-3-(RS)-(4-(4-fluorophenyl)piperidinylmethyl)-4-(RS)-(3-furanyl)pyrrolidine;
1-(2,3-Dichlorobenzoyl)-3-(SR)-(4-(4-fluorophenyl)piperidinylmethyl)-4-(RS)-(3-furanyl)pyrrolidine;
1-(2,3-Difluorobenzoyl)-3-(RS)-(4-(4-fluorophenyl)piperidinylmethyl)-4-(RS)-(3furanyl)pyrrolidine;
1-(2,3,4-Trifluorobenzoyl)-3-(RS)-(4-(4-fluorophenyl)piperidinylmethyl)-4-(RS)-(3-furanyl)pyrrolidine;
1-(2,3,4,5,6-Pentafluorobenzoyl)-3-(RS)-(4-(4-fluorophenyl)piperidinylmethyl)-4-(RS)-(3-furanyl)pyrrolidine;
1-(1-Naphthoyl)-3-(R)-(4-(4-fluorophenyl)piperidinylmethyl)-4-(R)-(3-furanyl)pyrrolidine;
1-(2,4-Dichlorobenzyl)-3-(S)-(4-hydroxy-4-(3-phenylpropyl)piperidinylmethyl)-4-(S)-(3-thienyl)pyrrolidine;
1-(2,4-Dichlorobenzyl)-3-(S)-(4-(4-fluorobenzyloxymethyl)piperidinyl-methyl)-4-(S)-(3-thienyl)pyrrolidine;
1-(2,3-Dichlorobenzyl)-3-(S)-(4-(4-fluorophenyl)piperidinylmethyl)-4-(S)-(3-thienyl)pyrrolidine;
1-(2,4-Dichlorobenzyl)-3-(S)-4-(4-fluorophenyl)piperidinylmethyl)-4-(S)-(3-thienyl)pyrrolidine;
1-(2-Chlorobenzyl)-3-(S)-(4-(4-fluorophenyl)piperidinylmethyl)-4-(S)-(3-thienyl)pyrrolidine;
1-(3-Chlorobenzyl)-3-(S)-(4-(4-fluorophenyl)piperidinylmethyl)-4-(S)-(3-thienyl)pyrrolidine;
1-(4-Chlorobenzyl)-3-(S)-(4-(4-fluorophenyl)piperidinylmethyl)-4-(S)-(3-thienyl)pyrrolidine;
1-(4-Methylbenzyl)-3-(S)-(4-(4-fluorophenyl)piperidinylmethyl)-4-(S)-(3-thienyl)pyrrolidine;
1-(4-Nitrobenzyl)-3-(S)-(4-(4-fluorophenyl)piperidinylmethyl)-4-(S)-(3-thienyl)pyrrolidine;
1-(4-Trifluoromethylbenzyl)-3-(S)-(4-(4-fluorophenyl)piperidinylmethyl)-4-(S)-(3-thienyl)pyrrolidine;
1-(3,4-Dichlorobenzyl)-3-(S)-(4-(4-fluorophenyl)piperidinylmethyl)-4-(S)-(3-thienyl)pyrrolidine;
1-(2,3-Dimethylbenzyl)-3-(S)-(4-(4-fluorophenyl)piperidinylmethyl)-4-(S)-(3-thienyl)pyrrolidine;
1-(3-Trifluoromethyl-4-chlorobenzyl)-3-(S)-(4-(4-fluorophenyl)piperidinylmethyl)-4-(S)-(3-thienyl)pyrrolidine;
1-(1-Naphthylmethyl)-3-(R)-(4-(4-fluorophenyl)piperidinylmethyl)-4-(R)-(3-thienyl)pyrrolidine;
1-(4-Nitrobenzyl)-3-(R)-(4-(4-fluorophenyl)piperidinylmethyl)-4-(R)-(3-thienyl)pyrrolidine;
1-(4-Methylbenzyl)-3-(R)-(4-(4-fluorophenyl)piperidinylmethyl)-4-(R)-(3-thienyl)pyrrolidine;
1-(1-n-propyl-7-indolecarbonyl)-3-(R)-4-(4-fluorophenyl)piperidinylmethyl)-4-(R)-(3-thienyl)pyrrolidine;
1-(1-(N,N-Dimethylaminoethyl)-7-indolecarbonyl)-3-(R)-4-(4-fluorophenyl)-piperidinylmethyl)-4-(R)-(3-thienyl)pyrrolidine;
1-(1-Cyanomethyl-7-indolecarbonyl)-3-(R)-4-(4-fluorophenyl)piperidinylmethyl)-4-(R)-(3-thienyl)pyrrolidine;
1-(1-(2-Acetoxyethyl)-7-indolecarbonyl)-3-(R)-4-(4-fluorophenyl)piperidinylmethyl)-4-(R)-(3-thienyl)pyrrolidine;
1-(1-(2-Methoxyethyl)-7-indolecarbonyl)-3-(R)-4-(4-fluorophenyl)piperidinylmethyl)-4-(R)-(3-thienyl)pyrrolidine;
1-(1-(2-Phthalimidoethyl)-7-indolecarbonyl)-3-(R)-4-(4-fluorophenyl)-piperidinylmethyl)-4-(R)-(3-thienyl)pyrrolidine;

1-(1-(2-Aminoethyl)-7-indolecarbonyl)-3-(R)-4-(4-fluorophenyl)piperidinylmethyl)-4-(R)-(3-thienyl) pyrrolidine;
1-(1-(2-Methylsulfonylaminoethyl)-7-indolecarbonyl)-3-(R)-4-(4-fluorophenyl)-piperidinylmethyl)-4-(R)-(3-thienyl)pyrrolidine;
1-(1-(2-Acetylaminoethyl)-7-indolecarbonyl)-3-(R)-4-(4-fluorophenyl)-piperidinylmethyl)-4-(R)-(3-thienyl) pyrrolidine;
1-(1-(2-Methoxycarbonylaminoethyl)-7-indolecarbonyl)-3-(R)-4-(4-fluorophenyl)piperidinylmethyl)-4-(R)-(3-thienyl)pyrrolidine;
1-(1-(2-Carboxyethyl)-7-indolecarbonyl)-3-(R)-4-(4-fluorophenyl)piperidinylmethyl)-4-(R)-(3-thienyl) pyrrolidine;
1-(1-(2-Carboxamidoethyl)-7-indolecarbonyl)-3-(R)-4-(4-fluorophenyl)-piperidinylmethyl)--4-(R)-(3-thienyl) pyrrolidine;
1-(1-(2-Methylsulfonamidocarbonylethyl)-7-indolecarbonyl)-3-(R)-4-(4-fluorophenyl) piperidinylmethyl)-4-(R)-(3-thienyl)pyrrolidine;
1-(1-(2-Methylsulfonamidocarbonylmethyl)-7-indolecarbonyl)-3-(R)-4-(4-fluorophenyl) piperidinylmethyl)-4-(R)-(3-thienyl)pyrrolidine;
1-(1-(3-Ethoxycarbonylpropyl)-7-indolecarbonyl)-3-(R)-4-(4-fluorophenyl)-piperidinylmethyl)-4-(R)-(3-thienyl) pyrrolidine;
1-(1-(3-Carboxypropyl)-7-indolecarbonyl)-3-(R)-4-(4-fluorophenyl)-piperidinylmethyl)-4-(R)-(3-thienyl) pyrrolidine;
1-(1-Methyl-7-indolemethyl)-3-(R)-4-(4-fluorophenyl) piperidinylmethyl)-4-(R)-(3-thienyl)pyrrolidine;
1-(2-Methyl-1-Naphthoyl)-3-(R)-4-(4-fluorophenyl) piperidinylmethyl)-4-(R)-(3-thienyl)pyrrolidine;
1-(4-Fluoro-1-naphthoyl)-3-(R)-4-(4-fluorophenyl) piperidinylmethyl)-4-(R)-(3-thienyl)pyrrolidine;
1-(7-Benzoxazolecarbonyl)-3-(R)-4-(4-fluorophenyl) piperidinylmethyl)-4-(R)-(3-thienyl)pyrrolidine;
1-(2-Methyl-7-benzoxazolecarbonyl)-3-(R)-4-(4-fluorophenyl)piperidinylmethyl)-4-(R)-(3-thienyl) pyrrolidine;
1-(4-Benzoxazolecarbonyl)-3-(R)-4-(4-fluorophenyl) piperidinylmethyl)-4-(R)-(3-thienyl)pyrrolidine;
1-(2-Methyl-4-benzoxazolecarbonyl)-3-(R)-4-(4-fluorophenyl)piperidinylmethyl)-4-(R)-(3-thienyl) pyrrolidine;
1-(1,4-Benzpyrazine-4-carbonyl)-3-(R)-4-(4-fluorophenyl) piperidinylmethyl)-4-(R)-(3-thienyl)pyrrolidine;
1-(Imidazo[1,2-a]pyridine-7-carbonyl)-3-(R)-4-(4-fluorophenyl)piperidinylmethyl)-4-(R)-(3-thienyl) pyrrolidine;
1-(2-Hydroxybenzimidazole-7-carbonyl)-3-(R)-4-(4-fluorophenyl)piperidinylmethyl)-4-(R)-(3-thienyl) pyrrolidine;
1-(3,4-Dichlorobenzoyl)-3-(RS)-(4-(4-(3-phenyl-2-oxopropyl)piperidinylmethyl)-4-(SR)-(3-thienyl) pyrrolidine;
1-(2,4-Dichlorobenzyl)-3-(RS)-(4-(4-(3-phenylpropyl) piperidinylmethyl)-4-(SR)-(3-thienyl)pyrrolidine;
1-(2,4-Dichlorobenzyl)-3-(S)-(4-(4-(3-phenyl-1-(RS)-methoxypropyl)piperidinylmethyl)-4-(S)-(3-thienyl) pyrrolidine;
1-(2,4-Dichlorobenzyl)-3-(S)-(trans-(3-hydroxy-4-(3-phenylpropyl))piperidinylmethyl)-4-(S)-(3-thienyl) pyrrolidine;
1-(2,4-Dichlorobenzyl)-3-(S)-(cis-(3-hydroxy-4-(3-phenylpropyl))piperidinylmethyl)-4-(S)-(3-thienyl) pyrrolidine;
1-(2,4-Dichlorobenzyl)-3-(S)-(4-(3-phenyl-2-oxopropyl) piperidinylmethyl)-4-(S)-(3-thienyl)pyrrolidine;
1-(2,4-Dichlorobenzyl)-3-(S)-(4-(3-phenylpropyl) piperidinylmethyl)-4-(S)-(3-thienyl)pyrrolidine;
1-(2,4-Dichlorobenzyl)-3-(S)-(4-(3-phenyl-2-(R,S)-fluoropropyl)piperidinylmethyl)-4-(S)-(3-thienyl) pyrrolidine;
1-(2,4-Dichlorobenzy)-3-(S)-(4-(benzylsulfonylmethyl) piperidinylmethyl)-4-(S)-(3-thienyl)pyrrolidine;
1-(2,4-Dichlorobenyl)-3-(S)-(4-(3-phenyl-2-(R,S)-hydroxypropyl)piperidinylmethyl)-4-(S)-(3-thienyl) pyrrolidine;
1-(2,4-Dichlorobenzyl)-3-(S)-(4-(3-pheny-2-(R,S)-methoxypropyl)piperidinylmethyl)-4-(S)-(3-thienyl) pyrrolidine;
1-(2,4-Dichlorobenzyl)-3-(S)-(4-(3-phenyl-2-hydroxypropyl)piperidinyl methyl)-4-(S)-(3-thienyl) pyrrolidine;
1-(2,4-Dichlorobenzyl)-3-(S)-(4-(3-(4-fluorophenyl)-2-hydroxypropyl)piperidinylmethyl)-4-(S)-(3-thienyl) pyrrolidine;
1-(2,4-Dichlorobenzyl)-3-(S)-(4-(3-chlorobenzyloxymethyl)piperidinylmethyl)-4-(S)-(3-thienyl)pyrrolidine;
1-(2,4-Dichlorobenzyl)-3-(S)-(4-(2,4-dichlorobenzyloxymethyl)piperidinylmethyl)-4-(S)-(3-thienyl)pyrrolidine;
1-(2,4-Dichlorobenzyl)-3-(S)-(4-(2-chlorobenzyloxymethyl)piperidinylmethyl)-4-(S)-(3-thienyl)pyrrolidine;
1-(2,4-Dichlorobenzyl)-3-(S)-(4-(3,4-dichlorobenzyoxymethyl)piperidinylmethyl)-4-(S)-(3-thienyl)pyrrolidine;
1-(2,4-Dichlorobenzyl)-3-(S)-(4-(4-methylbenzyloxymethyl)piperidinylmethyl)-4-(S)-(3-thienyl)pyrrolidine;
1-(2,4-Dichlorobenzyl)-3-(S)-(4-(4-chlorobenzyloxymethyl)piperidinylmethyl)-4-(S)-(3-thienyl)pyrrolidine;
1-(2,4-Dichlorobenzyl)-3-(S)-(4-(methoxybenzyloxymethyl)piperidinylmethyl)-4-(S)-(3-thienyl)pyrrolidine;

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing spiro-substituted azacycles as modulators of chemokine receptor activity. In particular, these compounds are useful as modulators of the chemokine receptors, including CCR-3 and/or CCR-5.

The utility of the compounds in accordance with the present invention as modulatorrs of chemokine receptor activity may be demonstrated by methodology known in the art, such as the assay for CCR-5 binding as disclosed by Van Riper, et al., *J. Exp. Med.*, 177, 851–856 (1993), and the assay for CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology,* 65 (9), 4887–4892 (1991).

In particular, the compounds of the following examples had activity in binding to the CCR-3 or the CCR-5 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, Such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis), trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-3 and/or CCR-5. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-3 and/or CCR-5. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical canier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-3 or CCR-5, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active inredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-sterodial antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenotibrate and benzafibrate), and probucol, (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1,β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the alt.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Intenferon | Glaxo Wellcome | Kaposi's sarcoma, HIV in combination w/ Retrovir |
| Ansamycin LM427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (−) 6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CT-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz, DMP-266 | DuPont-Merck Pharmaceuticais | HIV infection, AIDS, ARC (non-nucleoside reverse transcriptase inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcnptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, |

| Drug Name | Manufacturer | Indication |
|---|---|---|
| Lobucavir | Bristol-Myers Squibb | ARC (reverse transcriptase inhibitor); also with AZT CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonofonnate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interieukin-2 | Cetus | AIDS, in combination w/AZT |
| IL-2 Interleukin-2 | Hoffman-La Roche Immunex | AIDS, ARC, HIV, in combination w/AZT |
| W-2 Interleukin-2 (aldeslukin) | Chiron | AIDS, increase in CD4 cell counts |
| Immune Giobulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PF Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazoie | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (XbA & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Eriteral Nutrition | Norwich Eaton Pharmaceuticals | diarrhea and malabsorption related to AIDS |

It will be understood that the scope of combinations of the compounds of this invention with AIDS antivirals, immunomodulaltors, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT. 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran3-yloxycarbonylamino)-butyl)-N-isobutyl-benzenesulfonamide), N-(2(R)-hydroxy-1-(S)-indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94: and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC, (2) indinavir, and any of AZT and/or ddI and/or ddC.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

Several methods for preparing the compounds of this invention are illustrated in the following Schemes and Examples.

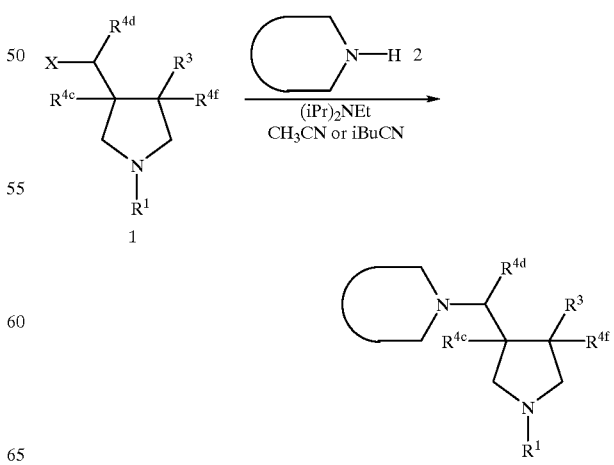

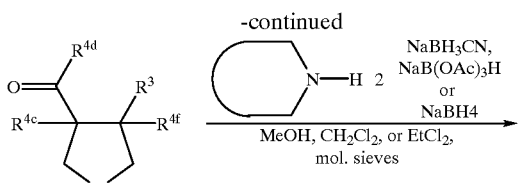

available commercially or can be prepared using the methods given below.

Alternatively, heterocycle 4, bearing a carbonyl group, can be combined with the cyclic amine 2 and the intermediate imine or iminium species is reduced to tertiary amine 3 under homogenous conditions (e.g. using sodium cyanoborohydride, sodium borohydride, or sodium triacetoxyborohydride) or in the presence of hydrogen and a heterogeneous catalyst (e.g. palladium on carbon or Raney nickel).

In an alternative embodiment of the present invention, heterocycle 5, bearing an activated acyl side chain (wherein X', for example, is a chloride or bromide atom, or is a hydroxybenzotriazole residue from activation of the corresponding carboxylic acid with HOBt in the presence of a suitable carbodiimide) is allowed to react with cyclic amine 2 to provide the corresponding tertiary amide 6. Compound 6 can then be treated with a suitable reducing agent (e.g. diborane; borane in THF; borane dimethylsulfide, or lithium aluminum hydride) to provide the desired product 7.

SCHEME 2

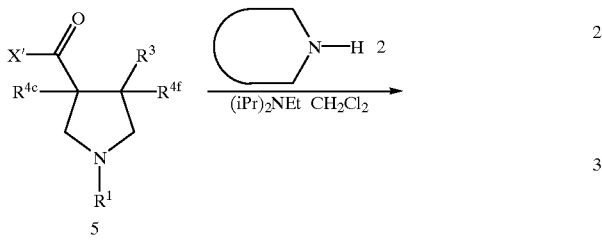

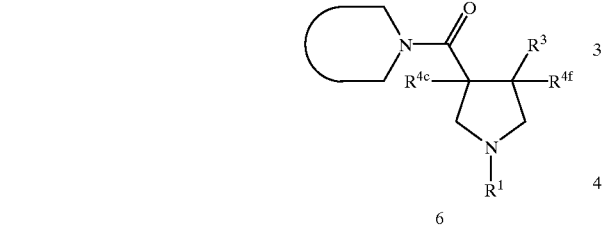

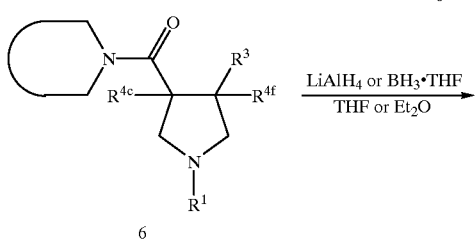

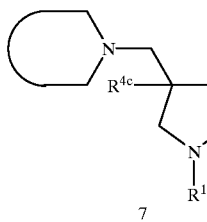

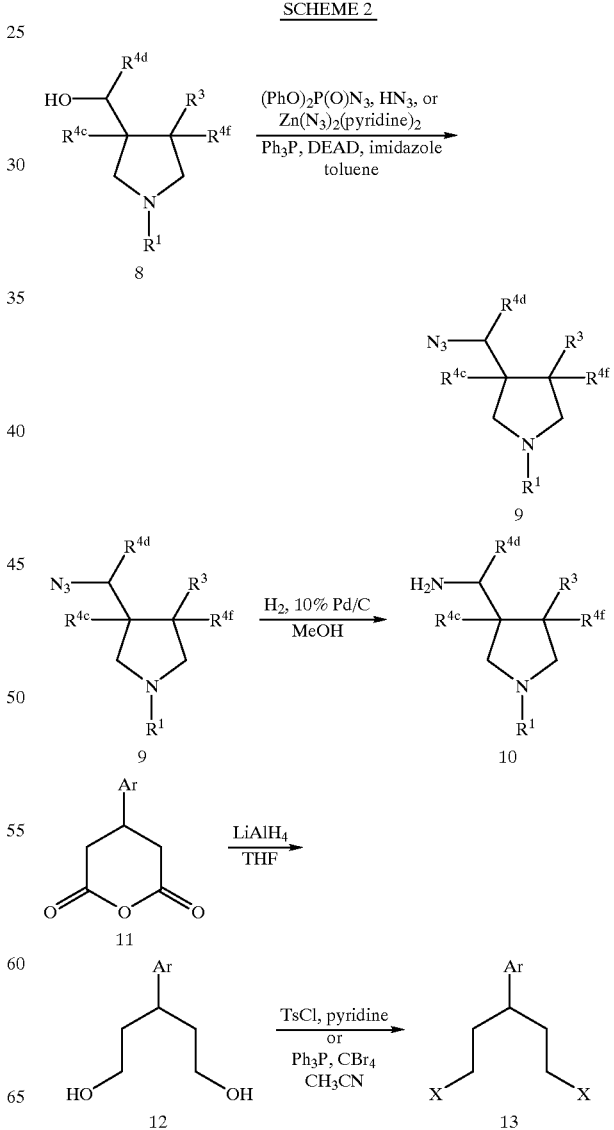

In one protocol, the compounds of the present invention are prepared by alkylating heterocycle 1 (wherein X is a leaving group such as, for example, bromide, iodide, methanesulfonate, p-toluenesulfonate, trifluoromethanesulfonate) with cyclic amine 2 under appropriate conditions to provide compound 3. Cyclic amine 2 is

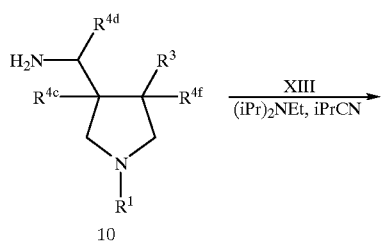

An alternative preparation of the target compounds is carried out as shown in Scheme 2. Treatment of alcohol 8 with zinc azide bis(pyridine) complex in the presence of triphenylphosphine and diethyl azodicarboxylate, or with diphenylphosphoryl azide, or with hydrazoic acid, provides azide 9. Reduction of 9, for example, with hydrogen and palladium on carbon, affords primary amine 10. This amine can be doubly alkylated with a bis-electrophile such as 13 under basic conditions, to provide the compound 14. Bis-electrophiles can be prepared from substituted glutaric anhydride derivatives such as 11 by reduction to diol 12 followed by double activation, using, for example, p-toluenesulfonyl chloride in pyridine, or triphenylphosphine carbon tetrabromide in acetonitrile, to provide 13 (where X=Br or OTs).

SCHEME 3

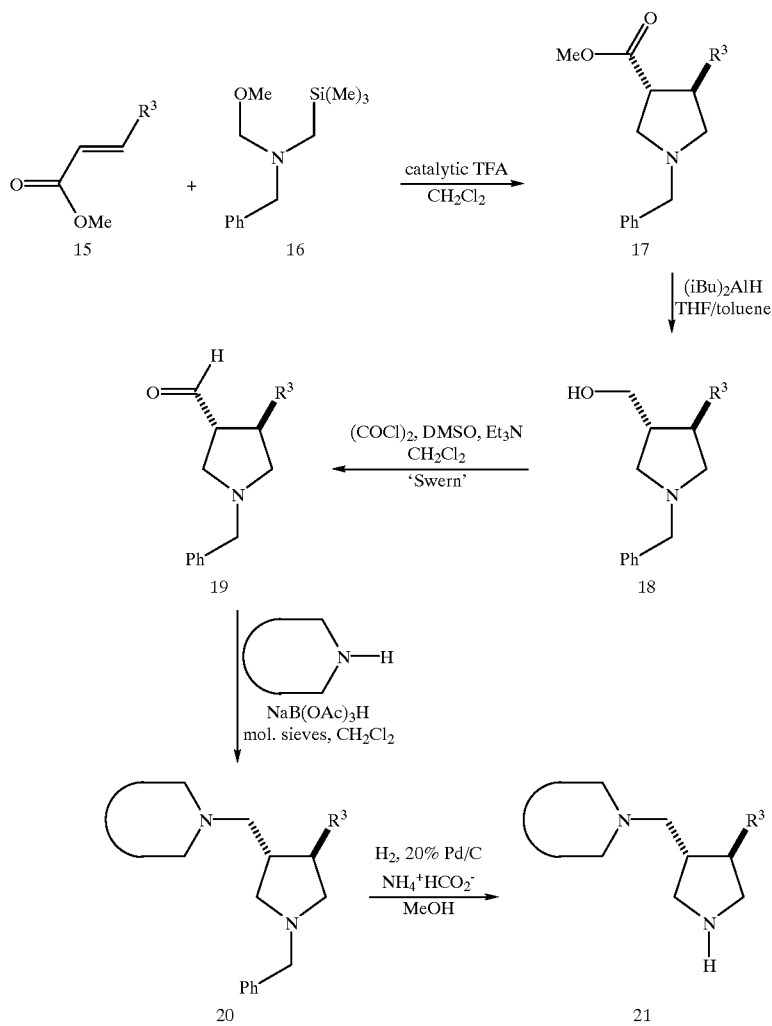

'The preparation of compounds within the scope of the instant invention which bear a 1,3,4-trisubstituted pyrrolidine framework is detailed in Scheme 3. Treatment of a trans-cinnamic ester such as 15 with N-benzyl-N-methoxymethyl-N-(trimethylsilyl)-methylamine(16) in the presence of a catalytic amount of an acid such as TFA, titanium tetrafluoride lithium fluoride or cesium fluoride according to the procedure of Padwa et al (*J. Org. Chem.* 1987, 52, 235) preferentially affords the 3,4-trans pyrrolidine 17. Executing this sequence starting from the cis-cinnamic ester results in preferential formation of the 3,4-cis pyrrolidine. Reduction of ester 17 with diisobutylaluminum hydride, lithium aluminium hydride, or sodium bis(2-methoxycthoxy)aluminum hydride, provides the primary alcohol 18. Oxidation of 18 to the aldehyde 19 can be carried out under numerous conditions, such as with the Swern reaction, with DMSO and oxalyl chloride at low temperature, followed by triethylamine, or with various chromium trioxide-based reagents (see March J. "Advanced Organic Chemistry", 4th ed., John Wiley & Sons, New York, pp. 1167–1171 (1992)). Reductive amination with cyclic amine 2 provides diamine 20. Alternatively, The N-benzyl group is cleaved in a hydrogen atmosphere in the presence of 10% palladium on carbon or with Pearlmans' catalyst [Pd(OH)$_2$/C] to provide the secondary amine 21.

In cases when certain substituents are labile to hydrogenolysis conditions, alternative methods to remove the benzyl group of compound 20 are described in Scheme 4. Compound 20 may be converted to the allyloxycarbamate derivative by stirring with allylchloroformate at rt in a solvent such as THF (T. Shono, Y. Matsumura, J. Org. Chem., 1984, 48, 300) Subsequent reaction with hydrazine hydrate and KOH in ethylene glycol at elevated temperatures provides the amine 21. Compound 20 may also be converted to its 2,2,2,-trichloroethyloxy-carbamate derivative by stirring with 2,2,2-trichloroethylchloroformate in a solvent such as acetonitrile (V. H. Rawal, R. J. Jones, J. Org. Chem., 1987, 52, 19). This derivative is then converted to amine 21 by reaction with zinc powder in acetic acid a slightly elevated temperatures such as at 40° C.

SCHEME 4

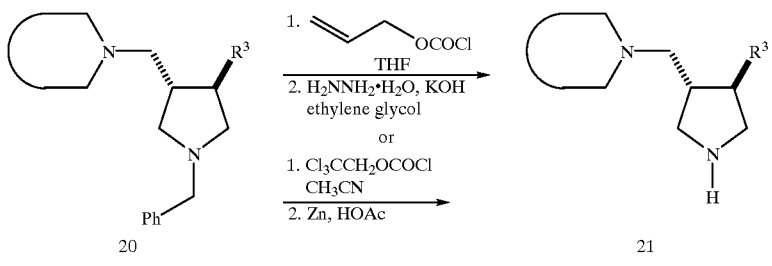

SCHEME 5

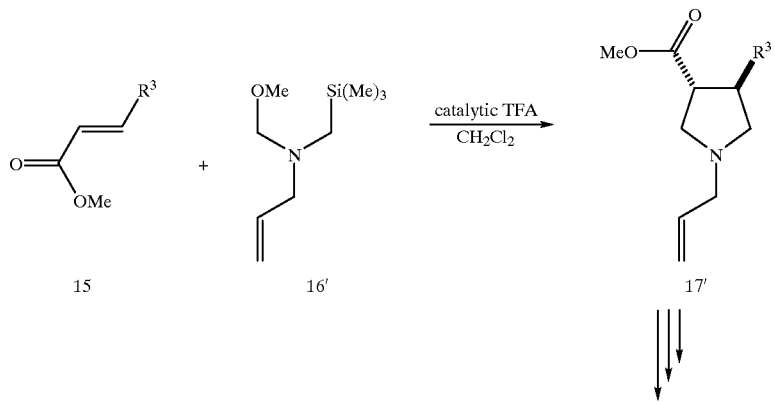

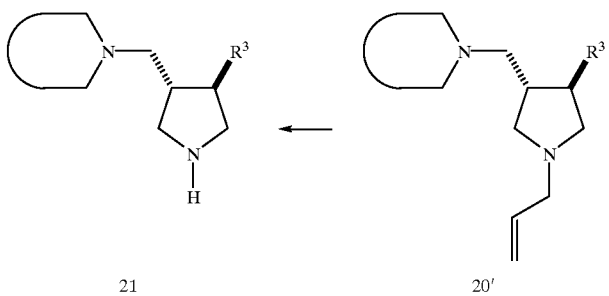

Scheme 5 describes a modification of Scheme 3 when substituents are not compatible with hydrogenolysis of the benzyl group of compound 20. In this variation, treatment of a trans-cinnamic ester 15 with N-allyl-N-methoxymethyl-N-(trimethylsilyl)-methylamine (16') according to procedures described in Scheme 3 provides N-allylpyrrolidine derivative 17'. The reagent N-allyl-N-methoxymethyl-N-(trimethylsilyl)-methylamine is prepared after procedures described by Padwa et al (*J. Org. Chem.* 7. 1985, 50, 4006 and *J. Org. Chem.* 1987, 52, 235) Subsequent elaboration as described in Scheme 3 gives compound 20'.

sulfonate, etc. carried out under standard conditions to provide N-alkylated pyrrolidine 22. Alternatively, compound 22 is acylated with, for example, acid chlorides or bromides, or activated esters utilizing a variety of the standard coupling conditions to give amide 23. For example, reaction of compound 22 and a carboxylic acid with BOP-Cl and triethylamine in a solvent such as methylene chloride is a commonly used procedure. The sulfonamide 24 is prepared under standard conditions by exposing 21 to an alkyl or aryl sulfonyl chloride in the presence of a suitable base to neutralize the formed hydrogen chloride.

SCHEME 6

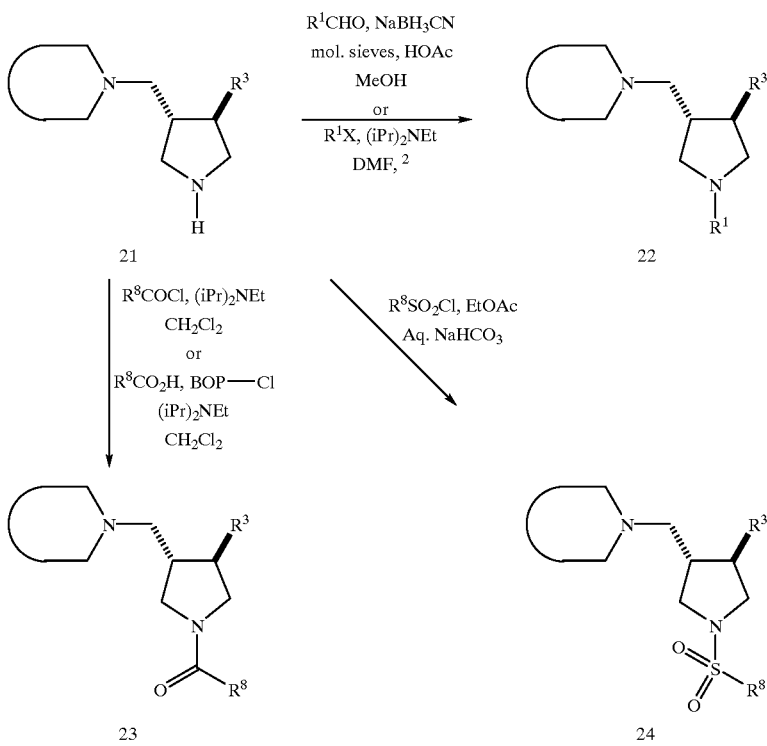

The unsubstituted pyrrolidine 21 may be further functionalized as shown in Scheme 6. Reductive amination with suitable aldehydes under standard conditions provides the tertiary amine 22. The pyrrolidine nitrogen may be alkylated with a suitable halide, methanesulfonate, p-toluene-

SCHEME 7

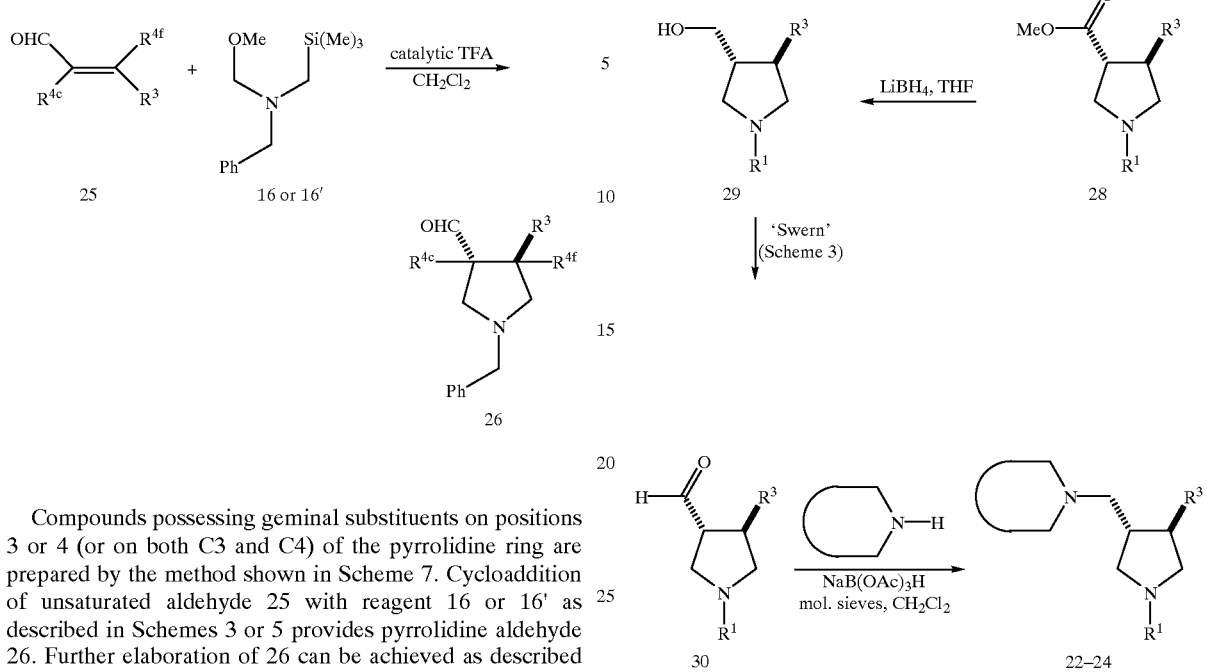

Compounds possessing geminal substituents on positions 3 or 4 (or on both C3 and C4) of the pyrrolidine ring are prepared by the method shown in Scheme 7. Cycloaddition of unsaturated aldehyde 25 with reagent 16 or 16' as described in Schemes 3 or 5 provides pyrrolidine aldehyde 26. Further elaboration of 26 can be achieved as described in the previous Schemes.

SCHEME 8

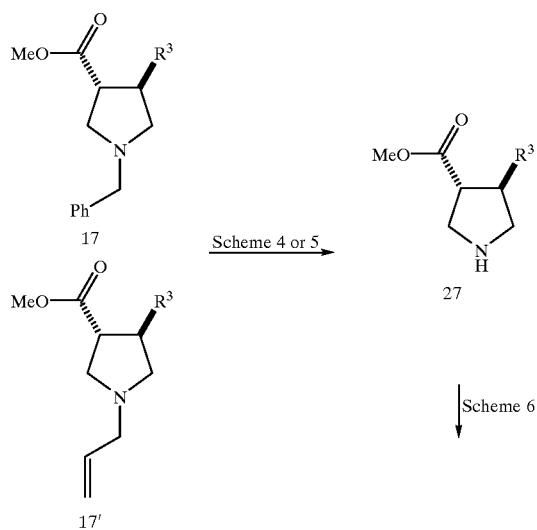

An alternative approach to the synthesis of chemokine modulators is described in Example 8. Ester derivatives 17 (Scheme 3) or 17' (Scheme 5) are first debenzylated or deallylated by procedures described in Schemes 3, 4 or 5 to give secondary amine derivative 27. Compound 27 can then be elaborated as described in Scheme 6 to provide compound 28. The ester group of 28 can be selectively reduced with a reagent such as lithium borohydride in THF to give the alcohol 29 which is then converted to aldehyde 30 under Swern conditions as described in Scheme 3. Aldehyde 39 is then converted to derivative 22 (or 23 or 24) by reductive amination (Scheme 3).

SCHEME 9

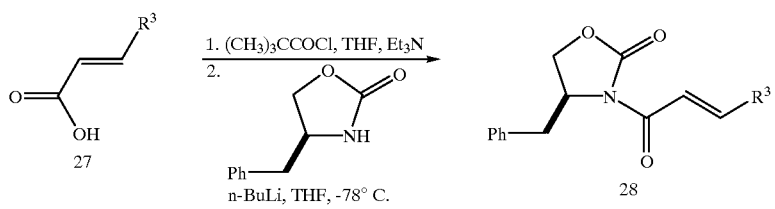

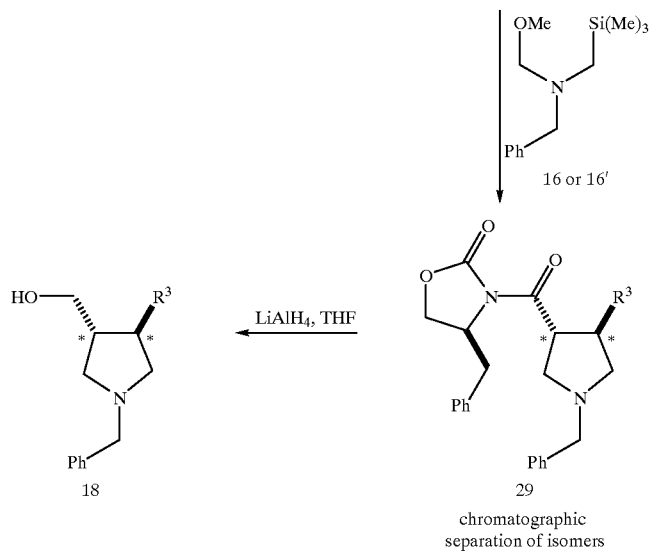

The preparation of optically active compounds described in Scheme 9 follows procedures described by Ma et.al., (*Tetrahedron: Assymmetry* 1997, 8, 883). Reaction of a trans-acrylic acid with oxalyl chloride or pivaloyl chloride and triethylamine in THF provide the mixed anhydride intermediate. This is then treated with the lithium salt of an appropriate chiral auxiliary such as (S)-benzyl-2-oxazolidinone in THF at reduced temperatures, such as −78° C. to give amide 28. This acrylamide is then reacted with N-benzyl-N-methoxymethyl-N-(trimethylsilyl)-methylamine (16) or N-allyl-N-methoxymethyl-N-(trimethylsilyl)-methylamine (16') as described in Schemes 3 and 5, respectively, to give pyrrolidine intermediate 29 or the corresponding N-allyl derivative. Modest diastercoselectivity is achieved in these cyclizations as shown by Ma et al. However, the separate optically active isomers may be easily obtained by simple chromatography on silica el. Reaction of the selected diastereomer 29 with LiAlH$_4$ in THF at 0° C. provides the optically active version of compound 18 which is further elaborated as described in the previous Schemes.

The various piperidine derivatives, when not commercially available, are prepared as described in the following Schemes.

SCHEME 10

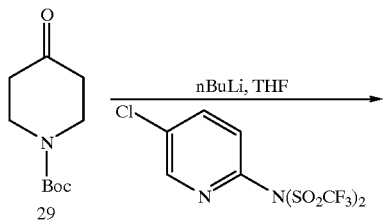

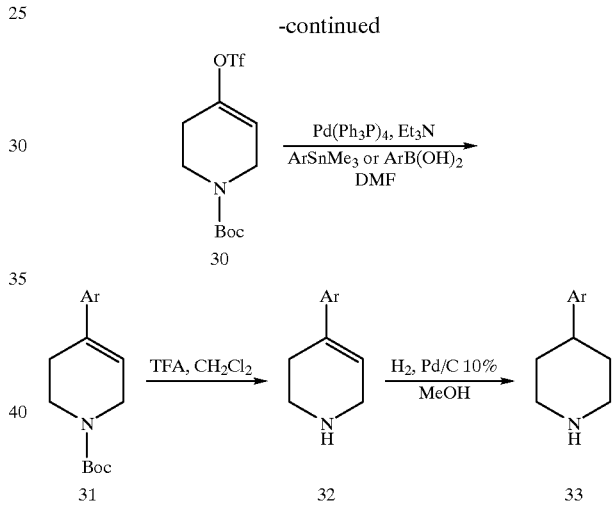

The synthesis of 4-arylpiperidine groups is presented in Scheme 10. Enolate formation of the 4-piperidone derivative 29 followed by formation of the vinyl triflate with either 2-[N,N-bis(trifluoromethyl sulfonyl)amino]-5-chloropyridine or with N-phenyltriflimide provides triflate ether 30. Palladium-mediated coupling with a suitable aryl stannane or aryl boronic acid provides the tetrahydropyridine derivative 31. The Boc protecting group can be removed with TFA to give amine 32 which is then hydrogenated under standard conditions to give piperidine 33. Alternatively, tetrahydropyridine derivative 31 is first hydrogenated and then deprotected. Modification of the aryl group of compound 31 or 33 is achieved using appropriate chemical modification schemes.

SCHEME 11

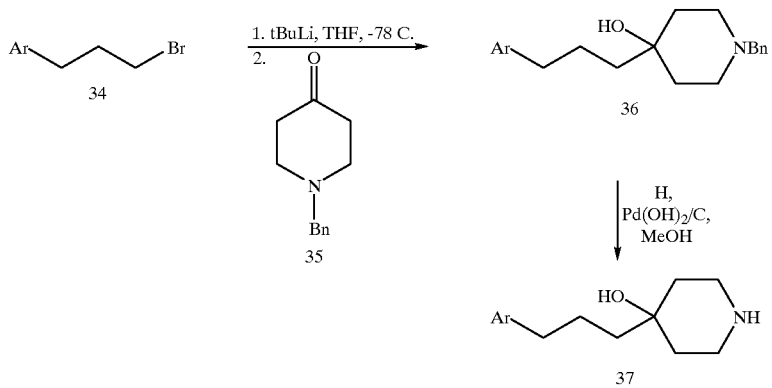

A method of preparing 4-(3-aryl-1-propyl)-4-hydroxypiperidine derivatives is described in Scheme 11. A suitable 3-arylpropyl halide 34 in THF at −78° C. is reacted with a base such as t-butyl lithium. This is then reacted with a protected 4-piperidone derivative such as N-benzyl-4-piperidone 35 to give the arylpropylpiperidine derivative 36. Deprotection by hydrogenation with Pd(OH)$_2$/C (Pearlman's catalyst) gives piperidine derivative 37 which can be reacted with compound 19 as described in Scheme 3.

A method of preparing 4-aryloxyethylpiperidine derivatives is described in Scheme 12. Reaction of commercially available N-benzyl-4-hydroxyethylpiperidine with an appropriate aryl alcohol under standard Mitsunobu conditions, followed by deprotection gives the corresponding piperidine derivative. The corresponding mercapto derivative is prepared by reaction of compound 38 with an aryldisulfide and tri-n-butylphosphine in THF with heating at reflux to give compound 41. Compound 41 is then converted to compound 42 as described in Scheme 4.

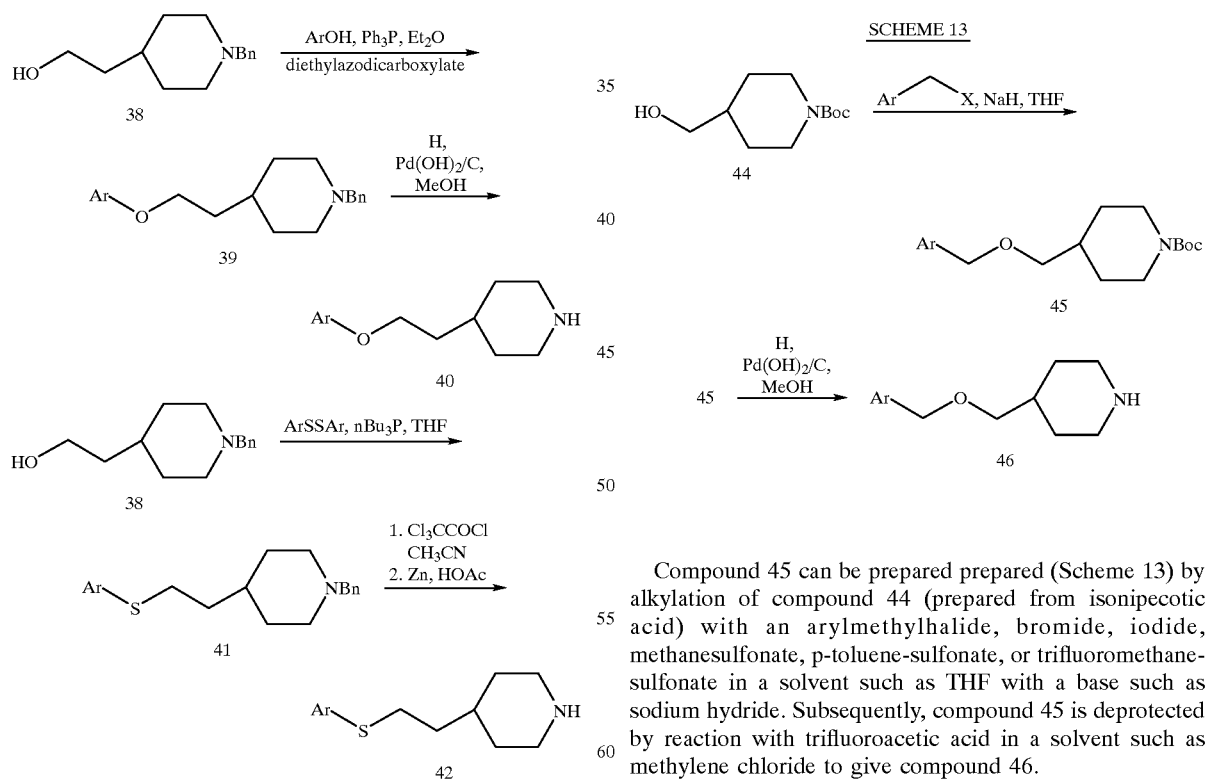

Compound 45 can be prepared prepared (Scheme 13) by alkylation of compound 44 (prepared from isonipecotic acid) with an arylmethylhalide, bromide, iodide, methanesulfonate, p-toluene-sulfonate, or trifluoromethane-sulfonate in a solvent such as THF with a base such as sodium hydride. Subsequently, compound 45 is deprotected by reaction with trifluoroacetic acid in a solvent such as methylene chloride to give compound 46.

SCHEME 14

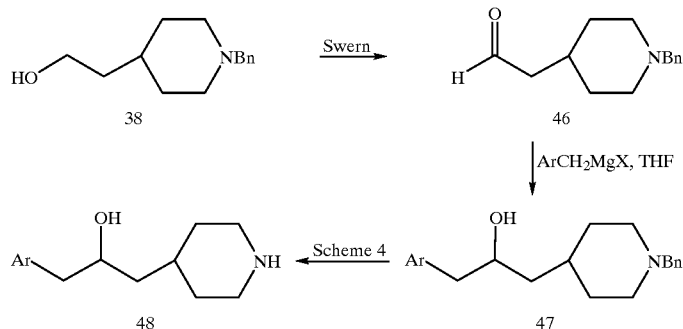

In Scheme 14, the preparation of 4-(3-aryl-2-hydroxypropyl) piperidines is described. Compound 38 is converted to aldehyde 46 by the Swern-type conditions (oxalyl chloride, DMSO, Et$_3$N). Reaction of compound 46 with Grignard reagents or other related nucleophiles gives hydroxy derivative 47. Compound 47 is then converted to piperidine 48 by procedures described in Scheme 4.

is warmed to room temperature and stirring is continued until reaction is complete.

Esters (compound 49) can be prepared by reaction of a pre-formed carboxylic acid chloride with compound 47 in a basic solvent such as pyridine or triethylamine. The acid chlorides, when not purchased, are prepared by stirring the carboxylic acids in reagents such as oxayl chloride or

SCHEME 15

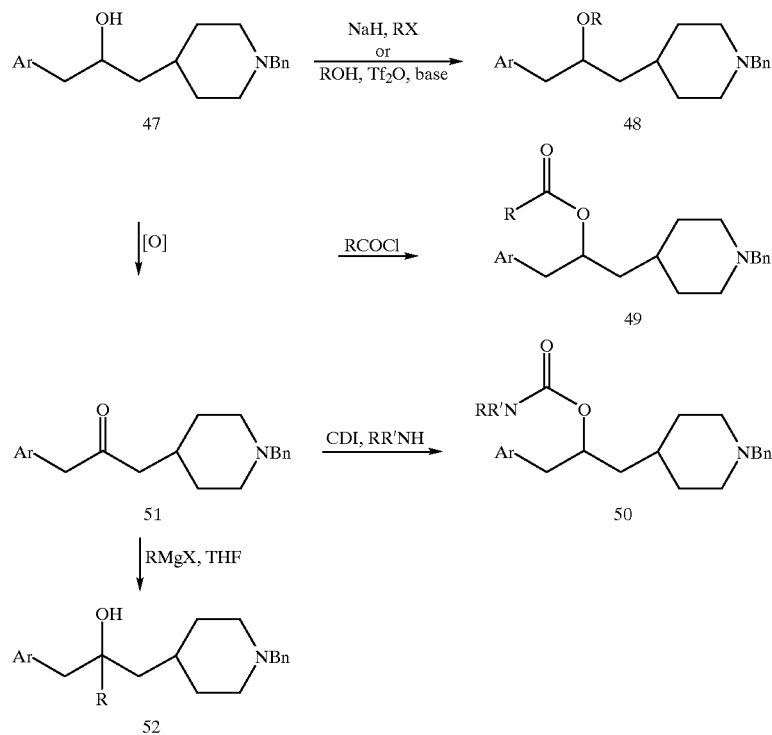

Compound 47 can be further derivatized as depicted in Scheme 15. Ether derivatives 48 can be prepared by reaction with an alkylhalide, tosylate or triflate in the presence of a base such as sodium hydride in an aprotic inert solvent such as THF. Alternatively, an excess of silver oxide (Ag$_2$O) is used in place of the base. In an alternate procedure, reaction of an alcohol with trifluoromethane sulfonic anhydride (Tf$_2$O, triflic anhydride) in dichloromethane at reduced temperature, preferably −78° C. gives the preformed triflate. To this solution is added compound 47, the reaction mixture thionyl chloride. C4 sulfonate derivatives are prepared in a similar manner by reaction with sulfonyl chlorides.

C4 carbamate and carbonate derivatives (compound 52) are prepared by first reacting compound 47 with carbonyldilmidazole (CDI) to obtain the imidazolecarbonyl intermediate which is then reacted with an amine (R$^1$R$^2$NH) or an alcohol to give the corresponding carbonate or carbamate derivatives.

Compound 47 can be oxidized to the corresponding ketone 51 by any number of standard conditions. It can then be reaction with Grignard reagents or related nucleophiles (as in Scheme 14) to give the tertiary hydroxy derivative 52. This alcohol can then be further modified as described in this scheme.

SCHEME 16

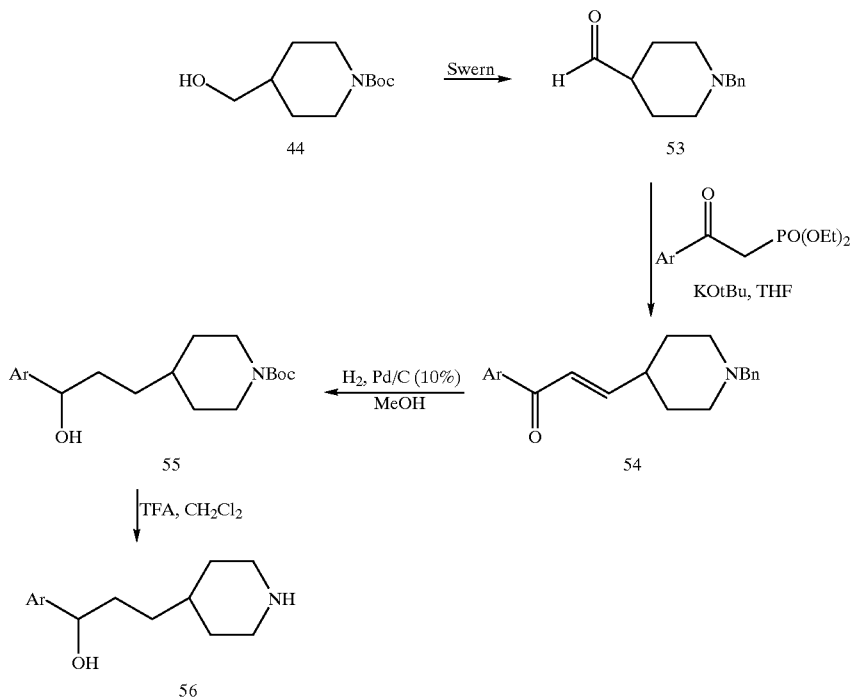

In Scheme 16, the preparation of 4-(3-phenyl-3-hydroxypropyl) piperidines is described. Oxidation of compound 44 under Swern conditions gives aldehyde derivative 53. It is then reacted with diethyl(2-aryl-2-oxoethyl) phosphonate and a base such as KOtBu in a solvent such as THF to give the conjugated ketone derivative 54. Reduction with hydrogen in the presence of Pd/C preferentially at 50 psi gives the hydroxy compound 55 which is converted to piperidine derivative 56 as previously described. Prior to deprotection, compound 55 can be further modified as depicted in Scheme 15.

SCHEME 17

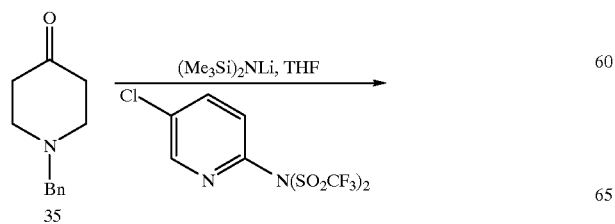

-continued

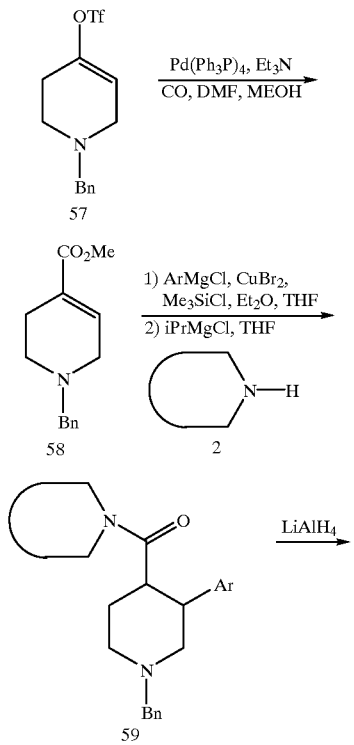

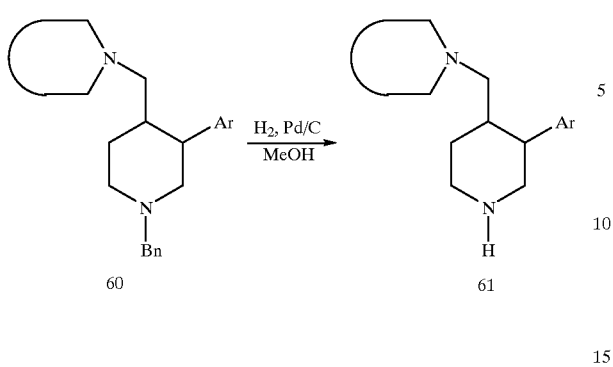

The synthesis of a framework for piperidine-based chemokine receptor modulators is given in Scheme 17. Enolate formation of the 4-piperidone derivative 35 followed by formation of the vinyl triflate with either 2-[N,N-bis(trifluoromethylsulfonyl)amino]-5-chloropyridine or with N-phenyltriflimide provides compound 57. Palladium-catalysed carbonylation in the presence of methanol then affords unsaturated ester 58. Conjugate addition of an aryl magnesium halide reagent in the presence of a copper catalyst and chlorotrimethylsilane to this species, followed by treatment with the magnesium salt of a suitable cyclic amine, then yields amide 59. Reduction with LiAlH$_4$ or borane.THF affords the tertiary amine 60, which is hydrogenated under standard conditions to the secondary piperidine 61. This compound is alkylated, acylated or sulfonated by analogy to the conditions described for compound 21 in Scheme 4.

SCHEME 18

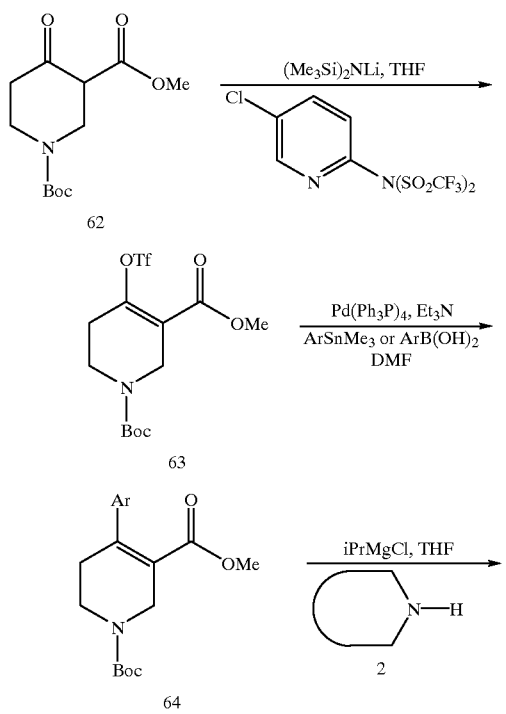

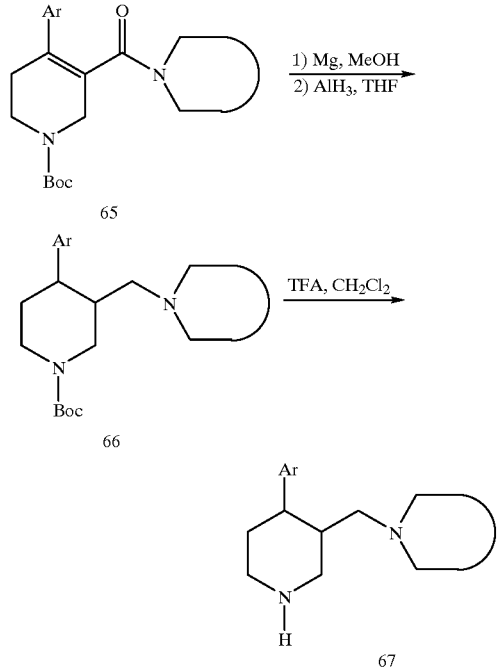

Synthesis of a piperidine derivative with an alternate presentation of the 3- and 4-substituents is given in Scheme 18. Formation of the enolate of ketoester 62 (prepared from commercially available 3-carbomethoxy-4-oxopiperidine and Boc anhydride) followed by addition of either 2-[N,N-bis(trifluoro-methylsulfonyl)amino]-5-chloropyridine or N-phenyltriflimide provides vinyl triflate 63. Palladium-mediated coupling with a suitable aryl stannane or aryl boronic acid provides unsaturated ester 64. Treatment of this compound with the magnesium salt of a suitable cyclic amine then affords amide 65, which can be reduced successively with magnesium metal in methanol followed by alane in THF, to provide the tertiary amine 66. Removal of the Boc group under standard acidic conditions yields secondary amine 67, which can be alkylated, acylated or sulfonated by analogy to the conditions described in Scheme 6.

SCHEME 19

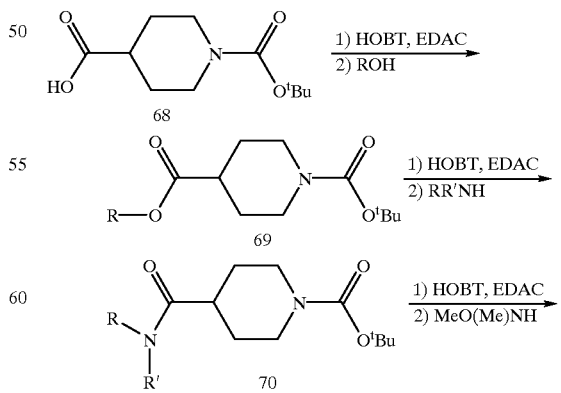

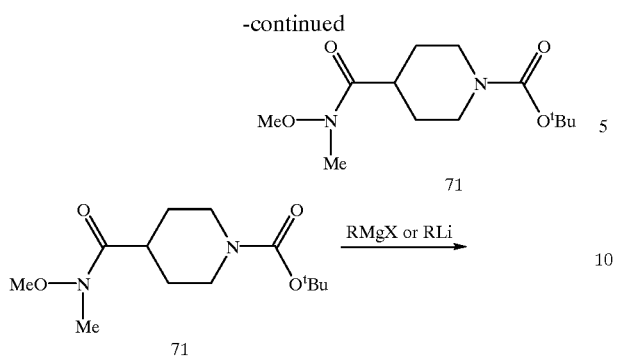

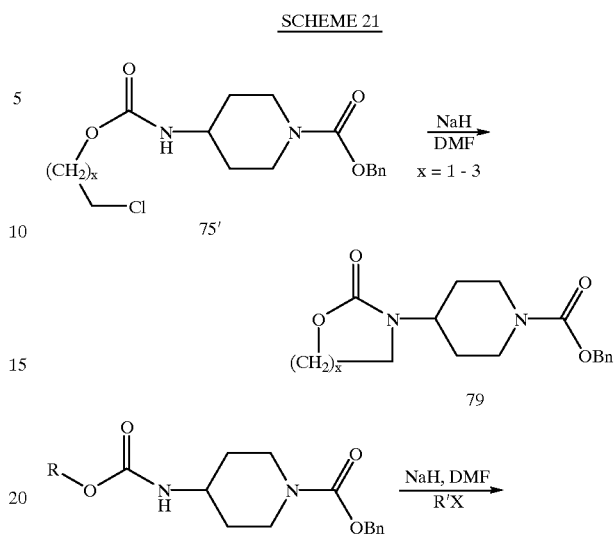

SCHEME 21

The cyclic amine II employed in the preceding Schemes can be obtained commercially in many cases or is prepared by a number of procedures. For example, as shown in Scheme 19, compound 68, the N-t-butoxycarbonyl protected form of isonipecotic acid (4-piperidine-carboxylic acid) is activated under standard conditions, for example with a carbodimide, and converted into ester 69 or amide 70. Alternatively, acid 68 is converted into the N-methyl-N-methoxy amide, 71, which upon reaction with organomagnesium and organolithium reagents forms the ketone 72. The Boc group of 69, 70 and 72 is removed under acidic conditions to provide the corresponding secondary amines.

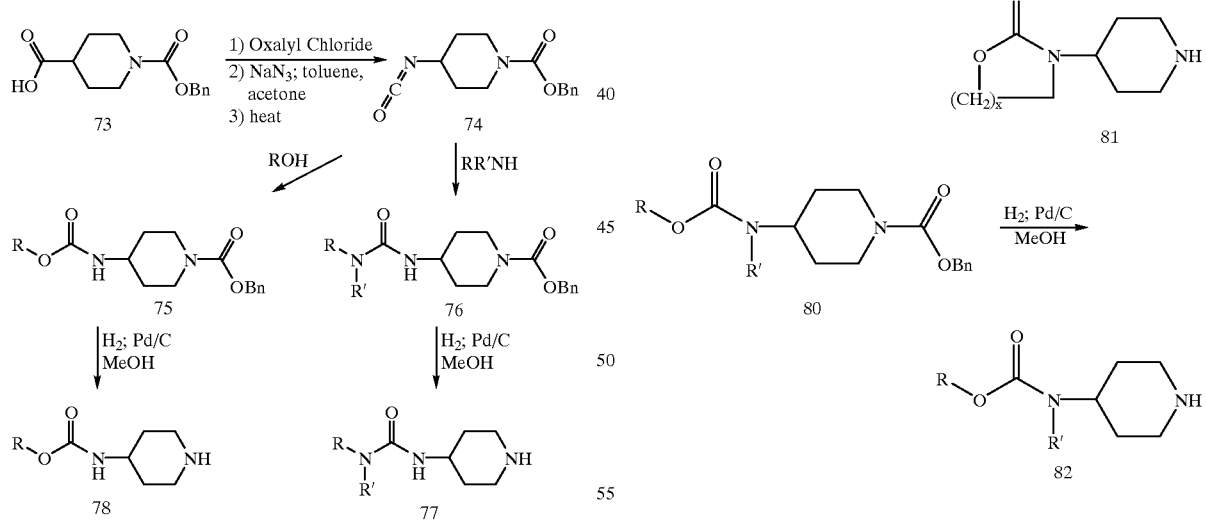

Alternatively, CBZ-protected piperidine 73 is allowed to react with oxalyl chloride and then sodium azide, to provide the corresponding acyl azide, which can then be thermally rearranged to isocyanate 74 (Scheme 20). Compound 74 is treated with an alcohol ROH or an amine RR'NH to form carbamate 75 or urea 76, respectively, each of which is deprotected with hydrogen in the presence of palladium on carbon to secondary amines 77 or 78.

If the carbamate 75 has R=—$(CH_2)_xCH_2Cl$, where x=1–3, then treatment with a suitable base, such as sodium hydride, lithium hexamethyldisilazide or potassium t-butoxide, can induce cyclization to compound 79 (Scheme 21). For other R groups, carbamate 75 is treated with an alkylating agent R'X, where R'=primary or secondary alkyl, allyl, propargyl or benzyl, while X=bromide, iodide, tosylate, mesylate or trifluoromethanesulfonate, in the presence of a suitable base, such as sodium hydride, lithium hexamethyldisilazide or potassium t-butoxide, to give derivative 80; a similar process can be employed for urea 76. In each case, removal of the CBZ protecting group under standard conditions provides the secondary amines 81 and 82.

SCHEME 22

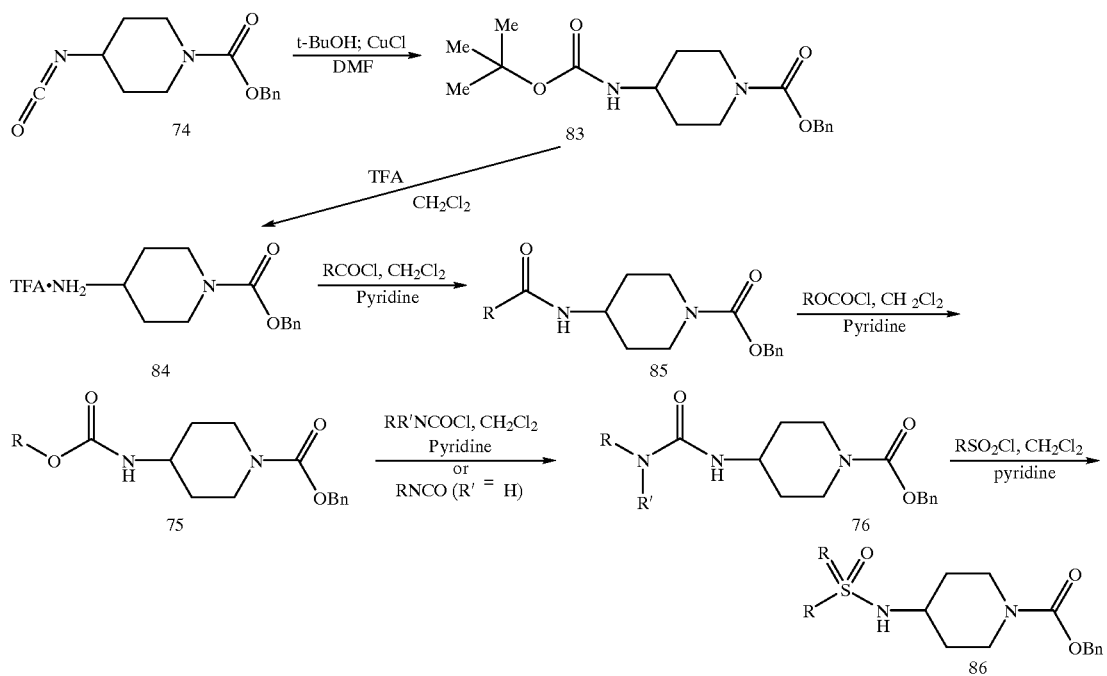

Additional derivatization of a piperidine with nitrogen functionality at C4 is carried out as shown in Scheme 22. For example, if the ring nitrogen is protected with a CBZ group, as with isocyanate 74, treatment with tert-butyl alcohol in the presence of copper(I) chloride, provides Boc derivative 83. This compound is selectively deprotected to the free amine 84. This amine is acylated with an acid chloride, a chloroformate, an isocyanate, or a carbamyl chloride, to provide compounds 85, 75 or 76. Alternatively, amine 84 is sulfonated with an alkyl or arylsulfonyl chloride, to give sulfonamide 86. Compounds 85 and 86 optionally is alkylated under the conditions given above. As shown in Scheme 21, removal of the CBZ group under reductive conditions gives the desired secondary amines.

SCHEME 23

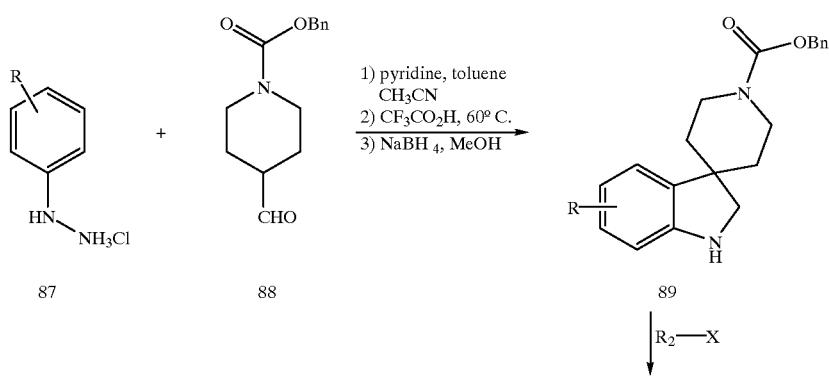

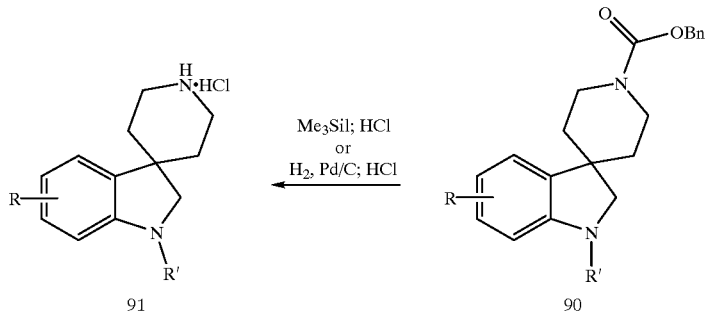

Substituted spiro(indoline-3,4'-piperidine) derivatives can be prepared as shown in Scheme 23 starting from the substituted phenylhydrazine 87 and the aldyhyde 88. Following the Fischer indole reaction and reduction of the intermediate imine with a mild reducing agent such as sodium borohydride, the indoline 89 can be combined with an electrophile such as an acyl chloride or a sulfonyl chloride. The protecting group on compound 90, for example a benzyloxycarbonyl group, can be removed by treatment with hydrogen in the presence of palladium on carbon or by exposure to trimethylsilyl iodide, to give the deprotected substituted spiro(indoline-3,4'-piperidine) 91.

SCHEME 24

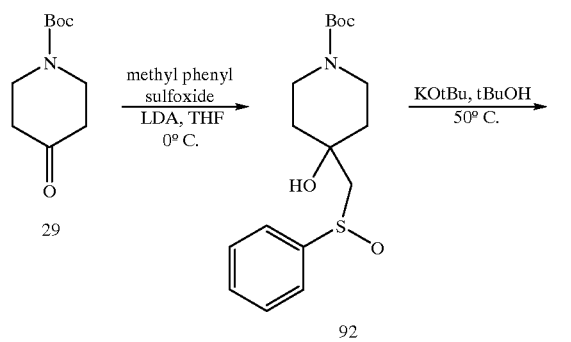

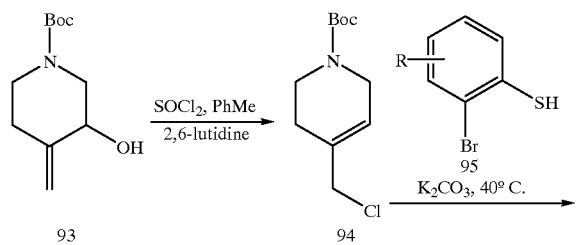

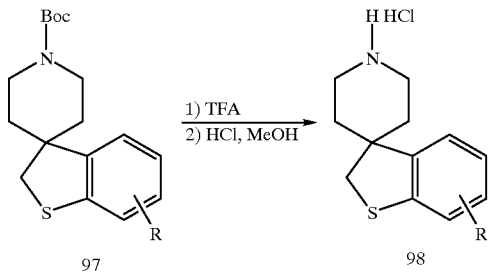

Preparation of spiro(2,3-dihydrobenzothiophene-3,4'-piperidine) derivatives is shown in Scheme 24. Reaction piperidone 29 with the lithium salt of methyl phenyl sulfoxide affords adduct 92. Base-mediated elimination-rearrangement and basic cleavage provides the allylic alcohol 93. The alcohol is converted to rearranged allylic chloride 94 with thionyl chloride in toluene in the presence of 2,6-lutidine as a proton scavenger. Displacement of the chloride with the 2-bromothiophenol 95 provides allylic sulfide 96, which can be cyclized under radical conditions to give spiro(2,3-dihydrobenzothiophene-3,4'-piperidine) 97. Cleavage of the t-butoxycarbonyl group under standard conditions, such as trifluoroacetic acid, then provides the desired spirocycle 98.

SCHEME 25

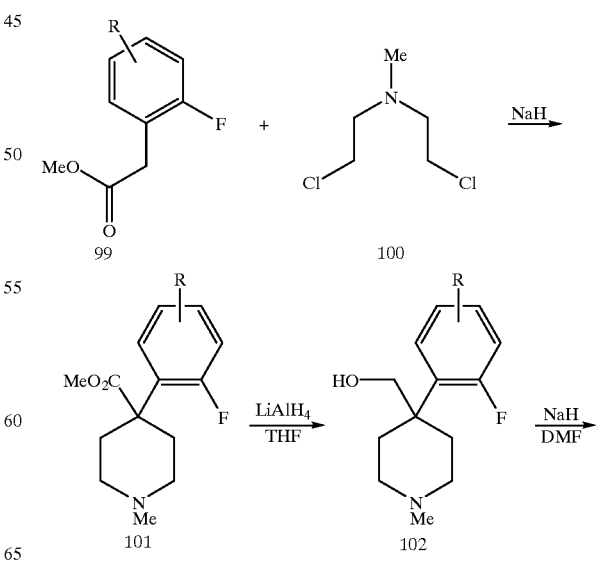

-continued

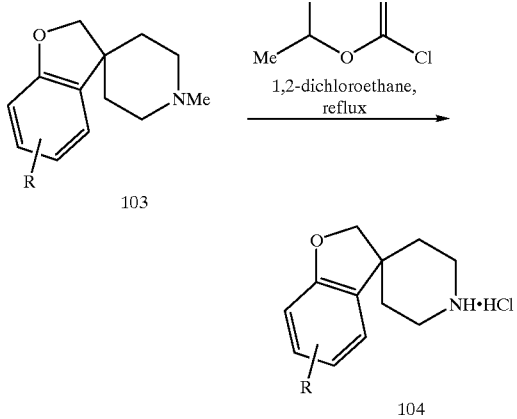

Spiro(2,3-dihydrobenzofuran-3,4'-piperidine) derivatives are prepared as illustrated in Scheme 25. Treatment of an appropiately substituted ester of 2-fluorophenylacetate 99 with mechlorethamine hydrochloride 100 under basic conditions provides piperidine 101, which on treatment with a strong reducing agent such as lithium aluminum hydride produces the corresponding 4-(hydroxymethyl) compound 102. Cyclization with base provides benzofuran 103, and cleavage of the N-methyl group is then carried out using 1-chloroethyl chloroformate or other suitable N-demethylating agents, to provide the desired intermediate 104.

SCHEME 26

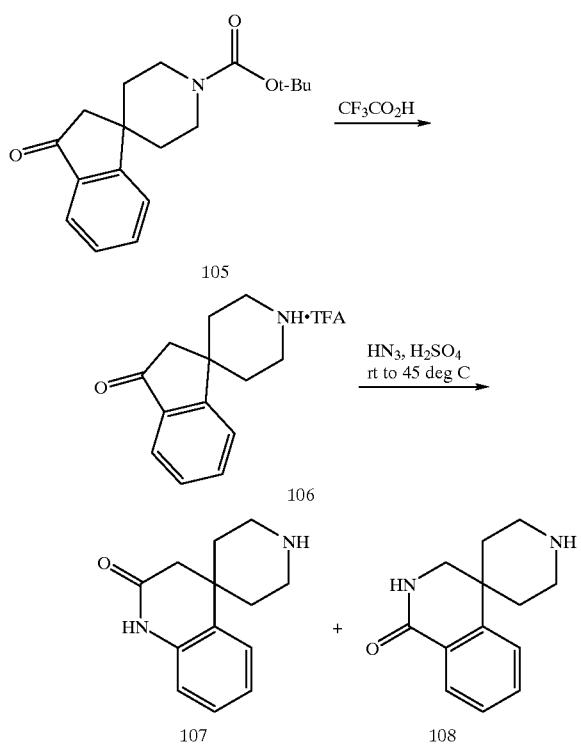

Spiro(2-oxo-1,2,3,4-tetrahydroquinoline-4,4'-piperidine) and spiro(1-oxo-1,2,3,4-tetrahydroisoquinoline-4,4'-piperidine) are prepared as shown in Scheme 26. Starting from the spiro(2-oxoindane-3,4'-piperidine) LXXXVIII (described in Claremon, D. A. et al, European Patent 0 431 943 943 A2, Evans, B. E. et al, U.S. Pat. No. 5,091,387, Davis, L. et al, U.S. Pat. No. 4,420,485, all of which are incorporated by reference, and Parham et al, Journal of Organic Chemistry, 41, 2628 (1976)), deprotection of the piperidine nitrogen is carried out by treatment with acid, for example trifluoroacetic acid, to provide ketone 106. After protection as the trifluoroacetamide, the product is exposed to hydrazoic acid in the presence of sulfuric acid. Heating of this mixture effects a Schmidt rearrangement, to provide both tetrahydroquinoline 107 and the tetrahydroisoquinoline 108. These spiro compounds are then separated and coupled to functionalized aldehydes by the methodology given above.

Cyclic amines (compound 2) which are 4-arylpiperazines functionality are prepared using methods described in the following Schemes. Starting materials are made from known procedures or as illustrated. Substituted purines are prepared as disclosed in U.S. Pat. No. 5,057,517; imidazo(1.2-a) pyrazinyl, as disclosed in U.S. Pat. No. 4,242,344; (1,2,4)-triazolo(1.5-a)pyrazinyl as disclosed in J. Org. Chem, 1974, 39, 2143 and J. C. S. Perkin I, 1980, 506; 1,7-naphthyridinyl as disclosed in J. Org. Chem. 1963, 28, 1753; furo(3.2-c) pyridinyl as disclosed in J. Heterocyclic Chem., 1982 ,19, 1207; and substituted 6-H-7,8-dihydro-thiopyrano(3.2-d) pyrimidyl as disclosed in Arch. Int. Pharmacodyn. 1986, 280, pp302–313.

Optionally, Compound III formed in the alkylation step is further modified in subsequent reactions. In one illustration of such an approach, the piperazine fragment may contain a nitro group, which is reduced to the amine after the coupling step. The resulting amine is further modified by acylation to provide the desired compounds. The piperazine fragment may also contain a protecting group such as a benzyl ester or a t-butyl ester. After reductive amination the protecting group is removed and the resulting acid is further reacted to provide additional analogs. Alternatively, the aldehyde portion may also contain a protecting group such as a t-butoxycarbonyl for an amino function. After reductive amination, the t-butoxycarbonyl group is removed by treatment with a strong acid such as trifluoroacetic acid, formic acid or hydrochloric acid and the resulting amine may be acylated to provide other analogs.

The piperazine starting materials used in the coupling reaction are prepared using methods described in the literature; more specifically as described in U.S. Pat. Nos. 5,057, 517; 4,242,344; J. Org. Chem, 1974, 39, 2143 and J. C. S. Perkin I, 1980, 506; J. Org. Chem. 1963, 28, 1753; J. Heterocyclic Chem., 1982, 19, 1207; Arch. Int. Pharmacodyn. 1986, 280, pp302–313; Meurer, L. C. et al., J. Med. Chem., 1992, 35, 3845–3857. None of these published compounds are disclosed to be chemokine receptor modulators. Alternatively, the piperazine substrates is prepared as illustrated in Schemes 27–30.

SCHEME 27

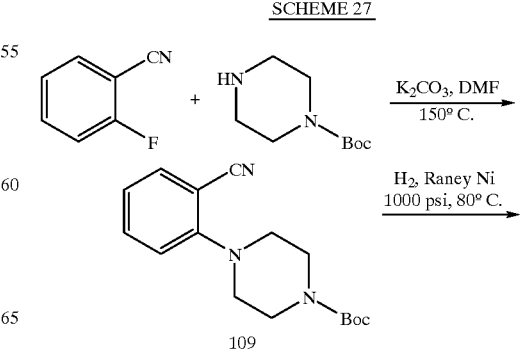

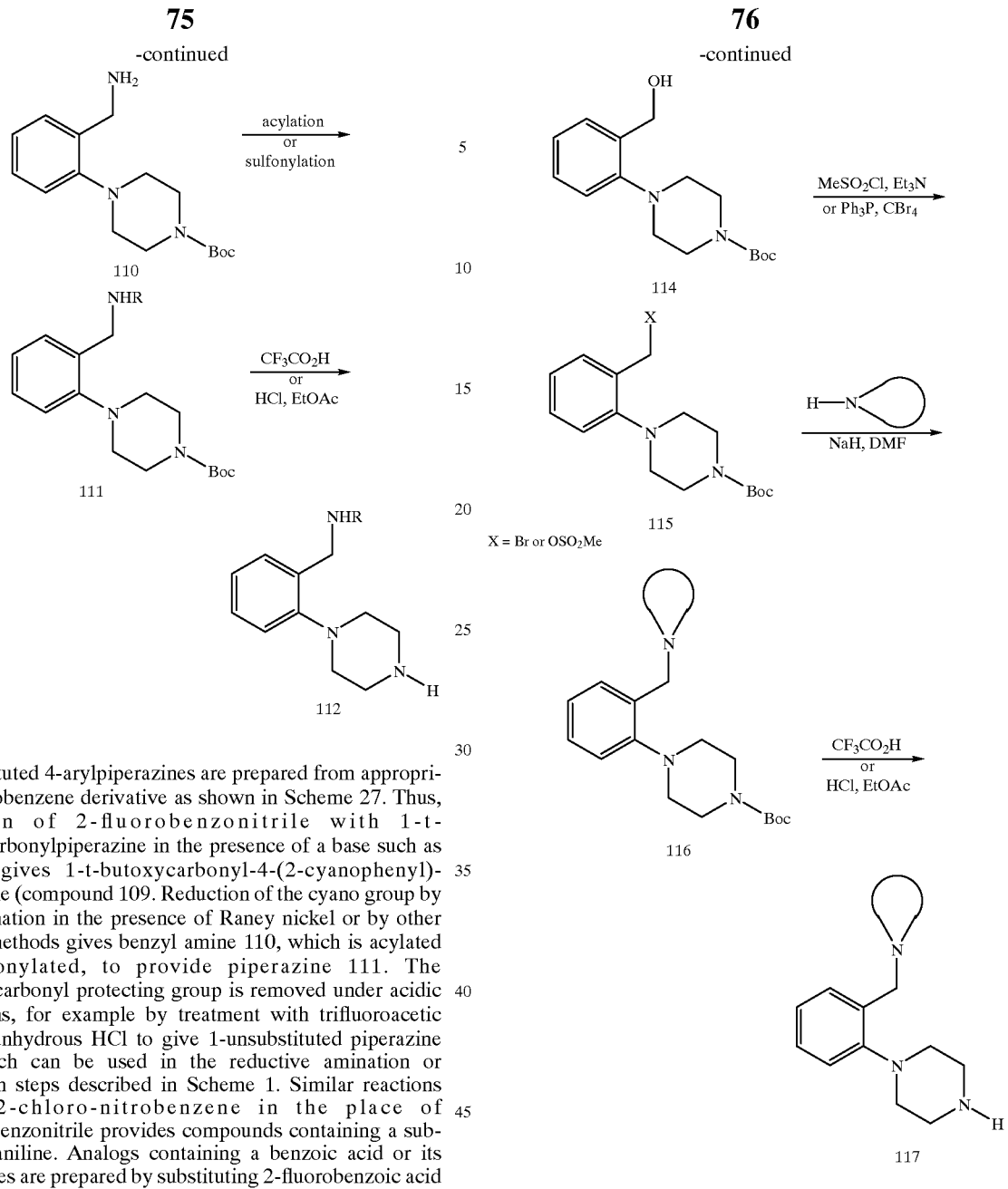

Substituted 4-arylpiperazines are prepared from appropriate fluorobenzene derivative as shown in Scheme 27. Thus, reaction of 2-fluorobenzonitrile with 1-t-butoxycarbonylpiperazine in the presence of a base such as $K_2CO_3$ gives 1-t-butoxycarbonyl-4-(2-cyanophenyl)-piperazine (compound 109. Reduction of the cyano group by hydrogenation in the presence of Raney nickel or by other known methods gives benzyl amine 110, which is acylated or sulfonylated, to provide piperazine 111. The t-butoxycarbonyl protecting group is removed under acidic conditions, for example by treatment with trifluoroacetic acid or anhydrous HCl to give 1-unsubstituted piperazine 112 which can be used in the reductive amination or alkylation steps described in Scheme 1. Similar reactions using 2-chloro-nitrobenzene in the place of 2-fluorobenzonitrile provides compounds containing a substituted aniline. Analogs containing a benzoic acid or its derivatives are prepared by substituting 2-fluorobenzoic acid in this sequence.

SCHEME 28

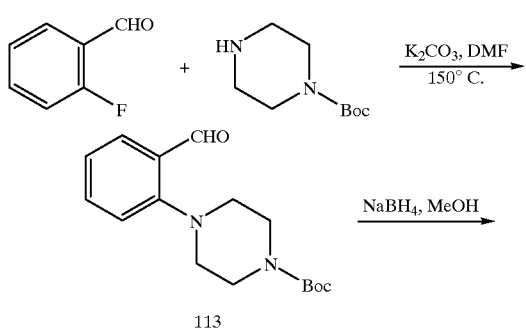

Arylpiperazine derivatives containing heterocyclic substituents are synthesized as shown in Scheme 28. Reaction between 2-fluorobenzaldehyde and 1-t-butoxycarbonylpiperazine gives 1-t-butoxycarbonyl-4-(2-formylphenyl)-piperazine compound 113. Reduction of this aldehyde and treatment of the alcohol 114 with methanesulfonyl chloride gives 115 (X=mesylate), while treatment of 114 with triphenylphosphine and carbon tetrabromide gives 115 (X=bromide). Displacement of the leaving group by a heterocycle such as imidazole in the presence of a base provides piperazine 116. Removal of the t-butoxycarbonyl protecting group under standard anhydrous acidic conditions furnishes compound 117 which is used in the coupling reactions described in Scheme 1.

SCHEME 29

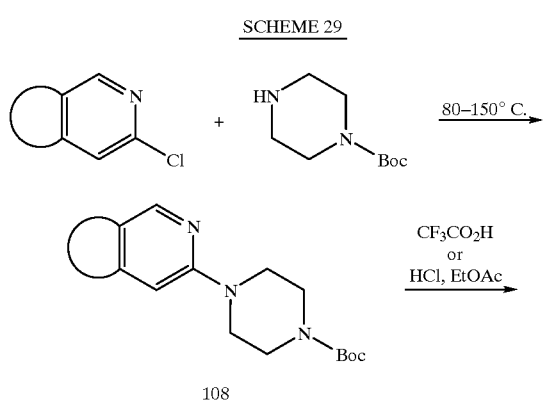

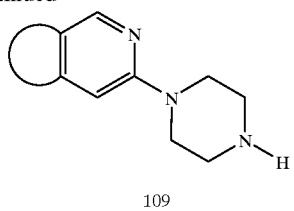

Preparation of piperazines containing a heteroaryl substituent is outlined in Scheme 29. Reaction of 1-t-butoxycarbonyl-piperazine with a chloro substituted heteroaromatic compound such as 8-chloro-1,7-naphthyridine or 8-chloro-(1,2,4)-triazolo(1,5-a)pyrazine gives N-protected piperazine 108. Removal of the t-bytoxycarbonyl protecting group under standard conditions by treatment with acid provides piperazine 109 for use in the coupling steps outlined in Scheme 1.

SCHEME 30

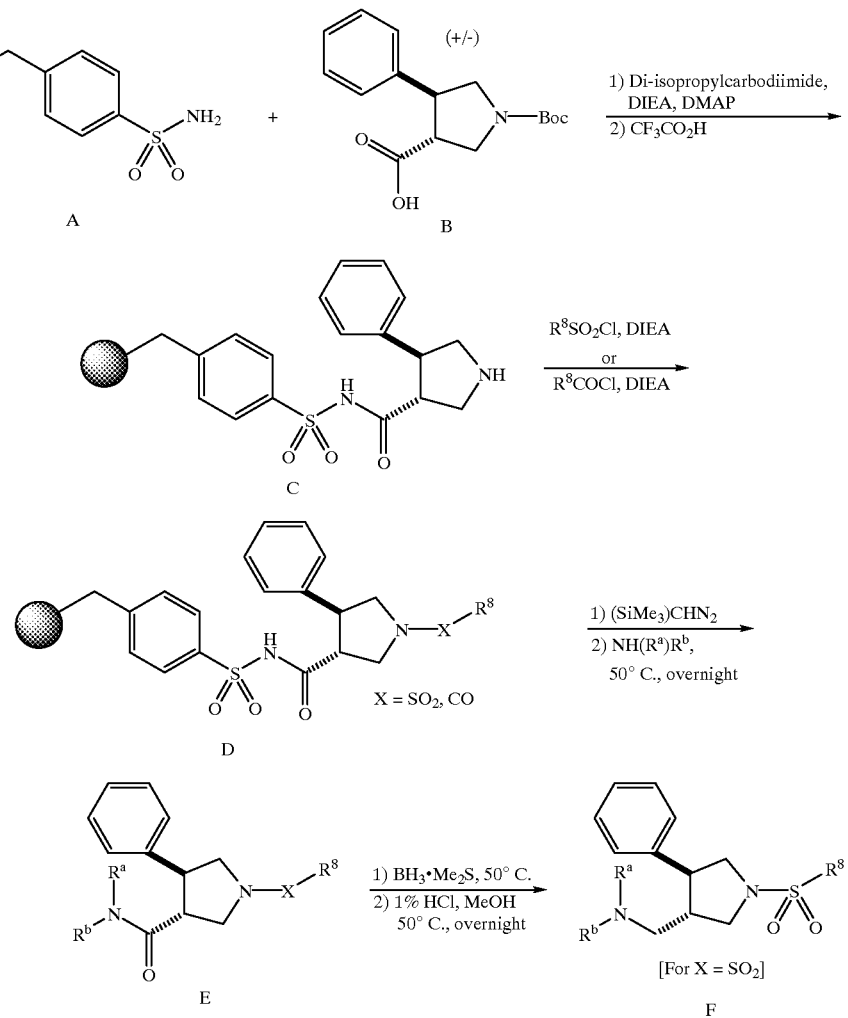

-continued

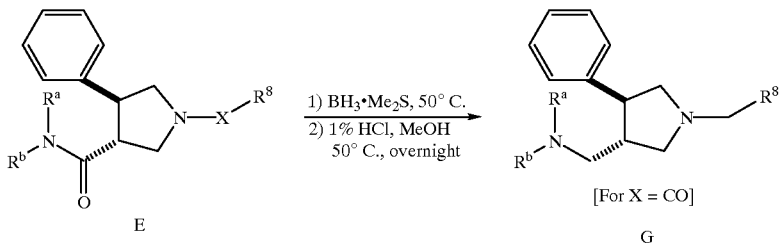

Preparation of target pyrrolidines using solid support technology is outlined in Scheme 22. Coupling of intermediate B to a commercially available 4-sulfamylbenzoyl polystyrene resin A (or a alkyl sulfamyl resin) is carried out with di-isopropylcarbodiimide or with other activating agents, for example dicyclohexylcarbodiimide, EDAC, oxalyl chloride, etc. Agents that result in the formation of the symmetrical anhydride from B (which then serves as the acylating agent) are also suitable for this purpose. Removal of the Boc group is carried out with trifluoroacetic acid or other acidic reagents, to give resin-bound pyrrolidine C. This intermediate is then coupled with sulfonyl chlorides or carbonyl chlorides in the presence of a suitable amine, preferably a hindered tertiary amine such as diisopropylethylamine (DIEA), lutidine, DBU, etc., to provide the N-functionalized pyrrolidine D. Alkylation of the acyl sulfonamide nitrogen can be carried out with trimethylsilyldiazomethane, diazomethane, with bromoacetonitrile in the presence of DBU and DMF, or under Mitsunobu conditions with a phenol such as pentafluorophenol. Reaction of the resulting N-alkylated intermediate with an amine NH($R^a$)$R^b$ at a temperature between 0 and 140° C., preferably around 50° C., for 4–24 hr, preferably about 14 hr, then cleaves the pyrrolidine from the resin as amide E. Reduction of the newly formed amide (and other amide functionality, if present) with borane methyl sulfide complex (or other hydride reducing agents, such as borane-pyridine, borane-THF, lithium aluminum hydride, lithium di-(sec) butyl borohydride, etc) followed by hydrolysis with dilute hydrogen chloride in methanol at a temperature between 0 and 140° C., preferably around 50° C., for 4–24 hr, preferably about 14 hr, provides either sulfonamide F or amine G.

Cyclic amines (compound II) from Scheme 1 which are spirocyclic piperidines are prepared using azacyclic starting materials prepared using methods described in the literature; more specifically, as described in Claremon, D. A. et al, European Patent Publication 0 431 943, Evans, B. E. et al, U.S. Pat. No. 5,091,387, Davis, L. et al, U.S. Pat. No. 4,420,485, and Parham et al, *Journal of Organic Chemistry*, 41, 2628 (1976). None of the compounds in the foregoing references are alleged to be chemokine receptor modulators.

In some cases the order of carrying out the foregoing reaction schemes may be varied to facilitate the reaction or to avoid unwanted reaction products. The following examples are provided for the purpose of further illustration only and are not intended to be limitations on the disclosed invention.

EXAMPLE 1

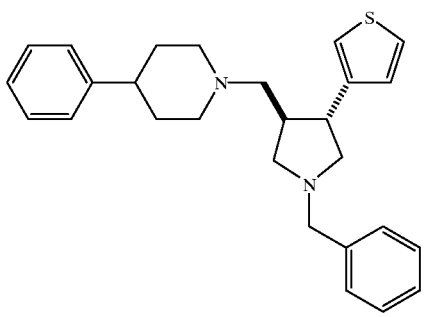

1-Benzyl-3-(RS)-(4-phenylpiperidinylmethyl)-4-(RS)-(3-thienyl)pyrrolidine

Step A

Methyl-3-(3-thienyl)acrylate

To a solution of 5.1 g (33 mmol) of 3-(3-thienyl)acrylic (Aldrich) in 75 mL of methanol at rt was slowly added 4.8 mL (66 mmol) of thionyl chloride and the reaction mixture was stirred at reflux for 2.5 h. The reaction mixture was concentrated, redissolved in methylene chloride ($CH_2Cl_2$), washed with $NaHCO_3$, dried over $MgSO_4$, filtered though a pad of silica and evaporated to give 6.7 g of the title compound as a off-white solid which was used without further purification. $^1$H NMR ($CDCl_3$) δ7.69 (d, 1H, J=16.0 Hz), 7.51 (d, 1H, J=2.8 Hz), 7.35 (d of d, 1H, J=5.2, 2.9 Hz), 7.31 (d, 1H, J=5.1 Hz), 6.28 (d, 1H, J=15.8 Hz), 3.81 (s, 3H).

Step B

1-Benzyl-3-(SR)-carbomethoxy-4-(RS)-(3-thienyl)pyrrolidine

To a solution of 1.74 g (10.4 mmol) of methyl-3-(3-thienyl) acrylate, 3.68 g (15.5 mmol) of N-(methoxymethyl)-N-trimethylsilyl methyl)benzylamine in 30 mL of $CH_2Cl_2$ at 0° C. was added 0.1 mL of trifluoroacetic acid and the reaction mixture was stirred for 4 h. The reaction mixture was diluted with sat'd $NaHCO_3$ and extracted twice with $CH_2Cl_2$. The combined organic fractions were dried over $Na_2SO_4$, filtered and the filtrate was concentrated. The residue was purified by chomatography (silica, EtOAc: hexanes, 1:15 to 1:4) to give 1.4 g of the title compound. $^1$H NMR ($CDCl_3$) δ7.28–7.39 (m, 7H), 7.09 (d, 1H, J=3.9 Hz), 3.72 (s, 3H).

Step C

1-Benzyl-3-(SR)-hydroxymethyl-4-(RS)-(3-thienyl)pyrrolidine

To a solution of 0.55 g (1.84 mmol) of 1-benzyl-3-(SR)-carbomethoxy-4-(RS)-(3-thienyl)pyrrolidine in 30 mL of THF at 0° C. was added 1.84 mL (1.84 mmol) of a 1M solution of lithium aluminum hydride in THF and the reaction was stirred at rt for 12 h. To the reaction mixture was then added 5 mL of EtOAc and 2 mL of 2N NaOH. The reaction mixture was extracted with ether and the combined organic fractions were washed with 2N NaOH solution and sat'd NaCl. The organic fractions were dried over $Na_2SO_4$, filtered and the filtrate was concentrated to give 0.49 g of the title compound which was used without further purification. $^1$H NMR ($CDCl_3$) δ7.28–7.36 (m, 7H), 7.03 (d, 1H, J=4.1 Hz), 3.66–3.78 (m, 5H).

Step D

1-Benzyl-3-(SR)-formyl-4-(RS)-(3-thienyl) pyrrolidine

To a solution of 0.31 mL (3.6 mmol) of oxalyl chloride in 20 mL of $CH_2Cl_2$ at −78° C. was added 0.51 mL (7.2 mmol) of DMSO and the reaction mixture was stirred. After 10 min., a solution of 0.49 g (1.8 mmol) of 1-benzyl-3-(RS)-hydroxymethyl-4-(SR)-(3-thienyl)pyrrolidine in 20 mL of $CH_2Cl_2$ was then added. After stirring for 10 min. at −78° C., the reaction was allowed to warm to rt. The reaction mixture was poured into ether and extracted twice with sat'd $NaHCO_3$ solution and once with sat'd NaCl solution. The organic fraction was dried over $Na_2SO_4$, filtered and the filtrate was concentrated to give 0.49 g of the title compound. $^1$H NMR ($CDCl_3$) δ9.75 (d, 1H, J=2.1 Hz), 7.27–7.36 (m, 6H), 7.03–7.07 (m, 2H), 3.78 (q, 1H, J=6.8 Hz), 3.72 (d, 1H, J=13.1 Hz), 3.68 (d, 1H, J=12.8 Hz).

Step E

4-Phenylpiperidine

A mixture of 20.5 g (104.9 mmol) of 4-phenyltetrahydropyridine hydrochloride (Aldrich) and 0.5 g of 10% Pd/C in 40 mL of $H_2O$ and 160 mL of EtOH was stirred under hydrogen at 45 psi for 2 h. The reaction mixture was then filtered though a thin pad of celite eluting with EtOH and $H_2O$. The filtrate was concentrated and the residue was stirred in 75 mL of ether. To it at 0° C. was added 5 g of solid NaOH. The layers were separated and the aqueous layer was extracted with ether. The combined organic fractions were washed with sat'd NaCl solution, dried over $Na_2SO_4$, filtered and the filtrate was concentrated. The residue was crystalized from cold heptane to give 10 g of the title compound. $^1$H NMR ($CDCl_3$) δ7.33 (t, 2H, J=7.7 Hz), 7.25–7.28 (m, 3H), 6.90 (bs, 1H), 3.65 (d, 2H, J=12.6 Hz), 3.04 (d of d,2H, J=13.0, 2.5 hz), 2.78 (t of d, 1H, J=12.1, 3.2 Hz), 2.21–2.30 (m,2H), 2.05 (d, 2H, J=14.0 Hz).

Step F

1-Benzyl-3-(RS)-(4-phenylpiperidinylmethyl)-4-(RS)-(3-thienyl)pyrrolidine

To a solution of 0.13 g (0.48 mmol) of 1-benzyl-3-(SR)-formyl-4-(RS)-(3-thienyl)pyrrolidine and 0.13 g (0.67 mmol) of 4-phenylpiperidine in 2 mL of dichloroethane and 0.1 mL of $Et_3N$ at rt was added 0.21 g (0.96 mmol) of sodium triacetoxyborohydride. After stirring for 3 h at rt, the reaction mixture was partitioned between $CH_2Cl_2$ and sat'd $NaHCO_3$. The organic fraction was dried over $Na_2SO_4$, filtered and the filtrate was concentrated. The residue was purified by chomatography (silica, acetone: hexanes, 1:3) to give 0.23 g of the title compound. $^1$H NMR $CDCl_3$) δ7.21–7.44 (m, 11H), 7.07–7.13 (m, 2H), 3.74 (d, 1H, J=12.8 Hz), 3.67 (d, 1H, J=13.1 Hz). Mass Spectrum (CI) m/e=417 (M+1).

EXAMPLE 2

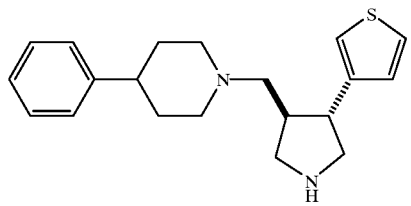

3-(SR)-(4-Phenylpiperidinylmethyl)-4-(RS)-(3-thienyl) pyrrolidine

Step A

1-Allyloxycarbamoyl-3-(RS)-(4-phenylpiperidinylmethyl)-4-(RS)-(3-thienyl) pyrrolidine A solution of 0.27 g (0.65 mmol) of 1-benzyl-3-(RS)-(4-phenylpipeidinylmethyl)-4-(RS)-(3-thienyl)pyrrolidine and 0.28 mL of allylchloroformate (Aldrich) in 4 mL of THF was stirred at rt for 1.2 h. The reaction mixture was then concentrated and the residue was purified by HPLC (Waters RCM silica 25×100 mm, 0.1% $iPr_2NH$ in t-butylmethylether: hexanes, 2.25 to 6.0 ml/min) to give 0.19 g of the title compound. $^1$H NMR ($CDCl_3$) δ7.21–7.33 (m, 11H), 7.08 (d, 1H, J=2.1 Hz), 7.01 (d, 1H, J=5.1 Hz), 5.95–6.02 (m, 1H), 5.21–5.37 (m, 2H), 4.64 (t, 2H, J=7.1 Hz).

Step B 3-(SR)-(4-phenylpiperidinylmethyl)-4-(RS)-(3-thienyl)pyrrolidine

A solution of 0.19 g (0.47 mmol) of 1-allyloxycarbamoyl-3-(SR)-(4-phenylpiperidinylmethyl)-4-(RS)-(3-thienyl) pyrrolidine, 0.52 g (9.4 mmol) KOH and 0.23 mL (4.7 mmol) of hydrazine hydrate in 5 mL of ethylene glycol was heated at 140° C. for 12 h. The reaction mixture was cooled to rt and diluted with ether. The reaction mixture was washed 3 times with $H_2O$, dried over $Na_2SO_4$, filtered and the filtrate was concentrated to give 0.13 g of the title compound. $^1$H NMR ($CDCl_3$) δ7.22–7.37 (m, 7H), 7.04 (d, 1H, J=4.3 Hz), 3.32–3.39 (m, 2H), Mass Spectrum (CI) m/e=327 (M+1).

EXAMPLE 3

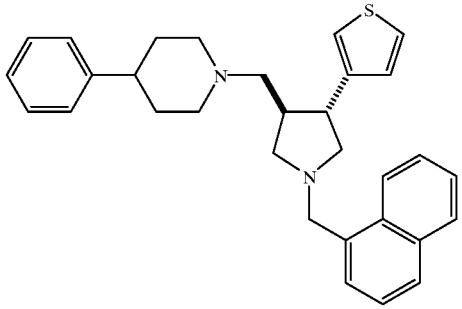

1-(1-Naphthylmethyl)-3-(RS)-(4-phenylpiperidinylmethyl)-4-(RS)-(3-thienyl) pynolidine To a solution of 0.023 g (0.071 mmol) of 3-(SR)-(4-phenyl piperidinylmethyl)-4-(RS)-(3-thienyl)prrolidine and 0.012 mL (0.085 mmol) of 1-naphthaldehyde (Aldrich) in 2 mL of dichloroethane at rt was added 0.036 g (0.17 mmol) of sodium triacetoxyborohydride and the reaction mixture was stirred overnight at rt. The reaction mixture was diluted with CH$_2$Cl$_2$ and was washed with sat'd NaHCO$_3$ solution. The organic fractions were dried over Na$_2$SO$_4$, filtered and the filtrate was concentrated. The residue was purified by chomatography (silica, EtOAc: hexanes, 1:6 to 1:2) to give the title compound. $^1$H NMR CDCl$_3$) δ8.45 (d, 1H, J=8.2 Hz), 7.92 ((d, 1H, J=8.0 Hz), 7.84 (d, 1H, J=8.2 Hz), 7.13 (d of d, 1H, J=5.1, 1.2 Hz), 7.07 (d, 1H, J=2.8 Hz), 4.17 (d, 1H, J=12.9 Hz), 4.11 (d, 1H, J=13.0 Hz); Mass Spectrum (CI) m/e 467 (M+1).

EXAMPLE 4

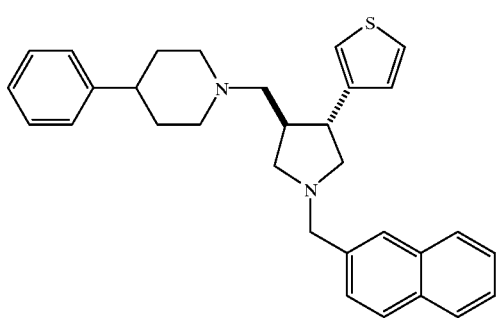

1-(2-Naphthylmethyl)-3-(RS)-(4-phenylpiperidnylmethyl)-4-(RS)-(3-thienyl)pyrrolidine The title compound was prepared from 3-(SR)-(4-phenylpiperidinylmethyl)-4-(RS)-(3-thienyl)pyrrolidine and 2-naphthaldehyde as described in Example 3. Mass Spectrum (CI) m/e 467 (M+1).

EXAMPLE 5

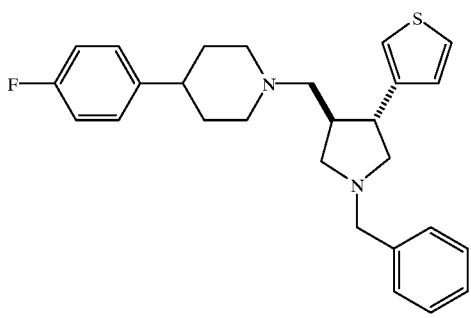

1-Benzyl-3-(RS)-(4-(4-fluorophenyl)piperidinylmethyl)-4-(RS)-(3-thienyl)pyrrolidine The title compound was prepared from 1-benzyl-3-(SR)-formyl-4-(RS)-(3-thienyl)pyrrolidine and 4-(4-fluorophenyl)piperidine according to procedures described in Example 1. 4-(4-fluorophenyl)piperidine was prepared according to procedures used to prepare 4-phenylpiperidine in Example 1. Mass Spectrum (CI) m/e 435 (M+1).

EXAMPLE 6

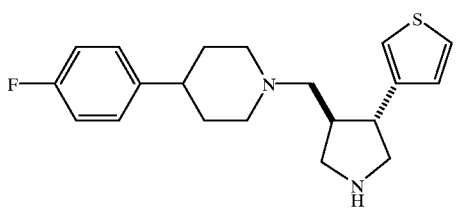

3-(SR)-(4-(4-Fluorophenyl)pipeidinylmethyl)-4-(RS)-(3-thienyl)pyrrolidine

The title compound was prepared from 1-benzyl-3-(RS)-(4-(4-fluorophenyl)piperidinylmethyl)-4-(RS)-(3-thienyl)pyrrolidine as described in Example 2.

The title compound may also be prepared according the the following procedures.

Step A

N-allyl-N-(trimethylsilylmethyl)amine

To 118 mL (1.57 mol) of allylamine warmed at 40° C. in an inert atmosphere was very slowly added 100 mL (0.72 mol) of chloromethyl trimethylsilane (approximate rate of 1 mL/min). The reaction mixture was slowly warmed to 70° C. and stirred for 24 h. The reaction mixture was cooled to 0° C. and to it was added water to break tip the gel and then 300 mL of 2N NaOH solution. The reaction mixture was extracted with ether. The combined organic fractions were washed with 500 mL of sat'd NaCl solution, dried over Na$_2$SO$_4$, filtered and the filtrate was concentrated. The residue was purified by distillation (bp 80–84° C. @ 100 torr) to give 75 g of the title compound.

Step B

N-Allyl-N-(methoxymethyl)-N-trimethylsilylmethyl)amine

To 75 g (0.57 mol) of N-allyl-N-(trimethylsilylmethyl)amine at 0° C. was slowly added 67 mL (0.88 mol) of aqueous formaldehyde (37% w/w). After stirring for 5 min, 65 mL (1.6 mol) of methanol was added followed by the addition of 94 g (0.68 mol) of K$_2$CO$_3$. The reaction mixture was warmed to rt and stirred for 12 h. The reaction mixture was partitioned between 300 mL of water and 300 mL of ether. The organic fraction was washed with water and sat. NaCl solution. The combined aqueous fractions were extracted with ether. The combined organic fractions were dried over Na$_2$SO$_4$, filtered and the filtrate was concentrated to give 89 g of the title compound which was used without further purification.

Step C

1-Allyl-3-(SR)-carbomethoxy-4-(RS)-(3-thienyl)pyrrolidine

To a solution of 5 g (29.7 mmol) of methyl-3-(3-thienyl)acrylate, 11.3 g (60.3 mmol) of N-allyl-N-(methoxymethyl)-N-trimethylsilylmethyl)amine in 50 mL of CH$_2$Cl$_2$ at 0° C. was added 0.3 mL of trifluoroacetic acid and the reaction mixture was stirred for 4 h while warming to rt. The reaction mixture was diluted with sat'd NaHCO$_3$ and extracted twice with 100 mL of ether. The combined organic fractions were washed with sat'd NaHCO$_3$ and NaCl solutions, dried over Na$_2$SO$_4$, filtered and the filtrate was concentrated. The residue was purified by chomatography (silica, EtOAc: hexanes, 1:3) to give 7.3 g of the title compound.

Step D

1-Allyl-3-(RS)-(4-(4-fluorophenyl) piperidinylmethyl)-4-(RS)-(3-thienyl)pyrrolidine The title compound was prepared as described in Example 1, Steps C, D and F.

Step E 3-(SR)-(4-(4-Fluorophenyl)piperidinylmethyl)-4-(RS)-(3-thienyl)pyrrolidine A mixture of 0.48 g (0.26 mmol) of 1-allyl-3-(RS)-(4-(4-fluorophenyl)piperidinylmethyl)-4-(RS)-(3-thienyl) pyrrolidine and 0.067 g (0.072 mmol) of Wilkinson's catalyst [Rh(PPh)$_3$Cl] in 20 mL of an 85% solution of CH$_3$CN and water was heated to 90° C. and stirred for 3 h. The reaction mixture was cooled to rt and concentrated. The residue was partitioned between EtOAc and water. The organic fraction was washed with sat. NaHCO$_3$, dried over Na$_2$SO$_4$, filtered and the filtrate was concentrated. The residue was purified by chomatography (silica, CHCl$_3$: MeOH: NH$_3$, 90: 10:1) to give the title compound. $^1$H NMR CDCl$_3$) δ7.28 (d of d, 1H, J=3.0, 4.8 Hz), 7.15–7.17 (m, 2H), 6.95–7.02 (m, 4H), 3.31–3.38 (m, 2H), 2.85–3.03 (m, 5H), 2.35–2.48 (m, 5H), 1.95–2.02 (m, 2H), 1.61–1.78 (m, 4H).

The following Examples 7 to 10 were prepared from 3-(SR)-(4-(4-fluoro phenyl)piperidinylmethyl)-4-(RS)-(3-thienyl)pyrrolidine and the corresponding aldehydes as demonstrated in Example 3.

EXAMPLE 7

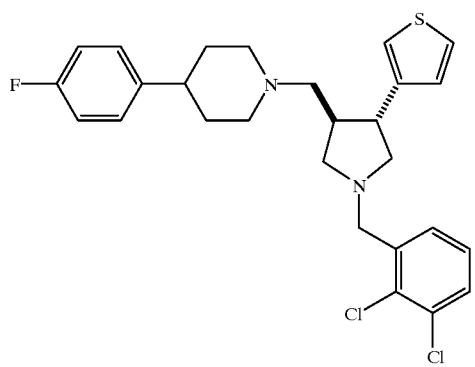

1-(2,3-Dichlorophenyl)methyl-3-(RS)-(4-(4-fluorophenyl)piperidinyl-methyl)-4-(RS)-(3-thienyl) pyrrolidine Mass Spectrum (CI) m/e 503 (M+1 35Cl, 35Cl) and 505 (M+1 35Cl, 37Cl).

EXAMPLE 8

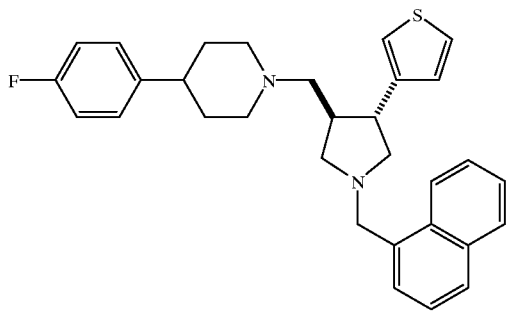

1-(1-Naphthylmethyl)-3-(RS)-(4-(4-fluorophenyl) piperdinylmethyl)-4-(RS)-(3-thienyl)pyrrolidine Mass Spectrum (CI) m/e 485 (M+1).

EXAMPLE 9

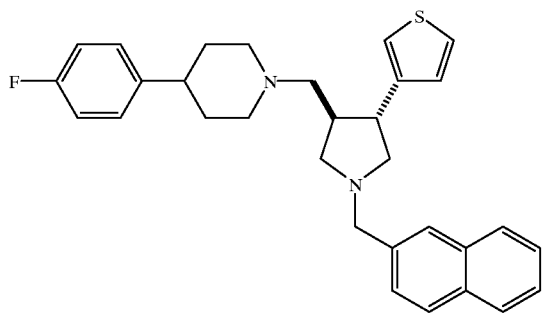

1-(2-Naphthylmethyl)-3-(RS)-(4-(4-fluorophenyl) piperidinylmethyl)-4-(RS)-(3-thienyl)pyrrolidine Mass Spectrum (CI) m/e 485 (M+1).

EXAMPLE 10

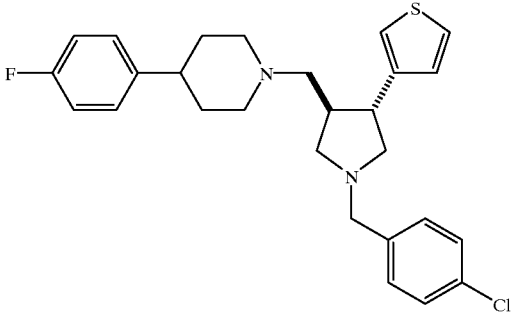

1-(4-Chlorobenzyl)-3-(RS)-(4-(4-fluorophenyl) piperidinylmethyl)-4-(RS)-(3-thienyl)pyrrolidine Mass Spectrum (CI) m/e=469 (M+1 35Cl) and 471 (M+1 37Cl).

EXAMPLE 11

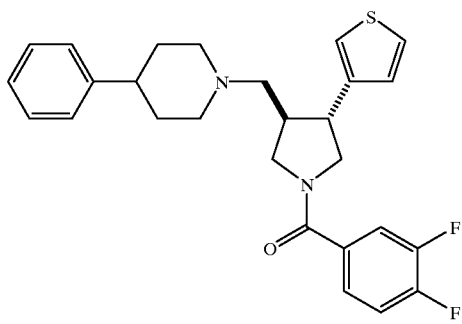

1-(3,4-Difluorobenzoyl)-3-(RS)-(4-phenylpiperidinylmethyl)-4-(RS)-(3-thienyl)pyrrolidine To a solution of 0.023 g (0.071 mmol) of 3-(SR)-(4-phenylpiperidinylmethyl)-4-(RS)-(3-thienyl)pyrrolidine and 0.079 mL of $Et_3N$ in 2 mL of $CH_2Cl_2$ was added 0.059 g (0.28 mmol) of 3,4-difluorobenzoyl chloride and the reaction mixture was stilled for 0.5 h. The reaction mixture was partitioned between $CH_2Cl_2$ and sat'd $NaHCO_3$ solution. The organic fraction was dried over $Na_2SO_4$, filtered and the filtrate was concentrated. The residue was purified by chomatography (silica, acetone: hexanes, 1:3) to give 0.026 g of the title compound. $^1H$ NMR ($CDCl_3$) δ7.17–7.49 (m, 9H), 7.13 and 7.08 (s, 1H), 7.04 and 6.99 (d, 1H, J=4.6 Hz),4.08–4.15 (m, 2H); Mass Spectrum (CI) m/e=482 (M+1).

EXAMPLE 12

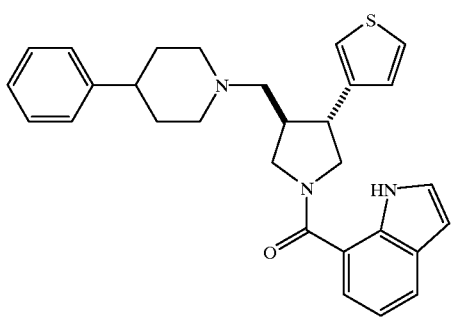

1-(7-Indolylcarbonyl)-3-(RS)-(4-phenylpiperidinylmethyl)-4-(RS)-(3-thienyl)pyrrolidine To a solution of 0.022 g (0.067 mmol) of 3-(SR)-(4-phenyl piperidinylmethyl)-4-(RS)-(3-thienyl)pyrrolidine and 0.016 g (0.1 mmol) of indole-7-carboxylic acid in 2 mL of $CH_2Cl_2$ and 0.037 mL (0.27 mmol) of triethylamine was added 0.022 g (0.087 mL) of BOP-Cl [Bis-(2-oxo-3-oxazolidinyl)phosphinic chloride] and the reaction mixture was stirred at rt for 5 h. The reaction mixture concentrated and purified by chomatography (silica, acetone: hexanes, 1:3 to 1:2) to give the title compound. $^1H$ NMR ($CDCl_3$) δ; 10.02 (bs, 1H), 7.79 (bs, 1H), 7.02–7.53 (m, 11H), 6.62 (bs, 1H), 4.15–4.19 (m, 2H); Mass Spectrum (CI) m/e=482 (M+1).

The following The following Examples 13 to 31 were prepared from 3-(SR)-(4-phenyl)piperidinylmethyl)-4-(RS)-(3-thienyl)pyrrolidine and the corresponding acid chloride or acid is demonstrated in Examples 11 and 12 respectively.

EXAMPLE 13

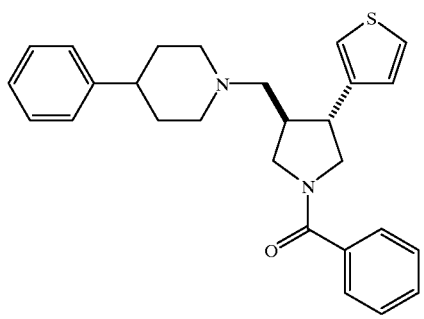

1-Benzoyl-3-(RS)-(4-phenylpiperidinylmethyl)-4-(RS)-(3-thienyl)pyrrolidine

Mass Spectrum (CI) m/e=467 (M+1)

EXAMPLE 14

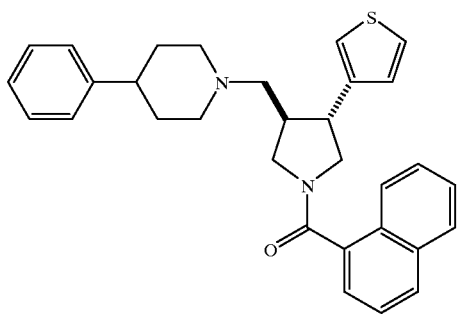

1-(1-Naphthoyl)-3-(RS)-(4-phenylpiperidinylmethyl)-4-(RS)-(3-thienyl)pyrrolidine Mass Spectrum (CI) m/e=481 (M+1)

EXAMPLE 15

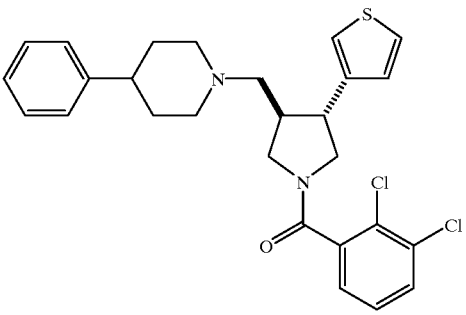

1-(2,3-Dichlorobenzoyl)-3-(RS)-(4-phenylpiperdinylmethyl)-4-(RS)-(3-thienyl)pyrrolidine Mass Spectrum (CI) m/e=499 (M+1, 35Cl, 35Cl) and 501 (M+1 35Cl, 37Cl)

EXAMPLE 16

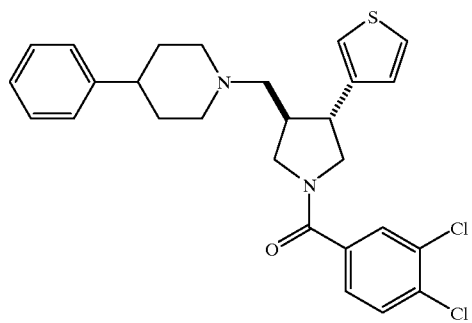

1-(3,4-Dichlorobenzoyl)-3-(RS)-(4-phenylpiperidinylmethyl)-4-(RS)-(3-thienyl)pyrrolidine Mass Spectrum (CI) m/e=499 (M+1, 35Cl, 35Cl), 501 (M+1 35Cl, 37Cl)

EXAMPLE 17

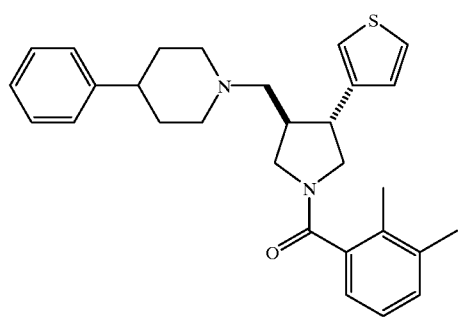

1-(2,3-Dimethylbenzoyl)-3-(RS)-(4-phenylpiperidinylmethyl)-4-(RS)-(3-thienyl)pyrrolidine Mass Spectrum (CI) m/e=459 (M+1)

EXAMPLE 18

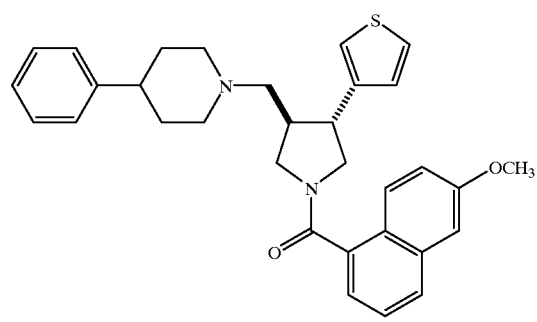

1-(6-Methoxy-1-naphthoyl)-3-(RS)-(4-phenylpiperidinylmethyl)-4-(RS)-(3-thienyl)pyrrolidine Mass Spectrum (CI) m/e=511 (M+1)

EXAMPLE 19

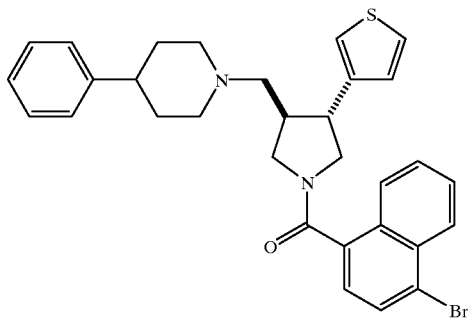

1-(4-Bromo-1-naphthoyl)-3-(RS)-(4-phenylpiperidinylmethyl)-4-(RS)-(3-thienyl)pyrrolidine Mass Spectrum (CI) m/e=559 (M+1,79 Br), 561 (81Br)

EXAMPLE 20

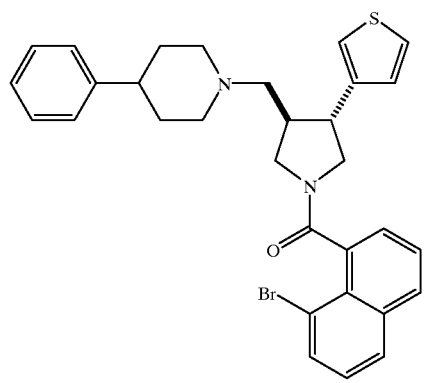

1-(8-Bromo-1-naphthoyl)-3-(RS)-(4-phenylpiperidinylmethyl)-4-(RS)-(3-thienyl)pyrrolidine Mass Spectrum (CI) m/e=559 (M+1,79 Br), 561 (81Br)

EXAMPLE 21

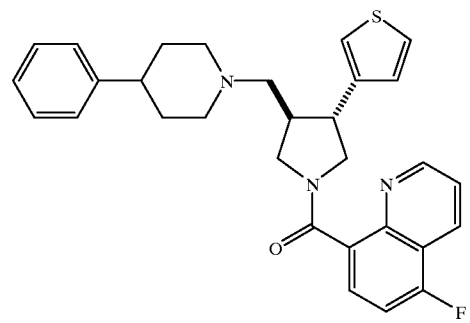

1-(4-Fluoro-1-naphthoyl)-3-(RS)-(4-phenylpiperidinylmethyl)-4-(RS)-(3-thienyl)pyrrolidine Mass Spectrum (CI) m/e=499 (M+1)

EXAMPLE 22

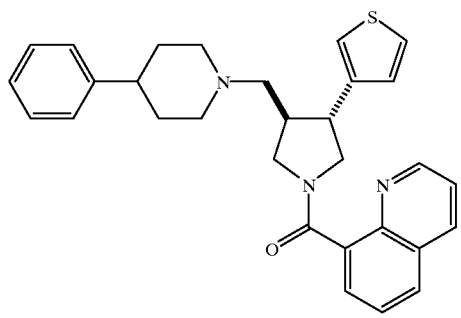

1-(8-Quinolinecarbonyl)-3-(RS)-(4-phenylpiperidinyimethyl)-4-(RS)-(3-thienyl) pyrrolidine Mass Spectrum (CI) m/e=482 (M+1)

EXAMPLE 23

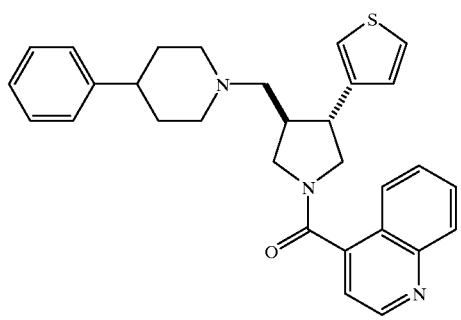

1-(4-Quinolinylcarbonyl)-3-(RS)-(4-phenylpiperidinylmethyl)-4-(RS)-(3-thieny) pyrrolidine Mass Spectrum (CI) m/e=482 (M+1)

EXAMPLE 24

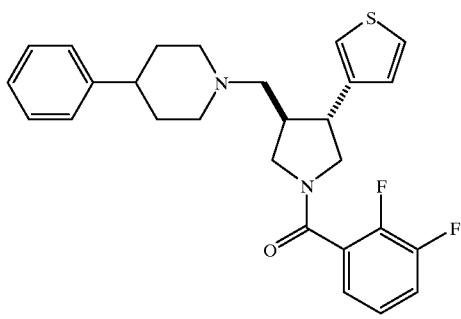

1-(2,3-Difluorobenzoyl)-3-(RS)-(4-phenylpiperidinylmethyl)-4-(RS)-(3-thienyl) pyrrolidine Mass Spectrum (CI) m/e=467 (M+1)

EXAMPLE 25

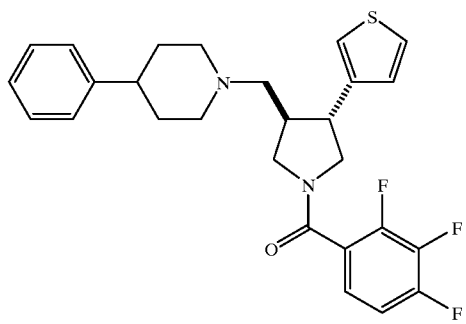

1-(2,3,4-Trifuorobenzoyl)-3-(RS)-(4-phenylpiperidinylmethyl)-4-(RS)-(3-thienyl) pyrrolidine Mass Spectrum (CI) m/e=485 (M+1)

EXAMPLE 26

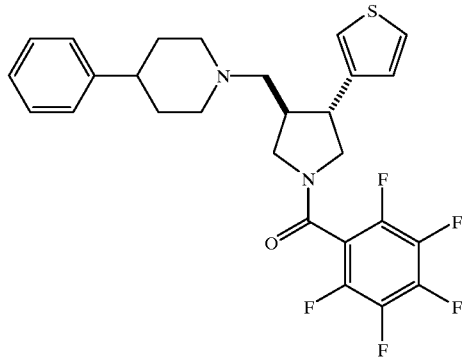

1-(2,3,4,5,6-Pentafluorobenzoyl)-3-(RS)-(4-phenylpiperidinylmethyl)-4-(RS)-(3-thienyl) pyrrolidine Mass Spectrum (CI) m/e=521 (M+1)

EXAMPLE 27

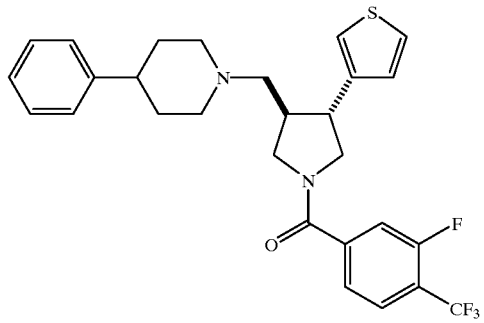

1-(3-Fluoro-4-trifluoromethylbenzoyl)-3-(RS)-(4-phenylpiperidinyl-methyl)-4-(RS)-(3-thienyl) pyrrolidine Mass Spectrum (CI) m/e=517 (M+1)

EXAMPLE 28

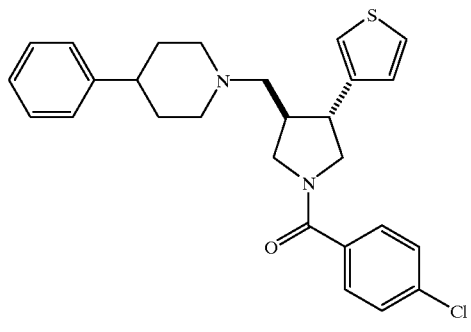

1-(4-Chlorobenzoyl)-3-(RS)-(4-phenylpiperidinylmethyl)-4-(RS)-(3-thienyl)pyrrolidine Mass Spectrum (CI) m/e=465 (M+1, 35Cl), 467 (M+1 37Cl)

EXAMPLE 29

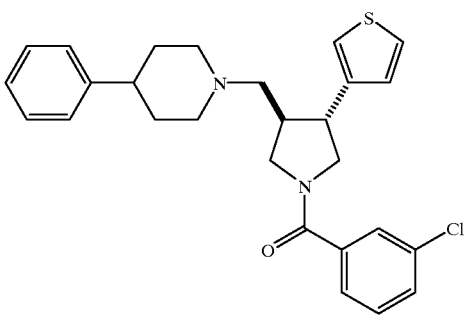

1-(3-Chlorobenzoyl)-3-(RS)-(4-phenylpiperidinylmethyl)-4-(RS)-(3-thienyl)pyrrolidine Mass Spectrum (CI) m/e=465 (M+1, 35Cl), 467 (M+1 37Cl)

EXAMPLE 30

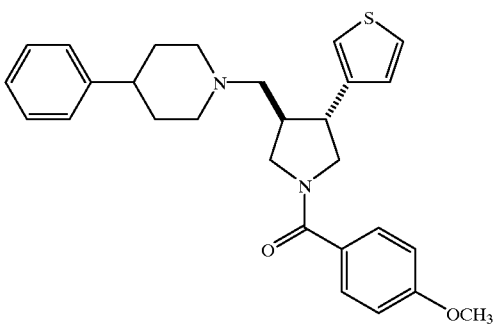

1-(4-Methoxybenzoyl)-3-(RS)-(4-phenylpiperidinylmethyl)-4-(RS)-(3-thienyl)pyrrolidine Mass Spectrum (CI) m/e=461 (M+1)

EXAMPLE 31

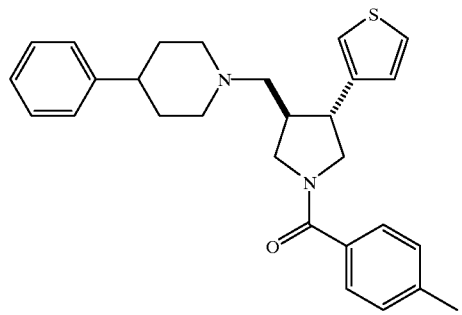

1-(4-Methylbenzoyl)-3-(RS)-(4-phenylpiperidinylmethyl)-4-(RS)-(3-thienyl)pyrrolidine Mass Spectrum (CI) m/e=445 (M+1)

The following The following Examples 32 to 78 were prepared from 3-(SR)-(4-(4-fluorophenyl)piperidinylmethyl)-4-(RS)-(3-thienyl)pyrrolidine and the corresponding acid chloride or acid as demonstrated in Examples 11 and 12 respectively. The acid chlorides, acids or their aldehyde or hydroxymethyl precursors are commercially available and were purchased from Aldrich, Maybridge, Avocado, Lancaster or TCI chemical companies.

EXAMPLE 32

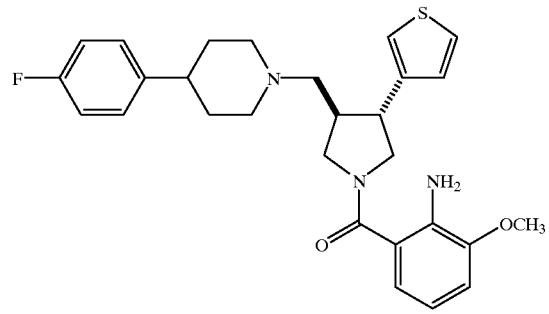

1-(2-Amino-3-methoxybenzoyl)-3-(RS)-(4-(4-fluorophenyl)piperidinyl-methyl)-4-(RS)-(3-thienyl)pyrrolidine Mass Spectrum (CI) m/e=494 (M+1)

EXAMPLE 33

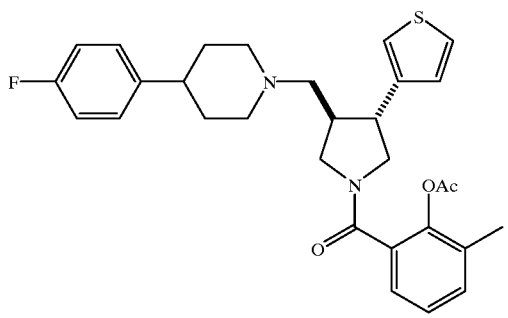

1-(2-Acetoxy-3-methylbenzoyl)-3-(RS)-(4-(4-fluorophenyl)piperidinyl-methyl)-4-(RS)-(3-thienyl)pyrrolidine Mass Spectrum (CI) m/e=521 (M+1)

EXAMPLE 34

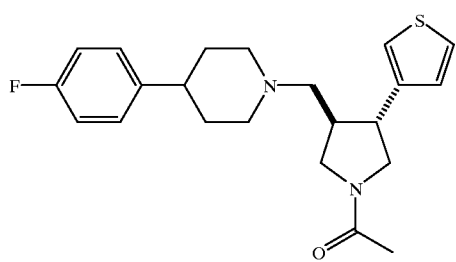

Acetyl-3-(RS)-(4-(4-fluorophenyl)piperidinylmethyl)-4-(RS)-(3-thienyl)pyrrolidine Mass Spectrum (CI) m/e=397 (M+1)

EXAMPLE 35

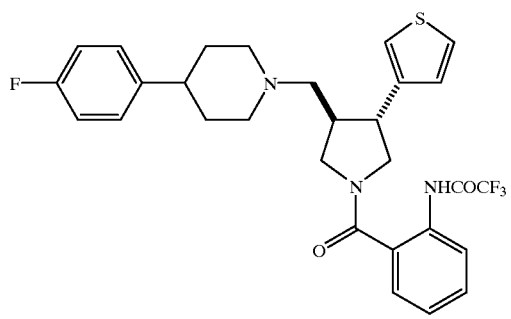

1-(2-Trifluoroacetylaminobenzoyl)-3-(RS)-(4-(4-fluorophenyl)-piperidinylmethyl)-4-(RS)-(3-thienyl)pyrrolidine Mass Spectrum (CI) m/e=560 (M+1)

EXAMPLE 36

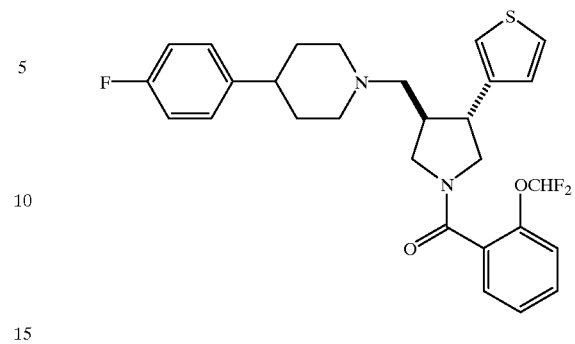

1-(2-Dilfluoromethoxybenzoyl)-3-(RS)-(4-(4-fluorophenyl)piperidinyl-methyl)-4-(RS)-(3-thienyl)pyrrolidine Mass Spectrum (CI) m/e=515 (M+1)

EXAMPLE 37

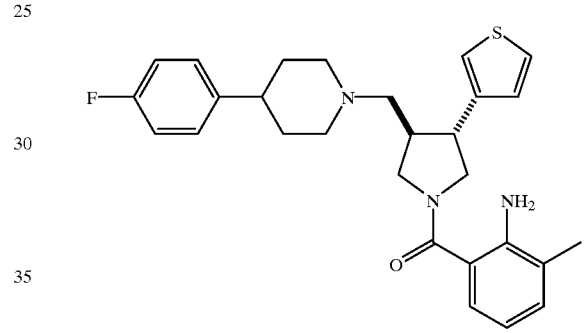

1-(2-Amino-3-methylbenzoyl)-3-(RS)-(4-(4-fluorophenyl)piperidinyl-methyl)-4-(RS)-(3-thienyl)pyrrolidine Mass Spectrum (CI) m/e=478 (M+1)

EXAMPLE 38

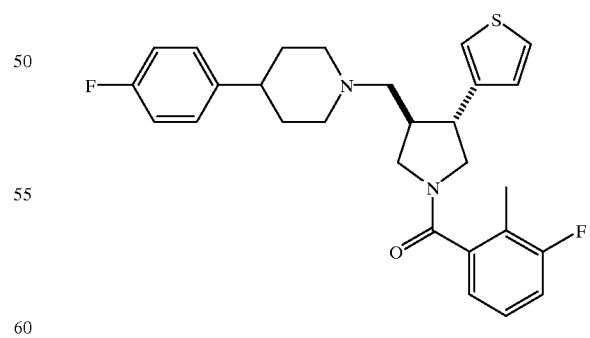

1-(2-Methyl-3-fluorobenzoyl)-3-(RS)-(4-(4-fluorophenyl)piperidinyl-methyl)-4-(RS)-(3-thienyl)pyrrolidine Mass Spectrum (CI) m/e=481 (M+1)

EXAMPLE 39

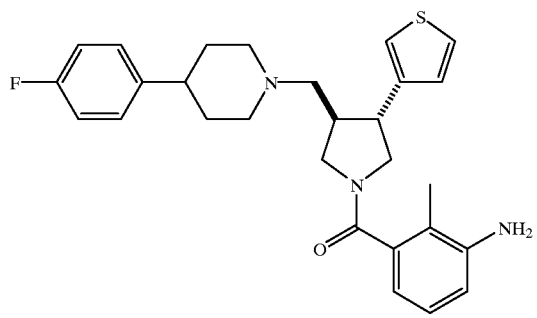

1-(2-Methyl-3-aminobenzoyl)-3-(RS)-(4-(4-fluorophenyl)piperidinyl-methyl)-4-(RS)-)-(3-thienyl)pyrrolidine Mass Spectrum (CI) m/e=478 (M+1)

EXAMPLE 40

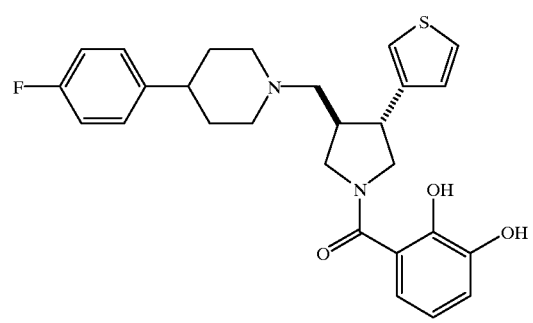

1-(2,3-Dihydroxybenzoyl)-3-(RS)-(4-(4-fluorophenyl)piperidinylmethyl)-4-(RS)-(3-thienyl) pyrrolidine Mass Spectrum (CI) m/e=481 (M+1)

EXAMPLE 41

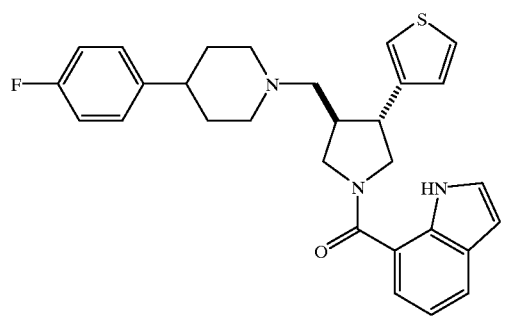

1-(7-Indolecarbonyl)-3-(RS)-(4-(4-fluorophenyl) piperidinylmethyl)-4-(RS)-(3-thienyl)pyrrolidine Mass Spectumn (CI) m/e=488 (M+1)

EXAMPLE 42

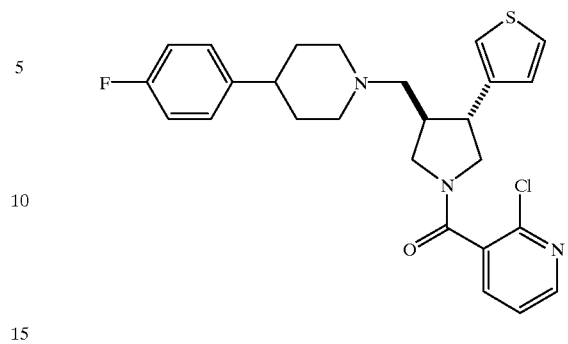

1-(2-Chloro-3-pyridylcarbonyl)-3-(RS)-(4-(4-fluorophenyl)piperidinyl-methyl)-4-(RS)-(3-thienyl) pyrrolidine Mass Spectrum (CI) m/e=484 (M+1 35Cl) and 486 (M+1 37Cl)

EXAMPLE 43

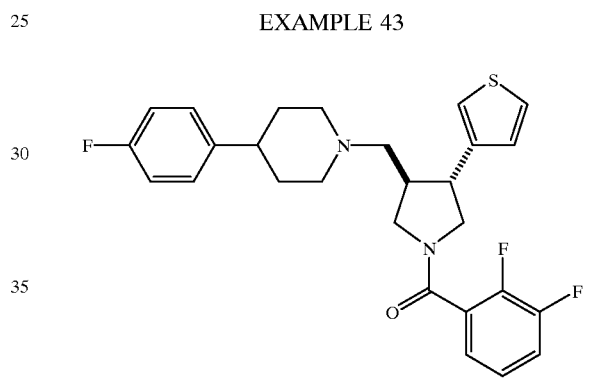

1-(2,3-Difluorobenzoyl)-3-(RS)-(4-(4-fluorophenyl) piperidinylmethyl)-4-(RS)-(3-thienyl)pyrrolidine Mass Spectrum (CI) m/e=485 (M+1)

EXAMPLE 44

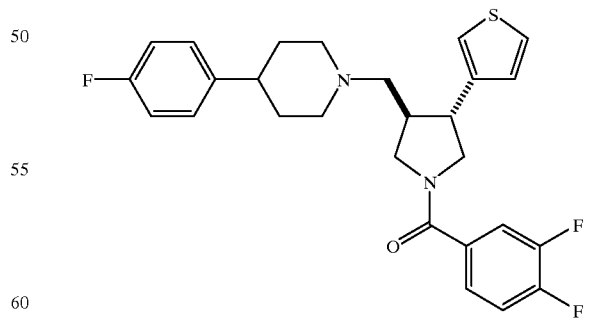

1-(3,4-Difluorobenzoyl)-3-(RS)-(4-(4-fluorlophenyl) piperidinylmethyl)-4-(RS)-(3-thienyl)pyrrolidine Mass Spectrum (CI) m/e=485 (M+1)

EXAMPLE 45

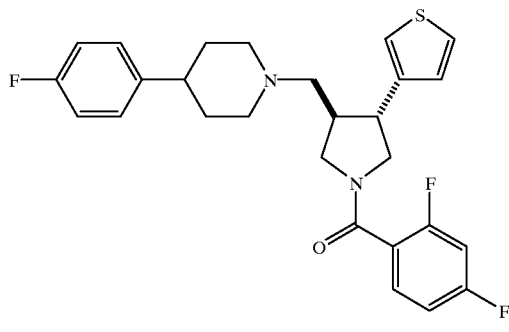

1-(2,4-Difluorobenzoyl)-3-(RS)-(4-(4-fluorophenyl) piperidinylmethyl)-4-(RS)-(3-thienyl)pyrrolidine Mass Spectrum (CI) m/e=485 (M+1)

EXAMPLE 46

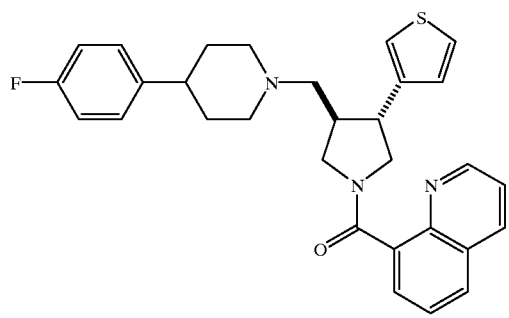

1-(8-Quinolinylcarbonyl)-3-(RS)-(4-(4-fluorophenyl)piperidinylmethyl)-4-(RS)-(3-thienyl) pyrrolidine Mass Spectrum (CI) m/e=500 (M+1)

EXAMPLE 47

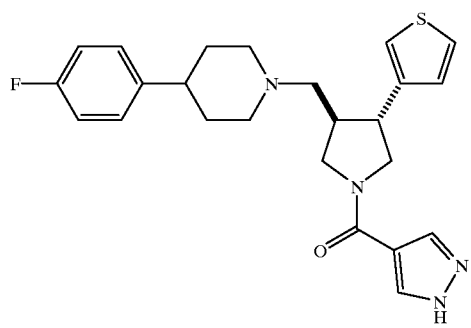

1-(4-Pyrazolylcarbonyl)-3-(RS)-(4-(4-fluorophenyl) piperidinylmethyl)-4-(RS)-(3-thienyl)pyrrolidine Mass Spectrum (CI) m/e=439 (M+1)

EXAMPLE 48

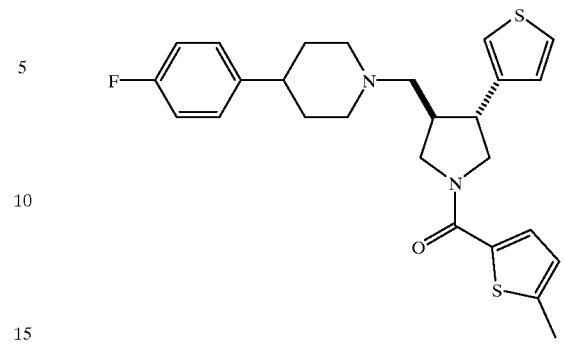

1-(5-Methyl-2-thienylcarbonyl)-3-(RS)-(4-(4-fluorophenyl)piperidinyl-methyl)-4-(RS)-(3-thienyl) pyrrolidine Mass Spectrum (CI) m/e=469 (M+1)

EXAMPLE 49

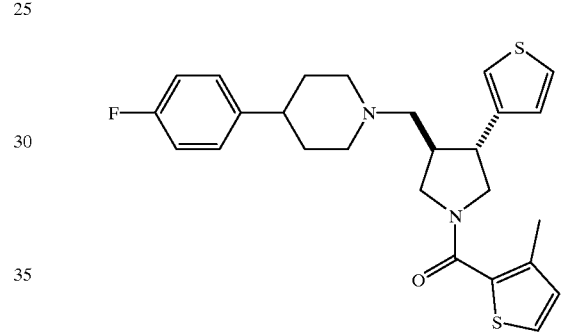

1-(3-Methyl-2-thienylcarbonyl)-3-(RS)-(4-(4-fluorophenyl)piperidinyl-methyl)-4-(RS)-(3-thienyl) pyrrolidine Mass Spectrum (CI) m/e=469 (M+1)

EXAMPLE 50

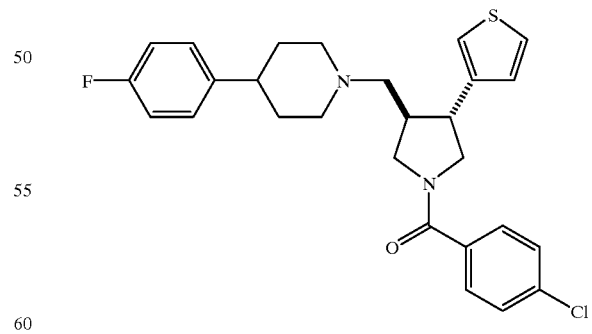

1-(4-Chlorobenzoyl)-3-(RS)-(4-(4-fluorophenyl) piperidinylmethyl)-4-(RS)-(3-thienyl)pyrrolidine Mass Spectrum (CI) m/e=483 (M+1 35Cl) and 485 (M+1 37Cl)

EXAMPLE 51

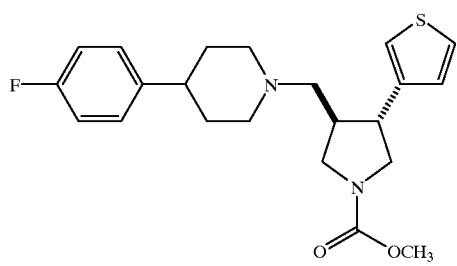

1-Methoxycarbonyl-3-(RS)-(4-(4-fluorophenyl)piperidinylmethyl)-4-(RS)-(3-thienyl)pyrrolidine Mass Spectrum (CI) m/e=403 (M+1)

EXAMPLE 52

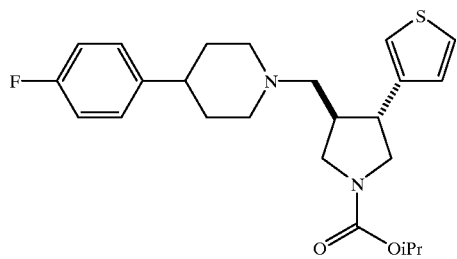

1-Isopropyloxycarbonyl-3-(RS )-(4-(4-fluorophenyl)piperidinylmethyl)-4-(RS)-(3-thienyl)pyrrolidine Mass Spectrum (CI) m/e=431 (M+1)

EXAMPLE 53

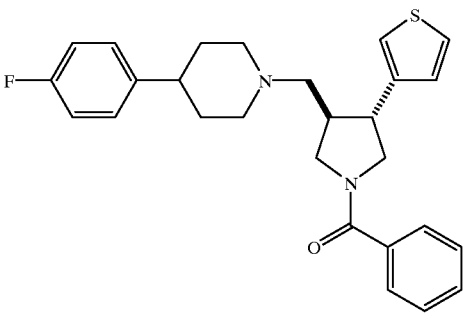

1-Benzoyl-3-(RS)-(4-(4-fluorophenyl)piperidinylmethyl)-4-(RS)-(3-thienyl)pyrrolidine Mass Spectrum (CI) m/e=449 (M+1)

EXAMPLE 54

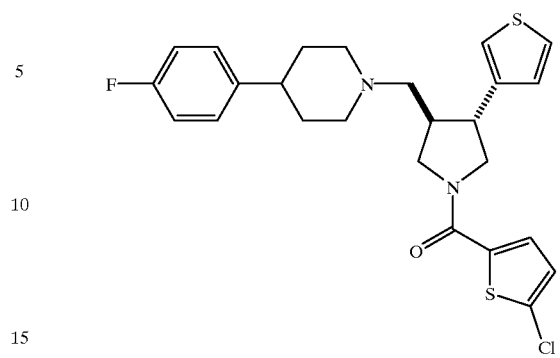

1-(5-Chloro-2-thienylcarbonyl)-3-(RS)-(4-(4-fluorophenyl)piperidinylmethyl)-4-(RS)-(3-thienyl)pyrrolidine Mass Spectrum (CI) m/e=489 (M+1 35Cl), 491 (35Cl 37Cl)

5-Chloro-2-thiophene carboxylic acid is commercially available from Lancaster or Avocado.

EXAMPLE 55

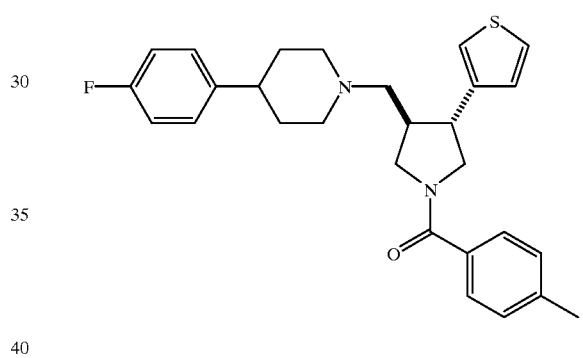

1-(4-Methylbenzoyl)-3-(RS)-(4-(4-fluorophenyl)piperidinylmethyl)-4-(RS)-(3-thienyl)pyrrolidine Mass Spectrum (CI) m/e=463 (M+1)

EXAMPLE 56

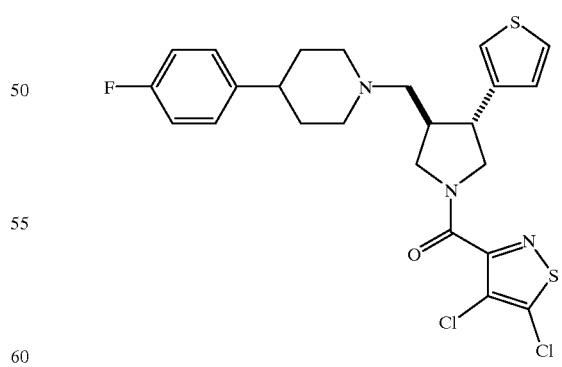

1-(4,5-Dichloro-3-thiazolylcarbonyl)-3-(RS)-(4-(4-fluorophenyl)piperidinylmethyl)-4-(RS)-(3-thienyl)pyrrolidine Mass Spectrum (CI) m/e=524 (M+1 35Cl 35Cl) and 526 (M+1 35Cl 37Cl)

EXAMPLE 57

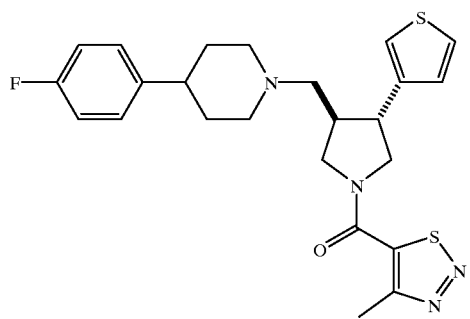

1-(4-Methyl-5-thiadizolylcarbonyl)-3-(RS)-(4-(4-fluorophenyl)piperidinylmethyl)-4-(RS)-(3-thienyl) pyrrolidine Mass Spectrum (CI) m/e=471 (M+1)

EXAMPLE 58

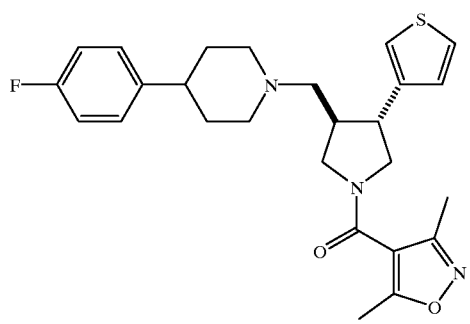

1-(4-Methyl-5-thiadizolylcarbonyl )-3-(RS)-(4-(4-fluorophenyl)piperidinylmethyl)-4-(RS)-(3-thienyl) pyrrolidine Mass Spectrum (CI) m/e=468 (M+1)

EXAMPLE 59

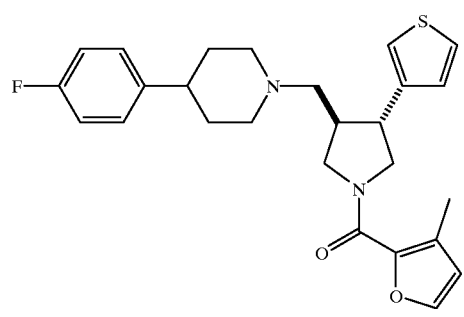

1-(3-Methyl-2-furanylcarbonyl)-3-(RS)-(4-(4-fluorophenyl)piperidinylmethyl)-4-(RS )-(3-thienyl) pyrrolidine Mass Spectrum (CI) m/e=453 (M+1)

EXAMPLE 60

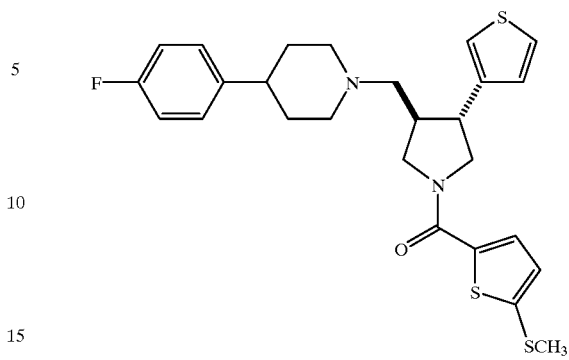

1-(5-Methylthio-2-thienylcarbonyl)-3-(RS)-(4-(4-fluorophenyl)piperidinylmethyl)-4-(RS)-(3-thienyl) pyrrolidine Mass Spectrum (CI) m/e=501 (M+1)

EXAMPLE 61

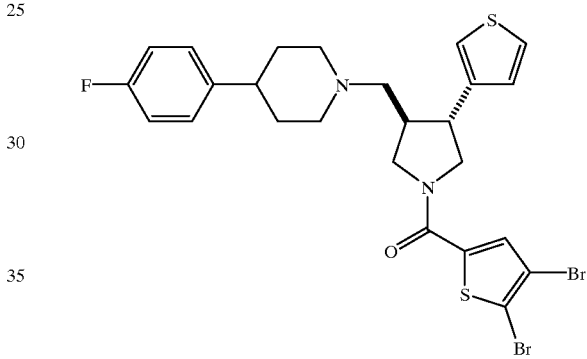

1-2,3-Dibromo-5-thienylcarbonyl)-3(RS)-(4-(4-fluorophenyl)piperidinylmethyl)-4-(RS)-(3-thienyl) pyrrolidine Mass Spectrum (CI) m/e=611 (M+1,79Br 79Br), 613 (M+1, 79Br 81Br).

EXAMPLE 62

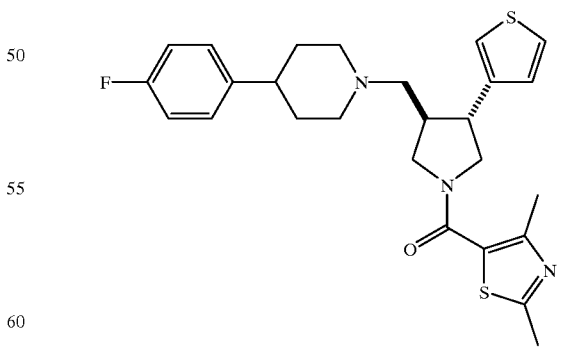

1-(2,4-Dimethyl-5-thiazolylcarbonyl)-3-(RS)-(4-(4-fluorophenyl)piperidinylmethyl)-4-(RS)-(3-thienyl) pyrrolidine Mass Spectrum (CI) m/e=484 (M+1)

EXAMPLE 63

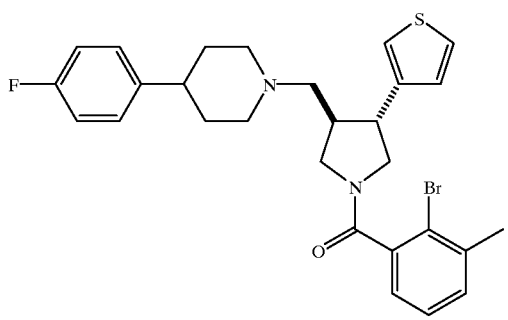

1-(2-Bromo-3-methylbenzoyl)-3-(RS)-(4-(4-fluorophenyl)piperidinylmethyl)-4-(RS)-(3-thienyl) pyrrolidine Mass Spectrum (CI) m/e=541 (M+1, 79Br) and 543 (M+1, 81Br).

EXAMPLE 64

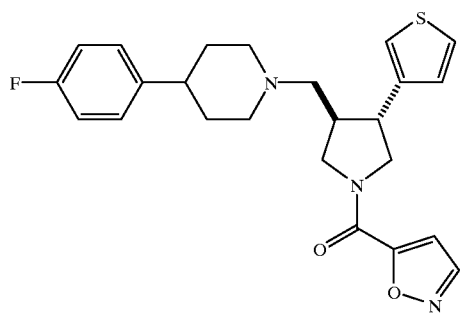

1-(5-Isoxazolylcarbonyl)-3-(RS)-(4-(4-fluorophenyl) piperidinylmethyl)-4-(RS)-(3-thienyl)pyrrolidine Mass Spectrum (CI) m/e=440 (M+1)

EXAMPLE 65

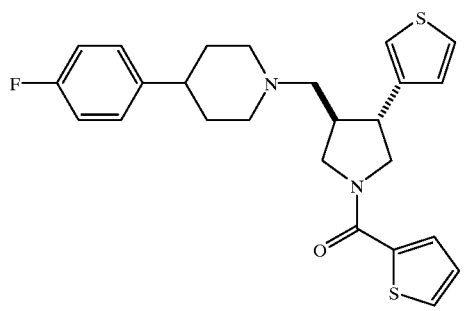

1-(2-Thienylcarbonyl)-3-(RS)-(4-(4-fluorophenyl) piperidinylmethyl)-4-(RS)-(3-thienyl)pyrrolidine Mass Spectrum (CI) m/e=455 (M+1)

EXAMPLE 66

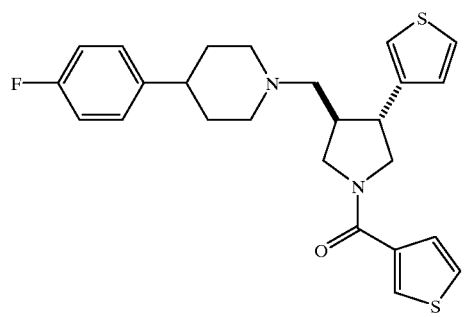

1-(3-Thienylcarbonyl)-3-(RS)-(4-(4-fluorophenyl) piperidinylmethyl)-4-(RS)-(3-thienyl)pyrrolidine Mass Spectrum (CI) m/e=455 (M+1)

EXAMPLE 67

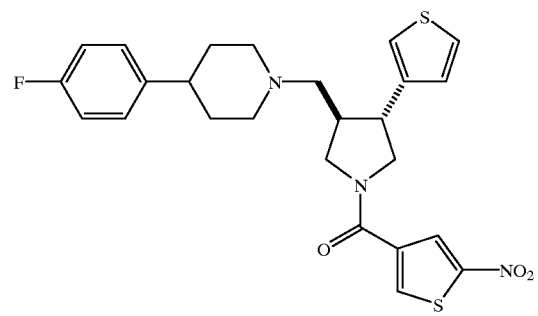

1-(2-Nitro-4-thienylcarbonyl)-3-(RS)-(4-(4-fluorophenyl)piperidinylmethyl)-4-(RS)-(3-thienyl) pyrrolidine Mass Spectrum (CI) m/e=500 (M+1)

EXAMPLE 68

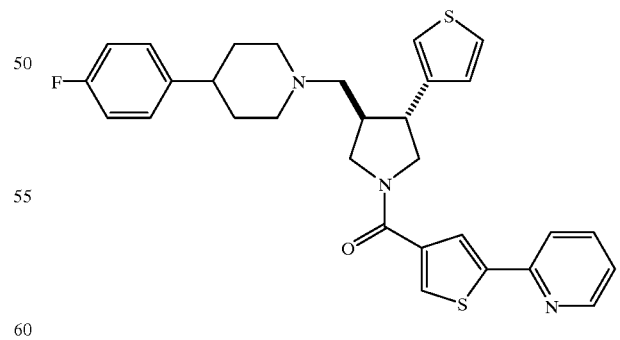

1-(2-(2-pyridyl)-4-thienylcarbonyl)-3-(RS)-(4-(4-fluorophenyl)piperidinylmethyl)-4-(RS)-(3-thienyl) pyrrolidine Mass Spectrum (CI) m/e=532 (M+1)

EXAMPLE 69

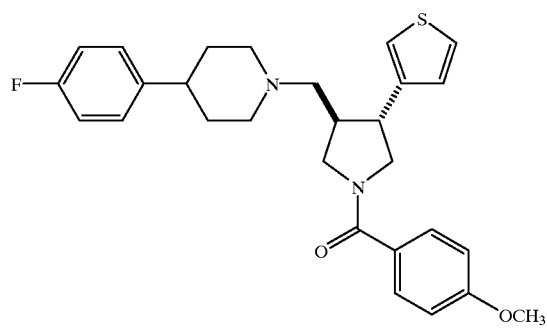

1-(4-Methoxybenzoyl)-3-(RS)-(4-(4-fluorophenyl)
piperidinylmethyl)-4-(RS)-(3-thienyl)pyrrolidine Mass Spectrum (CI) m/e=479 (M+1)

EXAMPLE 70

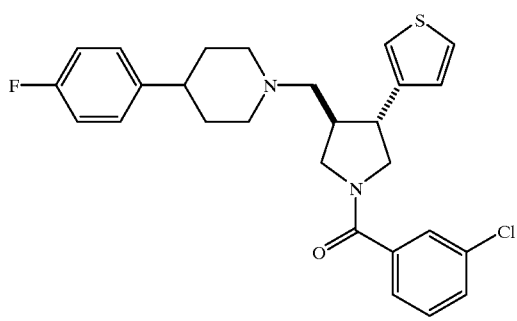

1-(3-Chlorobenzoyl)-3-(RS)-(4-(4-fluorophenyl)
piperidinylmethyl)-4-(RS)-(3-thienyl)pyrrolidine Mass Spectrum (CI) m/e=483 (M+1 35Cl), 485 (M+1 37Cl)

EXAMPLE 71

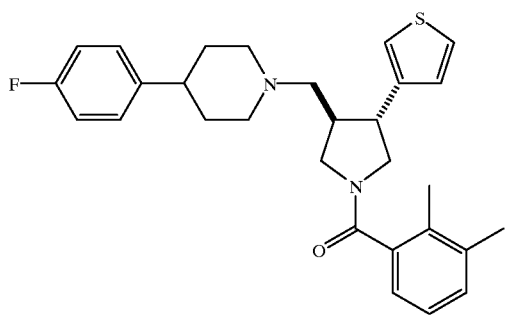

1-(2,3-Dimethylbenzoyl)-3-(RS)-(4-(4-fluorophenyl)
piperidinylmethyl)-4-(RS)-(3-thienyl)pyrrolidine Mass Spectrum (CI) m/e=477 (M+1)

EXAMPLE 72

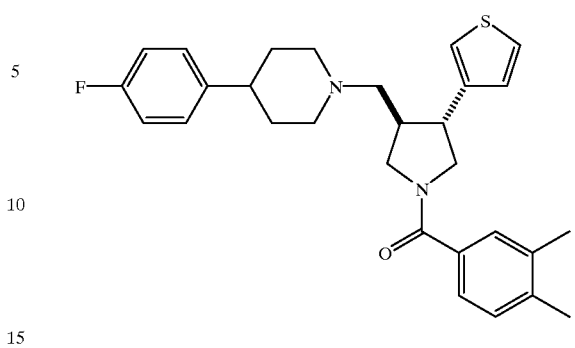

1-(3,4-Dimethylbenzoyl)-3-(RS)-(4-(4-fluorophenyl)
piperidinylmethyl)-4-(RS)-(3-thienyl)pyrrolidine Mass Spectrum (CI) m/e=477 (M+1)

EXAMPLE 73

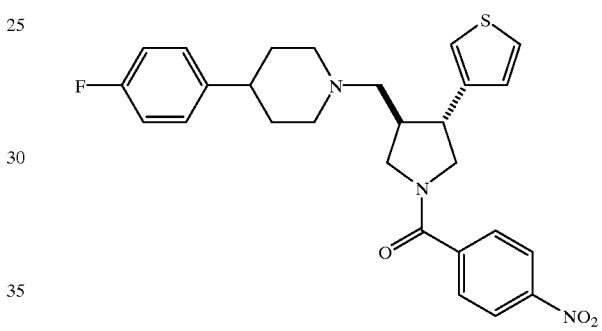

1-(4-Nitrobenzoyl)-3-(RS)-(4-(4-fluorophenyl)
piperidinylmethyl)-4-(RS)-(3-thienyl)pyrrolidine Mass Spectrum (CI) m/e=494 (M+1)

EXAMPLE 74

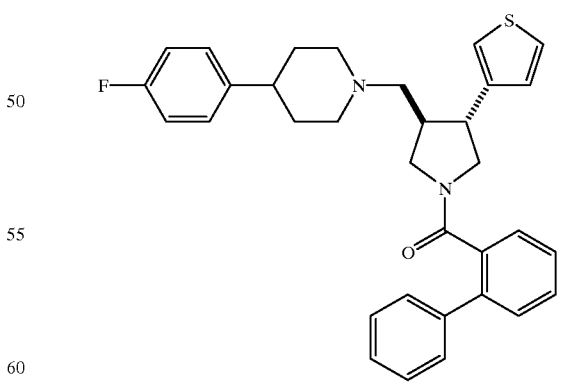

1-(2-Phenylbenzoyl)-3-(RS)-(4-(4-fluorophenyl)
piperidinylmethyl)-4-(RS)-(3-thienyl)pyrrolidine Mass Spectrum (CI) m/e=525 (M+1)

EXAMPLE 75

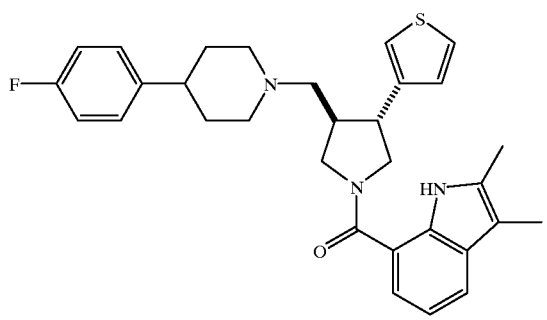

1-(2,3-Dimethyl-7-indolylcarbonyl)-3-(RS)-(4-(4-fluorophenyl)piperidinylmethyl)-4-(RS)-(3-thienyl)pyrrolidine Mass Spectrum (CI) m/e=516 (M+1)

EXAMPLE 76

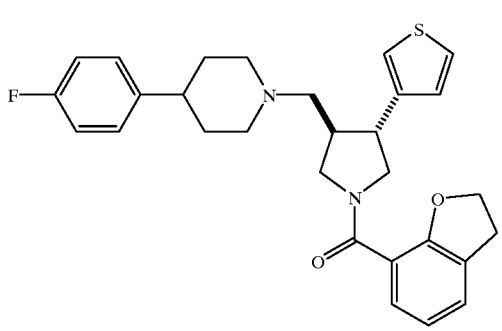

1-(7-Benzo-2,3-dihydrofuranylcarbonyl)-3-(RS)-(4-(4-fluorophenyl)piperidinylmethyl)-4-(RS)-(3-thienyl)pyrrolidine Mass Spectrum (CI) m/e=491 (M+1)

EXAMPLE 77

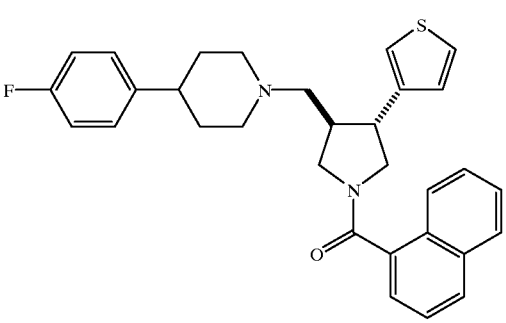

1-(1-Naphthoyl)-3-(RS)-(4-(4-fluorophenyl)piperidinylmethyl)-4-(RS)-(3-thienyl)pyrrolidine Mass Spectrum (CI) m/e=499 (M+1)

EXAMPLE 78

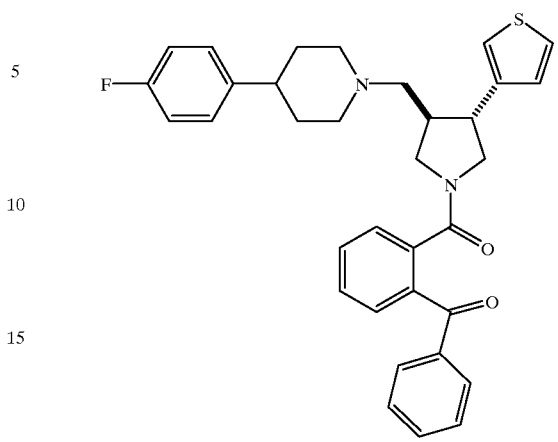

1-(2-benzoylbenzoyl)-3-(RS)-(4-(4-fluorophenyl)piperidinylmethyl)-4-(RS)-(3-thienyl)pyrrolidine Mass Spectrum (CI) m/e=593 (M+1)

The following Examples 79 to 87 were prepared from 3-(SR)-(4-(4-fluorophenyl)piperidinylmethyl)-4-(RS)-(3-thienyl)pyrrolidine and the corresponding acid chloride or acid as described in Examples 11 and 12 respectively. The preparation of the acids will be described.

EXAMPLE 79

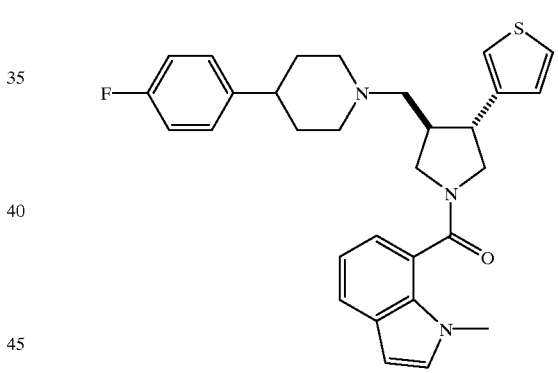

1-(1-Methyl-7-indolylcarbonyl)-3-(RS)-(4-(4-fluorophenyl)piperidinylmethyl)-4-(RS)-(3-thienyl)pyrrolidine Mass Spectrum (CI) m/e=502 (M+1)

Preparation of 1-methylindolyl-7-carboxylic acid and 1,3-Dimethylindole-7-carboxylic acid Step A Benzyl-indolyl-7-carboxylate To a solution of 0.25 g (1.55 mmol) of indole-7-carboxylic acid (Aldrich Rare and Fine Chemicals), 0.33 mL (3.1 mmol) of benzyl alcohol and 0.38 g (3.1 mmol) of DMAP in 5 mL of $CH_2Cl_2$ was added 0.59 g (3.1 mmol) of 1-[3-(dimethylamino)propyl]-3-ethylcarbodiimide hydrochloride and the reaction mixture was stirred for 12 h. The reaction mixture was concentrated and the residue was purified by chomatography (silica, hexanes: ether, 20:1) to give 0.37 g of the title compound.

Step B

Benzyl-1-methylindole-7-carboxylate and Benzyl-1,3-dimethylindole-7-carboxylate

To a mixture of 0.036 g (0.89 mmol) of NaH in 5 mL of THF at 0° C. was added 0.19 g (0.74 mmol) of benzyl-1-methyl-7-indolyl carboxylate. After stirring for 20 min, 0.21 g (1.49 mmol) of methyl iodide was added and the reaction mixture was warmed to rt and stirred for 3 h. The reaction mixture was diluted with ether, washed with sat'd NaHCO$_3$ solution, dried over Na$_2$SO$_4$, filtered and the filtrate was concentrated. The residue was purified by chomatography (silica, hexanes: ether, 50: 1) to give 0.065 g of benzyl-1-methylindole-7-carboxylate and 0.02 g of benzyl-1,3-dimethylindole-7-carboxylate.

Step C

1-Methylindole-7-carboxylic acid

A mixture of 0.65 g (0.25 mmol) of benzyl-1-methylindole-7-carboxylate (Step B) and 0.035 g of 10% Pd/C in 4 mL of a solution of 4.4% HCO$_2$H in MeOH was stirred for 2 h at rt. The reaction mixture was filtered though a thin pad of celite and concentrated to give the title compound. $^1$H NMR (CDCl$_3$) δ4.00 (s, 3H), 6.61 (d, 1H, J=3 Hz), 7.11 (d, 1H, J=3 Hz), 7.18 (t, 1H, J=8 Hz), 7.87 (d, 1H, J=8 Hz), 7.91 (d, 1H, J=8 Hz);

Step D 1,3-Dimethylindole-7-carboxylic acid

The title compound was prepared from Benzyl-1,3-dimethyl indole-7-carboxylate (Step B) as described in Step C. $^1$H NMR (CDCl$_3$) δ2.32 (s, 3H), 3.89 (s, 3H), 6.82 (s, 1H), 7.16 (t, 1H, J=8 Hz), 7.76 (d, 1H, J=8 Hz), 7.84 (d, 1H, J=8 Hz);

EXAMPLE 80

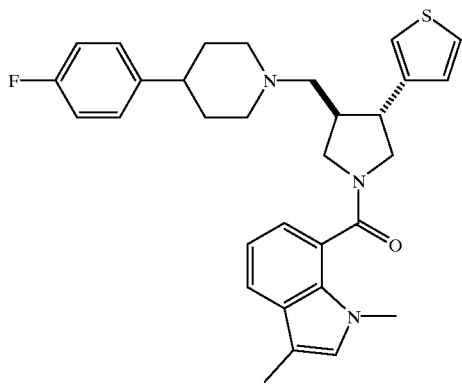

1-(1,2-Dimethyl-7-indolylcarbonyl)-3-(RS)-(4-(4-fluorophenyl)piperidinylmethyl)-4-(RS)-(3-thienyl) pyrrolidine Mass Spectrum (CI) m/e=516 (M+1)

The preparation of 1,3-Dimethylindole-7-carboxylic acid is described in Example 79, Step D.

EXAMPLE 81

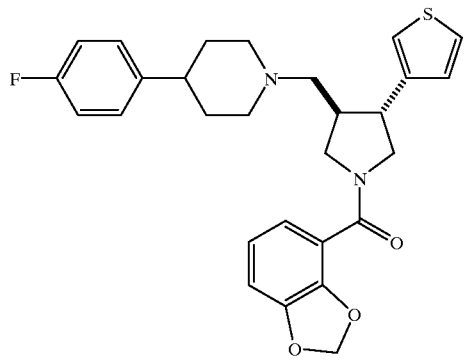

1-(2,3-Methylenedioxybenzoyl)-3-(RS)-(4-(4-fluorophenyl)piperidinylmethyl)-4-(RS)-(3-thienyl) pyrrolidine Mass Spectrum (CI) m/e=493 (M+1)

Preparation of 2,3-methylenedioxybenzoic acid

To a solution of 0.85 g (5.66 mmol) of 2,3-methylenedioxybenzaldehyde (Aldrich) in EtOH at 0° C. was added a solution of 2.12 g (12.45 mmol) of AgNO$_3$ in 7.5 mL of H$_2$O. To this was then added a solution of 1.74 g (31.4 mmol) of KOH in 12 mL of H$_2$O. After 2 h, the reaction mixture was filtered and the filter was washed with EtOH. The filtrate was concentrated and the pH was adjusted to pH=2 to 3 with 6N HCl. The title compound precipitated out and was isolated by filtration to give the title compound. $^1$H NMR (CDCl$_3$) δ6.16 (s, 2H), 6.92 (t, 1H, J=8 Hz), 7.04 (d, 1H, J=8 Hz), 7.48 (d, 1H, J=8 Hz);

EXAMPLE 82

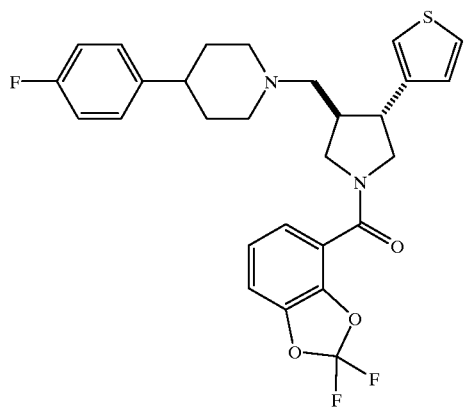

1-(2,3-Difluoroethylenedioxybenzoyl)-3-(RS)-(4-(4-fluorophenyl)piperidinylmethyl)-4-(RS)-(3-thienyl) pyrrolidine Mass Spectrum (CI) m/e=529 (M+1)

2,3-Difluoromethylenedioxybenzoic acid was prepared from 2,3-Difluoromethylenedioxybenzaldehyde according to procedures described in Example 81.

EXAMPLE 83

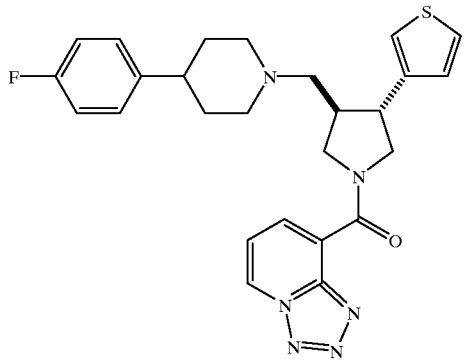

1-(([1,2,3,4]Tetrazolo[1,5a]pyridinoyl)-3-(RS)-(4-(4-fluorophenyl)piperidinylmethyl)-4-(RS)-(3-thienyl)pyrrolidine Step 1

1-(2-Chloro-3-pyridylcarbonyl)-3-(RS)-(4-(4-fluorophenyl)piperidinylmethyl)-4-(RS)-(3-thienyl)pyrrolidine.

A mixture of 0.105 g (0.3 mmol) of 3-(RS)-(4-(4-fluorophenyl)piperidinylmethyl)-4-(RS)-(3-thienyl)pyrrolidine, 0.082 mL (0.6 mmol) of triethylamine and 0.054 g (0.3 mmol) of 2-chloronicotinoyl chloride (Aldrich) in 6 mL of $CH_2Cl_2$ was stirred at rt for 4 h. The reaction mixture was concentrated and the residue was purified by chomatography (silica, hexanes: acetone=3:1) to afford 0.12 g of the title compound.

Step 2

1-(([1,2,3,4]Tetrazolo[1,5a]pyridinoyl)-3-(RS)-(4-(4-fluorophenyl)piperidinylmethyl)-4-(RS)-(3-thienyl)pyrrolidine A mixture of 0.12 g (0.25 mmol) of 1-(2-chloro-3-pyridyl carbonyl)-3-(RS)-(4-(4-fluorophenyl)piperidinylmethyl)-4-(RS)-(3-thienyl)pyrrolidine 0.025 g (0.38 mmol) of sodium azide and 0.021 g (0.38 mmol) of ammonium chloride in 4 mL of DMF and was heated at 100° C. for 36 h. The reaction mixture was diluted with $CH_2Cl_2$ and was washed with 20 mL of sat'd sodium bicarbonate. The organic fraction was dried over $Na_2SO_4$, filtered and the filtrate was concentrated. The residue was purified by chomatography [silica, $CH_2Cl_2$: EtOAc: (2N $NH_3$ in MeOH) 100:100:4] to afford the title compound.

Mass Spectrum (CI) m/e=491 (M+1)

EXAMPLE 84

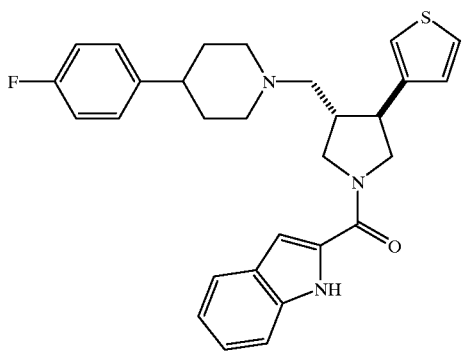

1-(2-Indolecarbonyl)-3-(RS)-(4-(4-fluorophenyl)piperidinylmethyl)-4-(RS )-(3-thienyl)pyrrolidine Mass Spectrum (CI) m/e=488 (M+1)

EXAMPLE 85

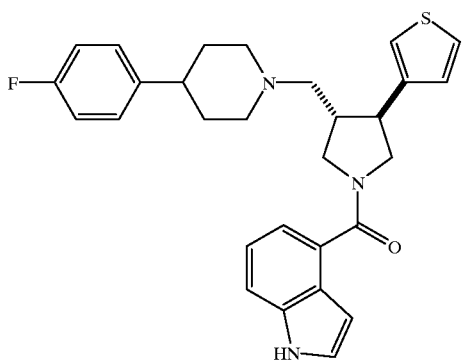

1-(4-Indolecarbonyl)-3-(RS)-(4-(4-fluorophenyl)piperidinylmethyl)-4-(RS)-(3-thienyl)pyrrolidine Mass Spectrum (CI) m/e=488 (M+1)

EXAMPLE 86

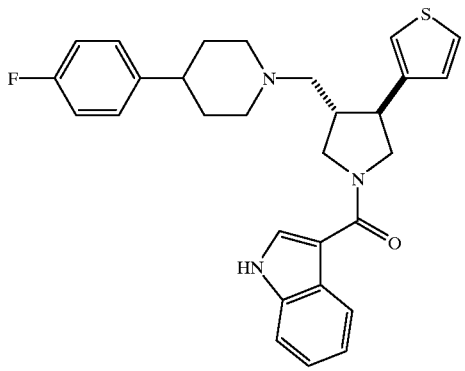

1-(3-Indolecarbonyl)-3-(RS)-(4-(4-fluorophenyl)piperidinylmethyl)-4-(RS)-(3-thienyl)pyrrolidine Mass Spectrum (CI) m/e=488 (M+1)

EXAMPLE 87

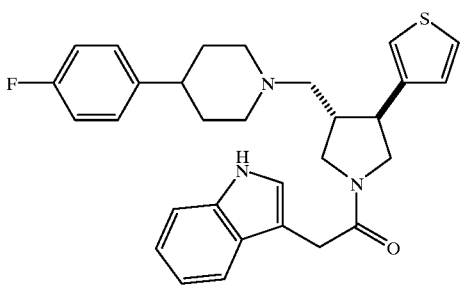

1-(3-Indolacteyl)-3-(RS)-(4-(4- fluorophenyl) piperidinylmethyl)-4-(RS)-(3-thienyl)pyrrolidine Mass Spectrum (CI) m/e=502 (M+1)

EXAMPLE 88

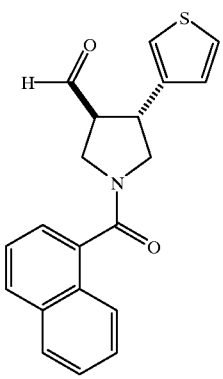

1-(1-Naphthoyl)-3-(SR)-formyl-4-(RS)-(3-thienyl) pyrrolidine

Step A

1-(2,2,2,-Trichloroethoxycarbonyl)-3-(RS)-carbomethoxy-4-(RS)-(3-thienyl)pyrrolidine A solution of 1.02 g (3.38 mmol) of 1-benzyl-3-(SR)-carbomethoxy-4-(RS)-(3-thienyl)pyrrolidine (Example 1) and 0.51 mL (3.72 mmol) of 2,2,2-trichloroethyl chloroformate in 15 mL of $CH_3CN$ was stirred at rt for 1.5 h. The reaction mixture was concentrated and the residue was purified by chomatography (silica, hexanes, ethyl acetate, 6:1) to give 1.1 g of the title compound. $^1H$ NMR ($CDCl_3$) δ3.21 (m, 1H), 3.58 (m, 1H), 3.716, 3.723 (s, 3H), 4.81 (m, 2H), 7.00 (m, 1H), 7.12 (s, 1H), 7.33 (m, 1H);

Step B

3-(RS)-Carbomethoxy-4-(SR)-(3-thienyl)pyrrolidine

To a solution of 1.1 g (2.9 mmol) of 1-(2,2,2,-trichloroethoxycarbonyl)-3-(SR)-carbomethoxy-4-(RS)-(3-thienyl)pyrrolidine in 30 mL of acetic acid at 40° C. was slowly added 0.5 g (7.6 mmol) of Zn powder and the reaction mixture was stirred a further 4 h at 40° C. The reaction mixture was filtered to remove the solid and the filter was washed with MeOH. The organic fraction was concentrated and the residue was purified by chomatography. (silica, $CH_2Cl_2$: MeOH: $NH_3$ (2M in MeOH),100:4:2) to give 0.61 g of the title compound. $^1H$ NMR ($CDCl_3$) δ2.92 (m, 1H). 3.02 (m, 1H), 3.29 (m, 2H), 3.48–3.62 (m, 2H), 3.72 (s, 3H), 6.99 (d, 1H, J=5 HZ), 7.05 (s, 1H), 7.31 (m, 1H);

Step C

1-(1-Naphthoyl)-3-(SR)-carbomethoxy-4-(RS)-thienyl-3-ylpyrrolidine

A solution of 0.3 g (1.42 mmol) of 3-(SR)-carbomethoxy-4-(RS)-(3-thienyl)pyrrolidine, 15.6 mL (1.56 mmol) of 1-naphthoyl chloride (0.1M solution of in THF), and 0.3 mL (2.13 mmol) of $Et_3N$ in 10 mL of $CH_2Cl_2$ was stirred at rt for 12 h. The reaction mixture was poured into 100 mL of $CH_2Cl_2$ and washed with sat'd $NaHCO_3$ solution. The combined organic fractions were dried over $MgSO_4$, filtered and the filtrate was concentrated. The residue was purified by chomatography (silica, hexanes: acetone, 8:1) to give 0.51 g of the title compound. $^1H$ NMR ($CDCl_3$) δ3.61, 3.76 (s, 3H), 7.48–7.92 (m, 8H);

Step D

1-(1-Naphthoyl)-3-(SR)-hydroxymethyl-4-(RS)-thiophen-3-ylpyrrolidine

A solution of 0.48 g (1.31 mmol) of 1-(1-naphthoyl)-3-(SR)-carbomethoxy-4-(RS)-(3-thienyl)pyrrolidine and 2.6 mL (5.24 mmol) of $LiBH_4$ (2M in THF) in 10 mL of THF was stirred at rt for 12 h. To the reaction mixture was added 50 mL of $CH_2Cl_2$ and 5 mL of 0.5N HCl. The fractions were partitioned and the aqueous fraction was extracted twice with $CH_2Cl_2$. The combined organic fractions were dried over $Na_2SO_4$, filtered and the filtrate was concentrated. The residue was purified by chomatography to give 0.41 g of the title compound. $^1H$ NMR ($CDCl_3$) δ3.45 (m, 2H), 7.47–7.90 (m, 8H);

Step E

1-(1-Naphthoyl)-3-(SR)-formyl-4-(RS)-thiophen-3-ylpyrrolidine

The title compound (0.44 g) was prepared from 0.45 g of 1-(1-naphthoyl)-3-(SR)-hydroxymethyl-4-(RS)-(3-thienyl) pyrrolidine according to procedures described in Example 1, Step D. $^1H$ NMR ($CDCl_3$) δ3.17–4.28 (m, 6H), 7.47–7.90 (m, 8H), 9.61, 9.78 (s, 1H);

EXAMPLE 89

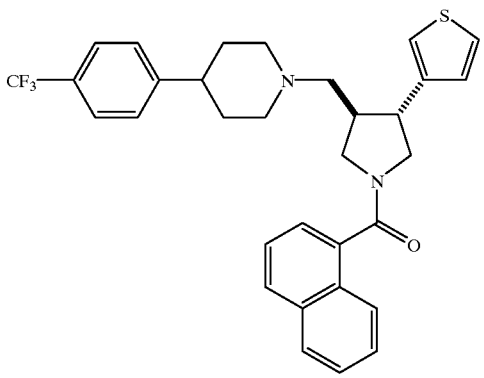

1-(1-Naphthoyl)-3-(RS)-(4-(4-trifluoromethylphenyl)piperidinylmethyl)-4-(RS)-(3-thienyl)pyrrolidine Step A

4-Trifluoromethylphenylboronic acid

To a solution of 1 mL (7.1 mmol) of 4-trifluoromethylphenyl bromide (JRD Fluoro Chemical LTD) in 20 mL of THF at −78° C. in a nitrogen atmosphere was added 7.1 mL (8.5 mmol) of nBuLi (1.6 M in THF). After stirring for 30 min, 2.5 mL (10.65 mmol) of triisopropyl borate (Aldrich) was slowly added and the reaction mixture was slowly warmed to rt. After 1 h at rt, the reaction mixture was concentrated and redissolved in 10 mL of a mixture of acetic acid and $H_2O$ (2:1). After stirring for 3 h, the reaction mixture was concentrated and redissolved in 100 mL of ethyl acetate. The solution was washed with sat'd $NaHCO_3$ solution, and the organic fraction was dried over $Na_2SO_4$, filtered and the filtrate was concentrated to give the title compound.

Step B 1-t-Butoxycarbonyl-4-trifluoromethylsulfonyloxy-1, 2,3,6-tetrahydropyridine To a solution of 14 mL of LDA (2M in THF) at −78° C. in a nitrogen atmosphere was slowly added 5 g (25 mmol) of 4-t-butoxycarbonyl piperidone. The reaction mixture was warmed to 0° C. and stirred for 3 h. The reaction mixture was then cooled to −78° C. and to it was slowly added a solution of 9.82 g (27.5 mmol) of $(CF_3SO_2)_2NPh$ (Aldrich) in 50 mL of THF. The reaction mixture was slowly warmed to 0° C. and stirred for 12 h. The reaction mixture was concentrated, redissolved in $CH_2Cl_2$ and filtered though a plug of alumina and the filtrate was concentrated to give 8.1 g of the title compound.

Step C 1-t-Butoxycarbonyl-4-(4-trifluoromethylphenyl)-1,2, 3,6-tetrahydropyridine To a solution of 0.66 g (2 mmol) of 1-t-butoxycarbonyl-4-trifluoromethylsulfonyloxy-1,2,3,6-tetrahydropyridine and 0.57 g (6 mmol) of 4-trifluoromethylphenylboronic acid in 6 mL of DME (dimethoxyethane) was added 2.5 mL (5 mmol) of a 2M solution of $Na_2CO_3$, 0.24 g (6 mmol) of LiCl and 0.115 g (0.1 mmol) of $Pd(PPh_3)_4$ and the reaction mixture was heated at reflux for 4 h. The reaction mixture was concentrated and dissolved in 10 mL of $CH_2Cl_2$. The solution was washed with sat'd $NaHCO_3$ solution, dried over $Na_2SO_4$, filtered and the filtrate was concentrated. The residue was purified by chomatography (silica, hexanes: ethyl acetate, 10:1) to give 0.4 g of the title compound. $^1H$ NMR ($CDCl_3$) δ1.51 (s, 9H), 2.54 (m, 2H), 3.67 (t, 2H, J=6 Hz), 4.12 (br, 2H), 6.14 (br, 1H), 7.47 (d, 2H, J=8 Hz), 7.59 (d, 2H, J=8 Hz);

Step D 4-(4-Trifluoromethylphenyl)-1,2,3,6-tetrahydropyridine

A solution of 0.4 g (0.112 mmol) of 1-t-butoxycarbonyl-4-(4-trifluoromethyl phenyl)-1,2,3,6-tetrahydropyridine in 1 mL of TFA and 3 mL of $CH_2Cl_2$ was stirred at rt for 1 h. The reaction mixture was then concentrated. A mixture of the residue and 0.1 g of 10% Pd/C in 20 mL of MeOH was hydrogenated at 45 psi for 4 h. The reaction mixture was flitered though a plug of celite and concentrated to give 0.54 g of the title compound. $^1H$ NMR ($CDCl_3$) δ1.94 (m,2H), 2.06 (m, 2H), 3.00 (m, 1H), 3.11 (m, 2H), 3.49 (m, 2H), 7.45 (d, 2H, J=8 Hz), 7.62 (d, 2H, J=8 Hz)

Step E 4-(4-Trifloromethylphenyl)piperidine

A mixture of 0.54 g (1.22 mmol) of 4-(4-trifluoromethylphenyl)-1,2,3,6-tetrahydropyridine and 0.1 g of 10% Pd/C in 20 mL of MeOH was stirred under a hydrogen atmosphere at 45 psi for 4 h. The reaction mixture was filtered through a thin pad of celite eluting with CH2Cl2. The solution was concentrated to give 0.26 g of the title compound.

Step F 1-(1-Naphthoyl)-3-(RS)-(4-(4-trifluoromethylphenyl)piperidinylmethyl)-4-(RS)-(3-thienyl)pyrrolidine The title compound was prepared from 1-(1-naphthoyl)-3-(SR)-formyl-4-(RS)-(3-thienyl)pyrrolidine (Example 82 and 4-(4-trifluoromethylphenyl)piperidine according to procedures described in Example 1, Step F. $^1H$ NMR ($CDCl_3$) δ7.34 (d, 2H, J=8 Hz), 7.58 (d, 2H, J=8 Hz); Mass Spectrum (CI) m/e=549 (M+1).

The following Examples 90 to 113 were prepared from 1-(1-naphthoyl)-3-(SR)-formyl-4-(RS)-(3-thienyl) pyrrolidine (Example 88) as described in Example 89. The arylpiperidine sidechains are commercially available or prepared as described in Example 89.

EXAMPLE 90

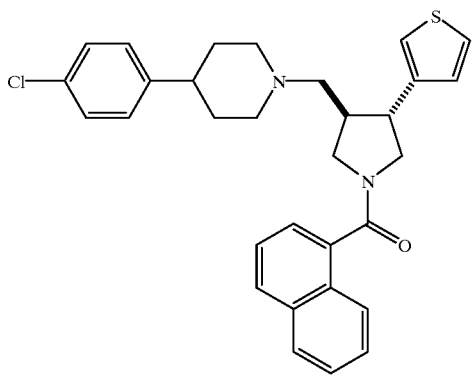

1-(1-Naphthoyl)-3-(RS)-(4-(4-chlorophenyl) piperidinylmethyl)-4-(RS)-(3-thienyl)pyrrolidine Mass Spectrum (CI) m/e=515 (M+1 35Cl) and 517 (M+1 37Cl)

EXAMPLE 91

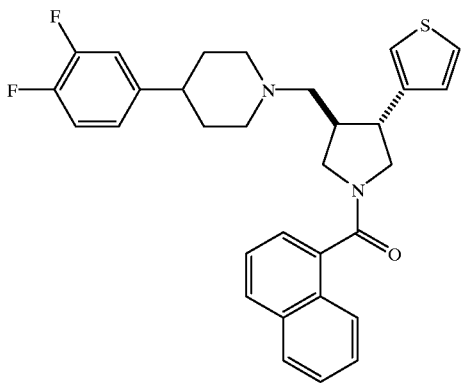

1-(1-Naphthoyl)-3-(RS)-(4-(3,4-difluorophenyl) piperidinylmethyl)-4-(RS)-(3-thienyl)pyrrolidine Mass Spectrum (CI) m/e=517 (M+1)

EXAMPLE 92

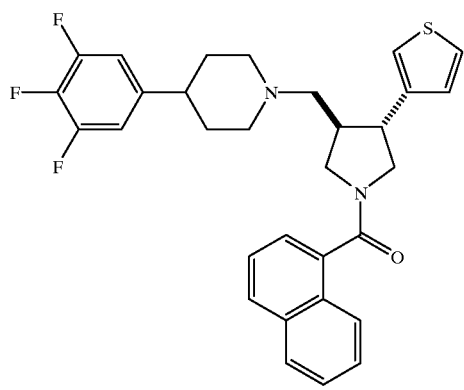

1-(1-Naphthoyl)-3-(RS)-(4-(3,4,5-trifluorophenyl)
piperidinylmethyl)-4-(RS)-(3-thienyl)pyrrolidine Mass Spectrum (CI) m/e=535 (M+1)

EXAMPLE 93

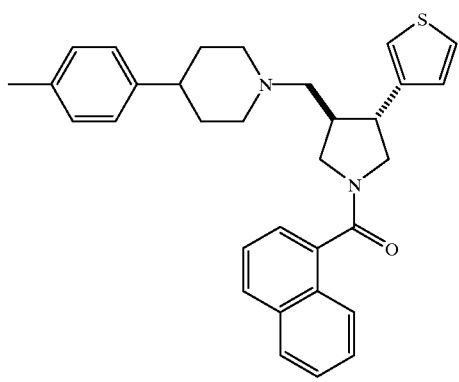

1-(1-Naphthoyl)-3-(RS)-(4-(4-methylphenyl)
piperidinylmethyl)-4-(RS)-(3-thienyl)pyrrolidine Mass Spectrum (CI) m/e=495 (M+1)

EXAMPLE 94

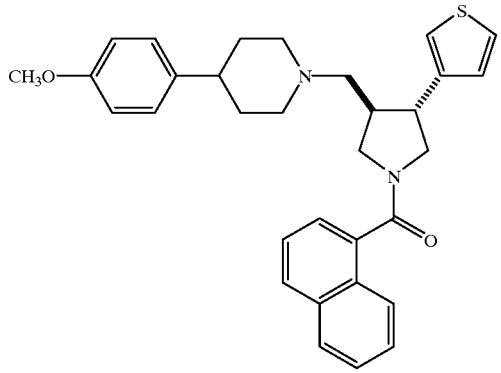

1-(1-Naphthoyl)-3-(RS)-(4-(4-methoxyphenyl)
piperidinylmethyl)-4-(RS)-(3-thienyl)pyrrolidine Mass Spectrum (CI) m/e=511 (M+1)

EXAMPLE 95

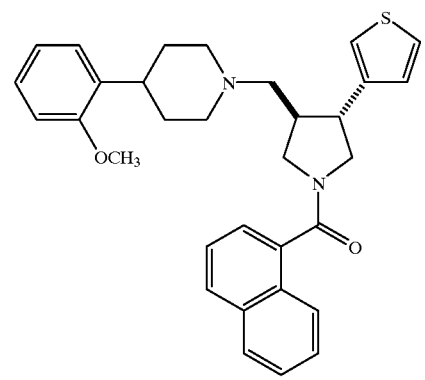

1-(1-Naphthoyl)-3-(RS)-(4-(2-methoxyphenyl)
piperidinylmethyl)-4-(RS)-(3-thienyl)pyrrolidine Mass Spectrum (CI) m/e=511 (M+1)

EXAMPLE 96

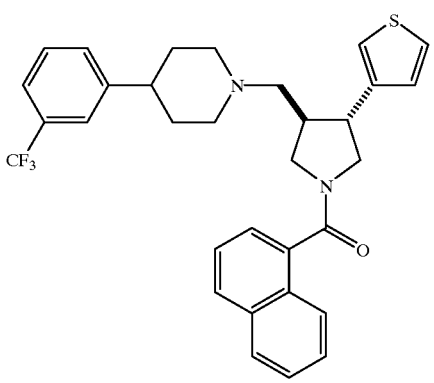

1-(1-Naphthoyl)-3-(RS)-(4-(3-
trifluoromethylphenyl)piperidinylmethyl)-4-(RS)-(3-
thienyl)pyrrolidine Mass Spectrum (CI) m/e=549 (M+1)

EXAMPLE 97

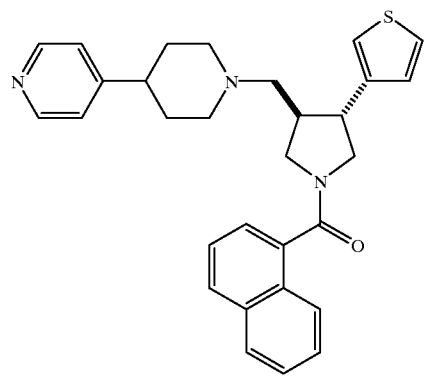

1-(1-Naphthoyl)-3-(RS)-(4-((4-pyridyl)
piperidinylmethyl)-4-(RS)-(3-thienyl)pyrrolidine Mass Spectrum (CI) m/e=482 (M+1)

EXAMPLE 98

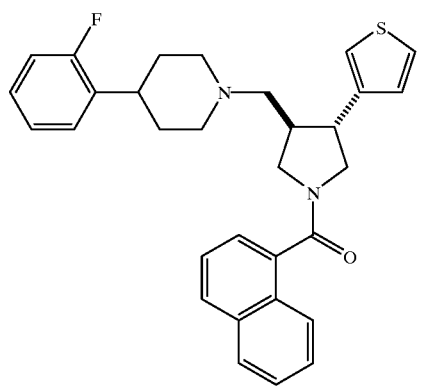

1-(1-Naphthoyl)-3-(RS)-(4-(2-fluorophenyl)
piperidinylmethyl)-4-(RS)-(3-thienyl)pyrrolidine Mass Spectrum (CI) m/e=499 (M+1)

EXAMPLE 99

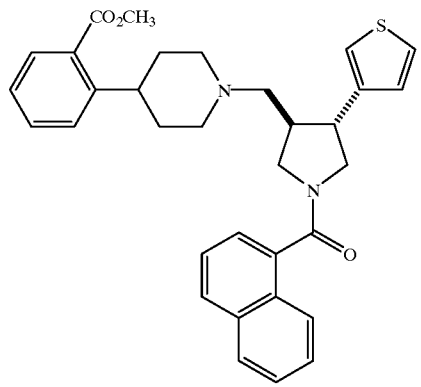

1-(1-Naphthoyl)-3-(RS)-(4-(2-carbomethoxyphenyl)
piperidinylmethyl)-4-(RS)-(3-thienyl)pyrrolidine Mass Spectrum (CI) m/e=539 (M+1)

EXAMPLE 100

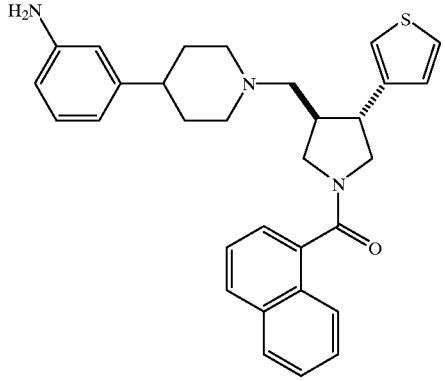

1-(1-Naphthoyl)-3-(RS)-(4-(3-aminophenyl)
piperidinylmethyl)-4-(RS)-(3-thienyl)pyrrolidine Mass Spectrum (CI) m/e=496 (M+1)

EXAMPLE 101

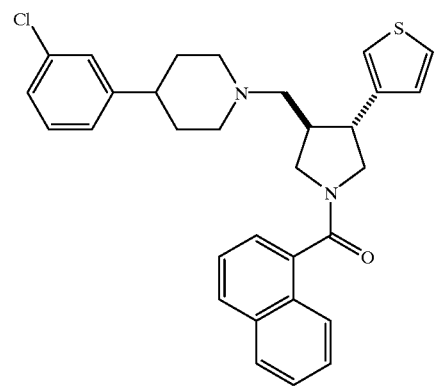

1-(1-Naphthoyl)-3-(RS)-(4-(3-chlorophenyl)
piperidinylmethyl)-4-(RS)-(3-thienyl)pyrrolidine Mass Spectrum (CI) m/e=515 (M+1 35Cl), 517 (M+1 37Cl).

EXAMPLE 102

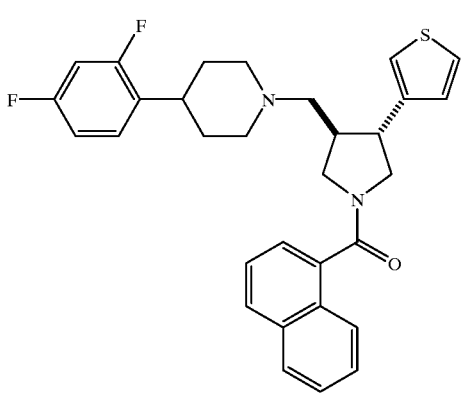

1-(1-Naphthoyl)-3-(RS)-(4-(2,4-difluorophenyl)
piperidinylmethyl)-4-(RS)-(3-thienyl)pyrrolidine Mass Spectrum (CI) m/e=517 (M+1)

EXAMPLE 103

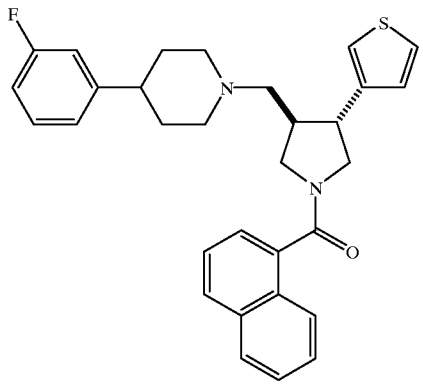

1-(1-Naphthoyl)-3-(RS)-(4-(3-fluorophenyl)
piperidinylmethyl)-4-(RS)-(3-thienyl)pyrrolidine Mass Spectrum (CI) m/e=499 (M+1)

EXAMPLE 104

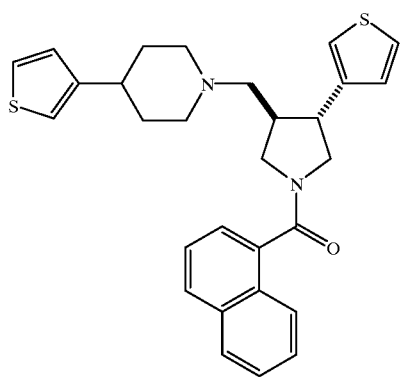

1-(1-Naphthoyl)-3-(RS)-(4-(3-thiophenyl)
piperidinylmethyl)-4-(RS)-(3-thienyl)pyrrolidine Mass Spectrum (CI) m/e=487 (M+1)

EXAMPLE 105

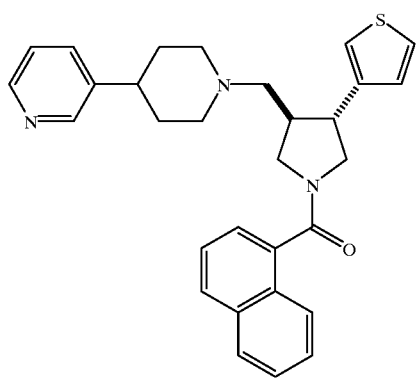

1-(1-Naphthoyl)-3-(RS)-(4-(3-pyridyl)
piperidinylmethyl)-4-(RS)-(3-thienyl)pynolidine Mass Spectrum (CI) m/e=482 (M+1)

EXAMPLE 106

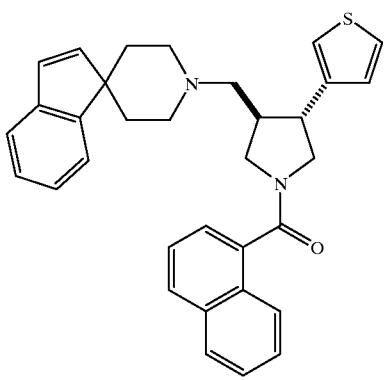

1-(1-Naphthoyl)-3-(RS)-(spiro[indenyl-3,4'piperidin-1'-yl]methyl)-4-(RS)-(3-thienyl)pyrrolidine Mass Spectrum (CI) m/e=505 (M+1) The spiroindenylpiperidine sidechain was prepared according to procedures described by Chambers, M. S. et al. in J. Med. Chem. 1992, 35, 2033–2039.

EXAMPLE 107

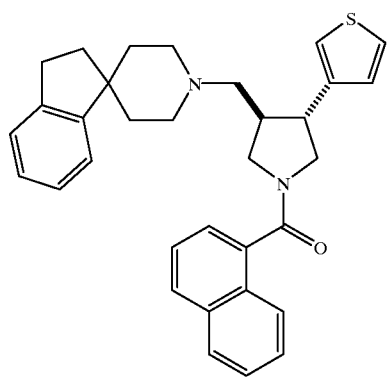

1-(1-Naphthoyl)-3-(RS)-(spiro[indanyl-3,4'piperidin-1'-yl]methyl)-4-(RS)-(3-thienyl)pyrrolidine Mass Spectrum (CI) m/e=507 (M+1)

Preparation of spiro[indanyl-3,4'piperidine

A mixture of 1.1 g (102 mmol) of spiro[indenyl-3, 4'piperidine and 100 mg of Pd/C (10%) in 50 mL of methanol was stirred in a hydrogen atmosphere (45 psi) for 18 h. The reaction mixture was then filtered and the filtrate was concentrated to give the title compound.

EXAMPLE 108

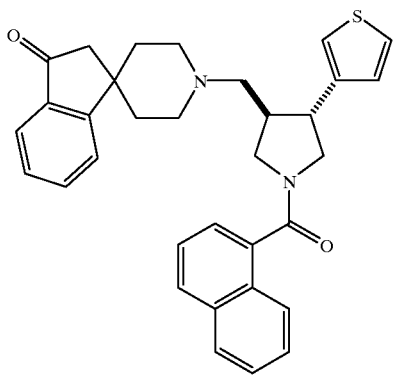

1-(1-Naphthoyl)-3-(RS)-(spiro[indan-1-one-3,4'piperidin-1'-yl]methyl)-4-(RS)-(3-thienyl)pyrrolidine Mass Spectrum (CI) m/e=521 (M+1)

Spiro(2-oxoindan-3,4'-piperidine was prepared as described by Clareman, D. A. et al European Patent 0 431 943 A2 and Evans, B. F. et al. U.S. Pat. No. 4,420,485.

EXAMPLE 109

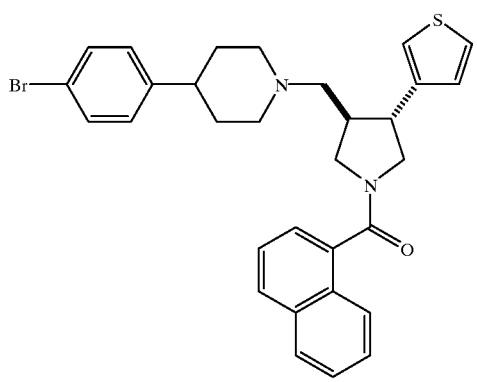

1-(1-Naphthoyl)-3-(RS)-(4-(4-bromophenyl)-
piperidinylmethyl)-4-(RS)-(3-thienyl)pyrrolidine Mass Spectrum (CI) m/e=559 (M+1)

Preparation of 4-(4-bromophenyl)piperidine

A solid mixture comprised of 2.65 g (16.4 mmol) of bromine adsorbed onto 5 g of $Al_2O_3$ was combined with a solid mixture of 1.05 g (6.56 mmol) of 4-phenylpiperidine adsorbed onto 5 g of $Al_2O_3$ and the combined mixture was stirred at rt for 2 h. The mixture was then put into a filter funnel and was eluted with $CH_2Cl_2$: EtOAc, 1:1 then $CH_2Cl_2$: MeOH:(2N $NH_3$ in MeOH), 100:4:2 to give 1.0 g of the title compound.

EXAMPLE 110

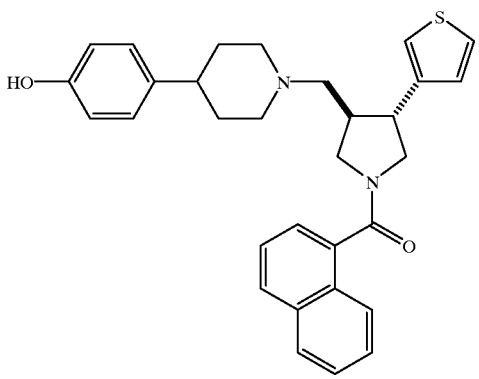

1-(1-Naphthoyl)-3-(RS)-(4-(4-hydroxyphenyl)-
piperidinylmethyl)-4-(RS)-(3-thienyl)pyrrolidine Mass Spectrum (CI) m/e=497 (M+1)

Preparation of 4-(4-Hydroxyphenyl)piperidine

To a solution of 0.49 g (1.68 mmol) of 1-t-Butoxycarbonyl-4-(4-methoxyphenyl)piperidine (used in Example 88) in 6 mL of $CHCl_3$ at −50° C., was added 5.04 mL (5.04 mmol) of $BBr_3$ (1M in $CH_2Cl_2$) and the reaction was stirred at −50° C. for 2 h. The reaction mixture was concentrated, and the residue was purified by chomatography (silica, $CH_2Cl_2$:MeOH:2M $NH_3$ in $CH_3OH$, 100:8:4 to give the title compound.

EXAMPLES 111 AND 112

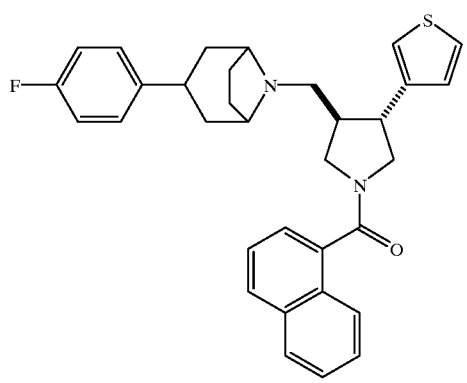

1-(1-Naphthoyl)-3-(RS)-(4-(4-fluorophenyl)-
tropanylmethyl)-4-(RS)-(3-thienyl)pyrrolidine The endo and exo isomers were separated by chomatography (silica, acetone: hexanes 1:2). Mass Spectrum (CI) m/e=525 (M+1)

Preparation of 4-(4-fluorophenyl)-tropane

The title compound was prepared as a 1:1 mixture of endo: exo isomers from 1-t-butoxycarbonyltropinone according to procedures described in Example 89.

EXAMPLE 113

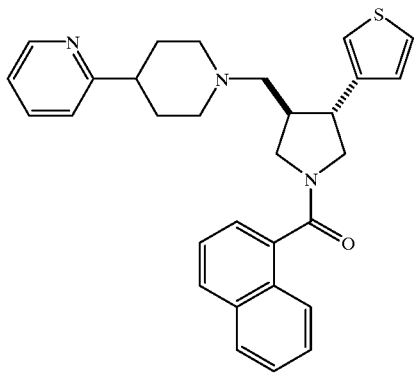

1(1-Naphthoyl)-3-(RS)-(4-(2-pyridyl)
piperidinylmethyl)-4-(RS)-(3-thienyl)pyrrolidine Mass Spectrum (CI) m/e=482 (M+1)

Preparation of 4-(2-pyridyl)piperidine

Step 1

1-Benzyl-4-(2-pyridyl)-1,2,3,6-tetrahydropyridine

A Solution of 2 g (12.8 mmol) of 4-(2-pyridyl)pyridine (Aldrich) and 2.18 g (12.8 mmol) of benzylbromide in 15 mL of DMF and 15 mL of $CH_3CN$ was stirred at 95° C. for 4 h. The reaction mixture was then concentrated and redissolved in 20 mL of methanol. To the reaction mixture at 0° C. was added 0.95 g, (25.6 mmol) of $NaBH_4$ and the reaction mixture was stirred for 1 h. The reaction was quenched with 6N HCl, and was partitioned between $CH_2Cl_2$ and 1N NaOH. The aqueous layer was extracted 3 times with $CH_2Cl_2$, dried over $Na_2SO_4$, filtered and the filtrate was concentrated. The residue was purified chomatography [silica, $CH_2Cl_2$:ethyl acetate:(2M $NH_3$ in MeOH), 100:100:2] to give 3.2 g of the title compound.

Step 2

4-(2-Pyridyl)piperidine

A mixture of 3.2 g (12.8 mmol) of 1-benzyl-4-(2-pyridyl)-1,2,3,6-tetrahydropyridine and 1.2 g of $Pd(OH)_2$/C in 25 mL of MeOH was hydrogenated at 50 psi for 6 h. The reaction mixture was filtered and the filtrate was concentrated. The residue was purified by chomatography [$CH_2Cl_2$:MeOH:(2M $NH_3$ in MeOH), 100:8:4) to give 1.86 g of the title compound.

The following Examples 114 to 119 were prepared from 1-(2,3-dichlorobenzoyl)-3-(SR)-formyl-4-(RS)-(3-thienyl)pyrrolidine or 1-(3,4-dichlorobenzoyl)-3-(SR)-formyl-4-(RS)-(3-thienyl)pyrrolidine as described in Examples 88 and 89.

EXAMPLE 114

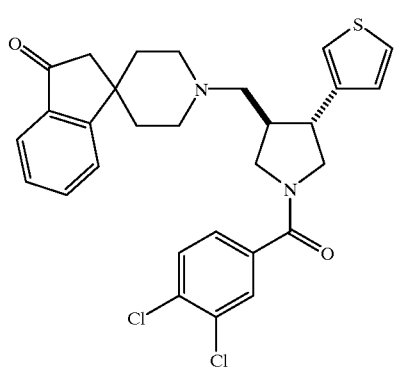

1-(3,4-Dichlorobenzoyl)-3-(RS)-(spiro[indan-1-one-3,4'piperidin-1'-yl]methyl)-4-(RS)-(3-thienyl)pyrrolidine Mass Spectrum (CI) m/e=539 (M+1 35Cl35Cl), 541 (M+1 35Cl,37Cl)

EXAMPLE 115

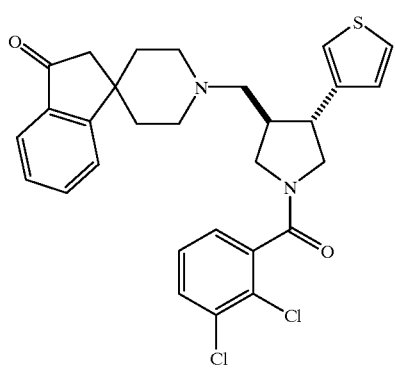

1-(2,3-Dichlorobenzoyl)-3-(RS)-(spiro[indan-1-one-3,4'piperidin-1'-yl]methyl)-4-(RS)-(3-thienyl)pyrrolidine Mass Spectrum (CI) m/e=539 (M+1 35Cl 35Cl) and 541 (M+1 35Cl,37Cl)

EXAMPLE 116

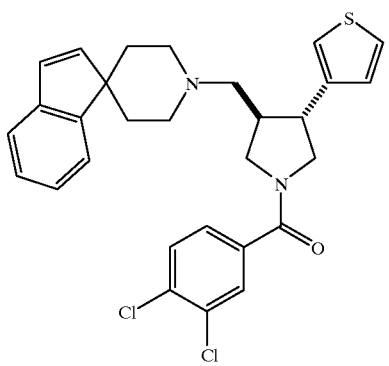

1-(3,4-Dichlorobenzoyl)-3-(RS)-(spiro[indenyl-3,4'piperidin-1'-yl]methyl)-4-(RS)-(3-thienyl)pyrrolidine Mass Spectrum (CI) m/e=523 (M+1 35Cl 35Cl) and 525 (M+1 35Cl, 37Cl)

EXAMPLE 117

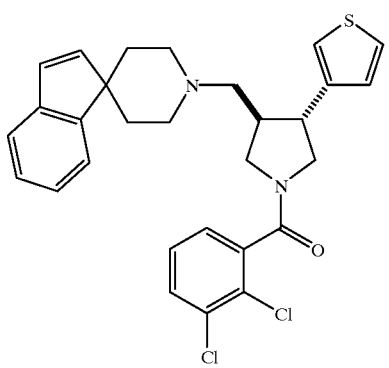

1-(2,3-Dichlorobenzoyl)-3-(RS)-(spiro[indenyl-3,4'piperidin-1'-yl]methyl)-4-(RS)-(3-thienyl)pyrrolidine Mass Spectrum (CI) m/e=523 (M+1 35Cl 35Cl) and 525 (M+1 35Cl, 37Cl)

EXAMPLE 118

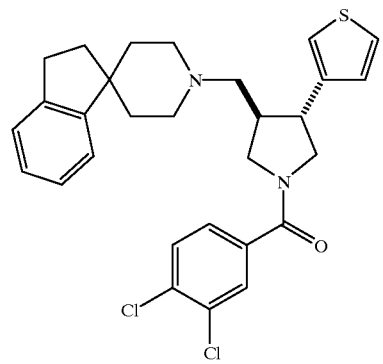

1-(3,4-Dichlorobenzoyl)-3-(RS)-(spiro[indanyl-3,
4'piperidin-1'-yl]methyl)-4-(RS)-(3-thienyl)
pyrrolidine Mass Spectrum (CI) m/e=525 (M+1 35Cl 35Cl) and 527 (M+1 35Cl, 37Cl)

EXAMPLE 119

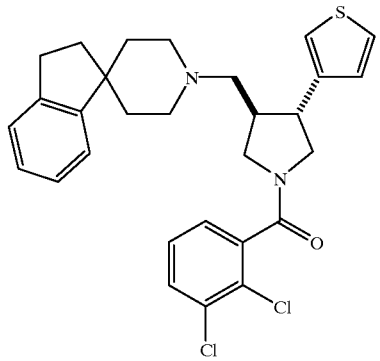

1-(2,3-Dichlorobenzoyl)-3-(RS)-(spiro[indanyl-3,
4'piperidin-1'-yl]methyl)-4-(RS)-(3-thienyl)
pyrrolidine Mass Spectrum (CI) m/e=525 (M+1 35Cl 35Cl) and 527 (M+1 35Cl, 37Cl)

EXAMPLES 120 AND 121

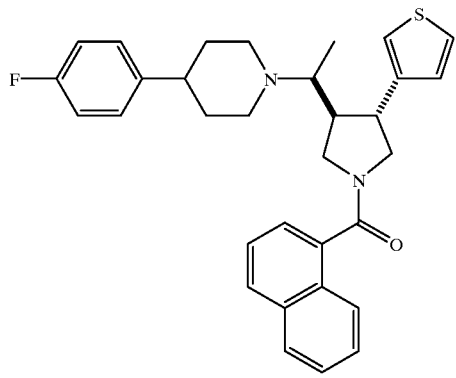

1-(1-Naphthoyl)-3-(RS)-(4-(4-fluorophenyl)-
piperidinyl-1-ethyl)-4-(RS)-(3-thienyl)pyrrolidine A solution of 0.16 g (0.47 mmol) of 1-(1-naphthoyl)-3-(SR)-formyl-4-(RS)-(3-thienyl)pyrrolidine (Example 88), and 0.085 g (0.47 mmol) of 4-(4-fluorophenyl)-piperidine in 10 mL of benzene was heated to reflux in a flask fitted with a Dean-Stark trap to azeotrope off the water. After 2 h, the benzene was removed by freeze-drying to give a white powder. The residue was redissolved in 6 mL of THF and the solution was cooled to −78° C. To this solution was added 0.56 mL (0.56 mmol) of a 1N solution of HCl in ether. The mixture was warmed to rt and stirred 30 min at rt. The mixture was then cooled to 0° C. and to it was added 1 mL (1.41 mmol) of methyl magnesium bromide (1N in THF). The reaction mixture was warmed to rt and stirred for 3 h at which time it was quenched with water. The reaction mixture was filtered though a thin layer of silica and concentrated. The residue was purified by chomatography (HPLC, Waters RCM 25×100, silica, hexanes: 0.1% iPr$_2$NH in t-butylmethylether, 8:2.25) to give the two isomers of the title compound.

Isomer #1
$^1$H NMR (CDCl$_3$) δ7.90–7.98 (m, 3H), 0.89 and 0.76 ( d, 3H, J=6.5 Hz)
Mass Spectrum (CI) m/e=513 (M+1)

Isomer #2
$^1$H NMR (CDCl$_3$) δ7.87–7.97 (m, 3H), 1.09 and 0.73 (d, 3H, J=6.5 Hz)
Mass Spectrum (CI) m/e=513 (M+1)

EXAMPLE 122

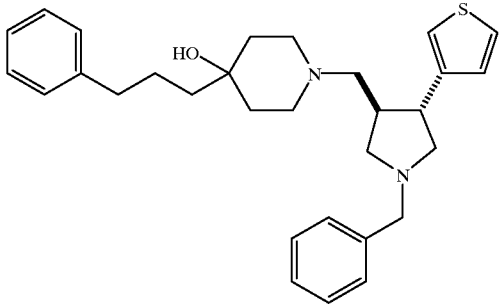

1-Benzyl-3-(RS)-(4-hydroxy-4-(3-phenylpropyl)
piperidinylmethyl)-4-(SR)-(3-thienyl)pyrrolidine Step 1

4-Hydroxy-4-(3-phenylpropyl)piperidine

Step 1A

1-Benzyl-4-hydroxy-4-(3-phenylpropyl)piperidine

To a solution of 3.8 mL (25 mmol) of 1-bromo-3-phenyl propane in 200 mL of ether at −78° C. was slowly added 30 mL (50 mmol) of t-BuLi (1.7 M in pentane). The reaction mixture was warmed to −20° C. for 15 min, then it was recooled to −78° C. To this reaction mixture was slowly added a solution of 2.61 g (13.8 mmol) of 1-benzyl-4-piperidone in 20 mL of ether. After 15 min, the reaction mixture was poured into, 200 mL of sat'd NH$_4$Cl solution. The reaction mixture was extracted with ethyl acetate and the combined organic fractions were washed with sat'd NaCl solution, dried over MgSO$_4$ filtered and the filtrate was concentrated. The residue was purified by chromatography (silica, hexanes: ethyl acetate, 1:1) to give 3.3 g of the title compound.

Step 1B

4-Hydroxy-4-(3-phenylpropyl)piperidine

A mixture of 3.3 g (10.7 mmol) of 1-benzyl-4-hydroxy-4-(3-phenylpropyl)piperidine and 0.5 g of Pd(OH)$_2$ (Pearlman's catalyst) in 80 mL of MeOH was hydrogenated at 50 psi for 24 h. The reaction mixture was filtered through a thin pad of celite and concentrated to give the title compound.

Step 2

1-Benzyl-3-(RS)-(4-hydroxy-4-(3-phenylpropyl)
piperidinylmethyl)-4-(SR)-(3-thienyl)pyrrolidine The title compound was prepared from 1-benzyl-3-(SR)-formyl-4-(SR)-thiophen-3-ylpyrrolidine and 4-hydroxy-4-(3-phenylpropyl)piperidine by procedures described in Example 1.

¹H NMR (CDCl₃) δ7.44 (d, 2H, J=6.7 Hz), 7.39 (t, 2H, J=7.5 Hz), 7.25–7.36 (m, 7H), 7.13 (d, 1H, J=4.8 Hz), 7.07 (d, 1H, J=2.5 Hz), 3.76 (d, 1H, J=13.1 Hz), 3.69 (d, 1H, J=13.0 Hz), 3.18 (q, 1H, J=6.1 Hz), 3.02 (t, 1H, J=8.7 Hz), 2.94 (t, 1H J=9.0 Hz), 2.47–2.70 (m, 10 H), 2.26–2.33 (m, 2H), 1.73–1.80 (m, 2 H), 1.51–1.66 (m, 6H). Mass Spectrum (ESI) m/e=385 (M+1)

EXAMPLE 123

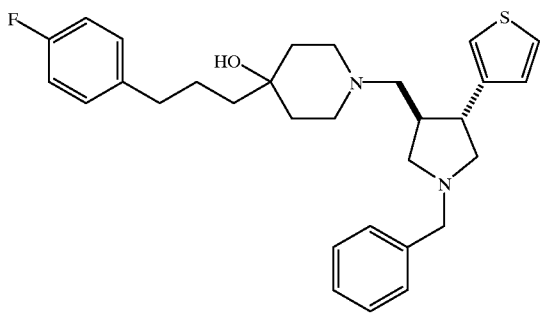

1-Benzyl-3-(RS)-(4-hydroxy-4-(3-(4-fluorophenyl)propyl)piperidinylmethyl)-4-(SR)-(3-thienyl)pyrrolidine The title compound was prepared as described in Example 6.

Mass Spectrum (ESI) m/e=493 (M+1)

Preparation of 4-hydroxy-4-(3-(4-fluorophenyl)propyl)piperidine

Step 1

3-(4-Fluorophenyl)propanol

A mixture of 2.5 g (15 mmol) of 4-fluorocinnamic acid and 0.06 g of (PPh₃)₃RhCl (Wilkinson's catalyst) in 5 mL of Et₃SiH was heated at 100° C. for 3 h. The reaction mixture was cooled to rt, and to it was added 20 mL of THF and 30 mL (30 mmol) of LiAlH₄ (1 M in THF) and the reaction mixture was stirred at 40° C. for 3 h. The reaction mixture was cooled to rt and to it was successively added 3 mL of H₂O, 3 mL of 15% KOH solution and 3 mL of H₂O. The reaction mixture was filtered and the Al-salts were washed with ethyl acetate. The combined organic fraction was dried over MgSO₄, filtered and the filtrate was concentrated. The residue was purified by chromatography (silica, hexanes: ethyl acetate, 4:1) to give 2.26 g of the title compound.

Step 2

3-(4-Fluorophenyl)propyliodide

To a solution of 2.26 g (14.65 mmol) of 3-(4-fluorophenyl propanol and 3.6 mL (44 mmol) of pyridine in 40 mL of CH₂Cl₂ at 0° C. was added 5.1 g (29.3 mmol) of methanesulfonic anhydride and the reaction mixture was sitirred for 4 h at rt. The reaction mixture was partitioned between 100 mL of CH₂Cl₂ and 20 of sat'd NaHCO₃ solution. The organic fraction was washed 3 times with sat'd NaHCO₃ solution and sat'd NaCl solution, dried over MgSO₄ and the filtrate was concentrated several times from heptane to remove pyridine. To the residue in 50 mL of acetone was added 6 g (44 mmol) of LiI and the reaction mixture was Stirred for 20 hr. The reaction mixture was poured into 200 mL of H₂O and extracted with ether. The combined organic fractions were washed with sat'd NaCl solution, dried over MgSO₄, filtered and the filtrate was concentrated. The residue was purified by chromatography (silica, hexanes: ethyl acetate, 9:1) to give 3.25 g of the title compound.

Step 3

4-Hydroxy-4-(3-(4-fluorophenyl)propyl)piperidine

The title compound was prepared from 3-(4-fluorophenyl propyliodide and 1-benzyl-4-piperidone as described in Example 122.

The following Examples 124 to 150 were prepared from 1-allyl-3-(SR)-formyl-4-(SR)-(3-thienyl)pyrrolidine according to procedures described in Examples 123. The substituents at C3 were prepared as described in Examples 122 or 123.

EXAMPLE 124

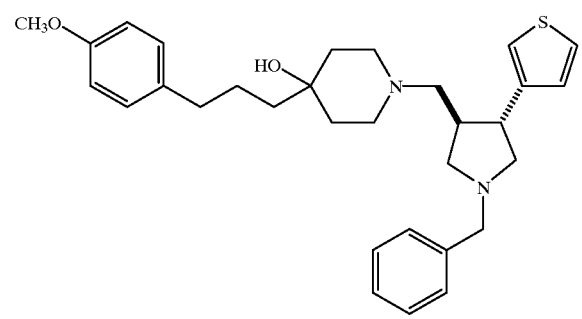

1-Benzyl-3-(RS)-(4-hydroxy-4-(3-(4-methoxyphenyl)propyl)piperidinylmethyl)-4-(SR)-(3-thienyl)pyrrolidine Mass Spectrum (ESI) m/e=505 (M+1)

EXAMPLE 125

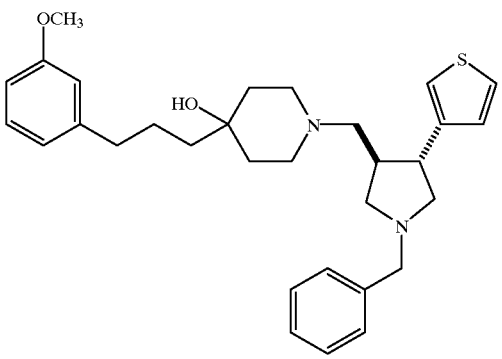

1-Benzyl-3-(RS)-(4-hydroxy-4-(3-(3-methoxyphenyl)propyl)piperidinylmethyl)-4-(SR)-(3-thienyl)pyrrolidine Mass Spectrum (ESI) m/e=505 (M+1)

EXAMPLE 126

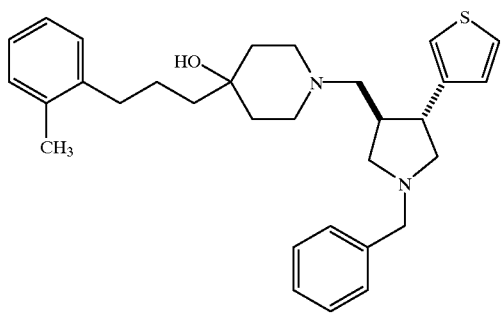

1-Benzyl-3-(RS)-(4-hydroxy-4-(3-(2-methylphenyl)propyl)piperidinylmethyl)-4-(SR)-(3-thienyl)pyrrolidine Mass Spectrum (ESI) m/e=489 (M+1)

EXAMPLE 127

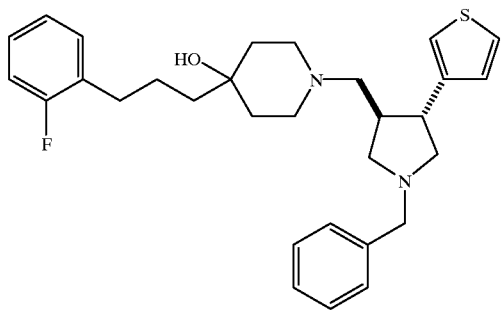

1-Benzyl-3-(RS)-(4-hydroxy-4-(3-(2-fluorophenyl)propyl)piperidinylmethyl)-4-(SR)-(3-thienyl)pyrrolidine Mass Spectrum (ESI) m/e=493 (M+1)

EXAMPLE 128

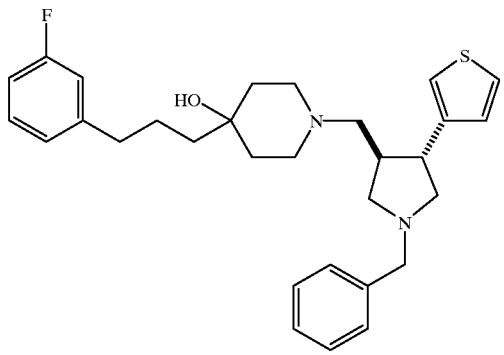

1-Benzyl-3-(RS)-(4-hydroxy-4-(3-(3-fluorophenyl)propyl)piperidinylmethyl)-4-(SR)-(3-thienyl)pyrrolidine Mass Spectrum (ESI) m/e=493 (M+1)

EXAMPLE 129

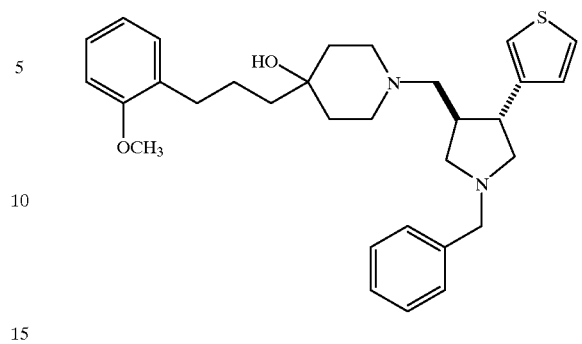

1-Benzyl-3-(RS)-(4-hydroxy-4-(3-(2-methoxyphenyl)propyl)piperidinylmethyl)-4-(SR)-(3-thienyl)pyrrolidine Mass Spectrum (ESI) m/e=505 (M+1)

EXAMPLE 130

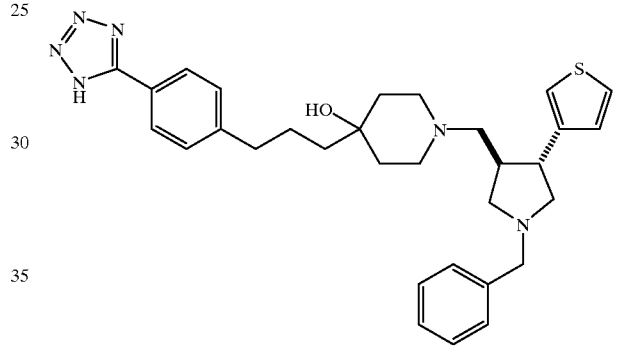

1-Benzyl-3-(RS)-(4-hydroxy-4-(3-(4-tetrazolylphenyl)propyl)piperidinylmethyl)-4-(SR)-(3-thienyl)pyrrolidine Mass Spectrum (ESI) m/e=543 (M+1)

EXAMPLE 131

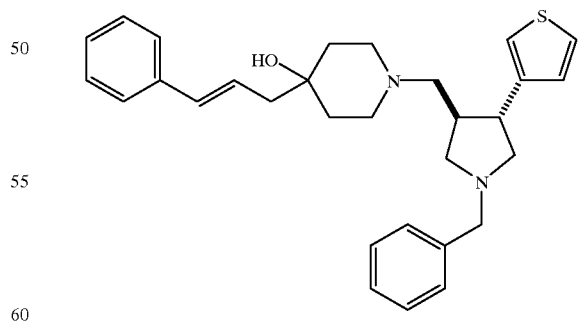

1-Benzyl-3-(RS)-(4-hydroxy-4-(3-phenylprop-2-enyl)piperidinylmethyl)-4-(SR)-(3-thienyl)pyrrolidine Mass Spectrum (ESI) m/e=473 (M+1)

EXAMPLE 132

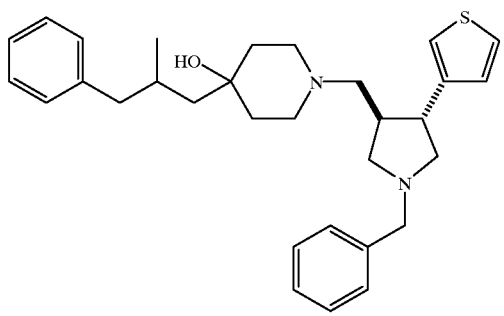

1-Benzyl-3-(RS)-(4-hydroxy-4-(2-methyl-3-phenylpropyl)piperidinylmethyl)-4-(SR)-(3-thienyl) pyrrolidine Mass Spectrum (ESI) m/e=489 (M+1)

EXAMPLE 133

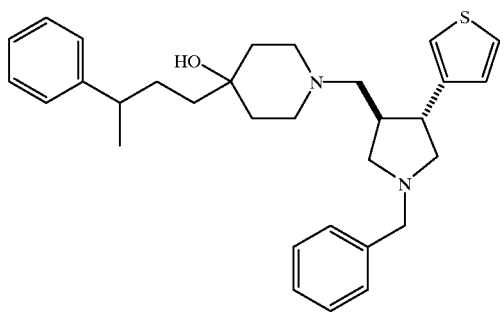

1-Benzyl-3-(RS)-(4-hydroxy-4-(3-methyl-3-phenylpropyl)piperidinylmethyl)-4-(SR)-(3-thienyl) pyrrolidine Mass Spectrum (ESI) m/e=489 (M+1)

The following Examples 134 to 151 were prepared from the corresponding pyrrolidine and benzaldehyde precursors according to procedures described in Example 3.

EXAMPLE 134

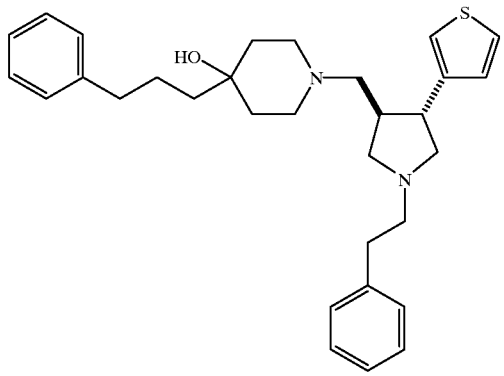

1-(2-Phenethyl)-3-(RS)-(4-hydroxy-4-(3-phenylpropyl)piperidinylmethyl)-4-(SR)-(3-thienyl) pyrrolidine Mass Spectrum (ESI) m/e=489 (M+1)

EXAMPLE 135

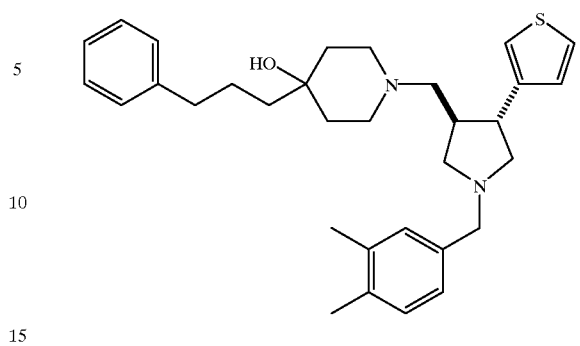

1-(3,4-Dimethylbenzyl)-3-(RS)-(4-hydroxy-4-(3-phenylpropyl)piperidinylmethyl)-4-(SR)-(3-thienyl) pyrrolidine Mass Spectrum (ESI) m/e=503 (M+1)

EXAMPLE 136

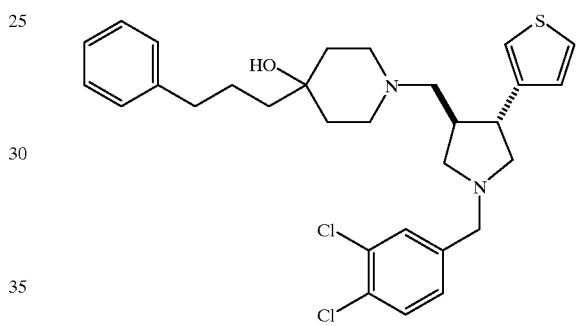

1-(3,4-Dichlorobenzyl)-3-(RS)-(4-hydroxy-4-(3-phenylpropyl)piperidinylmethyl)-4-(SR)-(3-thienyl) pyrrolidine Mass Spectrum (ESI) m/e=523 (M+1 35Cl, 37Cl), 525 (37Cl, 37Cl)

EXAMPLE 137

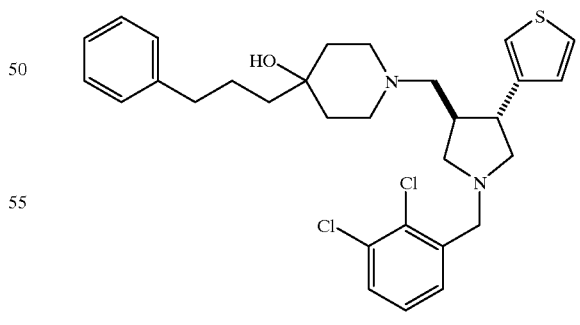

1-(2,3-Dichlorobenzyl)-3-(RS)-(4-hydroxy-4-(3-phenylpropyl)piperidinylmethyl)-4-(SR)-(3-thienyl) pyrrolidine Mass Spectrum (ESI) m/e=523 (M+1 35Cl, 37Cl, 525 (37Cl, 37Cl)

EXAMPLE 138

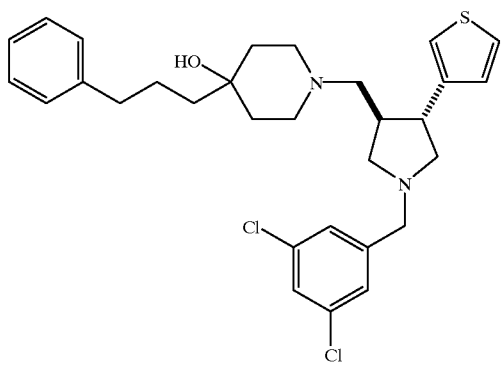

1-(3,5-Dichlorobenzyl)-3-(RS)-(4-hydroxy-4-(3-phenylpropyl)piperidinylmethyl)-4-(SR)-(3-thienyl) pyrrolidine Mass Spectrum (ESI) m/e=523 (M+1 35Cl), 525 (37Cl)

EXAMPLE 139

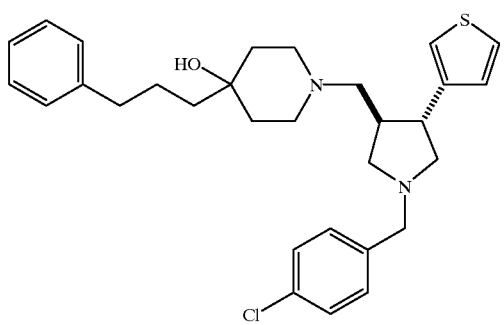

1-(4-Chlorobenzyl)-3-(RS)-(4-hydroxy-4-(3-phenylpropyl)piperidinylmethyl)-4-(SR)-(3-thienyl) pyrrolidine Mass Spectrum (ESI) m/e=509 (M+1 35Cl), and 511 (M+1, 37Cl)

EXAMPLE 140

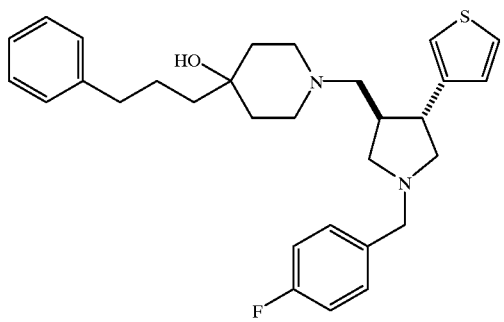

1-(4-Fluorobenzyl)-3-(RS)-(4-hydroxy-4-(3-phenylpropyl)piperidinylmethyl)-4-(SR)-(3-thienyl) pyrrolidine Mass Spectrum (ESI) m/e=493 (M+1)

EXAMPLE 141

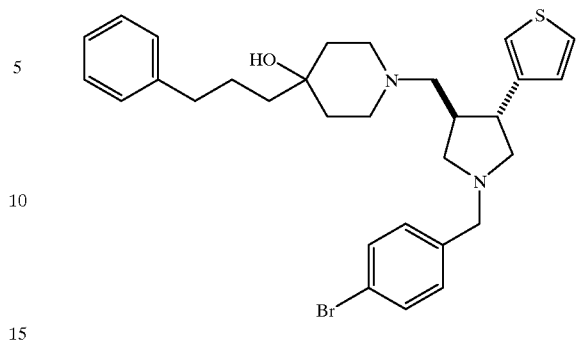

1-(4-Bromobenzyl)-3-(RS)-(4-hydroxy-4-(3-phenylpropyl)piperidinylmethyl)-4-(SR)-(3-thienyl) pyrrolidine Mass Spectrum (ESI) m/e=553 (M+1, 79 Br) and 555 (M+1, 81 Br)

EXAMPLE 142

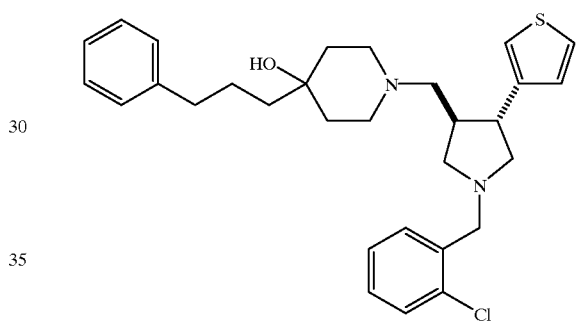

1-(2-Chlorobenzyl)-3-(RS)-(4-hydroxy-4-(3-phenylpropyl)piperidinylmethyl)-4-(SR)-(3-thienyl) pyrrolidine Mass Spectrum (ESI) m/e=509 (M+1 35Cl), and 511 (M+1, 37Cl)

EXAMPLE 143

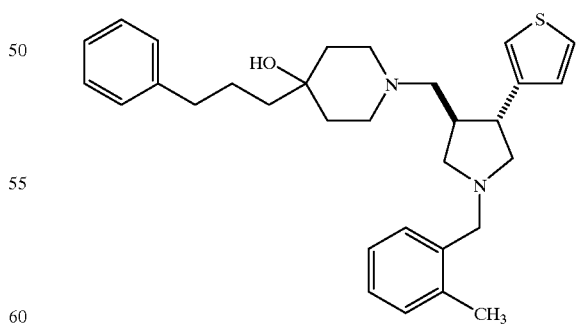

1-(2-Methylbenzyl)-3-(RS)-(4-hydroxy-4-(3-phenylpropyl)piperidinylmethyl)-4-(SR)-(3-thienyl) pyrrolidine Mass Spectrum (ESI) m/e=489 (M+1)

EXAMPLE 144

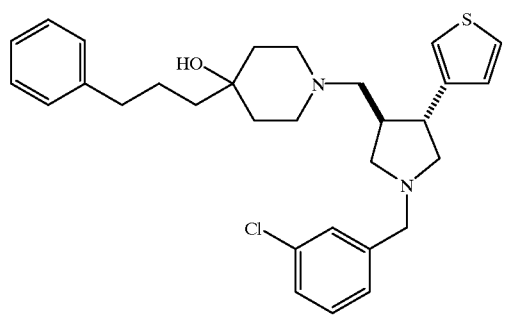

1-(3-Chlorobenzyl)-3-(RS)-(4-hydroxy-4-(3-phenylpropyl)piperidinylmethyl)-4-(SR)-(3-thienyl) pyrrolidine Mass Spectrum (ESI) m/e=509 (M+1 35Cl), and 511 (M+1, 37Cl)

EXAMPLE 145

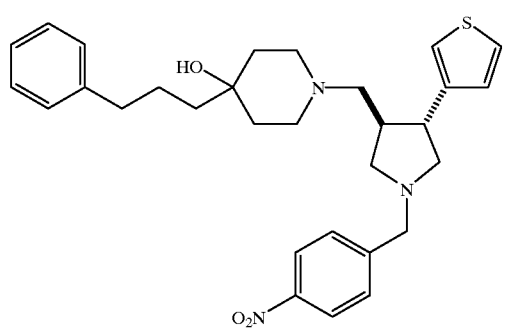

1-(4-Nitrobenzyl)-3-(RS)-(4-hydroxy-4-(3-phenylpropyl)piperidinylmethyl)-4-(SR)-(3-thienyl) pyrrolidine Mass Spectrum (ESI) m/e=520 (M+1)

EXAMPLE 146

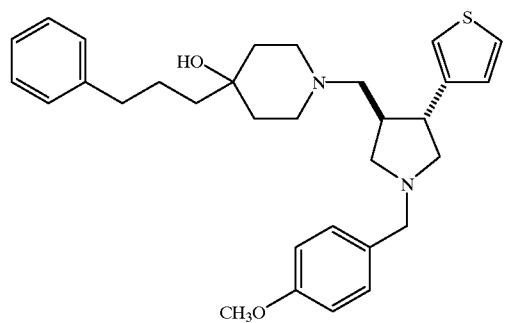

1-(4-Methoxybenzyl)-3-(RS)-(4-hydroxy-4-(3-phenylpropyl)piperidinylmethyl)-4-(SR)-(3-thienyl) pyrrolidine Mass Spectrum (ESI) m/e=505 (M+1)

EXAMPLE 147

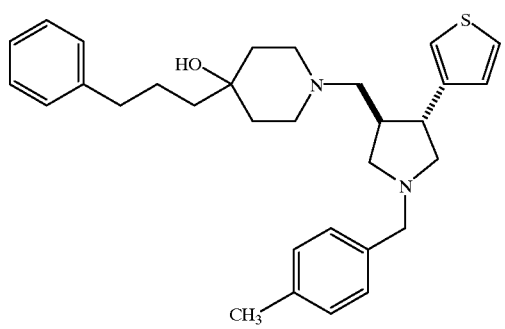

1-(4-Methylbenzyl)-3-(RS)-(4-hydroxy-4-(3-phenylpropyl)piperidinylmethyl)-4-(SR)-(3-thienyl) pyrrolidine Mass Spectrum (ESI) m/e=589 (M+1)

EXAMPLE 148

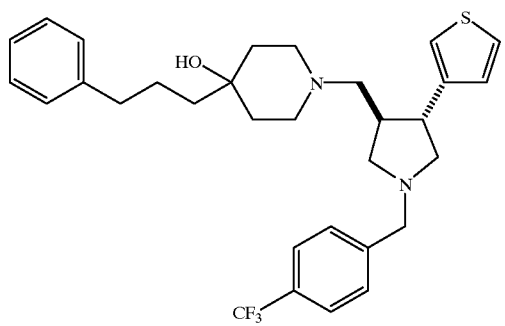

1-(4-Trifluoromethylbenzyl)-3-(RS)-(4-hydroxy-4-(3-phenylpropyl)piperidinylmethyl)-4-(SR)-(3-thienyl)pyrrolidine Mass Spectrum (ESI) m/e=489 (M+1)

EXAMPLE 149

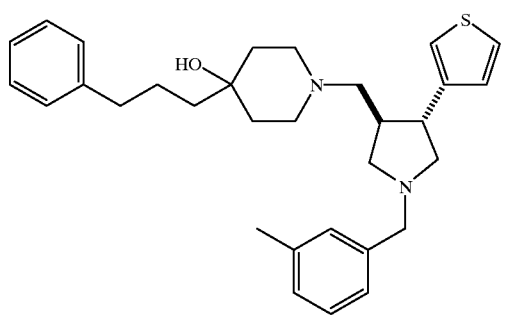

1-(3-Methylbenzyl)-3-(RS)-(4-hydroxy-4-(3-phenylpropyl)piperidinylmethyl)-4-(SR)-(3-thienyl) pyrrolidine Mass Spectrum (ESI) m/e=489 (M+1)

EXAMPLE 150

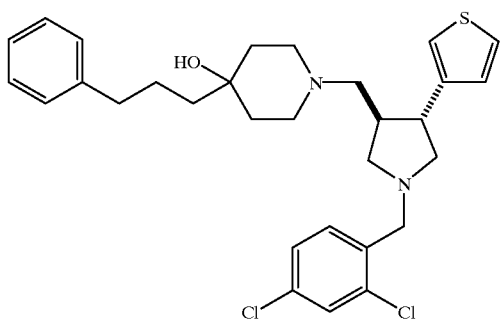

1-(2,4-Dichlorobenzyl)-3-(RS)-(4-hydroxy-4-(3-phenylpropyl)piperidinylmethyl)-4-(SR)-(3-thienyl) pyrrolidine Mass Spectrum (ESI) m/e=543 (M+1 35Cl, 37Cl), and 545 (M+1, 37Cl, 37Cl)

The following Examples 151 to 189 were prepared from the corresponding pyrrolidine and acid chloride or acid precursors according to procedures described in Examples 11 or 12.

EXAMPLE 151

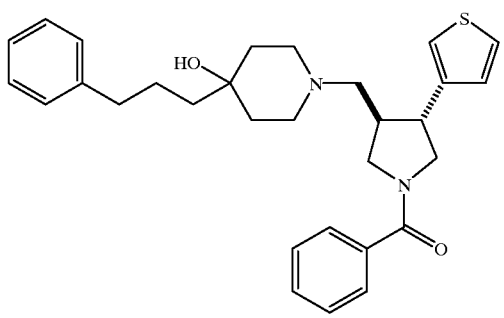

1-Benzoyl-3-(RS)-(4-hydroxy-4-(3-phenylpropyl) piperidinylmethyl)-4-(SR)-(3-thienyl)pyrrolidine Mass Spectrum (ESI) m/e=489 (M+1)

EXAMPLE 152

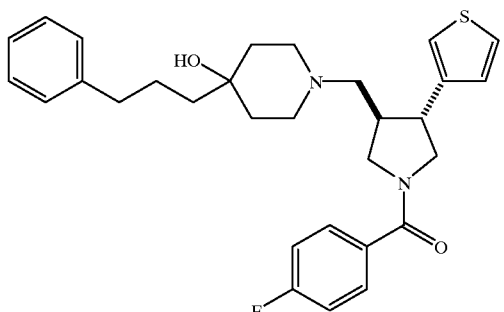

1-(4-Fluorobenzoyl)-3-(RS)-(4-hydroxy-4-(3-phenylpropyl)piperidinylmethyl)-4-(SR)-(3-thienyl) pyrrolidine Mass Spectrum (ESI) m/e=507 (M+1)

EXAMPLE 153

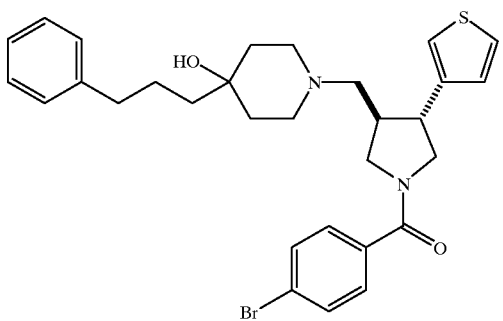

1-(4-Bromobenzoyl)-3-(RS)-(4-hydroxy-4-(3-phenylpropyl)piperidinylmethyl)-4-(SR)-(3-thienyl) pyrrolidine Mass Spectrum (ESI) m/e=567 (M+1 79 Br) and 569 (M+1, 81 Br)

EXAMPLE 154

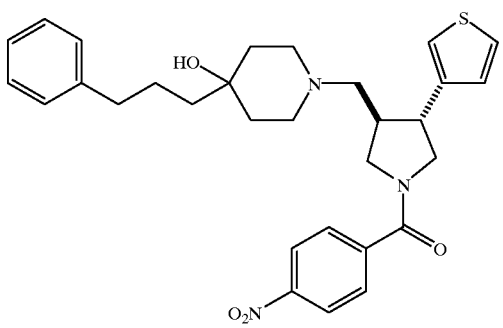

1-(4-Nitrobenzoyl)-3-(RS)-(4-hydroxy-4-(3-phenylpropyl)piperidinylmethyl)-4-(SR)-(3-thienyl) pyrrolidine Mass Spectrum (ESI) m/e=534 (M+1)

EXAMPLE 155

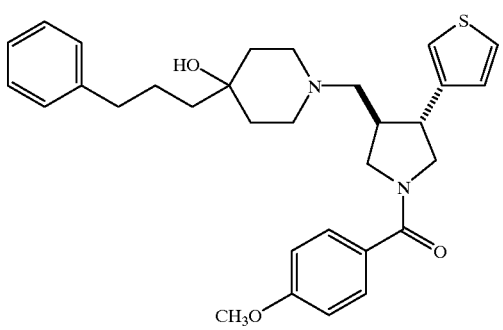

1-(4-Methoxybenzoyl)-3-(RS)-(4-hydroxy-4-(3-phenylpropyl)piperidinylmethyl)-4-(SR)-(3-thienyl) pyrrolidine Mass Spectrum (ESI) m/e=519 (M+1)

EXAMPLE 156

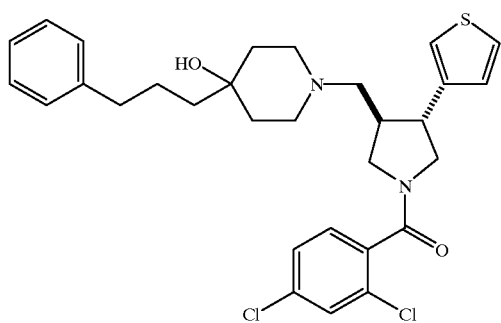

1-(2,4-Dichlorobenzoyl)-3-(RS)-(4-hydroxy-4-(3-phenylpropyl)piperidinylmethyl)-4-(SR)-(3-thienyl) pyrrolidine Mass Spectrum (ESI) m/e=557 (M+1 35Cl, 35Cl) and 559 (M+1 35Cl, 37Cl)

EXAMPLE 157

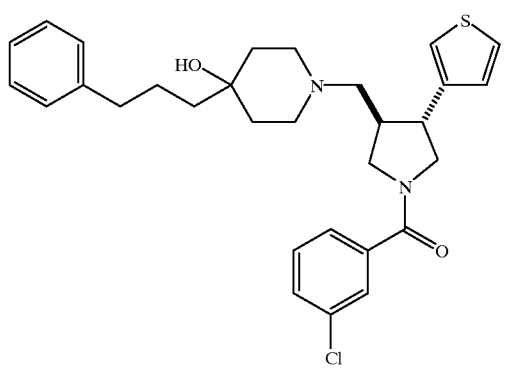

1-(3-Chlorobenzoyl)-3-(RS)-(4-hydroxy-4-(3-phenylpropyl)piperidinylmethyl)-4-(SR)-(3-thienyl) pyrrolidine Mass Spectrum (ESI) m/e=523 (M+1 35Cl) and 525 (M+1 37Cl)

EXAMPLE 158

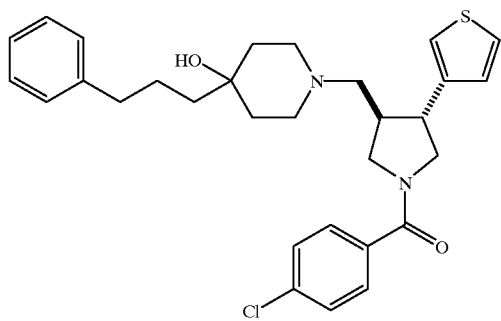

1-(4-Chlorobenzoyl)-3-(RS)-(4-hydroxy-4-(3-phenylpropyl)piperidinylmethyl)-4-(SR)-(3-thienyl) pyrrolidine Mass Spectrum (ESI) m/e=523 (M+1 35Cl) and 525 (M+1 37Cl)

EXAMPLE 159

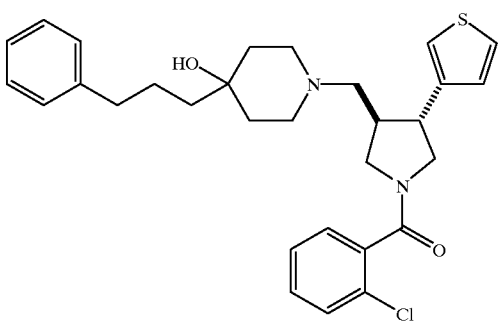

1-(2-Chlorobenzoyl)-3-(RS)-(4-hydroxy-4-(3-phenylpropyl)piperidinylmethyl)-4-(SR)-(3-thienyl) pyrrolidine Mass Spectrum (ESI) m/e=523 (M+1 35Cl) and 525 (M+1 37Cl)

EXAMPLE 160

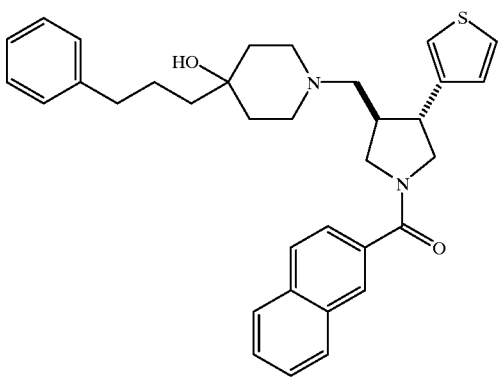

1-(2-Naphthoyl)-3-(RS)-(4-hydroxy-4-(3-phenylpropyl)piperidinylmethyl)-4-(SR)-(3-thienyl) pyrrolidine Mass Spectrum (ESI) m/e=539 (M+1)

EXAMPLE 161

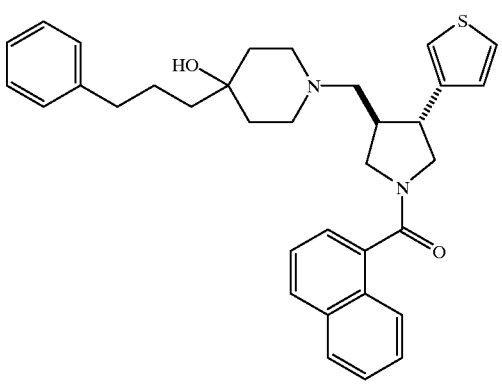

1-(1-Naphthoyl)-3-(RS)-(4-hydroxy-4-(3-phenylpropyl)piperidinylmethyl)-4-(SR)-(3-thienyl) pyrrolidine Mass Spectrum (ESI) m/e=539 (M+1)

EXAMPLE 162

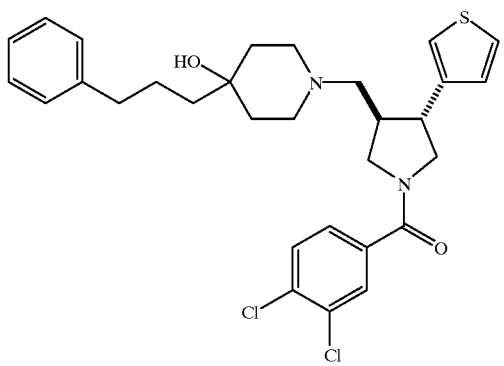

1-(3,4-Dichlorobenzoyl)-3-(RS)-(4-hydroxy-4-(3-phenylpropyl)piperidinylmethyl)-4-(SR)-(3-thienyl)pyrrolidine Mass Spectrum (ESI) m/e=557 (M+1 35Cl, 35 Cl), 559 (35Cl, 37Cl), 561 (37Cl, 37Cl)

EXAMPLE 163

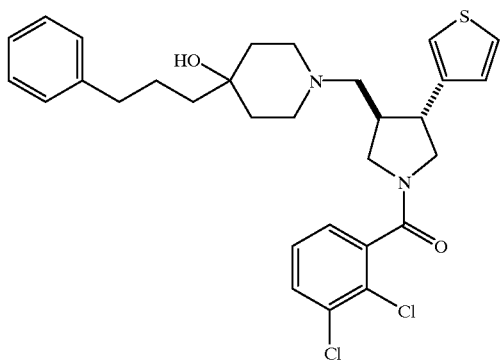

1-(2,3-Dichlorobenzoyl)-3-(RS)-(4-hydroxy-4-(3-phenylpropyl)piperidinylmethyl)-4-(SR)-(3-thienyl)pyrrolidine Mass Spectrum (ESI) m/e=557 (M+1 35Cl, 35 Cl), 559 (35Cl, 37Cl), 561 (37Cl, 37Cl)

EXAMPLE 164

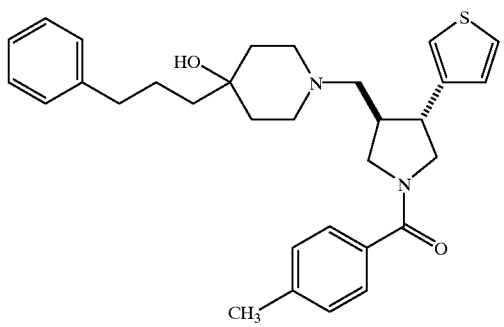

1-(4-Methylbenzoyl)-3-(RS)-(4-hydroxy-4-(3-phenylpropyl)piperidinylmethyl)-4-(SR)-(3-thienyl)pyrrolidine Mass Spectrum (ESI) m/e=503 (M+1)

EXAMPLE 165

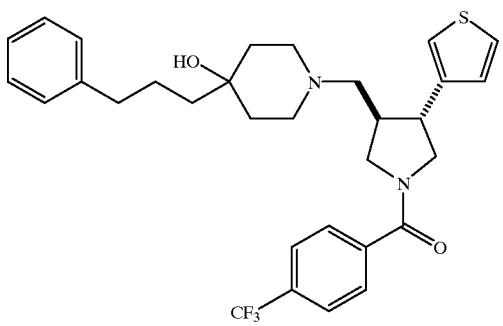

1-(4-Trifluoromethylbenzoyl)-3-(RS)-(4-hydroxy-4-(3-phenylpropyl)piperidinylmethyl)-4-(SR)-(3-thienyl)pyrrolidine Mass Spectrum (ESI) m/e=557 (M+1)

EXAMPLE 166

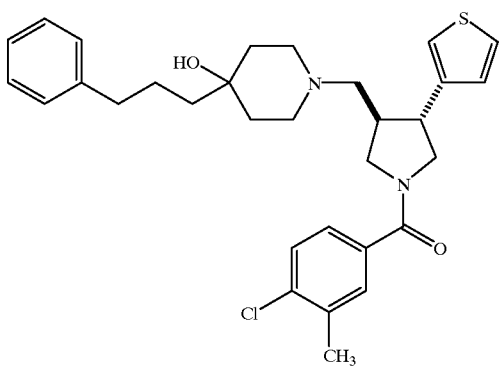

1-(4-Chloro-3-methylbenzoyl)-3-(RS)-(4-hydroxy-4-(3-phenylpropyl)piperidinylmethyl)-4-(SR)-(3-thienyl)pyrrolidine Mass Spectrum (ESI) m/e=537 (M+1 35Cl) and 539 (M+1 37Cl)

EXAMPLE 167

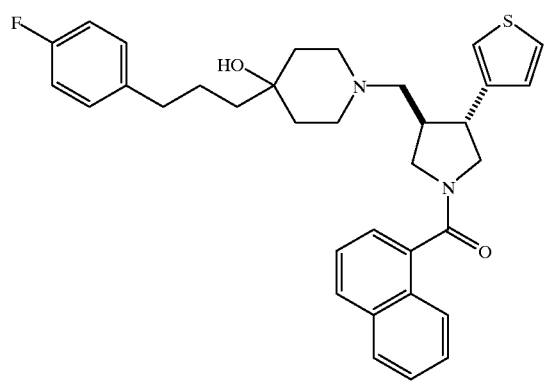

1-(1-Naphthoyl)-3-(RS)-(4-hydroxy-4-(3-(4-fluorophenyl)-1-propyl)piperidinylmethyl)-4-(SR)-(3-thienyl)pyrrolidine Mass Spectrum (ESI) m/e=557 (M+1)

EXAMPLE 168

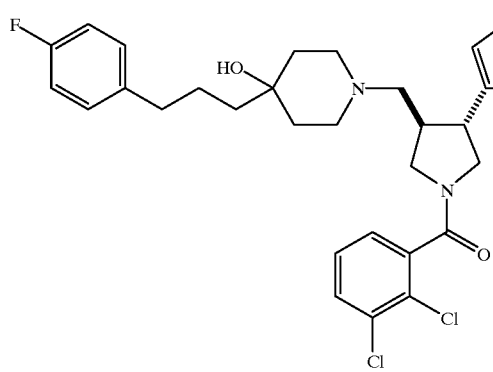

1-(2,3-Dichlorobenzoyl)-3-(RS)-(4-hydroxy-4-(3-(4-fluorophenyl)-1-propyl)piperidinylmethyl)-4-(SR)-(3-thienyl)pyrrolidine Mass Spectrum (ESI) m/e=575 (M+1 35Cl, 37Cl) and 577 (M+1 37Cl, 37Cl)

EXAMPLE 169

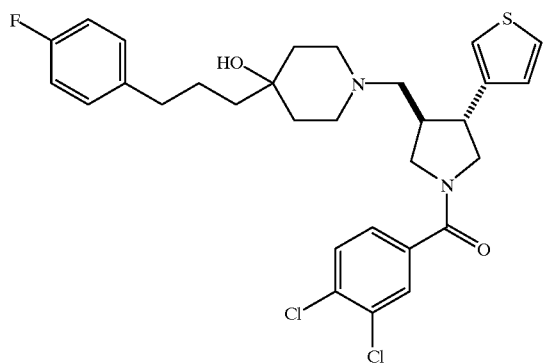

1-(3,4-Dichlorobenzoyl)-3-(RS)-(4-hydroxy-4-(3-(4-fluorophenyl)-1-propyl)piperidinylmethyl)-4-(SR)-(3-thienyl)pyrrolidine Mass Spectrum (ESI) m/e=575 (M+1 35Cl, 37Cl) and 577 (M+1 37Cl, 37Cl)

EXAMPLE 170

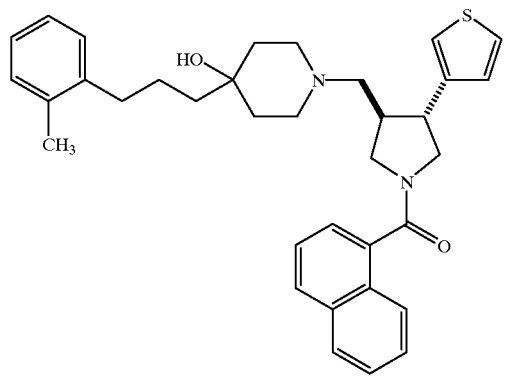

1-(1-Naphthoyl)-3-(RS)-(4-hydroxy-4-(3-(2-methylphenyl)-1-propyl)piperidinylmethyl)-4-(SR)-(3-thienyl)pyrrolidine Mass Spectrum (ESI) m/e=553 (M+1)

EXAMPLE 171

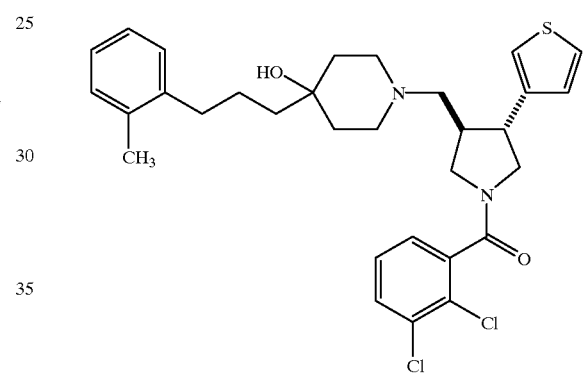

1-(2,3-Dichlorobenzoyl)-3-(RS)-(4-hydroxy-4-(3-(2-methylphenyl)-1-propyl)piperidinylmethyl)-4-(SR)-(3-thienyl)pyrrolidine Mass Spectrum (ESI) m/e=571 (M+1 35Cl, 35Cl) and 573 (M+1 37Cl, 37Cl)

EXAMPLE 172

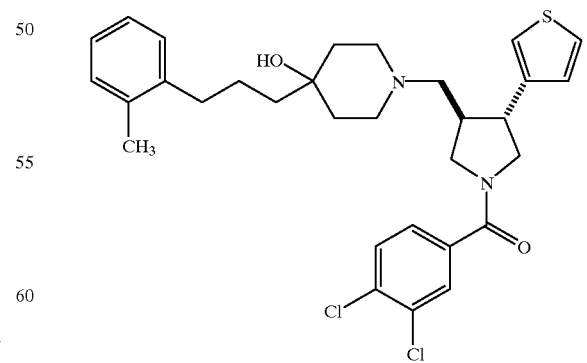

1-(3,4-Dichlorobenzoyl)-3-(RS)-(4-hydroxy-4-(3-(2-methylphenyl)-1-propyl)piperidinylmethyl)-4-(SR)-(3-thienyl)pyrrolidine Mass Spectrum (ESI) m/e=571 (M+1 35Cl, 37Cl) and 573 (M+1 37Cl, 37Cl)

EXAMPLE 173

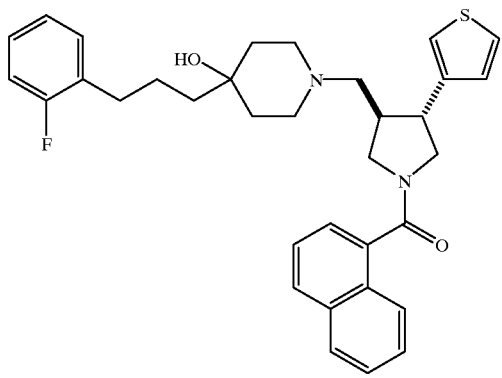

1-(1-Naphthoyl)-3-(RS)-(4-hydroxy-4-(3-(2-fluorophenyl)-1-propyl)piperidinylmethyl)-4-(SR)-(3-thienyl)pyrrolidine Mass Spectrum (ESI) m/e=557 (M+1)

EXAMPLE 174

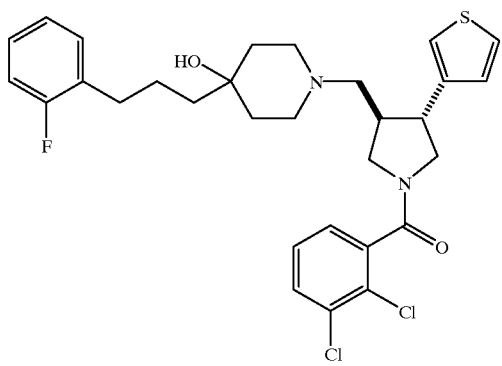

1-(2,3-Dichlorobenzoyl)-3-(RS)-(4-hydroxy-4-(3-(2-fluorophenyl)-1-propyl)piperidinylmethyl)-4-(SR)-(3-thienyl)pyrrolidine Mass Spectrum (ESI) m/e=575 (M+1 35Cl, 37Cl and 577 (M+1 37Cl, 37Cl)

EXAMPLE 175

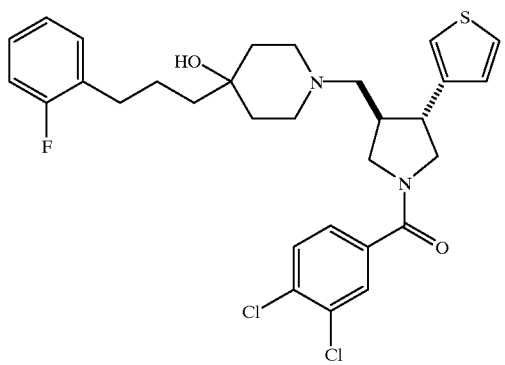

1-(3,4-Dichlorobenzoyl)-3-(RS)-(4-hydroxy-4-(3-(2-fluorophenyl)-1-propyl)piperidinylmethyl)-4-(SR)-(3-thienyl)pyrrolidine Mass Spectrum (ESI) m/e=575 (M+1 35Cl) and 577 (M+1 37Cl)

EXAMPLE 176

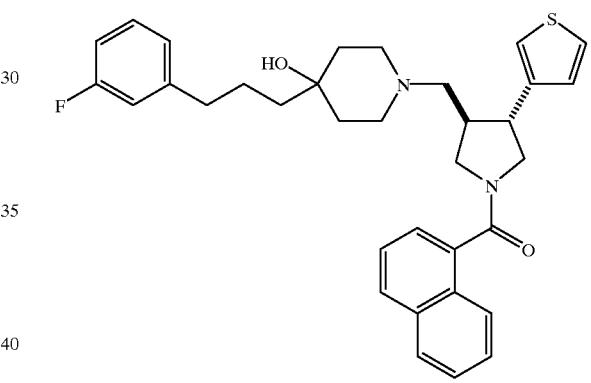

1-(1-Naphthoyl)-3-(RS)-(4-hydroxy-4-(3-(3-fluorophenyl)propyl) piperidinylmethyl)-4-(SR)-(3-thienyl)pyrrolidine Mass Spectrum (ESI) m/e=557 (M+1)

EXAMPLE 177

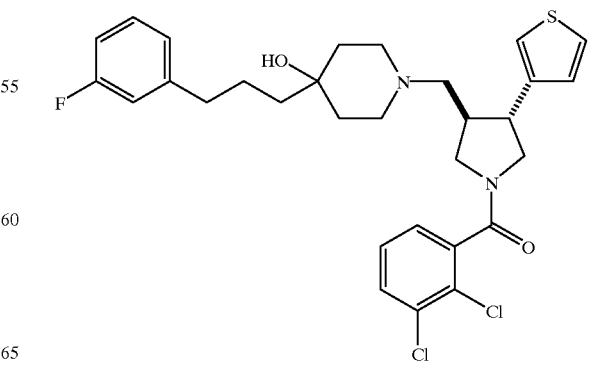

1-(2,3-Dichlorobenzoyl)-3-(RS)-(4-hydroxy-4-(3-(3-fluorophenyl)propyl)piperidinylmethyl)-4-(SR)-(3-thienyl)pyrrolidine Mass Spectrum (ESI) m/e=575 (M+1 35Cl, 37Cl) and 577 (M+1 37Cl, 37Cl)

EXAMPLE 178

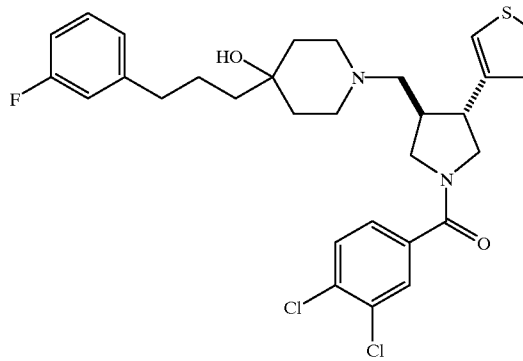

1-(3,4-Dichlorobenzoyl)-3-(RS)-(4-hydroxy-4-(3-(3-fluorophenyl)-1-propyl)piperidinylmethyl)-4-(SR)-(3-thienyl)pyrrolidine Mass Spectrum (ESI) m/e=575 (M+1 35Cl, 37Cl) and 577 (M+1 37Cl, 37Cl)

EXAMPLE 179

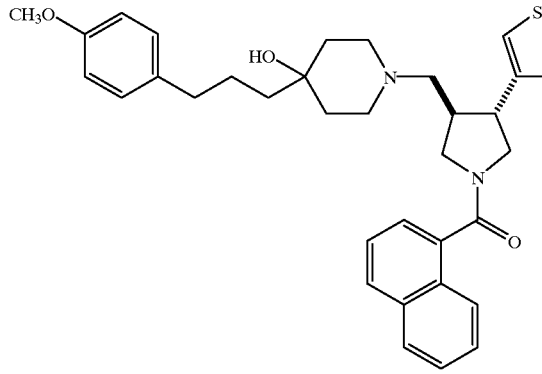

1-(1-Naphthoyl)-3-(RS)-(4-hydroxy-4-(3-(4-methoxyphenyl)propyl)piperidinylmethyl)-4-(SR)-(3-thienyl)pyrrolidine Mass Spectrum (ESI) m/e=569 (M+1)

EXAMPLE 180

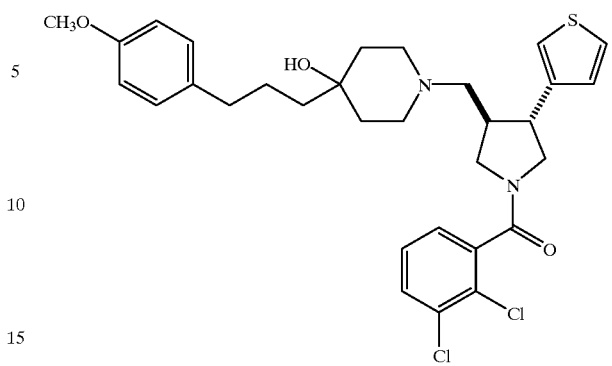

1-(2,3-Dichlorobenzoyl)-3-(RS)-(4-hydroxy-4-(3-(4-methoxyphenyl)propyl)piperidinylmethyl)-4-(SR)-(3-thienyl)pyrrolidine Mass Spectrum (ESI) m/e=587 (M+1 35Cl, 37Cl) and 589 (M+1 37Cl, 37Cl)

EXAMPLE 181

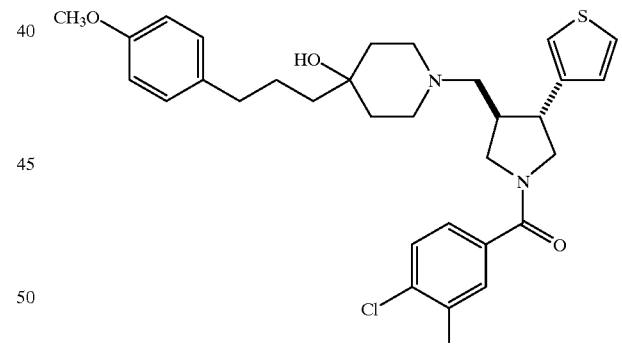

1-(3,4-Dichlorobenzoyl)-3-(RS)-(4-hydroxy-4-(3-(4-methoxyphenyl)propyl)piperidinylmethyl)-4-(SR)-(3-thienyl)pyrrolidine Mass Spectrum (ESI) m/e=587 (M+1 35Cl, 37Cl) and 589 (M+1 37Cl, 37Cl)

EXAMPLE 182

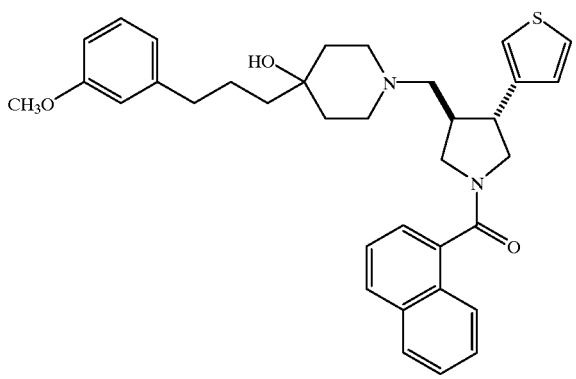

1-(1-Naphthoyl)-3-(RS)-(4-hydroxy-4-(3-(3-methoxyphenyl)propyl)piperidinylmethyl)-4-(SR)-(3-thienyl)pyrrolidine Mass Spectrum (ESI) m/e=557 (M+1)

EXAMPLE 183

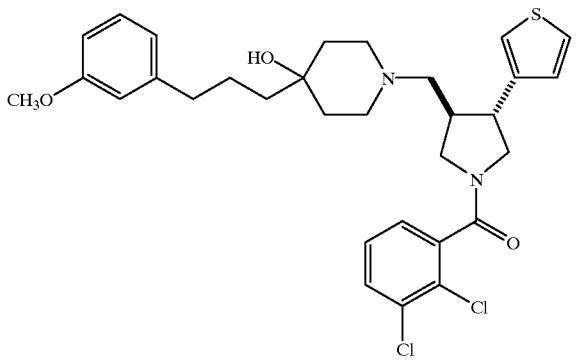

1-(2,3-Dichlorobenzoyl)-3-(RS)-(4-hydroxy-4-(3-(3-methoxyphenyl)propyl)piperidinylmethyl)-4-(SR)-(3-thienyl)pyrrolidine Mass Spectrum (ESI) m/e=587 (M+1 35Cl, 37Cl) and 589 (M+1 37Cl, 37Cl

EXAMPLE 184

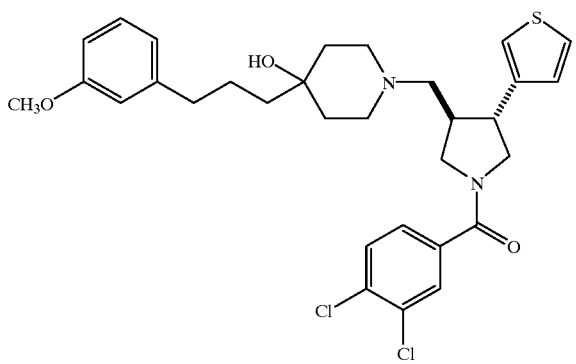

1-(3,4-Dichlorobenzoyl)-3-(RS)-(4-hydroxy-4-(3-(3-methoxyphenyl)propyl)piperidinylmethyl)-4-(SR)-(3-thienyl)pyrrolidine Mass Spectrum (ESI) m/e=587 (M+1 35Cl, 37Cl) and 589 (M+1 37Cl, 37Cl)

EXAMPLE 185

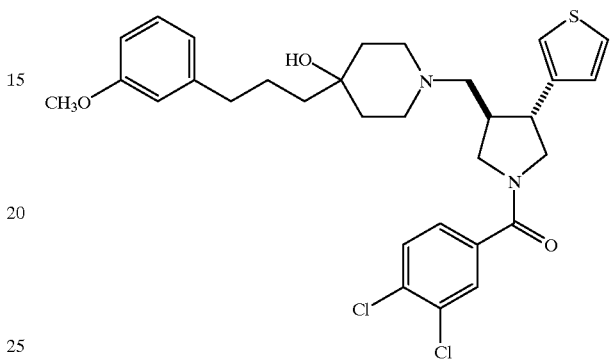

1-(3,4-Dichlorobenzoyl)-3-(RS)-(4-hydroxy-4-(3-(2-methoxyphenyl)propyl)piperidinylmethyl)-4-(SR)-(3-thienyl)pyrrolidine Mass Spectrum (ESI) m/e=587 (M+1 35Cl, 37Cl) and 589 (M+1 37Cl, 37Cl)

EXAMPLE 186

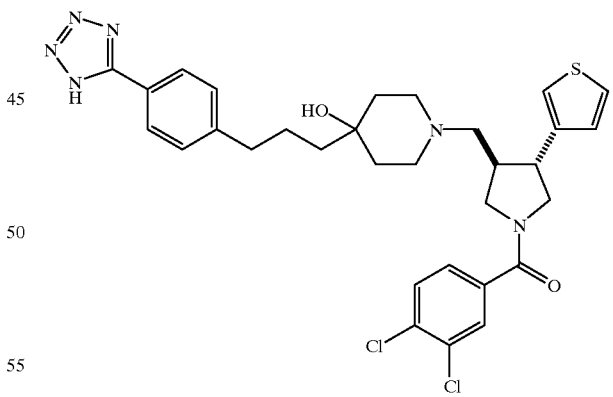

1-(3,4-Dichlorobenzoyl)-3-(RS)-(4-hydroxy-4-(3-(4-tetrazolylphenyl)propyl)piperidinylmethyl)-4-(SR)-(3-thienyl)pyrrolidine Mass Spectrum (ESI) m/e=625 (M+1 35Cl, 37Cl) and 627 (M+1 37Cl, 37Cl)

EXAMPLE 187

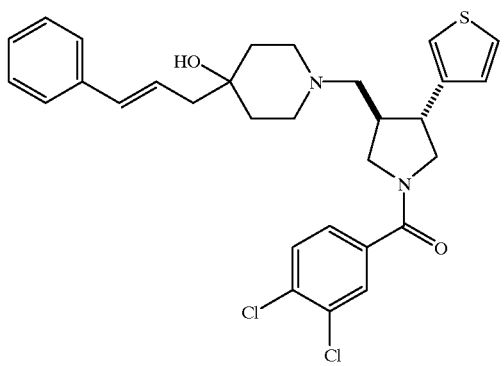

1-(3,4-Dichlorobenzoyl)-3-(RS)-(4-hydroxy-4-(3-phenyl-2-propenyl)piperidinylmethyl)-4-(SR)-(3-thienyl)pyrrolidine Mass Spectrum (ESI) m/e=555 (M+1 35Cl, 37Cl) and 557 (M+1 37Cl, 37Cl)

EXAMPLE 188

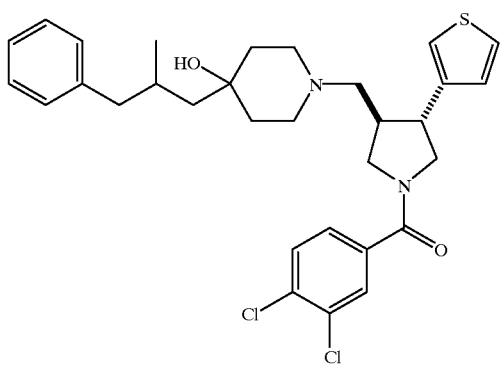

1-(3,4-Dichlorobenzoyl)-3-(RS)-(4-hydroxy-4-(2-methyl-3-phenylpropyl)piperidinylmethyl)-4-(SR)-(3-thienyl)pyrrolidine Mass Spectrum (ESI) m/e=571 (M+1 35Cl, 35Cl)

EXAMPLE 189

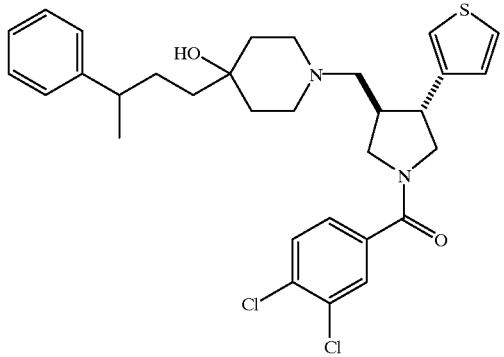

1-(3,4-Dichlorobenzoyl)-3-(RS)-(4-hydroxy-4-(3-methyl-3-phenylpropyl)piperidinylmethyl)-4-(SR)-(3-thienyl)pyrrolidine Mass Spectrum (ESI) m/e=571 (M+1 35Cl, 35Cl)

The following Examples 190 to 191 were prepared from 1-allyl-3-(SR)-formyl-4-(SR)-thiophen-3-ylpyrrolidine according to procedures described in Examples 123 or Examples 11 and 12. The source or preparation of the substituents at C3 will be described.

EXAMPLE 190

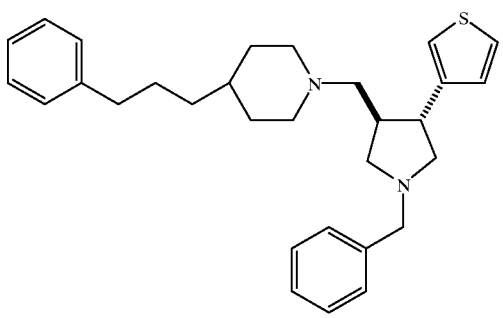

1-Benzyl-3-(RS)-(4-(3-phenylpropyl)piperidinylmethyl)-4-(SR)-(3-thienyl)pyrrolidine Mass Spectrum (ESI) m/e=459 (M+1)

4-(3-Phenylpropyl)piperidine is available form Aldrich Fine Chemicals.

EXAMPLE 191

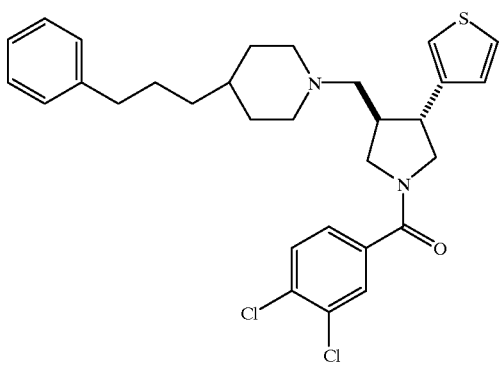

1-(3,4-Dichlorobenzoyl)-3-(RS)-(4-(3-phenylpropyl)piperidinylmethyl)-4-(SR)-(3-thienyl)pyrrolidine Mass Spectrum (ESI) m/e=541 (M+1 35Cl, 35Cl) and 543 (M+1 35Cl, 37Cl)

EXAMPLE 192

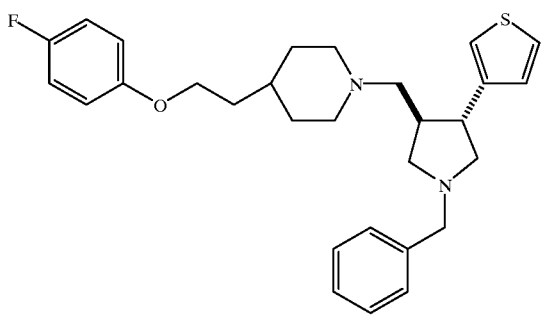

1-Benzyl-3-(RS)-(4-(2-(4-fluorophenoxy)ethyl) piperidinylmethyl)-4-(SR)-(3-thienyl)pyrrolidine Mass Spectrum (ESI) m/e=479 (M+1)

Preparation of 4-(2-(4-fluorophenoxy)ethyl) piperidine

Step 1

1-Benzyl-4-(2-(4-fluorophenoxy)ethyl)piperidine

To a solution of 1.5 g (6.84 mmol) of 1-benzyl-4-(2-hydroxy-1-ethyl)piperidine (Acros Chemical), 3.8 g (34.2 mmol) of 4-fluorophenol and 3.6 g (13.7 mmol) of triphenylphosphine in 25 mL of ether at 0° C. was slowly added dropwise 2.15 mL (13.7 mmol) of diethylazodicarboxylate (DEAD). The reaction mixture was allowed to warm to rt and was stirred for 12 h. To the reaction mixture was added 70 mL of ether and it was filtered through a thin pad of celite. The filtrate was washed with sat'd $Na_2CO_3$ solution and sat's NaCl solution. It was dried over $MgSO_4$, filtered and the filtrate concentrated. The residue was purified by chromatography (silica, hexanes: ethyl acetate, 4:1) to give 0.85 g of the title compound.

Step 2

4-(2-(4-fluorophenoxy)ethyl)piperidine

The title compound was prepared as described in Example 122.

EXAMPLE 193

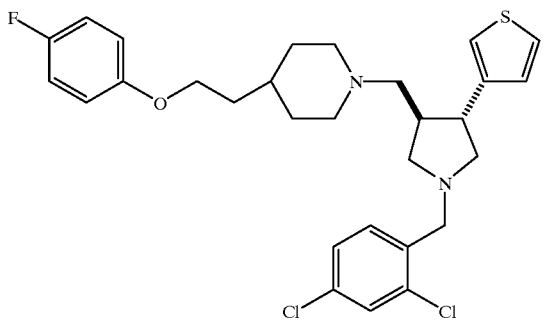

1-(2,4-Dichlorobenzyl)-3-(RS)-(4-(2-(4-fluorophenoxy)ethyl)piperidinylmethyl)-4-(SR)-(3-thienyl)pyrrolidine Mass Spectrum (ESI) m/e=529 (M+1 35Cl, 35Cl) and 531 (M+1 37Cl, 37Cl)

EXAMPLE 194

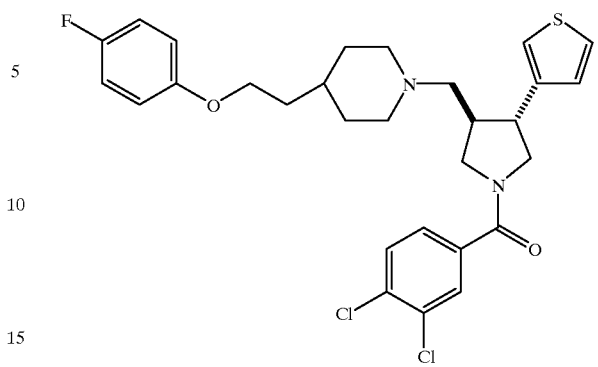

1-(3,4-Dichlorobenzoyl)-3-(RS)-(4-(2-(4-fluorophenoxy)ethyl)piperidinylmethyl)-4-(SR)-(3-thienyl)pyrrolidine Mass Spectrum (ESI) m/e=561 (M+1 35Cl, 35Cl) and 563 (M+1 35Cl, 37Cl)

EXAMPLE 195

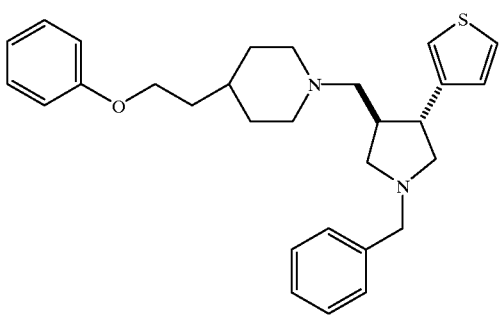

1-Benzyl-3-(RS)-(4-(2-phenoxy)ethyl) piperidinylmethyl)-4-(SR)-(3-thienyl)pyrrolidine Mass Spectrum (ESI) m/e=461 (M+1)

4-(2-Phenoxy-1-ethyl)piperidine was prepared as described in Example 193.

EXAMPLE 196

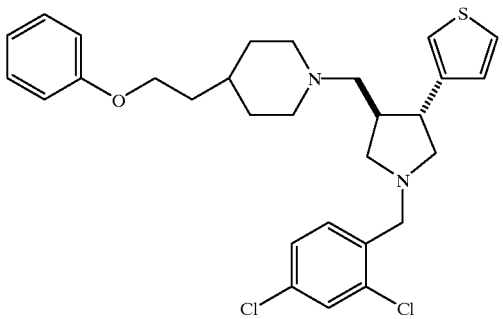

1-(2,4-Dichlorobenzyl)-3-(RS)-(4-(2-phenoxy)ethyl) piperidinylmethyl)-4-(SR)-(3-thienyl)pyrrolidine Mass Spectrum (ESI) m/e=529 (M+1 35Cl, 35Cl) and 531 (M+1 35Cl, 37Cl)

EXAMPLE 197

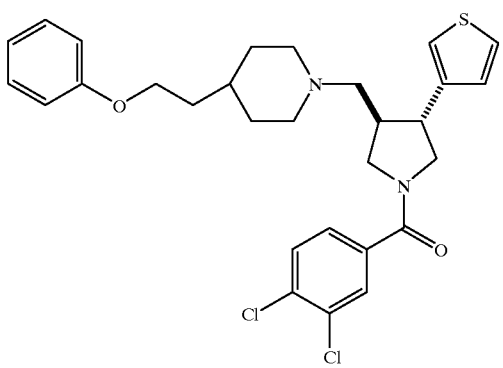

1-(3,4-Dichlorobenzoyl)-3-(RS)-(4-(2-(4-fluorophenoxy)ethyl)piperidinylmethyl)-4-(SR)-(3-thienyl)pyrrolidine Mass Spectrum (ESI) m/e=543 (M+1 35Cl, 35Cl) and 545 (M+1 35Cl, 37Cl)

EXAMPLE 198

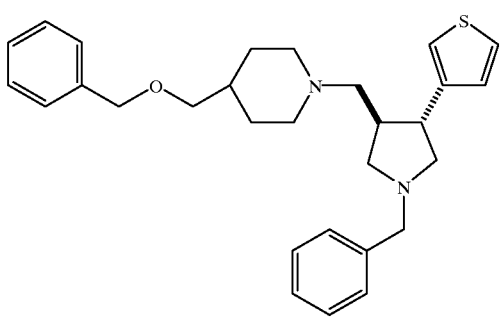

1-Benzyl-3-(RS)-(4-(benzyloxymethyl)piperdinylmethyl)-4-(SR)-(3-thienyl)pyrrolidine Mass Spectrum (ESI) m/e=461 (M+1)

4-(Benzyloxymethyl)piperidine is prepared according to proceudres described in Example 201.

EXAMPLE 199

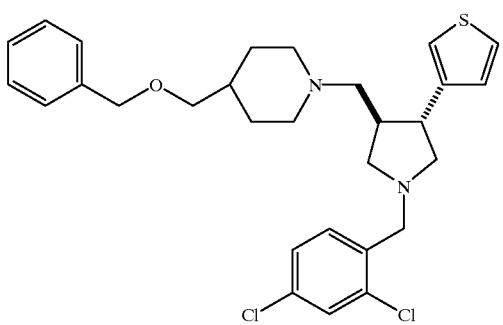

1-(2,4-Dichlorobenzyl)-3-(RS)-(4-(benzyloxymethyl)piperidinylmethyl)-4-(SR)-(3-thienyl)pyrrolidine Mass Spectrum (ESI) m/e=529 (M+1 35Cl) and 531 (M+1, 37Cl)

EXAMPLE 200

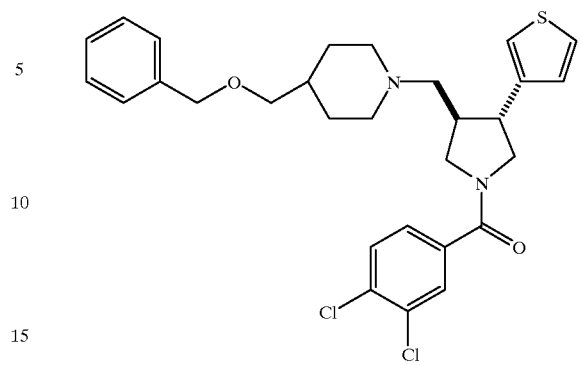

1-(3,4-Dichlorobenzoyl)-3-(RS)-(4-(benzyloxymethyl)piperidinylmethyl)-4-(SR)-(3-thienyl)pyrrolidine Mass Spectrum (ESI) m/e=543 (M+1 35Cl) and 545 (M+1 37Cl)

EXAMPLE 201

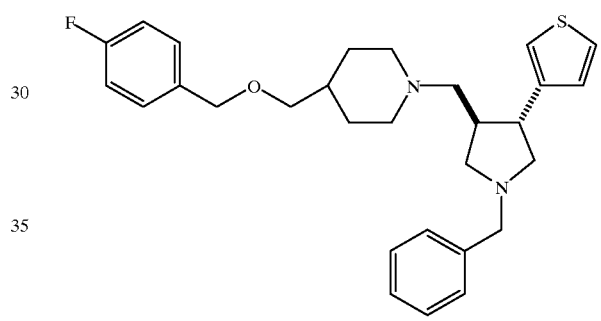

1-Benzyl-3-(RS)-(4-(4-fluorobenzyloxymethyl)piperidinylmethyl)-4-(SR)-(3-thienyl)pyrrolidine Mass Spectrum (ESI) m/e=479 (M+1)

Preparation of 4-(4-Fluorobenzyloxymethyl)piperidine

Step 1

4-Hydroxymethylpiperidine

To a mixture of 28.2 g (696.6 mmol) of LiAlH$_4$ in 800 mL of THF at rt was carefully added 30 g (232.2 mmol) of 4-carboxypiperidine (isonipecotic acid, Aldrich) and the reaction mixture was stirred at rt for 24 h. To the reaction mixture was slowly added 30 mL of H$_2$O over 2 h, followed by 30 mL of a 15% NaOH solution and 30 mL of H$_2$O. The mixture was diluted with ether filtered and the solids were triturated several times with ethyl acetate. The combined organic fractions were concentrated to give 22.2 g of the title compound.

Step 2

1-t-Butoxycarbonyl-4-hydroxymethylpiperidine

To a stirred mixture of 22.2 g (193 mmol) of 4-hydroxymethyl piperidine in 100 mL of CH$_2$Cl$_2$ and 75 mL of a 15% solution of NaOH was added a solution of 63.2 g (289 mmol) of Boc$_2$O in 50 mL of CH2Cl2 over 2 h. After stirring for a further 30 min, the reaction mixture was extracted with 15% NaOH solution and sat'd NaCl solution. The organic fraction was dried over MgSO4, filtered and the filtrate was concentrated. THe residue was purified by chromatography (silica, hexanes:ethyl acetate, 19:1, then 4:1, then 1:1) to give 25 g of the title compound.

Step 3

1-t-Butoxycarbonyl-4-(4-fluorobenzyloxymethyl) piperidine

To a solution of 0.75 g (6.02 mmol) of 4-fluorobenzylbromide and 0.58 g (2.7 mmol) of 1-t-butoxycarbonyl-4-hydroxymethylpiperidine in 5 mL of THF was added 0.136 g (5.4 mmol) of NaH in 3 portions over 30 min. After 3.5 h, 50 mL of $H_2O$ was added to the reaction mixture and it was extracted with ethyl acetate. The combined organic fractions were washed with sat'd Nacl solution, dried over $MgSO_4$, filtered and the filtrate was concentrated. The residue was purified by chromatography (silica, hexanes:ethyl aceate, 4:1) to give 0.84 g of the title compound.

Step 4

4-(4-Fluorobenzyloxymethyl)piperidine

To a solution of 0.89 g (2.35 mmol) of 1-t-butoxycarbonyl-4-(4-fluorobenzyloxymethyl)piperidine in 8 mL of $H_2O$ at rt was added 2 mL of TFA and the reaction mixture was stirred for 2 h. To the reaction mixture was added 50 mL of 0.5N $H_2SO_4$. After stirring vigorously for 5 min, the mixture was was washed with $CH_2Cl_2$. The aqueous fraction was made basic with solid $K_2CO_3$ and extracted with $CH_2Cl_2$. The combined organic fractions were washed with sat'd NaCl solution, dried over $MgSO_4$ and filtered. The filtrate was concentrated to give the title compound.

EXAMPLE 202

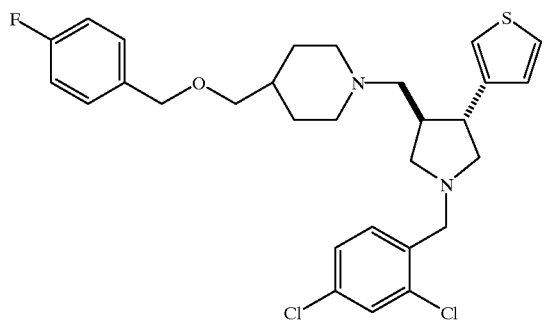

1-(2,4-Dichlorobenzyl)-3-(RS)-(4-(4-fluorobenzyloxymethyl)piperidinylmethyl)-4-(SR)-(3-thienyl)pyrrolidine Mass Spectrum (ESI) m/e=547 (M+1 35Cl) and 549 (M+1, 37Cl)

EXAMPLE 203

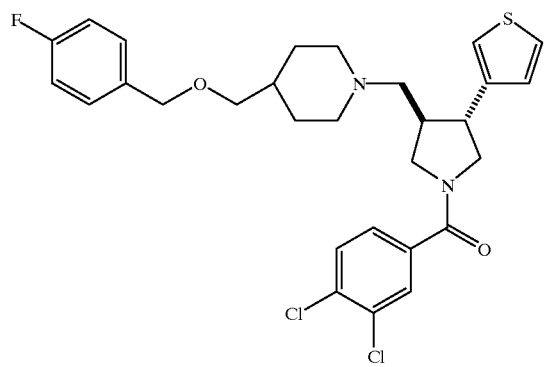

1-(3,4-Dichlorobenzoyl)-3-(RS)-(4-(4-fluorobenzyloxymethyl)piperidinylmethyl)-4-(SR)-(3-thienyl)pyrrolidine Mass Spectrum (ESI) m/e=561 (M+1 35Cl) and 563 (M+1 37Cl)

EXAMPLE 204

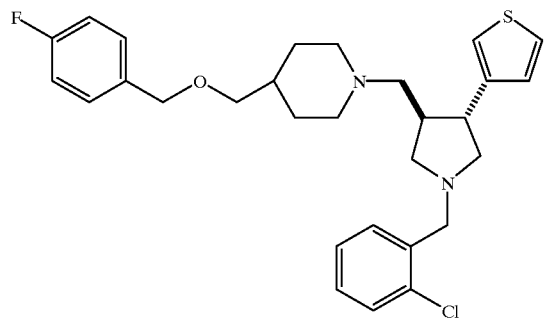

1-(2-Chlorobenzyl)-3-(RS)-(4-(4-fluorobenzyloxymethyl)piperidinylmethyl)-4-(SR)-(3-thienyl)pyrrolidine Mass Spectrum (ESI) m/e=513 (M+1 35Cl, 35Cl) and 515 (M+1 35Cl 37Cl)

EXAMPLE 205

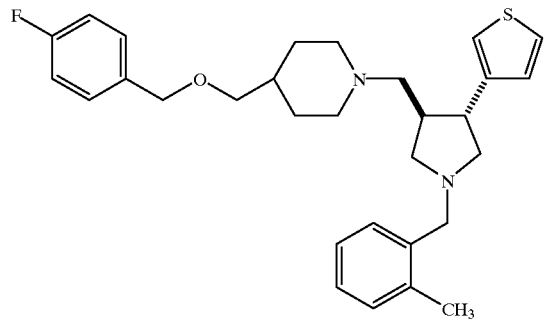

1-(2-Methylbenzyl)-3-(RS)-(4-(4-fluorobenzyloxymethyl)piperidinylmethyl)-4-(SR)-(3-thienyl)pyrrolidine Mass Spectrum (ESI) m/e=493 (M+1)

EXAMPLE 206

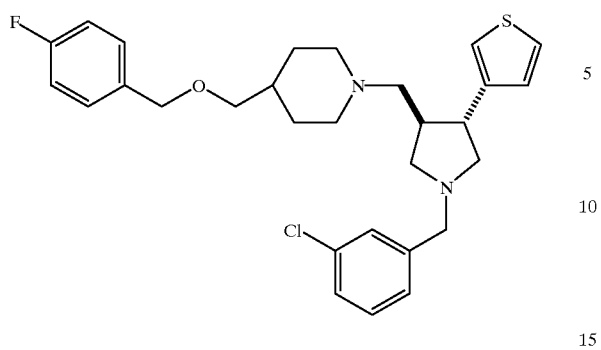

1-(3-Chlorobenzyl)-3-(RS)-(4-(4-fluorobenzyloxymethyl)piperidinylmethyl)-4-(SR)-(3-thienyl)pyrrolidine Mass Spectrum (ESI) m/e=513 (M+1 35Cl) and 515 (M+1, 37Cl)

EXAMPLE 207

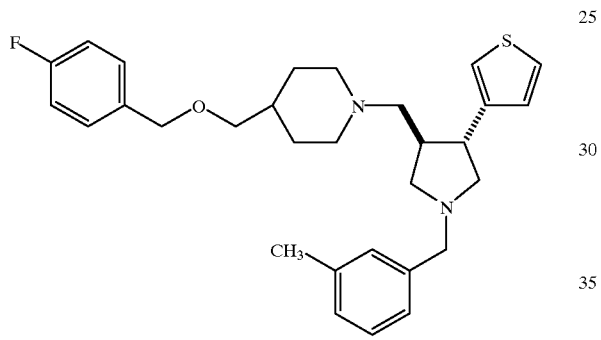

1-(3-Methylbenzyl)-3-(RS)-(4-(4-fluorobenzyloxymethyl)piperidinylmethyl)-4-(SR)-(3-thienyl)pyrrolidine Mass Spectrum (ESI) m/e=493 (M+1)

EXAMPLE 208

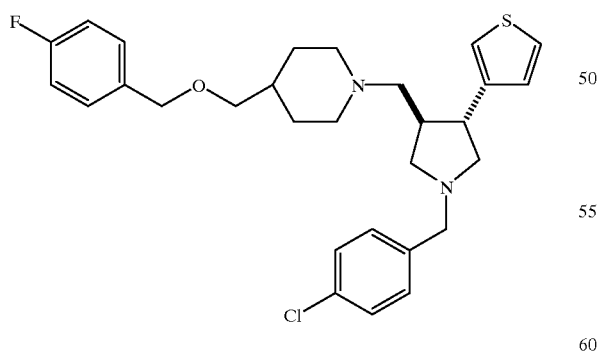

1-(4-Chlorobenzyl)-3-(RS)-(4-(4-fluorobenzyloxymethyl)piperidinylmethyl)-4-(SR)-(3-thienyl)pyrrolidine Mass Spectrum (ESI) m/e=513 (M+1 35Cl) and 515 (M+1 37Cl)

EXAMPLE 209

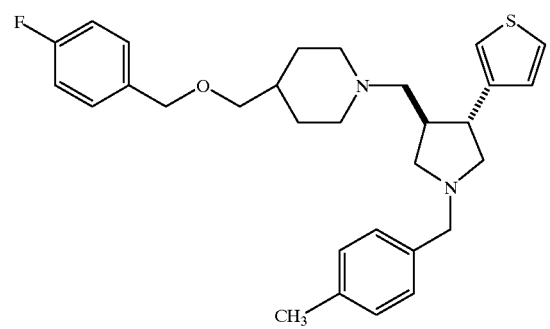

1-(4-Methylbenzyl)-3-(RS)-(4-(4-fluorobenzyloxymethyl)piperidinylmethyl)-4-(SR)-(3-thienyl)pyrrolidine Mass Spectrum (ESI) m/e=493 (M+1)

EXAMPLE 210

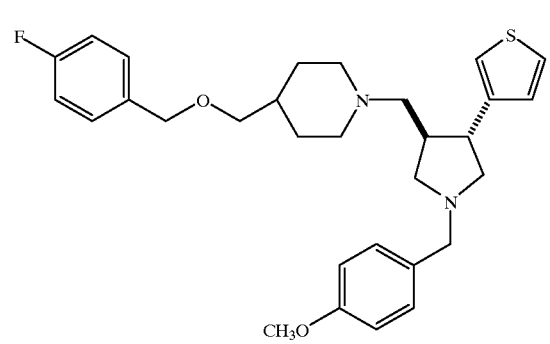

1-(4-Methoxybenzyl)-3-(RS)-(4-(4-fluorobenzyloxymethyl)piperidinylmethyl)-4-(SR)-(3-thienyl)pyrrolidine Mass Spectrum (ESI) m/e=509 (M+1)

EXAMPLE 211

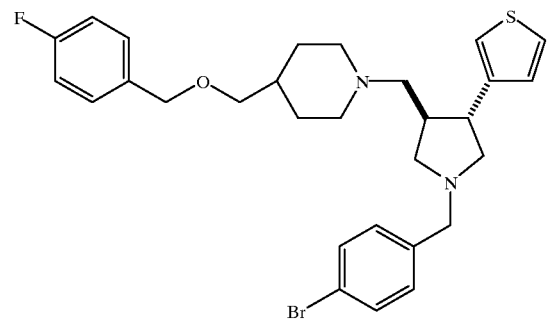

1-(4-Bromobenzyl)-3-(RS)-(4-(4-fluorobenzyloxymethyl)piperidinylmethyl)-4-(SR)-(3-thienyl)pyrrolidine Mass Spectrum (ESI) m/e=559 (M+1)

EXAMPLE 212

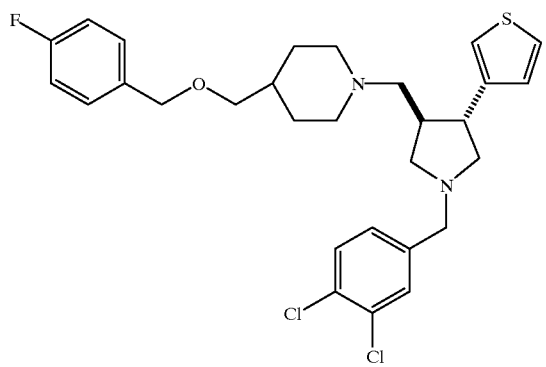

1-(3,4-Dichlorobenzyl)-3-(RS)-(4-(4-fluorobenzyloxymethyl)piperidinylmethyl)-4-(SR)-(3-thienyl)pyrrolidine Mass Spectrum (ESI) m/e=547 (M+1 35Cl, 35Cl), 549 (35Cl, 37Cl) and 551 (37Cl, 37Cl)

EXAMPLE 213

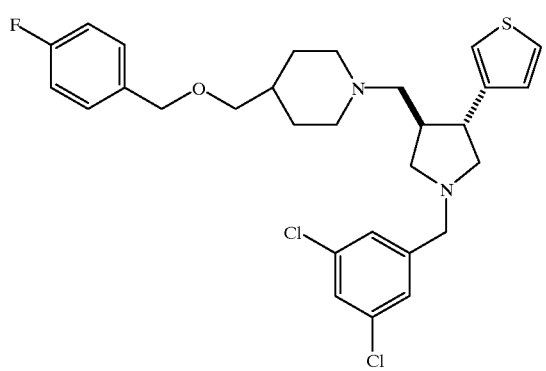

1-(3,5-Dichlorobenzyl)-3-(RS)-(4-(4-fluorobenzyloxymethyl)piperidinylmethyl)-4-(SR)-(3-thienyl)pyrrolidine Mass Spectrum (ESI) m/e=547 (M+1 35Cl, 35Cl), 549 (35Cl, 37Cl) and 551 (37Cl, 37Cl)

EXAMPLE 214

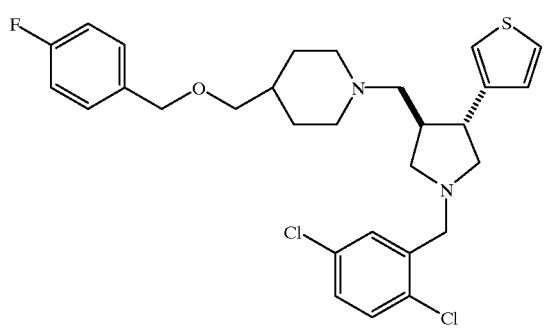

1-(2,5-Dichlorobenzyl)-3-(RS)-(4-(4-fluorobenzyloxymethyl)piperidinylmethyl)-4-(SR)-(3-thienyl)pyrrolidine Mass Spectrum (ESI) m/e=547 (M+1 35Cl, 35Cl), 549 (35Cl, 37Cl) and 551 (37Cl, 37Cl)

EXAMPLE 215

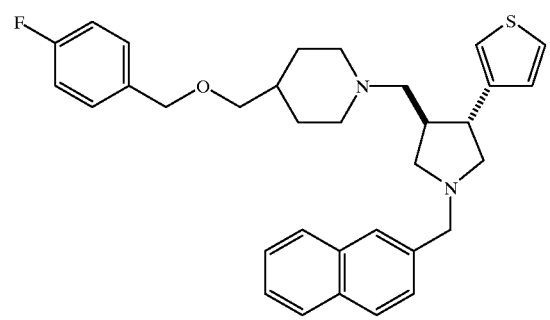

1-(2-Naphthyl)-3-(RS)-(4-(4-fluorobenzyloxymethyl)piperidinylmethyl)-4-(SR)-(3-thienyl)pyrrolidine Mass Spectrum (ESI) m/e=529 (M+1)

EXAMPLE 216

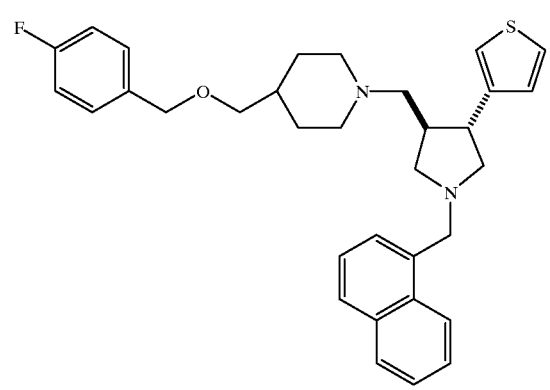

1-(1-Naphthylmethyl)-3-(RS)-(4-(4-fluorobenzyloxymethyl)piperidinylmethyl)-4-(SR)-(3-thienyl)pyrrolidine Mass Spectrum (ESI) m/e=529 (M+1)

EXAMPLE 218

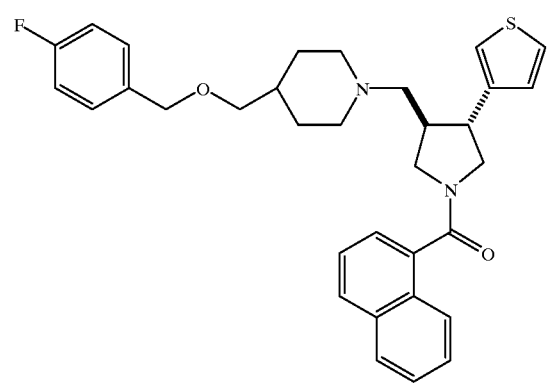

1-(1-Naphthoyl)-3-(RS)-(4-(4-fluorobenzyloxymethyl)piperidinylmethyl)-4-(SR)-(3-thienyl)pyrrolidine Mass Spectrum (ESI) m/e=543 (M+1)

EXAMPLE 219

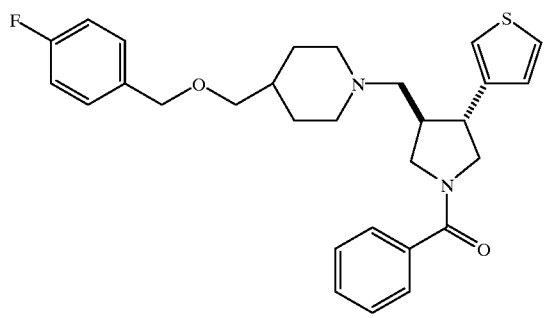

1-Benzoyl-3-(RS)-(4-(4-fluorobenzyloxymethyl)
piperidinylmethyl)-4-(SR)-(3-thienyl)pyrrolidine Mass Spectrum (ESI) m/e=493 (M+1)

EXAMPLE 220

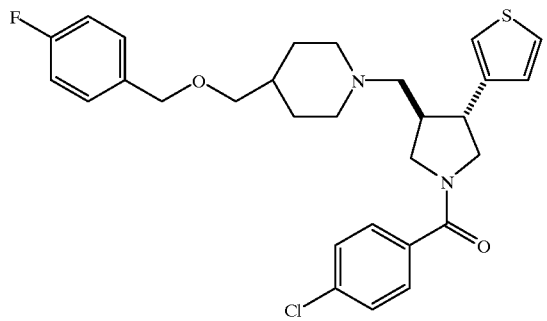

1-(4-Chlorobenzoyl)-3-(RS)-(4-(4-
fluorobenzyloxymethyl)piperidinylmethyl)-4-(SR)-
(3-thienyl)pyrrolidine Mass Spectrum (ESI) m/e=527 (M+1)

EXAMPLE 221

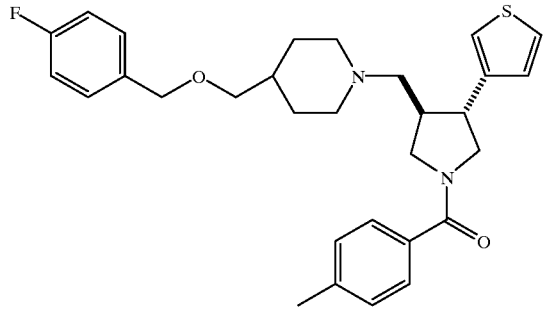

1-(4-Methylbenzoyl)-3-(RS)-(4-(4-
fluorobenzyloxymethyl)piperidinylmethyl)-4-(SR)-
(3-thienyl)pyrrolidine Mass Spectrum (ESI) m/e=507 (M+1)

EXAMPLE 222

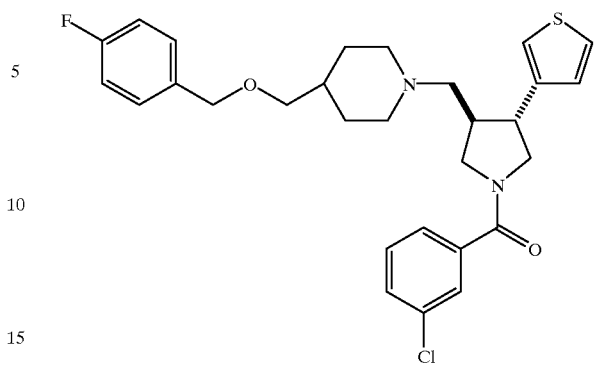

1-(3-Chlorobenzoyl)-3-(RS)-(4-(4-
fluorobenzyloxymethyl)piperidinylmethyl)-4-(SR)-
(3-thienyl)pyrrolidine Mass Spectrum (ESI) m/e=527 (M+1 35Cl) and 529
(M+1 37Cl)

EXAMPLE 223

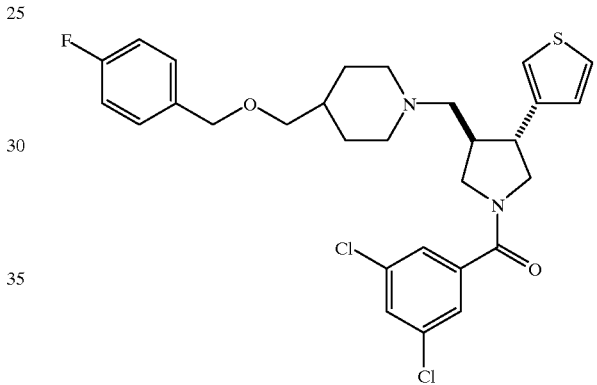

1-(2,6-Dichlorobenzoyl)-3-(RS)-(4-(4-
fluorobenzyloxymethyl)piperidinylmethyl)-4-(SR)-
(3-thienyl)pyrrolidine Mass Spectrum (ESI) m/e=561 (M+1 35Cl, 35Cl), 563
(M+1 35Cl, 37Cl) and 565 (M+1 37Cl, 37Cl)

EXAMPLE 224

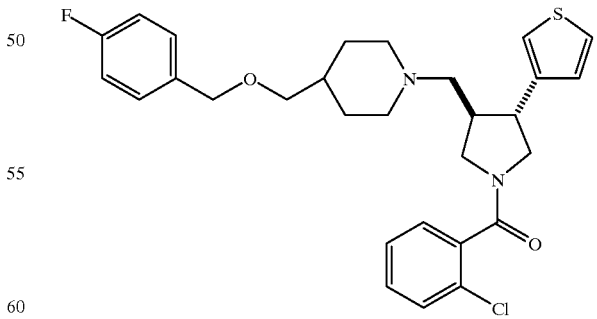

1-(2-Chlorobenzoyl)-3-(RS)-(4-(4-
fluorobenzyloxymethyl)piperidinylmethyl)-4-(SR)-
(3-thienyl)pyrrolidine Mass Spectrum (ESI) m/e=527 (M+1 35Cl) and 529
(M+1 37Cl)

EXAMPLE 225

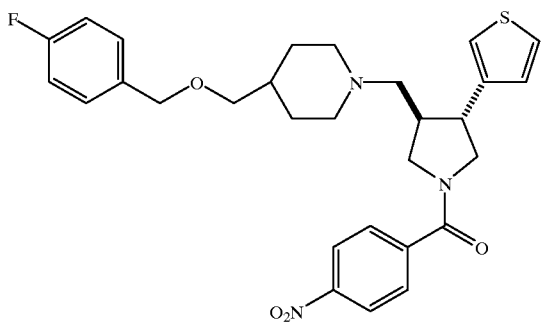

1-(4-Nitrobenzoyl)-3-(RS)-(4-(4-fluorobenzyloxymethyl)piperidinylmethyl)-4-(SR)-(3-thienyl)pyrrolidine Mass Spectrum (ESI) m/e=524 (M+1)

EXAMPLE 226

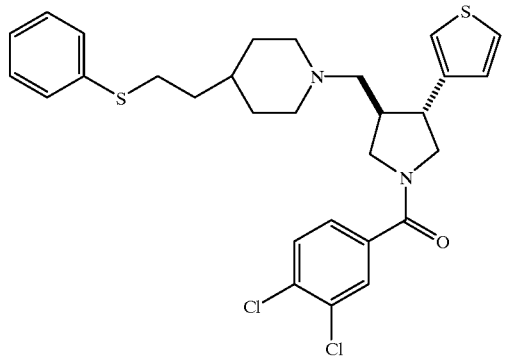

1-(3,4-Dichlorobenzoyl)-3-(RS)-(4-(2-(phenylmercapto)-1-ethyl)piperidinylmethyl)-4-(SR)-(3-thienyl)pyrrolidine Mass Spectrum (ESI) m/e=559 (M+1 35Cl, 35Cl) and 561 (M+1 35Cl, 37Cl)

Preparation of 4-(2-(Phenylmercapto)-1-ethyl)piperidine

Step 1

1-Benzyl-4-(2-(phenylmercapto)ethyl)piperidine

A solution of 1 g (4.56 mmol) of 1-benzyl-4-(2-hydroxyethyl)piperidine (Acros Chemical), 5 g (27.8 mmol) of diphenyldisulfide and 5.7 mL (27.9 mmol) of tri-n-butylphosphine in 35 mL of THF was heated at reflux for 46 h. The reaction mixture was concentrated and the residue was purified by chromatography (silica, hexanes:ehtyl acetate, 4:1) to give 1.32 g of the title compound.

Step 2

1-(2,2,2-Trichloroethoxycarbonyl)-4-(2-(phenylmercapto)ethyl)piperidine

A solution of 1.24 g (3.98 mmol) of 1-benzyl-4-(2-(phenylmercapto)-1-ethyl)piperidine and 0.61 mL (4.4 mmol) of 2,2,2-trichloroethylchloroformate in 10 mL of acetonitrile was stirred at rt for 2.5 h. The reaction mixture was concentrated and the residue was purified by chromatography (silica, hexanes:ehtyl acetate, 4:1) to give 1.48 g of the title compound.

Step 3

4-(2-(Phenylmercapto)ethyl)piperidine

To a solution of 1.47 g (3.71 mmol) of 1-(2,2,2-trichloroethoxycarbonyl)-4-(2-(phenylmercapto)ethyl)piperidine in 20 mL of glacial acetic acid was heated at 40° C. To this solution was added portionwise 2 g of zinc powder over a period of 1 h with vigorous stirring. After 24 h at 40° C., the reaction mixture was cooled to rt and carefully poured into 250 mL of sat'd NaHCO₃ solution. The mixture was extracted 5 times with CH₂Cl₂ and the combined organic fractions were washed with sat'd NaCl solution, and dried over MgSO₄ and filtered. The filtrate was concentrated to give the title compound.

EXAMPLE 227

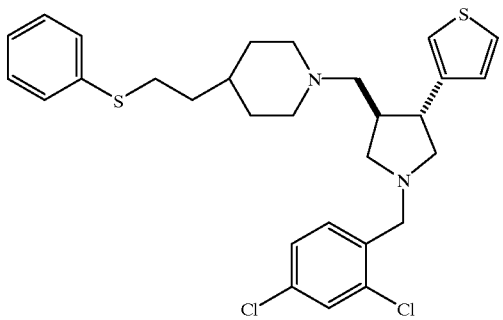

1-(2,4-Dichlorobenzyl)-3-(RS)-(4-(2-(phenylmercapto)ethyl)piperidinylmethyl)-4-(SR)-(3-thienyl)pyrrolidine Mass Spectrum (ESI) m/e=545 (M+1 35Cl, 35Cl) and 547 (M+1 35Cl, 37Cl)

EXAMPLE 228

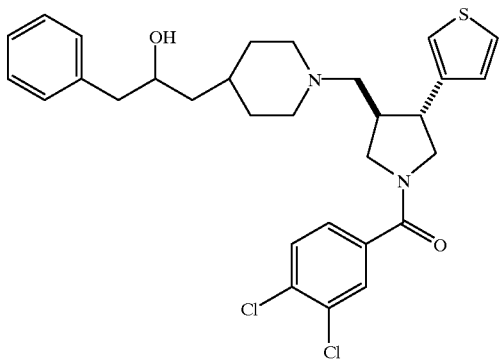

1-(3,4-Dichlorobenzoyl)-3-(RS)-(4-(4-(3-phenyl-2-hydroxy-1-propyl)piperidinylmethyl)-4-(SR)-(3-thienyl)pyrrolidine Mass Spectrum (ESI) m/e=557 (M+1 35Cl, 35Cl) and 559 (M+1 35Cl, 37Cl)

Preparation of 4-(3-phenyl-2-hydroxypropyl)piperidine

Step 1

1-Benzyl-4-(2-oxoethyl)piperidine

To a solution of 3 mL (34.4 mmol) of oxalyl chloride in 80 mL of CH$_2$Cl$_2$ at −78° C. was added a solution of 4.9 mL (68.8 mmol) of DMSO in 5 mL of CH$_2$Cl$_2$. After stirring for 10 min, a solution of 4 g (18.24 mmol) of 1-benzyl-4-(2-hydroxy-1-ethyl)piperidine (Acros Chemical) in 20 mL of CH$_2$Cl$_2$ was added dropwise. After 30 min, 12 mL (86.1 mmol) of Et$_3$N was added and the reaction mixture was allowed to warm to rt over a period of 30 min. To the reaction mixture was added 100 mL of H$_2$O and it was extracted with CH$_2$Cl$_2$. The combined organic fractions were washed with sat'd NaCl solution, and dried over MgSO$_4$ and filtered. The filtrate was concentrated to give 4 g of the title compound.

Step 2

1-Benzyl-4-(3-phenyl-2-hydroxypropyl)piperidine

To a solution of 4 g (18.24 mmol) of 1-Benzyl-4-(2-oxoethyl)piperidine in 40 mL of THF at 0° C. was added 20 mL (36.5 mmol) of benzyl magnesium chloride (2M in THF, Aldrich). THe reaction mixture was warmed to rt and stirred for 30 min. The reaction mixture was poured into 100 mL of sat'd NH$_4$Cl solution and extracted with EtOAc. The combined organic fractions were washed with sat'd Nacl solution, and dried over MgSO$_4$ and filtered. The filtrate was concentrated and purified by chromatography (silica, hexanes:ehtyl acetate, 4:1) to give 5.32 g of the title compound.

Step 3

4-(3-Phenyl-2-hydroxypropyl)piperidine

The benzyl group was removed as described in Example 226.

EXAMPLE 229

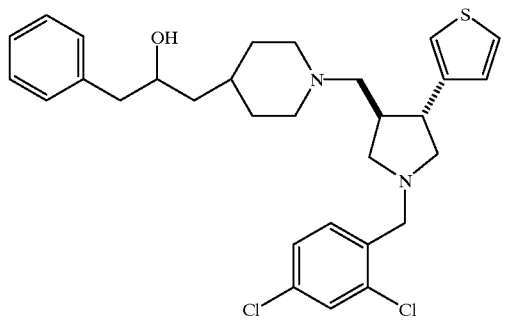

1-(2,4-Dichlorobenzyl)-3-(RS)-(4-(3-phenyl-2-hydroxypropyl)piperidinylmethyl)-4-(SR)-(3-thienyl)pyrrolidine Mass Spectrum (ESI) m/e=543 (M+1 35Cl, 35Cl), 545 (M+1 35Cl, 37Cl) and 547 (M+1, 37Cl, 37Cl).

EXAMPLE 230

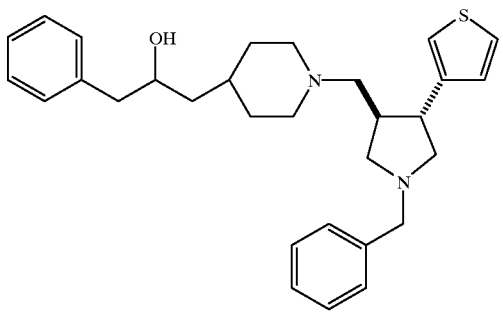

1-(2,4-Benzyl)-3-(RS)-(4-(3-phenyl-2-hydroxypropyl)piperidinylmethyl)-4-(SR)-(3-thienyl)pyrrolidine Mass Spectrum (ESI) m/e=475 (M+1)

EXAMPLE 231

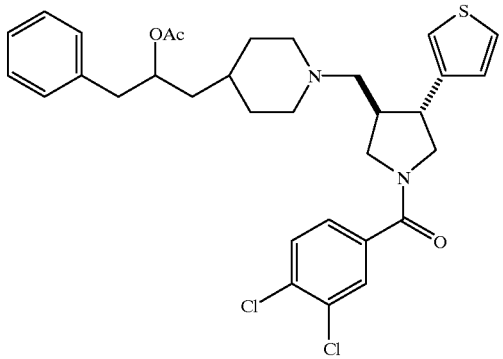

1-(3,4-Dichlorobenzoyl)-3-(RS)-(4-(4-(3-phenyl-2-acetoxypropyl)piperidinylmethyl)-4-(SR)-(3-thienyl)pyrrolidine A solution of 0.06 g (0.108 mmol) of 1-(3,4-dichlorobenzoyl)-3-(RS)-(4-(4-(3-phenyl-2-hydroxy-1-propyl)piperidinylmethyl)-4-(SR)-(3-thienyl)pyrrolidine, 0.2 mL of acetic anhydride and 0.25 mL of pyridine in 0.5 mL of CH$_2$Cl$_2$ was stirred at rt for 18 h. The reaction mixture was concentrated and azeotroped with heptane to remove pyridine. The residue was purified by chromatography (silica, acetone:hexanes, 1:10) to give the title compound.

Mass Spectrum (ESI) m/e=599 (M+1 35Cl, 35Cl) and 601 (M+1 35Cl, 37Cl).

EXAMPLE 232

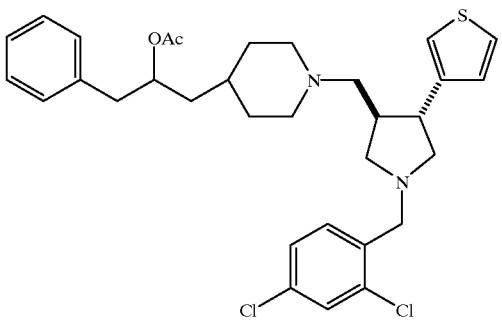

1-(2,4-Dichlorobenzyl)-3-(RS)-(4-(4-(3-phenyl-2-acetoxypropyl)piperidinylmethyl)-4-(SR)-(3-thienyl) pyrrolidine The title compound was prepared as described in Example 231.

Mass Spectrum (ESI) m/e=585 (M+1 35Cl, 35Cl) and 587 (M+1 35Cl, 37Cl).

EXAMPLE 233

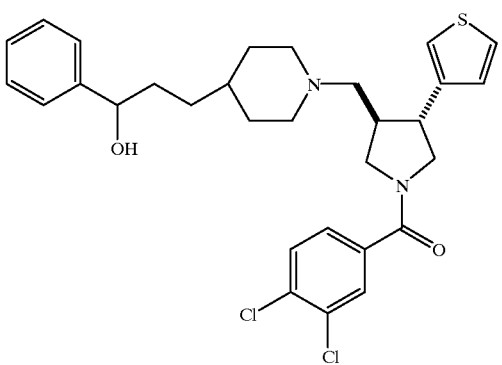

1-(3,4-Dichlorobenzoyl)-3-(RS)-(4-(4-(3-phenyl-3-hydroxypropyl)piperidinylmethyl)-4-(SR)-(3-thienyl)pyrrolidine Mass Spectrum (ESI) m/e=557 (M+1 35Cl, 35Cl), 559 (M+1 35Cl, 37Cl) and 561 (M+1, 37Cl, 37Cl).

Preparation of 4-(3-phenyl-3-hydroxypropyl) piperidine

Step 1

4-Hydroxymethylpiperidine

To a mixture of 28.2 g (696.6 mmol) of LiAlH$_4$ in 800 mL of THF at rt was carefully added 30 g (232.2 mmol) of 4-carboxypiperidine (isonipecotic acid, Aldrich) and the reaction mixture was stirred at rt for 24 h. To the reaction mixture was slowly added 30 mL of H$_2$O over 2 h, followed by 30 mL of a 15% NaOH solution and 30 mL of H$_2$O. The mixture was diluted with ether filtered and the solids were triturated several times with ethyl acetate. The combined organic fractions were concentrated to give 22.2 g of the title compound.

Step 2

1-t-Butoxycarbonyl-4-hydroxymethylpiperidine

To a stirred mixture of 22.2 g (193 mmol) of 4-hydroxymethylpiperidine in 100 mL of CH$_2$Cl$_2$ and 75 mL of a 15% solution of NaOH was added a solution of 63.2 g (289 mmol) of BOC$_2$O in 50 mL of CH$_2$Cl$_2$ over 2 h. After stirring for a further 30 min, the reaction mixture was extracted with 15% NaOH solution and sat'd Nacl solution. The organic fraction was dried over MgSO4, filtered and the filtrate was concentrated. The residue was purified by chromatography (silica, hexanes:ehtyl acetate, 19:1, then 4:1, then 1:1) to give 25 g of the title compound.

Step 3

1-t-Butoxycarbonyl-4-formylpiperidine

To a solution of 1.75 mL (20 mmol) of oxalyl chloride in 20 mL of CH$_2$Cl$_2$ at −78° C. was added a solution of 2.13 mL (30 mmol) of DMSO in 5 mL of CH$_2$Cl$_2$ and the reaction mixture was stirred for 20 min at −78° C. To this reaction mixture was then added a solution of 2.41 g (11.2 mmol) of 1-t-butoxycarbonyl-4-hydroxymethylpiperidine in 10 mL of CH$_2$Cl$_2$. After stittring for 30 min, 7 mL of Et$_3$N was then added and the reaction mixture was allowed to slowly warm to rt and stirred at rt for 1 h. To the reaction mixture was added 50 mL of H$_2$O and the mixture was extracted with CH$_2$Cl$_2$. The combined organic fractions were washed with sat'd NaCl solution, dried over MgSO$_4$, filtered and the filtrate was cocentrated give 2.45 g of the title compound which was used without further purification.

Step 4

1-t-Butoxycarbonyl-4-(3-phenyl-2-oxopropenyl) piperidine

To a mixture of 1.95 g (16.5 mmol) of KOtBu in 20 mL of THF at 0° C. was added a solution of 3.6 mL (16.6 mmol) of diethyl(2-oxo-2-phenethyl)phosphonate in 10 mL of THF. The reaction mixture was stirred for 15 min at 0° C. then was warmed to rt. To this mixture was added a solution of 2.39 g (11.2 mmol) of 1-t-butoxycarbonyl-4-formylpiperidine in in 10 mL of THF and the reaction mixture stirred for 3 h. The reaction mixture was then poured into 100 mL of sat'd NH4Cl solution and it was extracted with ethyl acetate. The combined organic fractions were washed with sat'd Nacl solution, dried over MgSO$_4$ and filtered. The filtrate was concentrated and the residue was purified by chromatography (silica, hexanes:ehtyl acetate, 5:1) to give 2.9 g of the title compound.

Step 5

1-t-Butoxycarbonyl-4-(3-phenyl-3-hydroxypropyl) piperidine

A mixture of 2 g of 1-t-butoxycarbonyl-4-(3-phenyl-2-oxopropenyl)piperidine and 0.5 g of 10% Pd/C in 50 mL of CH$_3$OH was hydrogenated at 50 psi for 15 h. The reaction mixture was then filtered through a thin pad of celite and the filtrate was concentrated. The residue was purified by chromatography (silica, hexanes:ehtyl acetate, 4:1) to give 1.5 g of the title compound.

Step 6

4-(3-Phenyl-3-hydroxypropyl)piperidine

To a solution of 1.48 g (4.66 mmol) of 1-t-butoxycarbonyl-4-(3-phenyl-3-hydroxypropyl)piperidine in 8 mL of CH$_2$Cl$_2$ at rt was added 2 mL of trifluoroacetic acid. After stirring for 2 h at rt, the reaction mixture was poured into 100 mL of sat'd NaHCO$_3$ solution and extracted with CH$_2$Cl$_2$. The combined organic fractions were dried over MgSO$_4$, filtered and the filtrate was concentrated to give 1.2 g of the title compound.

EXAMPLE 234

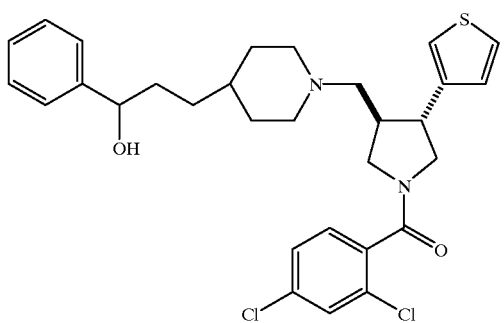

1-(2,4-Dichlorobenzyl)-3-(RS)-(4-(3-phenyl-3-hydroxypropyl)piperidinylmethyl)-4-(SR)-(3-thienyl)pyrrolidine Mass Spectrum (ESI) m/e=543 (M+1 35Cl, 35Cl), 545 (M+1 35Cl, 37Cl).

EXAMPLE 235

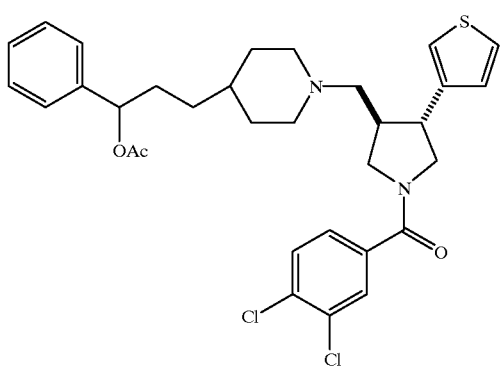

1-(3,4-Dichlorobenzoyl)-3-(RS)-(4-(4-(3-phenyl-3-acetoxypropyl)piperidinylmethyl)-4-(SR)-(3-thienyl)pyrrolidine The title compound was prepared as described in Example 231.

Mass Spectrum (ESI) m/e=599 (M+1 35Cl, 1 35Cl), 601 (M+1 35Cl, 37Cl).

EXAMPLE 236

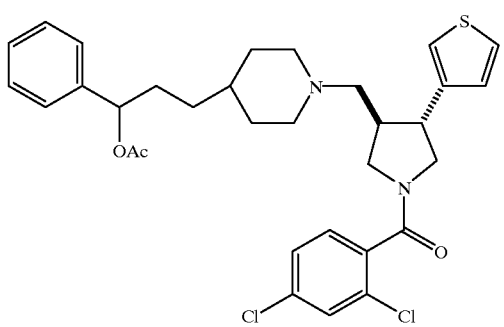

1-(2,4-Dichlorobenzyl)-3-(RS)-(4-(3-phenyl-3-acetoxypropyl)piperidinylmethyl)-4-(SR)-(3-thienyl)pyrrolidine The title compound was prepared as described in Example 231.

Mass Spectrum (ESI) m/e=585 (M+1 35Cl, 35Cl), 587 (M+1 35Cl, 37Cl).

EXAMPLE 237

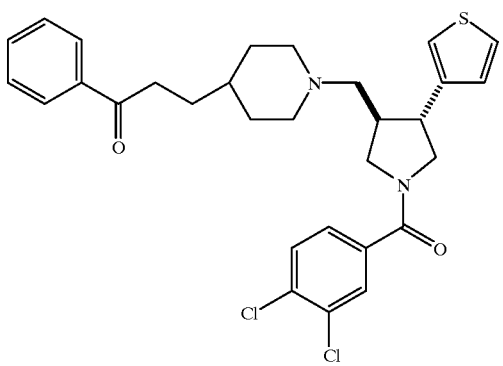

1-(2,4-Dichlorobenzyl)-3-(RS)-(4-(3-phenyl-3-oxopropyl)piperidinylmethyl)-4-(SR)-(3-thienyl)pyrrolidine The title compound was prepared from 1-(3,4-dichlorobenzoyl)-3-(RS)-(4-(4-(3-phenyl-3-hydroxypropyl)piperidinylmethyl)-4-(SR)-(3-thienyl)pyrrolidine (Example 233) according to procedures described in Example 233, Step 3.

Mass Spectrum (ESI) m/e=555 (M+1 35Cl, 35Cl), 557 (M+1 35Cl, 37Cl).

EXAMPLE 238

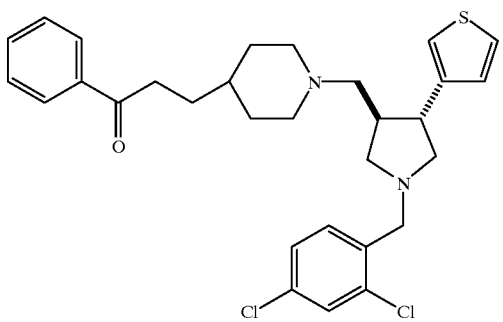

1-(2,4-Dichlorobenzyl)-3-(RS)-(4-(4-(3-phenyl-3-oxopropyl)piperidinylmethyl)-4-(SR)-(3-thienyl)pyrrolidine The title compound was prepared from 1-(2,4-dichlorobenzyl)-3-(RS)-(4-(3-phenyl-3-hydroxypropyl)piperidinylmethyl)-4-(SR)-(3-thienyl)pyrrolidine (Example 234) according to procedures described in Example 233, Step 3.

Mass Spectrum (ESI) m/e=541 (M+1 35Cl, 35Cl), 543 (M+1 35Cl, 37Cl) and 545 (M+1 37Cl, 37Cl)

EXAMPLE 239

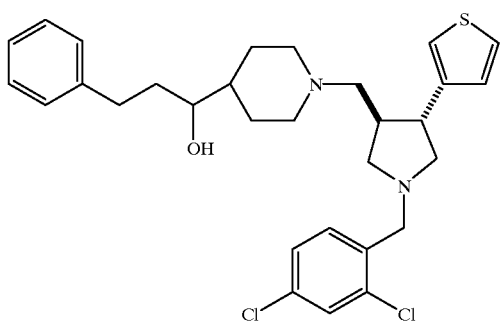

1-(2,4-Dichlorobenzyl)-3-(RS)-(4-(3-phenyl-1-hydroxypropyl)piperidinylmethyl)-4-(SR)-(3-thienyl)pyrrolidine Mass Spectrum (ESI) m/e=543 (M+1 35Cl, 35Cl), 545 (M+1 35Cl, 37Cl).

Preparation of 4-(3-phenyl-1-hydroxypropyl)piperidine

To a solution of 5 mL (34.5 mmol) of (2-iodoethyl)benzene in 100 mL of ether at −78° C. was added 42.6 mL (72.5 mmol) of t-butyl lithium. The reaction mixture was warmed to −20° C. for 20 min, then cooled to −78° C. TO this solution, was added a solution of 5.6 g (23.2 mmol) of 1-t-butoxy carbonyl-4-formylpiperidine in 50 mL of ether and the reaction mixture was stirred 15 min at −78° C. To the reaction mixture was added 150 mL of a sat'd solution of NH$_4$Cl and the mixture was extracted with ethyl acetate. The combined organic fractions were washed with sat'd NaCl solution, dried over MgSO$_4$, filtered and the filtrate was concentrated. Removal of the BOC protecting group was achieved as described in Example 233, Step 6 to give the title compound.

EXAMPLE 240

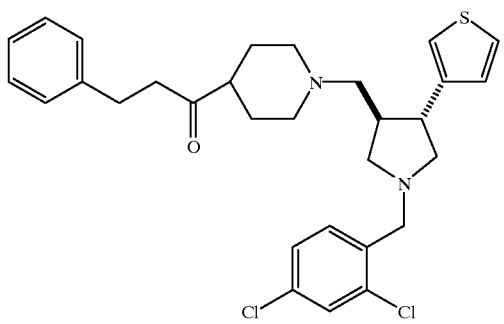

1-(2,4-Dichlorobenzyl)-3-(RS)-(4-(4-(3-phenyl-1-oxopropyl)piperidinylmethyl)-4-(SR)-(3-thienyl)pyrrolidine The title compound was prepared from 1-(2,4-dichlorobenzyl)-3-(RS)-(4-(3-phenyl-1-hydroxypropyl)piperidinylmethyl)-4-(SR)-(3-thienyl)pyrrolidine (Example 239) according to procedures described in Example 233, Step 3.

Mass Spectrum (ESI) m/e=541 (M+1 35Cl, 35Cl), 543 (M+1 35Cl, 37Cl) and 545 (M+1 37Cl, 37Cl)

EXAMPLE 241

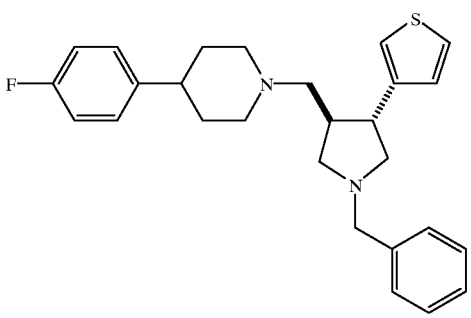

1-Benzyl-3-(R)-(4-(4-fluorophenyl)piperidinylmethyl)-4-(R)-(3-thienyl)pyrrolidine (RR)-stereoisomer of Example 5.

Step 1

N-trans-3-(3-Thienyl)acryloyl-4-(S)-benzyl-2-oxazolidinone

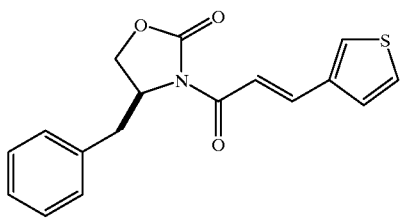

To a solution of 5 g (34 mmol) of 3-(3-thienyl)acrylic acid and 5.5 mL (39.7 mmol) of triethylamine in 160 mL of THF at 0° C was added 6.15 g (34.7 mmol) of pivaloyl chloride. The reaction mixture was allowed to warm to rt and was stirred for 2 h, then was cooled to −78° C.

Meanwhile, to a solution of 6.15 g (34.7 mmol) of (S)-benzyl-2-oxazolidinone in 60 mL of THF at −78° C. under nitrogen, was added 2.48 mL of nbutyllithium (1.6M, 39.7 mmol) and the solution was stirred for 30 min at −78° C. This was added via cannula to the first solution. After addition was complete, the solution was allowed to warm to room temperature for 2 h.

The reaction was quenched by addition of saturated aqueous NH$_4$Cl and the mixture was extracted with ethyl acetate. The organic layer was washed with brine, dried over MgSO$_4$, and filtered. The solution was concentrated and the residue was crystalized from hexanes to afford 8.43 g the title compound; $^1$H NMR (CDCl$_3$) δ7.92 (d, 1H, J=15.5 Hz), 7.76 (d, 1H, J=15.5 Hz), 7.62 (d, 1H, J=1.9 Hz), 4.79–4.83 (m, 1H)4.20–4.27 (m, 3H), 3.38 (d of d, 1H, J=13.5, 3.2 Hz), 2.87 (d of d, 1H, J=13.3, 9.4 Hz); Mass spectrum (ESI) m/e=435 (M+1).

Step 2

(S)-N-(1-Benzyl-4-(S)-(3-thienyl)-3-(R)-pyrrolidinylcarbonyl)-4-benzyl-2-oxazolidinone and
(S)-N-(1-Benzyl-4-(R)-(3-thienyl)-3-(S)-pyrrolidinylcarbonyl)-4-benzyl-2-oxazolidinone

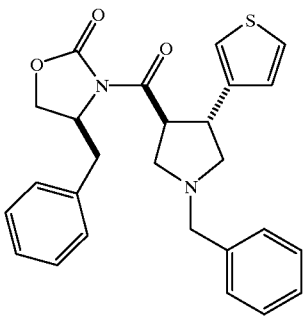

To a solution of 8.36 g (26.7 mmol) of N-trans-3-(3-thienyl)acryloyl-4-(S)-benzyl-2-oxazolidinone (Step 1) in 60 mL of CH$_2$Cl$_2$ at 0° C. was added 9.5 g (40 mmol) of N-(methoxymethyl-N-trimethylsilylmethylbenzylamine. Then 1 mL (13.4 mmol) of trifluoroacetic acid was added and the solution was stirred at 0° C for 1 h. The solution was poured into saturated NaHCO$_3$ solution and the layers were separated. The aqueous layer was washed with CH$_2$Cl$_2$ and the combined organic fractions were washed with brine, dried over MgSO$_4$, filtered, and the filtrate was concentrated. The residue was purified by chromatography (silica, ethyl acetate:hexanes, 1:4) to afford 7.7 g of the title compound (S)-N-[(1-Benzyl)-4-(S)-(3-thienyl)-3-(R)-pyrrolidinylcarbonyl]-4-benzyl-2-oxazolidinone. $^1$H NMR (CDCl$_3$) δ7.20–7.22 (m, 2H), 7.07–7.10 (m, 2H), 4.67–4.70 (m, 1H), 3.80 (d, 1H, J=13.1 Hz), 3.67 (d, 1H, J=13.1 Hz); Mass spectrum (ESI) m/e=447 (M+1); [α]$_D$=+114.7 (c=0.17, CHCl$_3$)

Futher elution afforded the title compound (S)-N-[(1-Benzyl)-4-(R)-(3-thienyl)-3-(S)-pyrrolidinylcarbonyl]-4-benzyl-2-oxazolidinone; $^1$H NMR (CDCl$_3$) d 7.11–7.16 (m, 4H), 4.69–4.74 (m, 1H), 3.79 (d, 1H, J=13.1 Hz), 3.69 (d, 1H, J=13.1 Hz); Mass spectrum (ESI) m/e=447 (M+1); [α]$_D$=+5.0 (c.=0.64, CHCl$_3$)

Step 3

1-Benzyl-3-(S)-hydroxymethyl-4-(R)-(3-thienyl)pyrrolidine

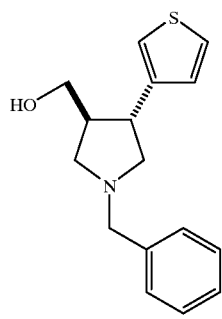

To a solution of 5.84 g (13.1 mmol) of (S)-N-[(1-Benzyl)-4-(R)-(3-thienyl)-3-(S)-pyrrolidinylcarbonyl]-4-benzyl-2-oxazolidinone (Step 2) in 60 mL of THF at 0° C. was added 15.7 mL (15.7 mmol) of a solution of LiAlH$_4$ (1.0 M in ether). The solution was stirred at room temperature for 3 h, then was quenched by addition of 5N NaOH solution. The mixture was diluted with ether and the organic fraction was washed twice with 5N NaOH solution. The combined organic fractions were dried over Na$_2$SO$_4$, filtered, and the filtrate concentrated. The residue was purified by chromatography (silica, acetone:hexanes, 1:6) to afford 3.22 g of the title compound. $^1$H NMR (CDCl$_3$) δ7.33–7.34 (m, 4H), 7.26–7.30 (m, 2H), 7.02–7.04 (m, 2H), 3.77 (d of d, 1H, J=10.3, 4.3 Hz), 3.68 (d of d, 1H, J=10.1, 5.0 Hz); Mass spectrum (ESI) m/e=274 (M+1); [α]$_D$=–13.6 (c.=1.60, CHCl$_3$).

Step 4

1-Benzyl-3-(S)-formyl-4-(R)-(3-thienyl)pyrrolidine

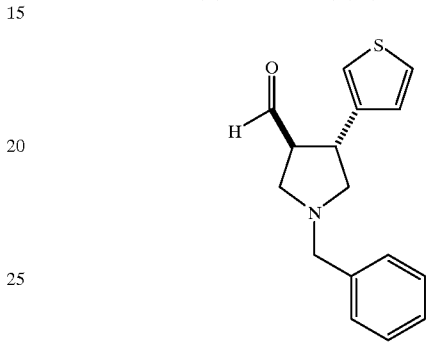

A solution of 2.04 mL (23.4 mmol) of oxalyl chloride in 40 mL of dry CH$_2$Cl$_2$ was cooled to –78° C. under nitrogen. To this was added 3.32 mL (46.8 mmol) of DMSO and the mixture was stirred at –78° C. for 15 min. A solution of 3.2 g (11.7 mmol) of 1-benzyl-3-(S)-hydroxymethyl-4-(R)-(3-thienyl)pyrrolidine in 20 mL of dry CH$_2$Cl$_2$ was added and the mixture was stirred at –78° C. for 15 min. Then 8.15 mL (58.5 mmol) of triethylamine were added and the solution was allowed to warm to room temperature over 1 h. The reaction mixture was diluted with 400 mL of ether, poured onto 200 mL of water and the layers were separated. The aqueous layer was washed with ether and the combined organic extracts were washed with saturated NaHCO$_3$ solution and brine. The organic fraction was dried over Na$_2$SO$_4$, filtered, and concentrated to afford the title compound, which was used directly in the next step.

Step 5

1-Benzyl-3-(R)-(4-(4-fluorophenyl)piperidinylmethyl)-4-(R)-(3-thienyl)pyrrolidine (RR)-stereoisomer of Example 5.

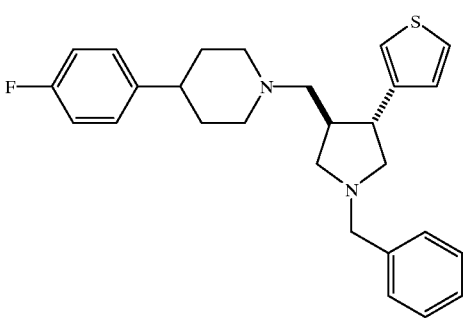

To a solution of 1.0 g (16.4 mmol) of 1-benzyl-3-(S)-formyl-4-(R)-(3-thienyl)pyrrolidine and 2.94 g (23.4 mmol) of 4-(4-fluorophenyl)piperidine in 50 mL of 1,2- dichlorethane was added 4.96 g (23.4 mmol) of sodium triacetoxyborohydride and the solution was stirred at rt for 16 h. The reaction was poured into 50 mL of saturated NaHCO$_3$ solution and the mixture was extracted with CH$_2$Cl$_2$. The combined organic extracts were washed with brine, dried over Na$_2$SO$_4$, filtered and concentrated. The residue was purified by chromatography (silica, acetone:hexanes, 1:3) to afford the title compound. $^1$H NMR (CDCl$_3$) δ6.97–7.10 (m, 4H), 3.72 (d, 1H, J=13.1 hz), 3.64 (d, 1H, J=13.0 Hz), 3.11–3.14 (m, 1H); Mass Spectrum (ESI) m/e 435 (M+1); [α]$_D$=−13.3 (c.=0.06, CHCl$_3$)

EXAMPLE 242

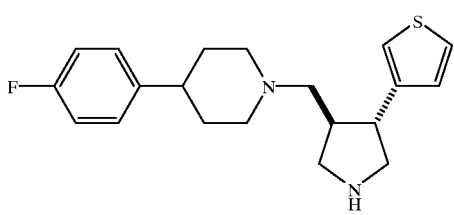

3-(S)-(4-(4-flurophenyl)piperidinylmethyl)-4-(R)-(3-thieny)pyrrolidine

Step 1

1-Methoxycarbonyl-3-(R)-(4-(4-fluorophenyl) piperidinylmethyl)-4-(R)-(3-thienyl)pyrrolidine To a solution of 4.35 g (10 mmol) of 1-benzyl-3-(R)-(4-(4-fluorophenyl)piperidinylmethyl)-4-(R)-(3-thienyl) pyrrolidine in 20 mL of THF at 0° C. was added 3.7 mL (26 mmol) of methylchloroformate and the reaction mixture was warmed to rt and stirred for 2 h. The reaction mixture was concentrated and the residue was purified by chromatography (silica, acetone: hexanes, 1:3) to give 3.5 g of the title compound.

Step 2

3-(S)-(4-(4-fluorophenyl)piperidinylmethyl)-4-(R)-(3-thienyl pyrrolidine

To a solution of 3.5 g (8.66 mmol) of 1-Methoxycarbonyl-3-(R)-(4-(4-fluorophenyl)piperidinylmethyl)-4-(R)-(3-thienyl)pyrrolidine in 30 mL of ethylene glycol was added 4.8 g (86 mmol) of KOH and 2.1 mL (43 mmol) of hydrazine hydrate and the reaction mixture was stirred at 140° C. for 10 h. The reaction mixture was then cooled and diluted with ether. The organic fraction was washed with sat'd NaHCO$_3$ and brine, dried over Na$_2$SO$_4$, filtered and concentrated to give the title compound. $^1$H NMR (CDCl$_3$) δ7.27–7.29 (m, 1H), 7.15–7.17 (m, 2H), 6.95–7.03 (m,4H), 3.31–3.38 (m, 2H); Mass Spectrum (ESI) m/e 345 (M+1); [α]$_D$=−47.0 (c.=0.45, CHCl$_3$).

EXAMPLE 243

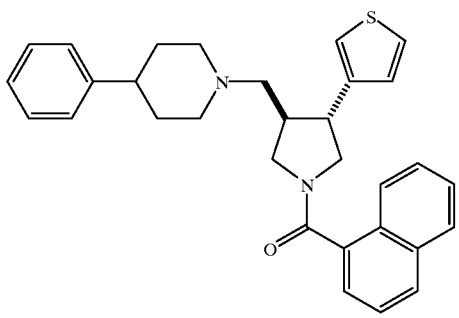

1-(1-Naphthoyl)-3-(R)-(4-phenylpiperidinylmethyl)-4-(R)-(3-thienyl)pyrrolidine

The title compound was obtained by separation of the stereoisomers of 1-(Naphthoyl)-3-(RS)-(4-phenylpiperidinylmethyl)-4-(RS)-(3-thienyl)pyrrolidine (Example 14) by HPLC chromatography (Daicel Chemical Industries LTD AD-chiral 250×20 mm I.D., iPrOH: hexanes, 6:4)

Mass Spectrum (CI) m/e=481 (M+1) [α]$_D$=−35.8 (c=1.06, CHCl$_3$)

EXAMPLE 244

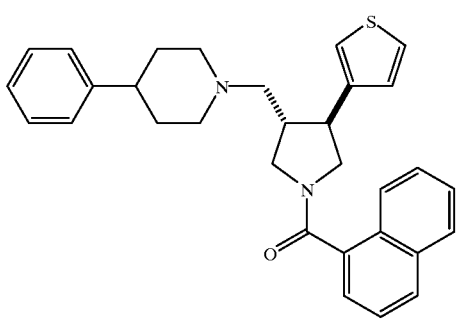

1-(Naphth-1-oyl)-3-(S)-(4-phenylpiperidinylmethyl)-4-(S)-(3-thienyl)pyrrolidine

The title compound was obtained by further elution of the HPLC chromatography of Example 243.

Mass Spectrum (CI) m/e=481 (M+1) [α]$_D$=+36.6 (c.= 0.095, CHCl$_3$)

The following compounds 245 to 257 were prepared from 3-(S)-(4-(4-fluorophenyl)piperidinylmethyl)-4-(R)-(3-thienyl)pyrrolidine and the corresponding acid chloride or acid as described in Examples 11 and 12, respectively. For those acids that were not commercially available, their preparations will be described.

EXAMPLE 245

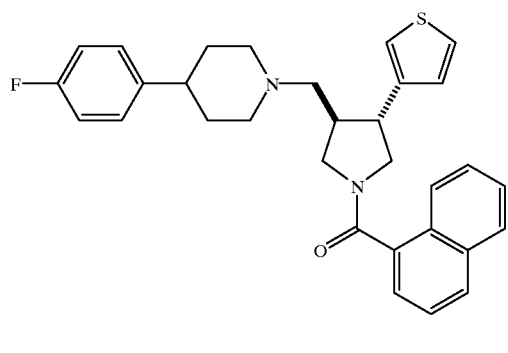

1-(1-Naphthoyl)-3-(R)-(4-(4-fluorophenyl)
piperidinylmethyl)-4-(R)-(3-thienyl)pyrrolidine Mass Spectrum (CI) m/e=499 (M+1) $[\alpha]_D$=−39.79 (c.= 0.95, CHCl$_3$)

EXAMPLE 246

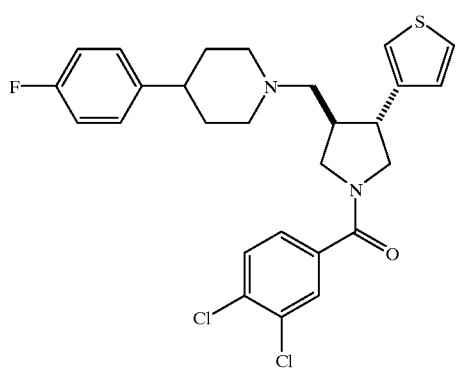

1-(3,4-Dichlorobenzoyl)-3-(R)-(4-(4-fluorophenyl)
piperidinylmethyl)-4-(R)-(3-thienyl)pyrrolidine Mass Spectrum (CI) m/e=517 (M+1 35Cl, 35Cl), 519 (M+1, 35Cl, 37Cl); $[\alpha]_D$ =−57.6 (HCl salt, c.=0.21, MeOH)

EXAMPLE 247

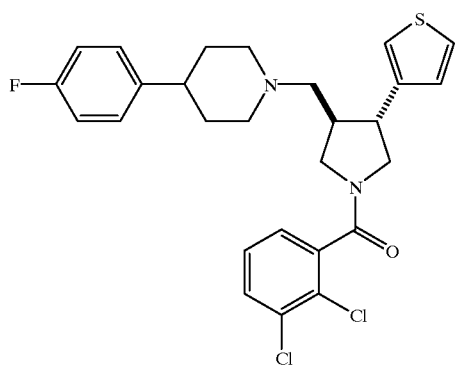

1-(2,3-Dichlorobenzoyl)-3-(R)-(4-(4-fluorophenyl)
piperidinylmethyl)-4-(R)-(3-thienyl)pyrrolidine Mass Spectrum (CI) m/e=517 (M+1 35Cl, 35Cl), 519 (M+1, 35Cl, 37Cl); $[\alpha]_D$=−33.6 (HCl salt, c.=0.21, MeOH)

EXAMPLE 248

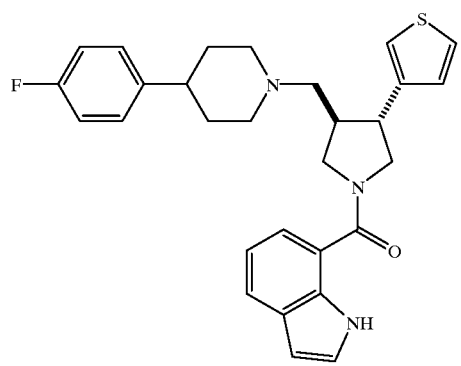

1-(7-Indolecarbonyl)-3-(R)-(4-(4-fluorophenyl)
piperidinylmethyl)-4-(R)-(3-thienyl)pyrrolidine Mass Spectrum (CI) m/e=488 (M+1); $[\alpha]_D$=−58.0 (c.= 0.8, HCl salt in MeOH)

EXAMPLE 249

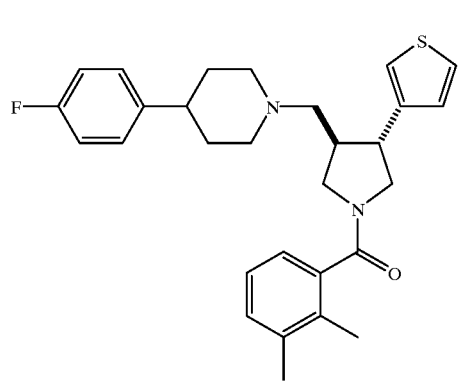

1-(2,3-Dimethylbenzoyl)-3-(R)-(4-(4-fluorophenyl)
piperidinylmethyl)-4-(R)-(3-thienyl)pyrrolidine Mass Spectrum (CI) m/e=477 (M+1); $[\alpha]_D$=−26.7 (c.= 0.468, HCl salt in MeOH)

EXAMPLE 250

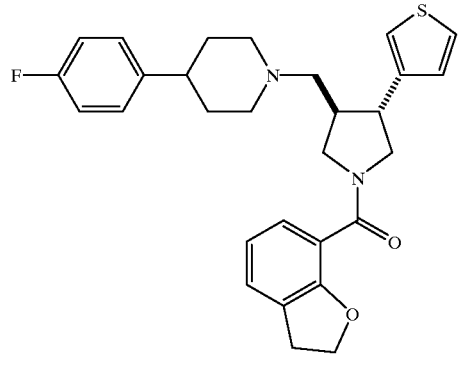

1-(7-2,3-Dihydrobenzofuranylcarbonyl)-3-(R)-(4-(4-fluorophenyl)piperidinylmethyl)-4-(R)-(3-thienyl)
pyrrolidine Mass Spectrum (CI) m/e =491 (M+1); $[\alpha]_D$=−59 (c.=0.28, HCl salt in MeOH)

EXAMPLE 251

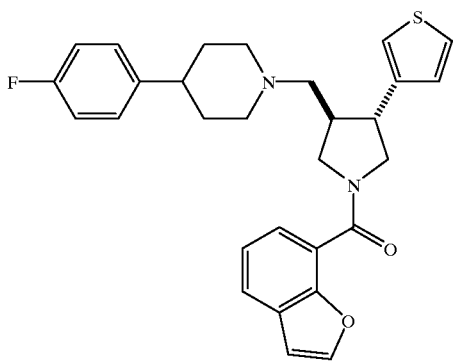

1-(7-Benzofuranylcarbonyl)-3-(R)-(4-(4-fluorophenyl)pipendinylmethyl)-4-(R)-(3-thienyl)pyrrolidine Mass Spectrum (CI) m/e=489 (M+1); $[\alpha]_D$=−54.9 (c.=0.40, HCl salt in MeOH)

Preparation of 7-benzofuranylcarboxylic acid

Step 1

7-Carbomethoxydihydrobenzofuran

A solution of 0.2 g (1.22 mmol) of 7-dihydrobenzofuran carboxylic acid, 0.13 g (1.22 mmol) of benzyl alcohol, 0.3 g (2.44 mmol) of DMAP and 0.46 g (2.44 mmol) of 1-[3-(dimethylamino)propyl]-3-ethyl carbodiimide hydrochloride in 5 mL of $CH_2Cl_2$ was stirred at rt for 12 h. The reaction mixture was partitioned between $CH_2Cl_2$ and water and the pH was adjusted to pH=1 with 1N HCl solution. The reaction mixture was extracted with $CH_2Cl_2$ and the combined organic fraction was dried over $MgSO_4$, filtered and the filtrate was concentrated. The residue was purified by chromatography (silica, hexanes: ethyl acetate, 6:1) to give 0.31 g of the title compound.

Step 2

7-Carbomethoxybenzofuran

A solution of 0.31 g (1.22 mmol) of 7-Carbomethoxy dihydrobenzofuran and 1.66 g (3.3 mmol) of DDQ in 25 mL of toluene was heated at reflux for 7 h. The reaction mixture was then cooled to rt, diluted with ether, and washed with 3×30 mL of sat'd $NaHCO_3$ solution. The organic fraction was dried over $MgSO_4$, filtered and the filtrate was concentrated. The residue was purified by chromatography (silica, hexanes: ethyl acetate, 9:1) to give 0.25 g of the title compound.

Step 3

7-Benzofuranylcarboxylic acid

A mixture of 0.25 g (0.99 mmol) of 7-Carbomethoxybenzofuran and 0.1 mL of $K_2CO_3$ (1N in water) in 6 mL of methanol was stirred at it for 24 h. The reaction mixture was filtered and the filtrate was concentrated. The residue was purified by chromatography (silica, hexanes: ethyl acetate, 4:1, then ethyl acetate: methanol, 9:1) to give 0.15 g of the title compound.

EXAMPLE 252

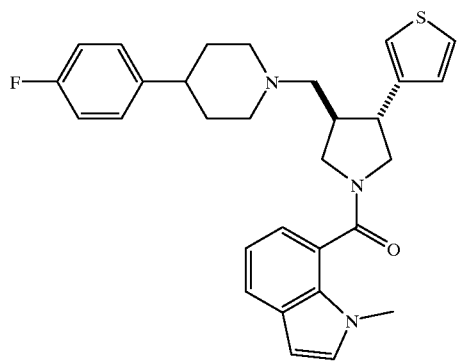

1-(N-methyl-7-indolecarbonyl)-3-(R)-(4-(4-fluorophenyl)plperidinylmethyl)-4-(R)-(3-thienyl)pyrrolidine Mass Spectrum (CI) m/e=502 (M+1); $[\alpha]_D$=−46.5 (c.=0.40, HCl salt in MeOH)

The preparation of N-methyl-7-indolylcarboxylic acid sidechain is described in Example 79.

EXAMPLE 253

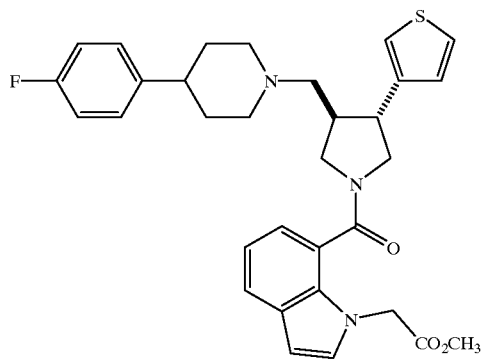

1-(1-Carbomethoxymethyl-7-indolecarbonyl)-3-(R)-(4-(4-fluorophenyl)piperidinylmethyl)-4-(R)-(3-thienyl)pyrrolidine To a suspension of 0.126 g (0.258 mmol) of 1-(7-indolecarbonyl)-3-(R)-(4-(4-fluorophenyl)piperidinylmethyl)-4-(R)-(3-thienyl)pyrrolidine in 6 mL of ether was added 0.082 g (0.31 mmol) of 18-crown-6 and 0.31 mL (0.31 mmol) of potassium t-butoxide (1M in t-BuOH). After stirring the reaction mixture at rt for 15 min, the reaction mixture was cooled to 0° C. and to it was added 0.034 mL (0.36 mmol) of methyl-2-bromoacetate. The reaction mixture was stirred at rt for 2 h. The reaction mixture was diluted with $CH_2Cl_2$ and washed with sat. $NaHCO_3$ solution. The organic fraction was dried over $Na_2SO_4$, filtered and the filtrate was concentrated and purified by chromatography (silica, hexanes: acetone, 3:1) to give the title compound.

$^1$H NMR ($CDCl_3$) δ7.67, 7.72 (d, 1H, J =8.0 Hz), 6.60, 6.64 (d, 1H, J=3Hz), 3.79, 3.74 (s, 3H); Mass Spectrum (CI) m/e=560 (M+1); $[\alpha]_D$=−56 (c.=0.32, MeOH)

EXAMPLE 254

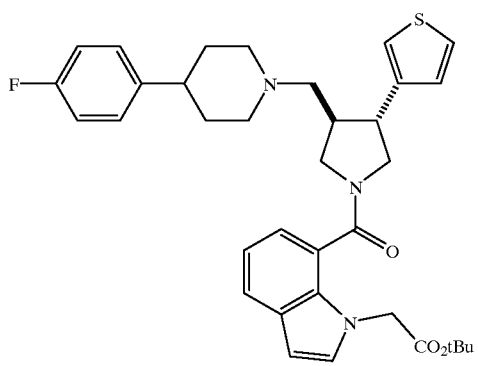

1-(1-t-Butoxycarbonylmethyl-7-indolecarbonyl)-3-(R)-(4-(4-fluorophenyl)piperidinylmethyl)-4-(R)-(3-thienyl)pyrrolidine The title compound was prepared as described in Example 13A. Mass Spectrum (CI) m/e=546 (M+1); $[\alpha]_D$=−65.0 (c.=0.20, HCl salt in MeOH)

EXAMPLE 255

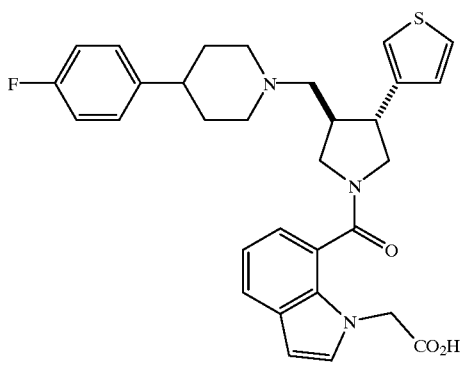

1-(1-Carboxymethyl-7-indolecarbonyl)-3-(R)-(4-(4-fluorophenyl)piperidinylmethyl)-4-(R)-(3-thienyl)pyrrolidine A solution of 0.185 g (0.307 mmol) of 1-(1-t-butoxycarbonyl methyl-7-indolecarbonyl)-3-(R)-(4-(4-fluorophenyl)piperidinylmethyl)-4-(R)-(3-thienyl)pyrrolidine in 6 mL of $CF_3CO_2H$ and 5 drops of $H_2O$ was stirred at rt for 1.5 h. The reaction mixture was concentrated and purified by chromatography (silica, $CH_2Cl_2$: ethyl acetate: $NH_3$ (2M in MeOH), 10:10:1, then $CH_2Cl_2$: MeOH: $NH_3$ (2M in MeOH) 100:8:4) to give the title compound.

Mass Spectrum (CI) m/e=545 (M+1); $[\alpha]_D$=−74.1 (c.=0.21, HCl salt in MeOH)

EXAMPLE 256

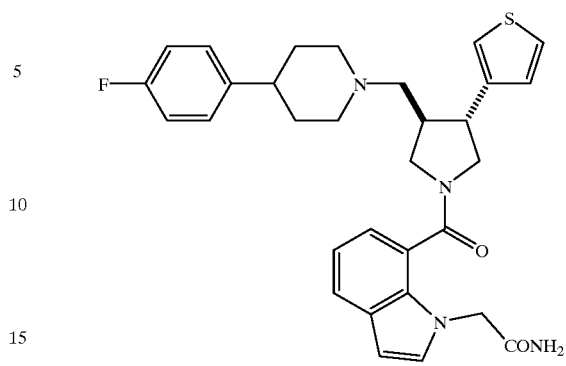

1-(1-Carboxamidomethyl-7-indolecarbonyl)-3-(R)-(4-(4-fluorophenyl)piperidinylmethyl)-4-(R)-(3-thienyl)pyrrolidine The title compound was prepared as described in Example 13A using 2-bromoacetamide.

Mass Spectrum (CI) m/e=531 (M+1); $[\alpha]_D$=−59.7 (c.=0.30, HCl salt in MeOH)

EXAMPLE 257

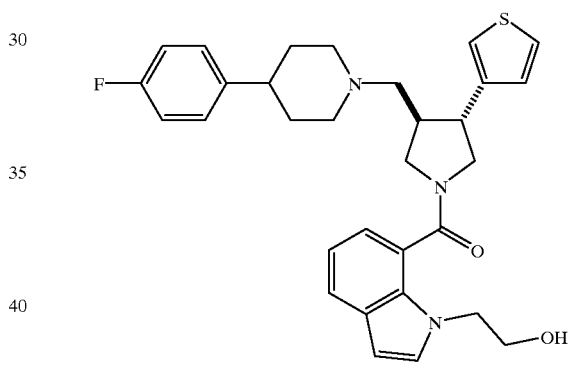

1-(1-(2-Hydroxyethyl)-7-indolecarbonyl)-3-(R)-(4-(4-fluorophenyl)piperidinylmethyl)-4-(R)-(3-thienyl)pyrrolidine A solution of 0.07 g (0.115 mmol) of 1-(1-t-butoxycarbonyl methyl-7-indolecarbonyl)-3-(R)-(4-(4-fluorophenyl)piperidinylmethyl)-4-(R)-(3-thienyl) pyrrolidine and 0.23 mL (0.46 mmol) of $LiBH_4$ (2M in THF) in 4 mL of THF was stirred at rt for 12 h. To the reaction mixture was slowly added 2 mL of sat. $NaHCO_3$ solution and the mixture was stirred st rt for 3 h. To this mixture was then added 30 mL of ether and the pH was adjusted to pH=10–11 with 5N NaOH solution. The reaction mixture was extracted with $CH_2Cl_2$. The organic fraction was dried over $Na_2CO_3$, filtered and the filtrate was concentrated. The residue was purified by chromatography (silica, $CH_2Cl_2$: ethyl acetate: $NH_3$ (2M in MeOH), 10:10:2) to give the title compound.

$^1$H NMR ($CDC_3$) δ6.58, 6.62 (d, 1H, J=4.0 Hz), 4.29 (m, 2H), 3.88 (m, 2H),

Mass Spectrum (CI) m/e=516 (M+1); $[\alpha]_D$=−50.9 (c.=0.43, HCl salt in MeOH)

The following Examples 258 to 261 were prepared using procedures described in Example 253.

EXAMPLE 258

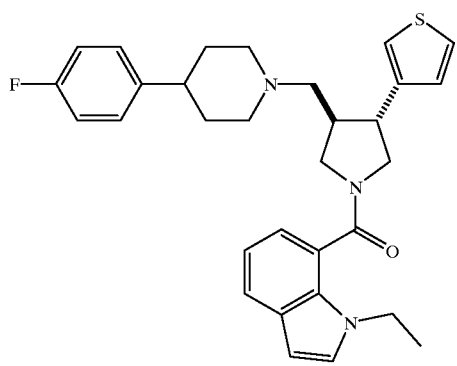

1-(1-Ethyl-7-indolecarbonyl)-3-(R)-(4-(4-fluorophenyl)piperidinylmethyl)-4-(R)-(3-thienyl) pyrrolidine Mass Spectrum (CI) m/e=516 (M+1); $[\alpha]_D$=−50.9 (c.= 0.43, HCl salt in MeOH).

EXAMPLE 259

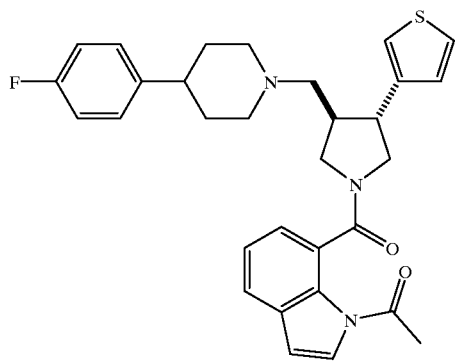

1-(1-Acetyl-7-indolecarbonyl)-3-(R)-(4-(4-fluorophenyl)piperidinylmethyl)-4-(R)-(3-thienyl) pyrrolidine Mass Spectrum (CI) m/e=530 (M+1); $[\alpha]_D$=−40.2 (c.= 0.41, HCl salt in MeOH)

EXAMPLE 260

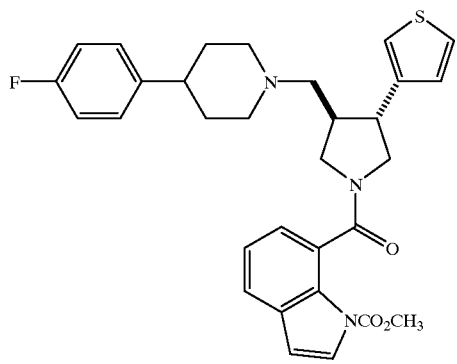

1-(1-Methoxycarbonyl-7-indolecarbonyl)-3-(R)-(4-(4-fluorophenyl) piperidinylmethyl)-4-(R)-(3-thienyl)pyrrolidine Mass Spectrum (CI) m/e=547 (M+1); $[\alpha]_D$=−42.9 (c.= 0.25, HCl salt in MeOH)

EXAMPLE 261

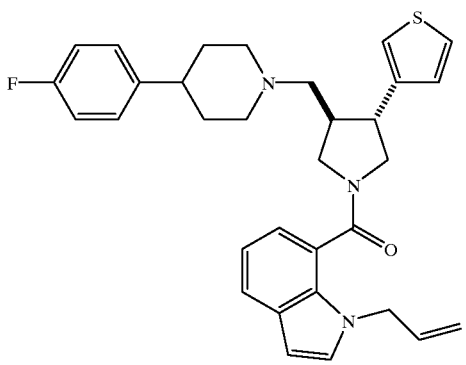

1-(1-Allyl-7-indolecarbonyl)-3-(R)-(4-(4-fluorophenyl)piperidinylmethyl)-4-(R)-(3-thienyl) pyrrolidine Mass Spectrum (CI) m/e=528 (M+1); $[\alpha]_D$=−68.5 (c.= 0.20, HCl salt in MeOH)

The following compounds of the Examples were prepared from 3-(R)-(4-(4-fluorophenyl)piperidinylmethyl)-4-(R)-(3-thienyl)-pyrrolidine and the corresponding acid chloride or acid as described in Examples 11 and 12, respectively. For those acids that were not commercially available, their preparations will be described.

EXAMPLE 262

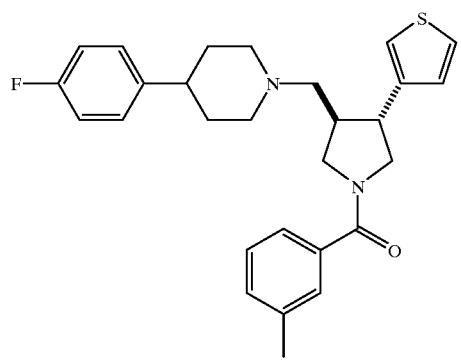

1-(3-Methylbenzoyl)-3-(R)-(4-(4-fluorophenyl) piperidinylmethyl)-4-(R)-(3-thienyl)pyrrolidine Mass Spectrum (CI) m/e=463 (M+1); $[\alpha]_D$=−46.5 (c.= 0.51, HCl salt in MeOH)

EXAMPLE 263

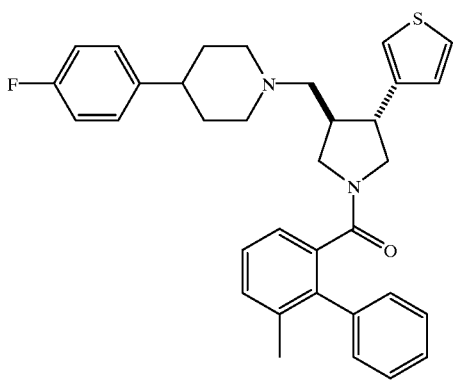

1-(3-Methyl-2-phenylbenzoyl)-3-(R)-(4-(4-fluorophenyl)piperidinylmethyl)-4-(R)-(3-thienyl) pyrrolidine Mass Spectrum (CI) m/e=539 (M+1); [α]$_D$=−9.0 (c.=0.53, HCl salt in MeOH)

Preparation of 3-Methyl-2-phenylbenzoic acid

Step 1

Benzyl-3-methyl-2-bromobenzoate

The title compound was prepared from 3-methyl-2-bromobenzoic acid as described in Example 11A, Step 1.

Step 2

Benzyl-3-methyl-2-phenylbenzoate

A mixture of 0.4 g (1.3 mmol) of benzyl-3-methyl-2-bromo benzoate, 0.24 g (1.95 mmol) of phenylboronic acid, 0.16 g (3.94 mmol) of LiCl, and 0.053 g (0.065 mmol) of [(C$_6$H$_5$)$_3$P]$_2$PdCl$_2$ in 8 mL of DME and 1.3 mL of Na$_2$CO$_3$ (2M in water) was heated at reflux for 6 h. The reaction mixture was cooled to rt, diluted with ether and washed with sat'd NaHCO$_3$ solution. The organic fraction was dried over Na$_2$SO$_4$, filtered and the filtrate was concentrated. The residue was chromatographed (silica, hexanes: ethyl acetate 100:2) to give 0.38 g of the title compound.

Step 3

3-Methyl-2-phenylbenzoic acid

A mixture of 0.35 g (1.18 mmol) of benzyl-3-methyl-2-phenylbenzoate and 0.25 g of 10% Pd/C in 8 mL of a 4.4% solution of HCO$_2$H in methanol was heated at reflux for 2 h. The reaction mixture was filtered through a thin layer of celite and concentrated to give 0.25 g of the title compound as a white solid.

EXAMPLE 264

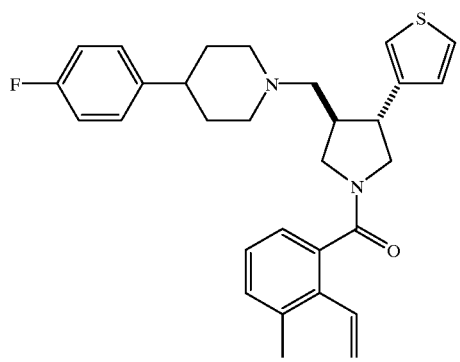

1-(2-Vinyl-3-methylbenzoyl)-3-(R)-(4-(4-fluorophenyl)piperidinylmethyl)-4-(R)-(3-thienyl) pyrrolidine Mass Spectrum (CI) m/e=489 (M+1); [α]$_D$=−18.8 (c.=0.41, HCl salt in MeOH)

Preparation of 3-Methyl-2-vinylbenzoic acid

Step 1

Benzyl-2-vinyl-3-methylbenzoate

A mixture of 0.425 g (1.39 mmol) of benzyl-3-methyl-2-bromo benzoate, 0.8 mL (2.78 mmol) of vinyltributyltin, 0.168 g (4.17 mmol) of LiCl, and 0.049 g (0.07 mmol) of PdCl$_2$(Ph$_3$P)$_2$ (Aldrich) in 6 mL of DME was stirred at 70° C. for reflux for 12 h. The reaction mixture was cooled to rt, diluted with ether and washed with sat'd NaHCO3 solution. The organic fraction was dried over Na$_2$SO$_4$, filtered and the filtrate was concentrated. The residue was chromatographed (silica, hexanes: ethyl acetate 100:2) to give 0.38 g of the title compound.

Step 2

3-Methyl-2-vinylbenzoic acid

The title compound was prepared from benzyl-2-vinyl-3-methylbenzoate as described in Example 251, Step 3.

EXAMPLE 265

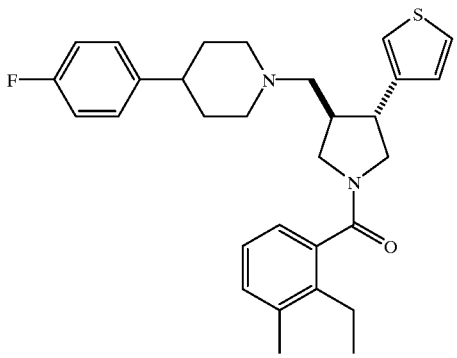

1-(2-Ethyl-3-methylbenzoyl)-3-(R)-(4-(4-fluorophenyl) piperidinylmethyl)-4-(R)-(3-thienyl) pyrrolidine Mass Spectrum (CI) m/e=490 (M+1); [α]$_D$=−22.1 (c.=0.20, HCl salt in MeOH)

Preparation of 2-Ethyl-3-methylbenzoic acid
Step 1

Methyl-2-vinyl-3-methylbenzoate

A solution of 0.35 g (1.37 mmol) of benzyl-2-vinyl-3-methylbenzoate and 1 mL of a saturated aqueous solution of $K_2CO_3$ in 6 mL of methanol was stirred for 48 h. The reaction mixture was concentrated and purified by chromatography (silica, hexanes: ethyl acetate, 20: 1, then $CH_2Cl_2$: MeOH: $NH_3$ (2M in MeOH) 100:4:2) to give 0.2 g of the title compound.
Step 2

Methyl-2-ethyl-3-methylbenzoate

A mixture of 0.105 g (0.6 mmol) of methyl-2-vinyl-3-methylbenzoate and 0.05 g of Pd/C 10% in 15 mL of ethyl acetate was hydrogenated at 50 psi for 2 h. The reaction mixture was filtered through a thin pad of celite and the filtrate was concentrated to give 0.1 g of the title compound.
Step 3

2-Ethyl-3-methylbenzoic acid

A solution of 0.1 g (0.58 mmol) of methyl-2-ethyl-3-methylbenzoate and 1.45 mL (1.45 mmol) of KOH (1M in $H_2O$) in 2 mL of MeOH was stirred at 40° C. for 12 h. The reaction mixture was concentrated and dissolved in 20 mL of $CH_2Cl_2$. The pH was adjusted to pH=2–3 with 2N HCl and the aqueous layer was extracted with $CH_2Cl_2$. The combined organic fractions were dired over $MgSO_4$, filtered and the filtrate was concentrated to give 0.095 gm of the title compound.

EXAMPLE 266

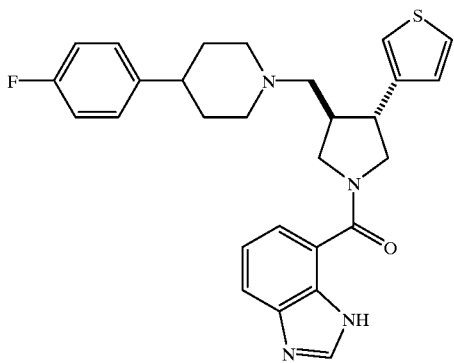

1-(7-benzimidazolecarbonyl)-3-(R)-(4-(4-fluorophenyl)piperidinylmethyl)-4-(R)-(3-thienyl) pyrrolidine Mass Spectrum (CI) m/e=489 (M+1); $[\alpha]_D$=−44.3 (c.= 0.75, HCl salt in MeOH)

Preparation of 7-benzimidazolecarboxylic acid
Step 1

2,3-diaminobenzoic acid

To a suspension of 2 g (9.4 mmol) of 2,3-di-nitrobenzoic acid in 20 mL of acetic acid at 0° C. was added a solution of 14.8 g (65 mmol) $SnCl_2$. 2 $H_2O$ in 7 mL of concentrated HCl. After stirring for 2 h at rt, the reaction mixture was concentrated. The residue was dissolved in 30 mL of $H_2O$ and the pH was adjusted to pH=12–13 with 6N NaOH. The mixture was filtered and the solid was washed with 0.1N HCl. The combined aqueous fractions were concentrated to give 1.4 g of the title compound.
Step 2

7-benzimidazolecarboxylic acid

A mixture of 0.745 g (4.9 mmol) of 2,3-diaminobenzoic acid hydrochloride in 20 mL of 96% formic acid was heated at reflux for 30 h. The reaction mixture was concentrated. The residue was dissolved in 15 mL of $H_2O$ and the pH was adjusted to pH=11–12 with 6N NaOH solution. The mixture was washed with 1:1 ether: ethyl acetate and the aqueous fraction was concentrated. The residue was dissolved in 20 mL of MeOH and filtered. The filtrate was concentrated to give 0.9 g of an orange solid. The solid was dissolved in $H_2O$ and the pH was adjusted to pH=6 with 1N HCl. The prepcipitated title compound was isolated by filtration.

EXAMPLE 267

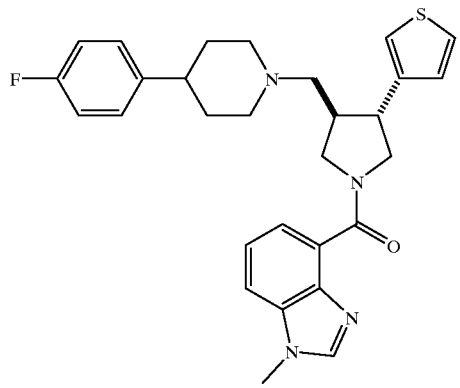

1-(1-methyl-4-benzimidazolecarbonyl)-3-(R)-(4-(4-fluorophenyl)piperidinylmethyl)-4-(R)-(3-thienyl) pyrrolidine The title compound was prepared as described in Example 253 to give a mixture of Example 267 and 268. The two compounds were separated by chromatography (silica, $CH_2Cl_2$: ethyl acetate: $NH_3$ (2M in MeOH), 100:100:8). Example 268 elutes first followed by Example 267.

Mass Spectrum (CI) m/e=503 (M+1); $[\alpha]_D$=−47.2 (c.= 0.27, HCl salt in MeOH)

EXAMPLE 268

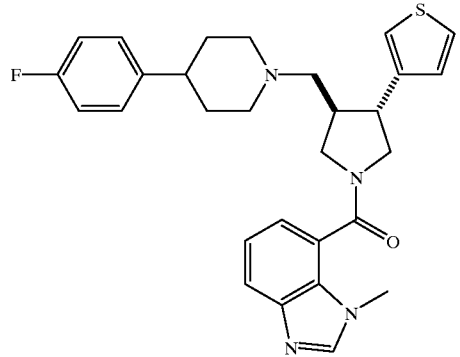

1-(1-methyl-7-benzimidazolecarbonyl)-3-(R)-(4-(4-fluorophenyl)piperidinylmethyl)-4-(R)-(3-thienyl) pyrrolidine Mass Spectrum (CI) m/e=503 (M+1); $[\alpha]_D$=+(c.=1.56, $CHCl_3$) $[\alpha]_D$=−49.1 (c.=0.238, HCl salt in MeOH)

Examples 269 and 270 were prepared and separated as described for Examples 268 and 269.

EXAMPLE 269

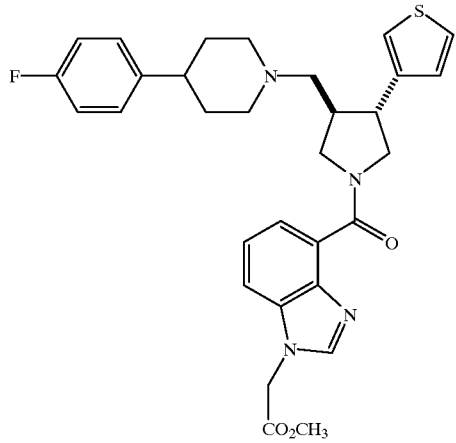

1-(1-(Methoxycarbonylmethyl)-4-benzimidazolecarbonyl)-3-(R)-(4-(4-fluoropheny)piperidinylmethyl)-4-(R)-(3-thienyl)pyrrolidine Mass Spectrum (CI) m/e=547 (M+1); $[\alpha]_D$=−42.8 (c.=0.28, HCl salt in MeOH).

EXAMPLE 270

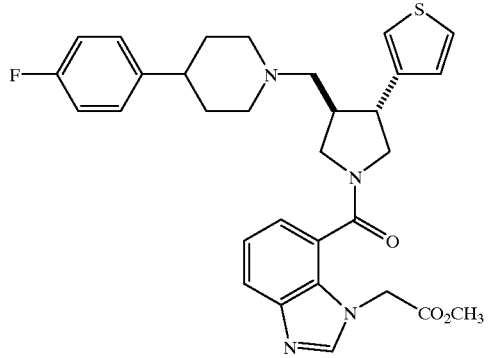

1-(1-(Methoxycarbonylmethyl)-7-benzimidazolecarbonyl)-3-(R)-(4-(4-fluorophenyl)piperidinylmethyl)-4-(R)-(3-thienyl)pyrrolidine Mass Spectrum (CI) m/e=561 (M+1); $[\alpha]_D$=−60 (c.=0.12, HCl salt in MeOH)

Examples 271 and 272 were prepared and separated as described in Examples 268 and 269.

EXAMPLE 271

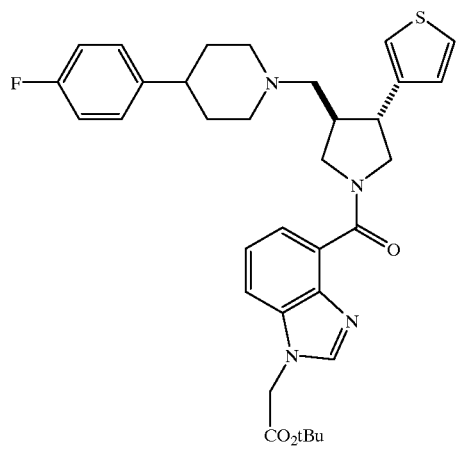

1-(1-(t-Butoxycarbonylmethyl)-4-benzimidazolecarbonyl)-3-(R)-(4-(4-fluorophenyl)piperidinylmethyl)-4-(R)-(3-thienyl)pyrrolidine Mass Spectrum (CI) m/e=547 (M+1)

EXAMPLE 272

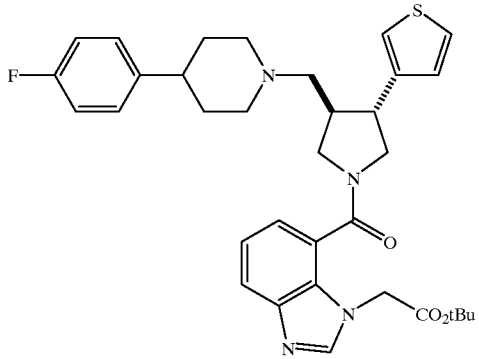

1-(1-(t-Butoxycarbonylmethyl)-7-benzimidazolecarbonyl)-3-(R)-(4-(4-fluorophenyl)piperidinylmethyl)-4-(R)-(3-thienyl)pyrrolidine Mass Spectrum (CI) m/e=603 (M+1)

Examples 273 and 274 were prepared from Examples 271 and 272, respectively, as described in Example 255.

EXAMPLE 273

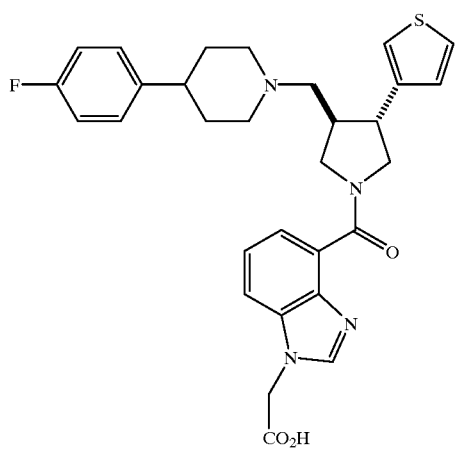

1-(1-(Carboxymethyl)-4-benzimidazolecarbonyl)-3-(R)-(4-(4-fluorophenyl)piperidinylmethyl)-4-(R)-(3-thienyl)pyrrolidine Mass Spectrum (CI) m/e=547 (M+1); $[\alpha]_D$=−44.0 (c.= 0.095 HCl salt in MeOH).

EXAMPLE 274

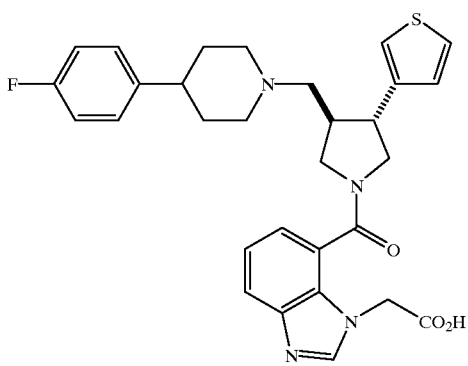

1-(1-(Carboxymethyl)-7-benzimidazolecarbonyl)-3-(R)-(4-(4-fluorophenyl)piperidinylmethyl)-4-(R)-(3-thienyl)pyrrolidine Mass Spectrum (CI) m/e=547 (M+1); $[\alpha]_D$=−42.8 (c.= 0.28, TFA salt in MeOH).

Examples 275 and 276 were prepared from Examples 33A and 34A as described in Example 257.

EXAMPLE 275

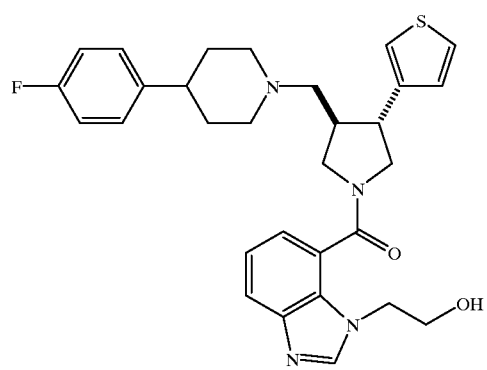

1-(1-(2-Hydroxyethyl)-7-benzimidazolecarbonyl)-3-(R)-(4-(4-fluorophenyl)piperidinylmethyl)-4-(R)-(3-thienyl)pyrrolidino Mass Spectrum (CI) m/e=533 (M+1); $[\alpha]_D$=−56 (C=0.25, HCl salt in MeOH).

EXAMPLE 276

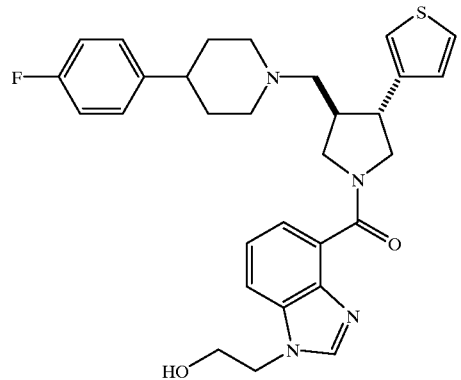

1-(1-(2-Hydroxyethyl)-4-benzimidazolecarbonyl)-3-(R)-(4-(4-fluorophenyl)piperidinylmethyl)-4-(R)-(3-thienyl)pyrrolidine Mass Spectrum (CI) m/e=533 (M+1); $[\alpha]_D$=−51 (c.= 0.205, HCl salt in MeOH).

The following Examples 277 to 278 were prepared from 3-(RS)-(4-phenylpiperidinylmethyl)-4-(RS)-(3-furanyl)pyrrolidine or 3-(RS)-(4-(4-fluorophenyl)piperidinylmethyl)-4-(RS)-(3-furanyl)pyrrolidine by procedures described in Examples 1, 10 and 11.

EXAMPLE 277

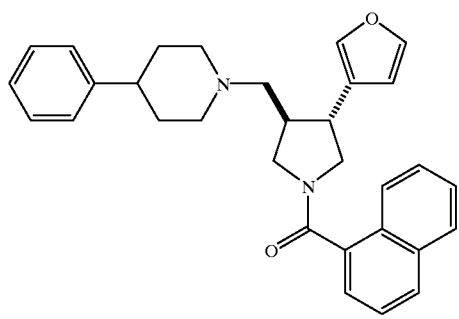

1-(1-Naphthoyl)-3-(RS)-(4-phenylpiperldinylmethyl)-4-(RS)-(3-furanyl)pyrrolidine Mass Spectrum (CI) m/e=465 (M+1)

EXAMPLE 278

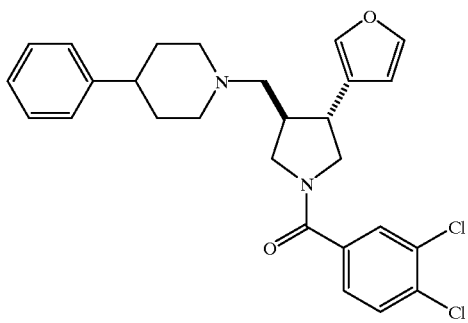

1-(3,4-Dichlorobenzoyl)-3-(RS)-(4-phenylpiperidinylmethyl)-4-(RS)-(3-furanyl)pyrrolidine Mass Spectrum (CI) m/e=483 (M+1, 35Cl, 35Cl), 485 (M+1, 35Cl, 37Cl)

EXAMPLE 279

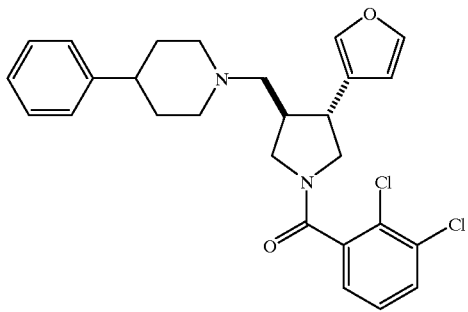

1-(2,3-Dichlorobenzoyl)-3-(RS )-(4-phenylpiperidinylmethyl)-4-(RS)-(3-furanyl)pyrrolidine Mass Spectrum (CI) m/e=483 (M+1, 35Cl, 35Cl), 485 (M+1, 35Cl, 37Cl)

EXAMPLE 280

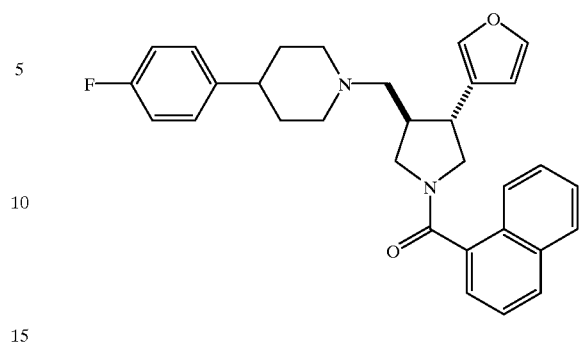

1-(1-Naphthoyl)-3-(RS)-(4-(4-fluorophenyl)piperdinylmethyl)-4-(RS)-(3-furanyl)pyrrolidine Mass Spectrum (CI) m/e=483 (M+1)

EXAMPLE 281

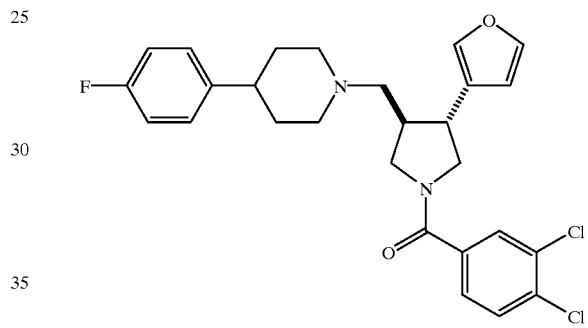

1-(3,4-Dichlorobenzoyl)-3-(RS)-(4-(4-fluorophenyl)piperidinylmethyl)-4-(RS)-(3-furanyl)pyrrolidine Mass Spectrum (CI) m/e=501 (M+1, 35Cl, 35Cl), 503 (M+1, 35Cl, 37Cl)

EXAMPLE 282

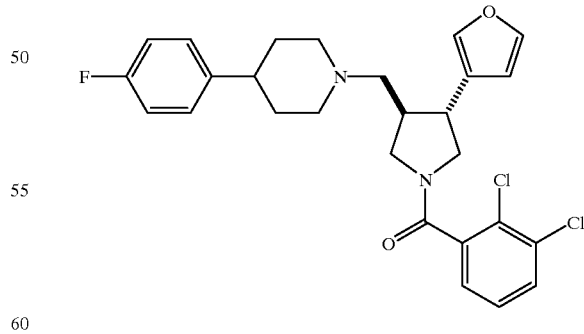

1-(2,3-Dichlorobenzoyl)-3-(SR)-(4-(4-fluorophenyl)piperidinylmethyl)-4-(RS)-(3-furanyl)pyrrolidine Mass Spectrum (CI) m/e=501 (M+1, 35Cl, 35Cl), 503 (M+1, 35Cl, 37Cl)

EXAMPLE 283

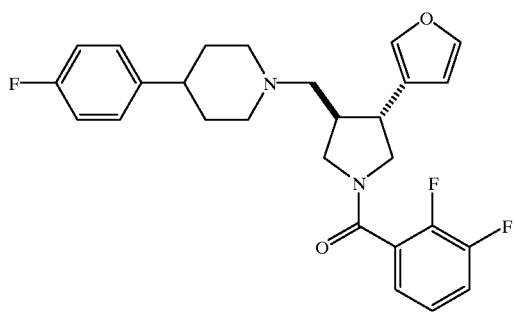

1-(2,3-Difluorobenzoyl)-3-(RS)-(4-(4-florophenyl) pipelidinylmethyl)-4-(RS)-(3-furanyl)pyrrolidine Mass Spectrum (CI) m/e=469 (M+1)

EXAMPLE 284

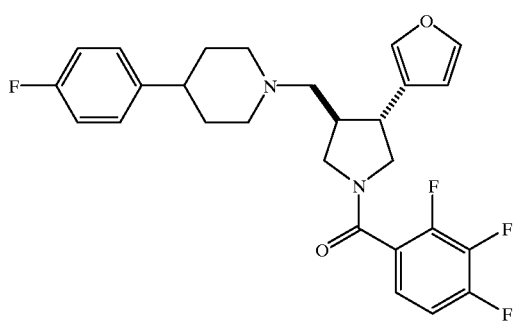

1-(2,3,4-Trifluorobenzoyl)-3-(RS)-(4-(4-fluorophenyl)peridinylmethyl)-4-(RS)-(3-furanyl) pyrrolidine Mass Spectrum (CI) m/e=487 (M+1)

EXAMPLE 285

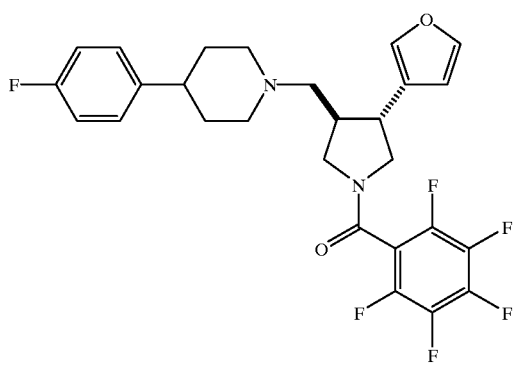

1-(2,3,4,5,6-Pentafluorobenzoyl)-3-(RS)-(4-(4-fluorophenyl)piperidinylmethyl)-4-(RS)-(3-furanyl) pyrrolidine Mass Spectrum (CI) m/e=523 (M+1)

EXAMPLE 286

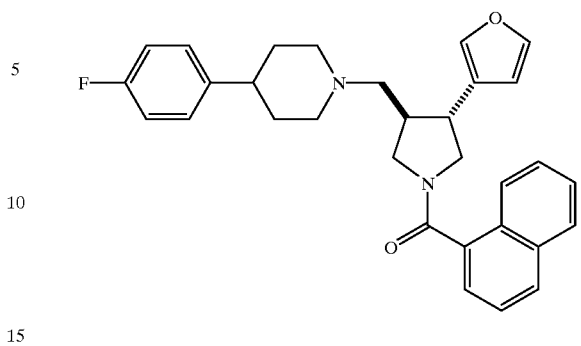

1-(1-Naphthoyl)-3-(R)-(4-(4-fluorophenyl) piperidinylmethyl)-4-(R)-(3-furanyl)pyrrolidine Mass Spectrum (CI) m/e=483 (M+1), $[\alpha]_D$=−45.5 (c.=0.56, HCl salt in MeOH).

The title compound was prepared as described in Examples 241, 242 and 243.

EXAMPLE 287

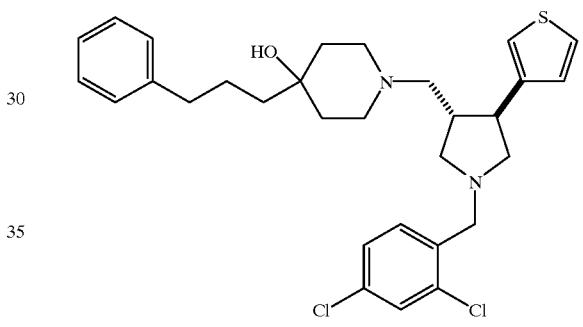

1-(2,4-Dichlorobenzyl)-3-(S)-(4-hydroxy-4-(3-phenylpropyl)piperidinylmethyl)-4-(S)-(3-thienyl) pyrrolidine (S,S stereoisomer of Example 150)

Step 1

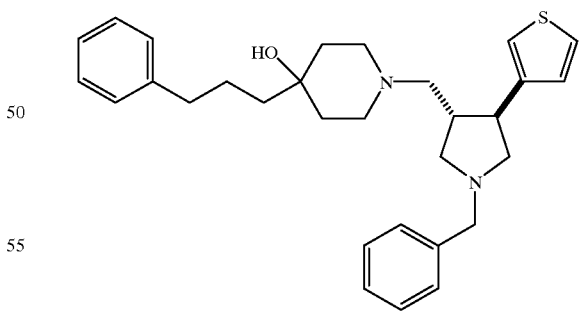

1-Benzyl-3-(S)-(4-hydroxy-4-(3-phenylpropyl) piperidinylmethyl)-4-(S)-(3-thienyl)pyrrolidine The title compound was prepared from 1-Benzyl-3-(R)-formyl-4-(S)-(3-thienyl)pyrrolidine [which was prepared from (S)-N-(1-benzyl-4-(S)-(3-thienyl)-3-(R)-pyrrolidinylcarbonyl)-4-benzyl-2-oxazolidinone (Example 241 Step 2)] and 4-hydroxy-4-(3-phenylpropyl)piperidine (Example 122, Step 1) by procedures analogous to those described in Example 241.

Step 2

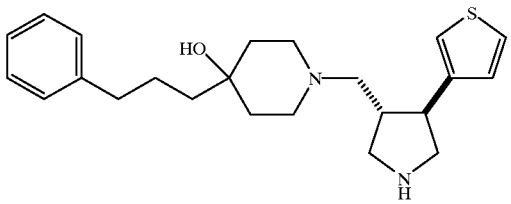

3-(R)-(4-hydroxy-4-(3-phenylpropyl) piperidinylmethyl)-4-(S)-(3-thienyl)pyrrolidine The title compound was prepared as described in Example 242.

Step 3

1-(2,4-Dichlorobenzyl)-3-(S)-(4-hydroxy-4-(3-phenylpropyl)piperidinylmethyl)-4-(S)-(3-thienyl) pyrrolidine The title compound was prepared as described in Examples 3 and 150.

Mass Spectrum (ESI) m/e=543 (M+1 35Cl, 37Cl), and 545 (M+1, 37Cl, 37Cl),

EXAMPLE 288

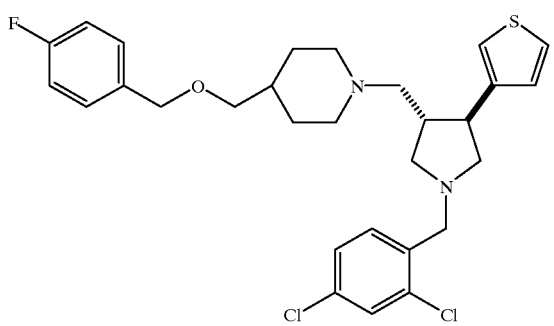

1-(2,4-Dichlorobenzyl)-3-(S )-(4-(4-fluorobenzyloxymethyl)piperidinylmethyl)-4-(S)-(3-thienyl)pyrrolidine (S,S stereoisomer of Example 202)

The title compound was prepared by procedures described in Examples 201, 202, and 287. Mass Spectrum (ESI) m/e=547 (M+1 35Cl) and 549 (M+1, 37Cl), $[\alpha]_D$=+12.5(c.= 1.37 CHCl$_3$).

EXAMPLE 289

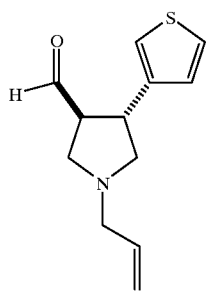

1-Allyl-3-(S)-formyl-4-(R)-(3-thienyl)pyrrolidine

The title compound was prepared according to procedures described in Example 241 with the change that N-methoxymethyl-N-trimethylsilylmethylallylamine replaces N-methoxymethyl-N-trimethylsilylmethylbenzylamine in Step 2.

EXAMPLE 290

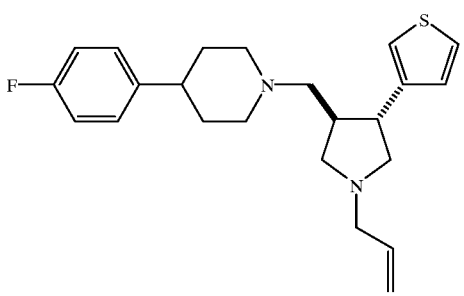

1-Allyl-3-(R)-(4-(4-fluorophenyl) piperidinylmethyl)-4-(R)-(3-thienyl)pyrrolidine.

The title compound was prepared from 1-allyl-3-(S)-formyl-4-(R)-(3-thienyl)pyrrolidine and 4-(4-fluorophenyl) piperidine by according to procedures described in Example 241, Step 5 with the change that 1-Allyl-3-(S)-formyl-4-(R)-(3-thienyl)pyrrolidine replaced 1-benzyl-3-(S)-formyl-4-(R)-(3-thienyl)pyrrolidine. $^1$H NMR (CDCl$_3$) is consistent with structure.

EXAMPLE 291

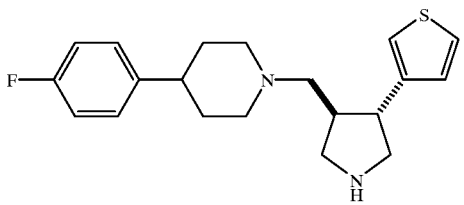

3-(S)-(4-(4-fluorophenyl)piperidinylmethyl)-4-(R)-(3-thienyl)pyrrolidine: alternate prep from Example 242.

A mixture of 1.2 g (3.2 mmol) of 1-Allyl-3-(R)-(4-(4-fluorophenyl)piperidinylmethyl)-4-(R)-(3-thienyl) pyrrolidine and 0.19 g (0.2 mmol) of Wilkinson's catalyst ([Rh(PPh)$_3$Cl] in 20 mL of an 85% solution of CH$_3$CN in water in a flask fitted with a short path distillation head and an addition funnel for added solvent was heated to reflux. As solvent is azeotroped off, more is added to maintain the original concentration. After stirring at reflux for 4 h, the reaction mixture was concentrated. To the residue was added 3 mL of 2 N HCl and this mixture was partitioned between EtOAc and water. The aqueous fraction was washed with EtOAc and was then made basic with 2 N NaOH solution. The aqueous fraction was then extracted with EtOAc. The combined organic fractions were washed with sat'd NaCl solution, dried over MgSO$_4$, filtered and the filtrate was concentrated to give the title compound which was used without further purification. Mass Spectrum (CI) m/e=345 (M+1)

EXAMPLE 292

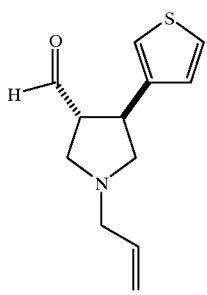

1-Allyl-3-(R)-formyl-4-(S)-(3-thienyl)pyrrolidine

The title compound was prepared according to procedures described in Example 241 with the change that N-methoxymethyl-N-trimethylsilylmethylallylamine replaces N-methoxymethyl-N-trimethylsilylmethylbenzylamine in Step 2.

EXAMPLE 293

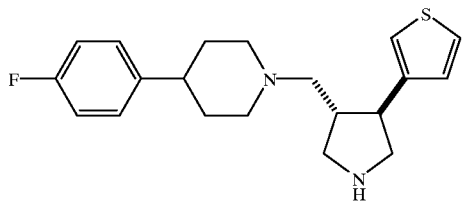

3-(R)-4-(4-fluorophenyl)piperidinylmethyl)-4-(S)-(3-thienyl)pyrrolidine

The title compound was prepared from 1-Allyl-3-(R)-formyl-4-(S)-(3-thienyl)pyrrolidine (Example 292) as described in Examples 290 and 292.

The following Examples 294 to 304 were prepared from 3-(R)-(4-(4-fluorophenyl)piperidinylmethyl)-4-(S)-3-thienyl)pyrrolidine (Example 293) and the corresponding aldehyde according to procedures described in Example 3.

EXAMPLE 294

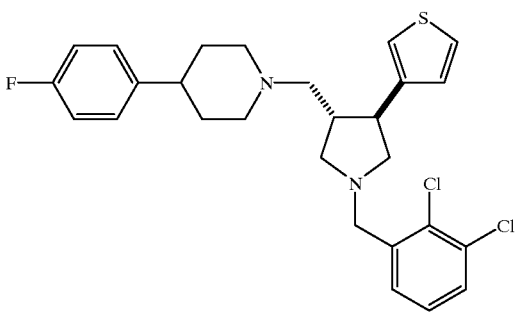

1-(2,3-Dichlorobenzyl)-3-(S)-(4-(4-fluorophenyl)piperidinylmethyl)-4-(S)-(3-thienyl)pyrrolidine.

Mass Spectrum (CI) m/e 503 (M+1, 35Cl, 35Cl), 505 (M+1(35Cl, 37Cl), 507 (M+1, 37Cl, 37Cl).

EXAMPLE 295

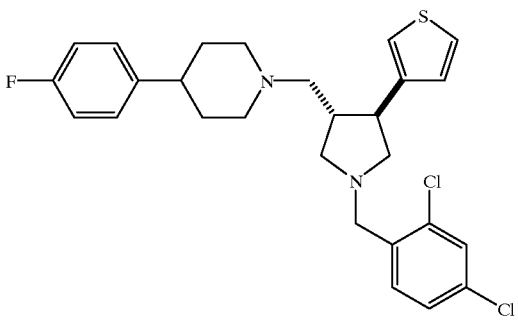

1-(2,4-Dichlorobenzyl)-3-(S)-4-(4-fluorophenyl)piperidinylmethyl)-4-(S)-(3-thienyl)pyrrolidine.

Mass Spectrum (CI) m/e 503 (M+1, 35Cl), 505 (M+1(35Cl, 37Cl), 507 (M+1, 37Cl, 37Cl).

EXAMPLE 296

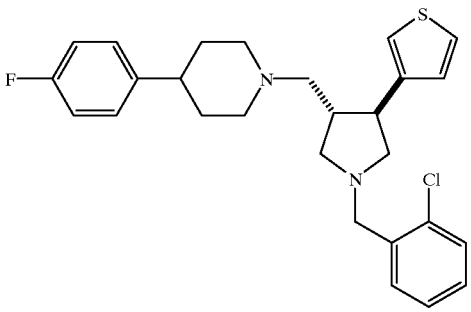

1-(2-Chlorobenzyl)-3-(S)-(4-(4-fluorophenyl)piperidinylmethyl)-4-(S)-(3-thienyl)pyrrolidine.

Mass Spectrum (CI) m/e=469 (M+1, 35Cl), 471 (M+1, 37Cl).

EXAMPLE 297

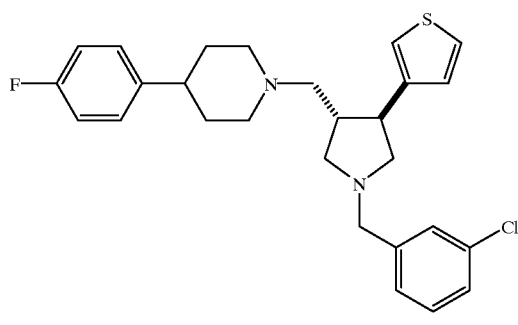

1-(3-Chlorobenzyl)-3-(S)-(4-(4-fluorophenyl)
piperidinylmethyl)-4-(S)-(3-thienyl)pyrrolidine.

Mass Spectrum (CI) m/e 469 (M+1, 35Cl), 471 (M+1, 37Cl).

EXAMPLE 298

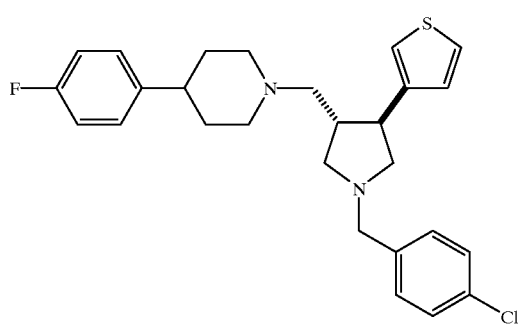

1-(4-Chlorobenzyl)-3-(S)-(4-(4-fluorophenyl)
piperidinylmethyl)-4-(S)-(3-thienyl)pyrrolidine.

Mass Spectrum (CI) m/e 469 (M+1, 35Cl), 471 (M+1, 37Cl).

EXAMPLE 299

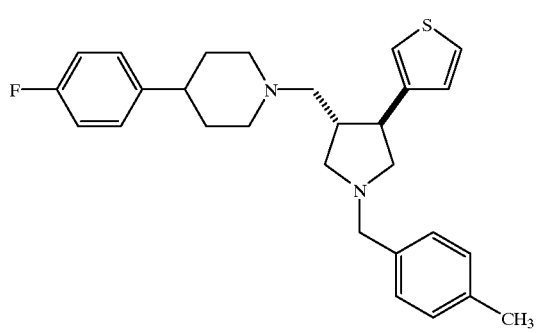

1-(4-Methylbenzyl)-3-(S)-(4-(4-fluorophenyl)
piperidinylmethyl)-4-(S)-(3-thienyl)pyrrolidine.

Mass Spectrum (CI) m/e 449 (M+1).

EXAMPLE 300

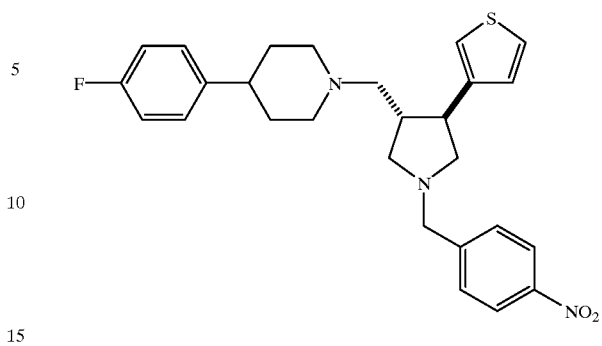

1-(4-Nitrobenzyl)-3-(S)-(4-(4-fluorophenyl)
piperidinylmethyl)-4-(S)-(3-thienyl)pyrrolidine.

Mass Spectrum (CI) m/e 480 (M+1).

EXAMPLE 301

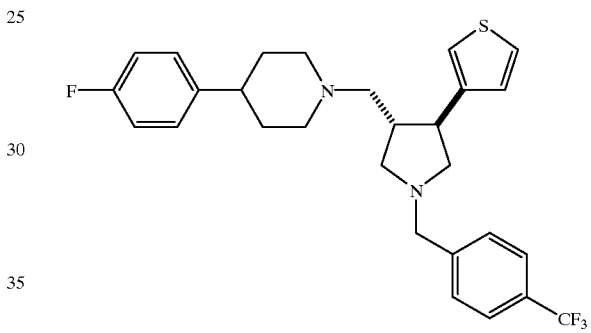

1-(4-Trifluoromethylbenzyl)-3-(S)-(4-(4-
fluorophenyl)piperidinylmethyl)-4-(S)-(3-thienyl)
pyrrolidine.

Mass Spectrum (CI) m/e 503 (M+1).

EXAMPLE 302

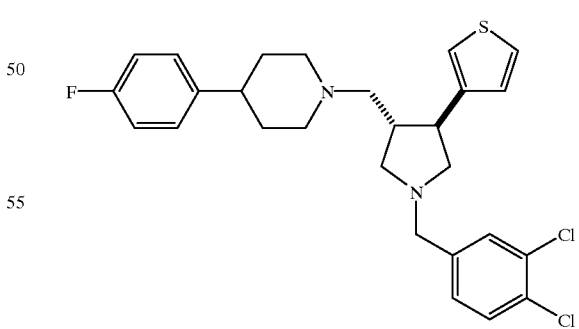

1-(3,4-Dichlorobenzyl)-3-(S)-(4-(4-fluorophenyl)
piperidinylmethyl)-4-(S)-(3-thienyl)pyrrolidine.

Mass Spectrum (CI) m/e 503 (M+1, 35Cl, 35Cl), 505 (M+1, 35Cl, 37Cl), 507 (M+1, 37Cl, 37Cl).

EXAMPLE 303

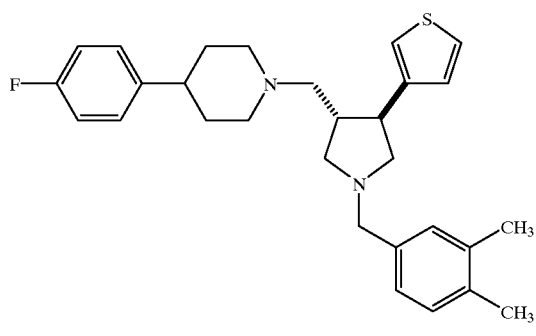

1-(2,3-Dimethylbenzyl)-3-(S)-(4-(4-fluorophenyl)
piperidinylmethyl)-4-(S)-(3-thienyl)pyrrolidine.

Mass Spectrum (CI) m/e 463 (M+1).

EXAMPLE 304

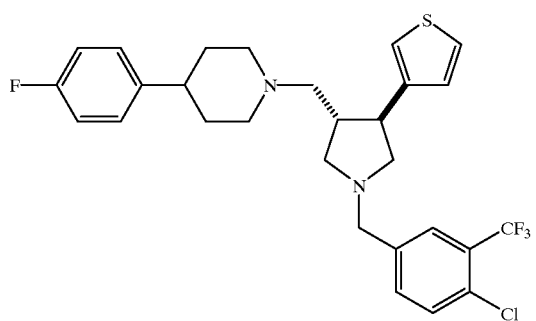

1-(3-Trifluoromethyl-4-chlorobenzyl)-3-(S)-(4-(4-fluorophenyl)piperidinylmethyl)-4-(S)-(3-thienyl)
pyrrolidine.

Mass Spectrum (CI) m/e 537 (M+1 35Cl), 539 (M+1 37Cl).

The following Examples 305 to 307 were prepared from 3-(S)-(4-(4-fluorophenyl)piperidinylmethyl)-4-(R)-3-thienyl)pyrrolidine (Example 291) and the corresponding aldehyde according to procedures described in Example 3.

EXAMPLE 305

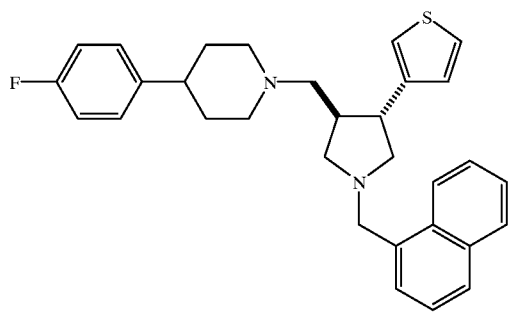

1-(1-Naphthylmethyl)-3-(R)-(4-(4-fluorophenyl)
piperidinylmethyl)-4-(R)-(3-thienyl)pyrrolidine.

Mass Spectrum (CI) m/e 485 (M+1)

EXAMPLE 306

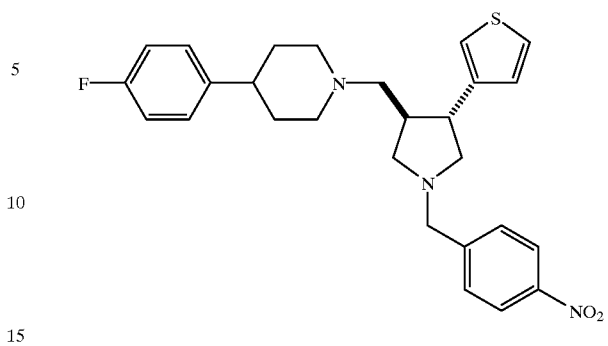

1-(4-Nitrobenzyl)-3-(R)-(4-(4-fluorophenyl)
piperidinylmethyl)-4-(R)-(3-thienyl)pyrrolidine.

Mass Spectrum (CI) m/e 480 (M+1).

EXAMPLE 307

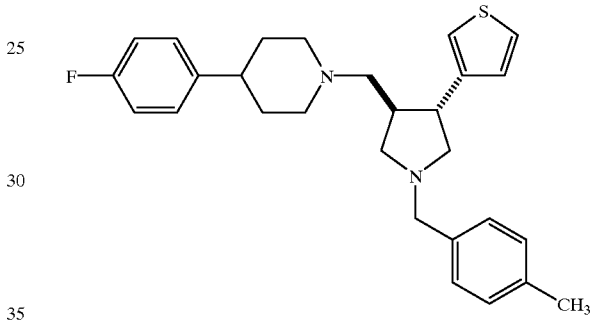

1-(4-Methylbenzyl)-3-(R)-(4-(4-fluorophenyl)
piperidinylmethyl)-4-(R)-(3-thienyl)pyrrolidine.

Mass Spectrum (CI) m/e 449 (M+1).

EXAMPLE 308

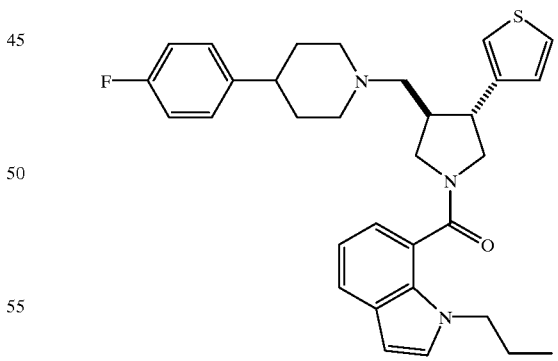

1-(1-n-propyl-7-indolecarbonyl)-3-(R)-4-(4-fluorophenyl)piperidinylmethyl)-4-(R)-(3-thienyl)
pyrrolidine The title compound was prepared from 1-(7-indolecabonyl)-3-(R)-4-(4-fluorophenyl)
piperidinylmethyl)-4-(R)-(3-thienyl)pyrrolidine (Example 248) and n-propyl iodide as described in Example 253. Mass Spectrum (CI) m/e 530 (M+1).

EXAMPLE 309

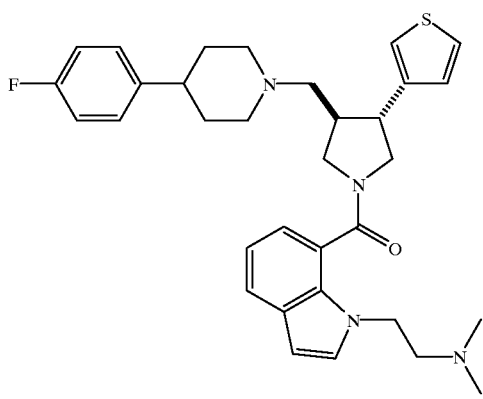

1-(1-(N,N-dimethylaminoethyl)-7-indolecarbonyl)-3-(R)-4-(4-fluorophenyl)piperidinylmethyl)-4-(R)-(3-thienyl)pyrrolidine The title compound was prepared from 1-(7-indolecabonyl)-3-(R)-4-(4-fluorophenyl)piperidinylmethyl)-4-(R)-(3-thienyl)pyrrolidine (Example 248) and N,N-dimethylaminoethyl iodide as described in Example 253. Mass Spectrum (CI) m/e 559 (M+1).

EXAMPLE 310

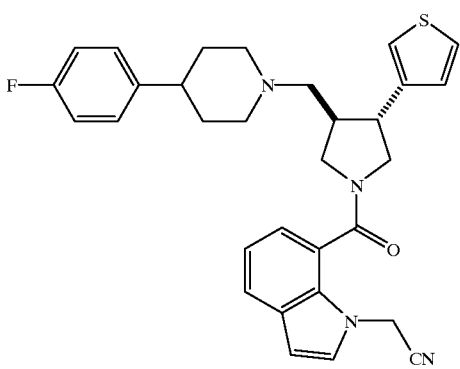

1-(1-cyanomethyl-7-indolecarbonyl)-3-(R)-4-(4-fluorophenyl)piperidinylmethyl)-4-(R)-(3-thienyl)pyrrolidine The title compound was prepared from 1-(7-indolecabonyl)-3-(R)-4-(4-fluorophenyl)piperidinylmethyl)-4-(R)-(3-thienyl)pyrrolidine (Example 248) and iodoacetonitrile as described in Example 253. Mass Spectrum (CI) m/e 526 (M+1).

EXAMPLE 311

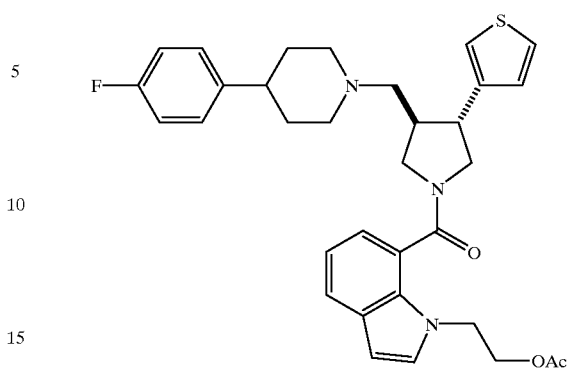

1-(1-(2-Acetoxyethyl)-7-indolecarbonyl)-3-(R)-4-(4-fluorophenyl)piperdinylmethyl)-4-(R)-(3-thienyl)pyrrolidine A solution of 0.01 g (0.018 mmol) of 1-(1-(2-Hydroxyethyl)-7-indolecarbonyl)3-(R)-4-(4-fluorophenyl)piperidinylmethyl)-4-(R)-(3-thienyl)pyrrolidine (Example 257), 0.002 mL (0.028 mmol) of acetic anhydride and 0.01 mL (0.072 mmol) of triethylamine in 4 mL of $CHCl_3$ was stirred at rt for 12 h.

The reaction mixture was concentrated and purified by chromatography (silica, $CH_2Cl_2$: EtOAc: $NH_3$ (2M in $CH_3OH$), 100: 100: 8) to give the title compound. Mass Spectrum (CI) m/e 574 (M+1).

EXAMPLE 312

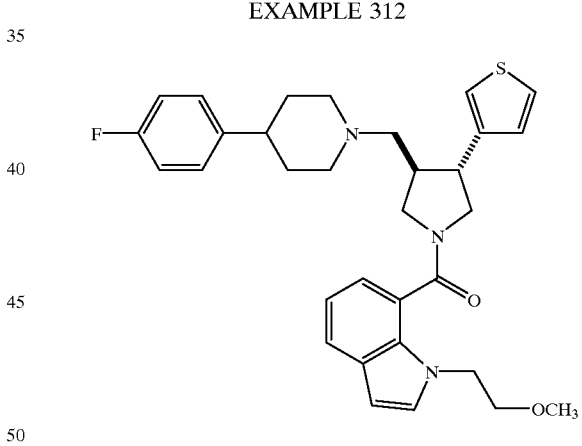

1-(1-(2-Methoxyethyl)-7-indolecarbonyl)-3-(R)-4-(4-fluorophenyl)piperidinylmethyl)-4-(R)-(3-thienyl)pyrrolidine A solution of 0.013 g (0.024 mmol) of 1-(1-(2-hydroxyethyl)-7-indolecarbonyl)3-(R)-4-(4-fluorophenyl)piperidinylmethyl)-4-(R)-(3-thienyl)pyrrolidine (Example 257), 0.0047 g (0.084 mmol) of KOH and 0.0034 g (0.024 mmol) of methyliodide in 2 mL of DMSO was stirred at rt for 2 h. The reaction mixture was diluted with EtOAc: ether (2:1) and washed with sat'd $NaHCO_3$ solution. The organic fractions were dried over $Na_2CO_3$ and filtered. The filtrate was concentrated and the residue was purified by chromatography (silica, $CH_2Cl_2$: EtOAc: $NH_3$ (2M in $CH_3OH$), 100:100:8) to give the title compound. Mass Spectrum (CI) m/e 546 (M+1).

EXAMPLE 313

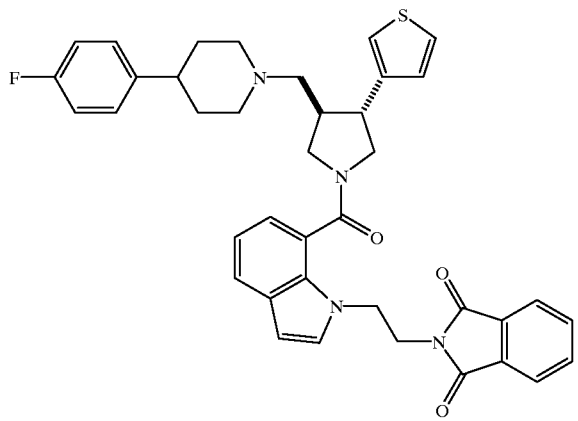

1-(1-(2-Phthalimidoethyl)-7-indolecarbonyl)-3-(R)-4-(4-fluorophenyl)piperidinylmethyl)-4-(R)-(3-thienyl)pyrrolidine To a solution of 0.22 g (0.414 mmol) of 1-(1-(2-hydroxyethyl)-7-indolecarbonyl)3-(R)-4-(4-fluorophenyl) piperidinylmethyl)-4-(R)-(3-thienyl)pyrrolidine (Example 257), 0.217 g (0.827 mmol) of triphenylphospine and 0.12 g (0.827 mmol) of phthalimide in 8 mL of THF at rt was added 0.13 mL (0.827 mmol) of diethylazodicarboxylate and the reaction mixture was stirred at rt for 12 h. The reaction mixture was partitioned between $CH_2Cl_2$ and water. The pH of the water layer was adjusted to pH=10–11 and was extracted three times with $CH_2Cl_2$. The organic fractions were dried over $Na_2SO_4$ and filtered. The filtrate was concentrated and the residue was purified by chromatography (silica, hexanes: EtOAc, 3:1) to give the title compound. Mass Spectrum (CI) m/e 660 (M+1).

EXAMPLE 314

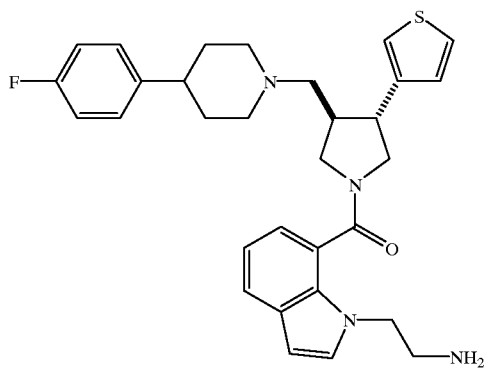

1-(1-(2-Aminoethyl)-7-indolecarbonyl)-3-(R)-4-(4-fluorophenyl)piperidinylmethyl)-4-(R)-(3-thienyl) pyrrolidine A solution of 0.235 g (0.356 mmol) of 1-(1-(2-Phthalimidoethyl)-7-indolecarbonyl)3-(R)-4-(4-fluorophenyl)piperidinylmethyl)-4-(R)-(3-thienyl)pyrrolidine and 0.114 g (3.56 mmol) of hydrazine hydrate 10 mL of $CH_3OH$ was stirred at rt for 3 h. The reaction mixture was concentrated and the residue was purified by chromatography (silica, $CH_2Cl_2$:EtOAc:$NH_3$ (2M in $CH_3OH$), 100:100:8) to give the title compound. Mass Spectrum (CI) m/e 531 (M+1).

EXAMPLE 315

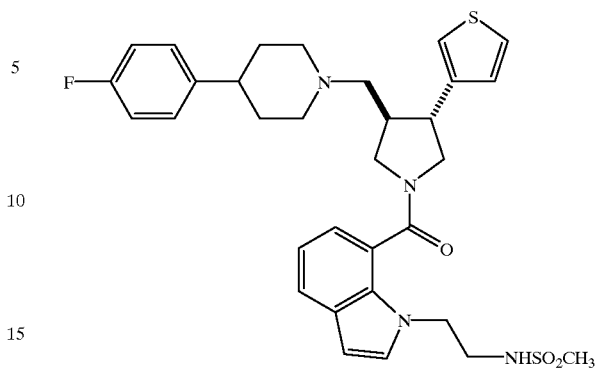

1-(1-(2-methylsulfonylaminoethyl)-7-indolecarbonyl)-3-(R)-4-(4-fluorophenyl) piperidinylmethyl)-4-(R)-(3-thienyl)pyrrolidine A solution of 0.02 g (0.038 mmol) of 1-(1-(2-aminoethyl)-7-indolecarbonyl)3-(R)-4-(4-fluorophenyl) piperidinylmethyl)-4-(R)-(3-thienyl)pyrrolidine, 0.0045 mL (0.056 mmol) of methanesulfonyl chloride, and 0.016 mL (0.114 mmol) of triethylamine in 2 mL of $CH_2Cl_2$ was stirred at rt for 12 h. The reaction mixture was concentrated and the residue was purified by chromatography (silica, $CH_2Cl_2$:EtOAc:$NH_3$ (2M in $CH_3OH$), 100:100:8) to give the title compound. Mass Spectrum (CI) m/e 609 (M+1).

EXAMPLE 316

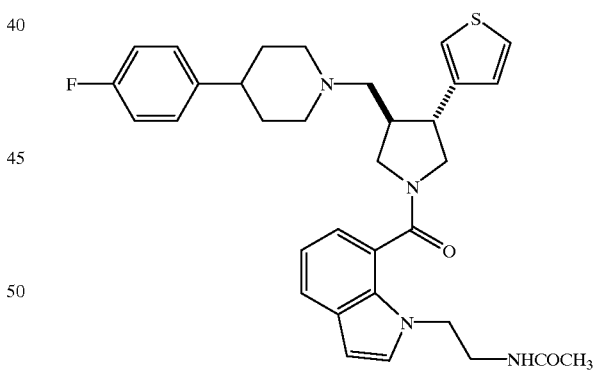

1-(1-(2-Acetylaminoethyl)-7-indolecarbonyl)-3-(R)-4-(4-fluorophenyl)piperidinylmethyl)-4-(R)-(3-thienyl)pyrrolidine The title compound was prepared from 1-(1-(2-aminoethyl)-7-indolecarbonyl)3-(R)-4-(4-fluorophenyl) piperidinylmethyl)-4-(R)-(3-thienyl)pyrrolidine and acetyl chloride as described in Example 315. Mass Spectrum (CI) m/e 573 (M+1).

EXAMPLE 317

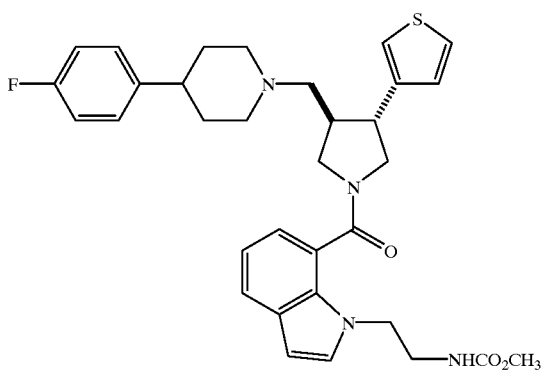

1-(1-(2-Methoxycarbonylaminoethyl)-7-indolecarbonyl)-3-(R)-4-(4-fluorophenyl)piperidinylmethyl)-4-(R)-(3-thienyl)pyrrolidine The title compound was prepared from 1-(1-(2-aminoethyl)-7-indolecarbonyl)3-(R)-4-(4-fluorophenyl)piperidinylmethyl)-4-(R)-(3-thienyl)pyrrolidine and methylchloroformate as described in Example 315. Mass Spectrum (CI) m/e 589 (M+1).

EXAMPLE 318

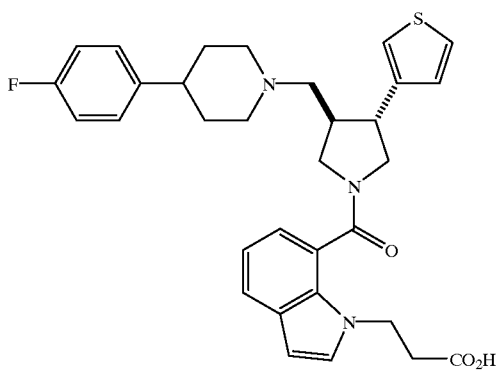

1-(1-(2-Carboxyethyl)-7-indolecarbonyl)-3-(R)-4-(4-fluorophenyl)piperidinylmethyl)-4-(R)-(3-thienyl)pyrrolidine A mixture of 0.115 g (0.235 mmol) of 1-(7-indolecarbonyl)-3-(R)-4-(4-fluorophenyl)piperidinylmethyl)-4-(R)-(3-thienyl)pyrrolidine (Example 248), 0.023 mL (0.21 mmol) of methyl-3-bromopropionate and 0.066 g (1.18 mmol) of KOH in 3 mL of DMSO was stirred at rt for 3 h. The reaction mixture was diluted with 40 mL of ether and 3 mL of water. The water layer was allowed to sit overnight at rt, whereupon the title compound crystallized out and was isolated by filtration. Mass Spectrum (CI) m/e 560 (M+1).

EXAMPLE 319

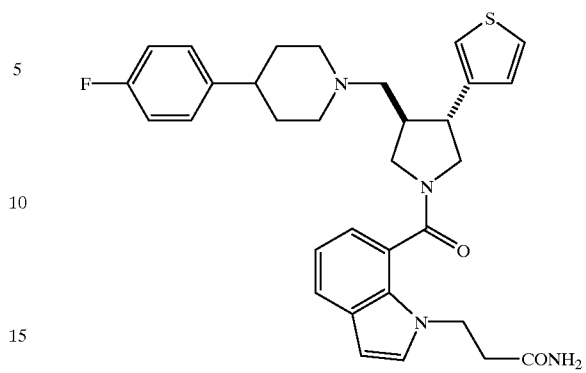

1-(1-(2-Carboxamidoethyl)-7-indolecarbonyl)-3-(R)-4-(4-fluorophenyl)piperidinylmethyl)-4-(R)-(3-thienyl)pyrrolidine A mixture of 0.140 g (0.25 mmol) of 1-(1-(2-carboxyethyl)-7-indolecarbonyl)-3-(R)-4-(4-fluorophenyl)piperidinylmethyl)-4-(R)-(3-thienyl)pyrrolidine, 0.097 g (0.5 mmol) of 1-[3-(dimethylamino)propyl]-3-ethylcarbodiimide hydrochloride and 2 mL of a 0.5M solution of ammonia in dioxane in 4 mL of THF was stirred at rt for 12 h. The reaction mixture was concentrated and the residue was purified by chromatography (silica, $CH_2Cl_2$:EtOAc:$NH_3$ (2M in $CH_3OH$), 100:100:10) to give the title compound. Mass Spectrum (CI) m/e 559 (M+1).

EXAMPLE 320

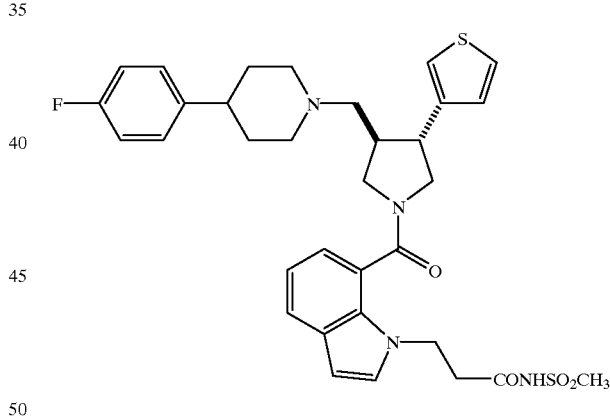

1-(1-(2-Methylsulfonamidocarbonylethyl)-7-indolecarbonyl)-3-(R)-4-(4-fluorophenyl)piperidinylmethyl)-4-(R)-(3-thienyl)pyrrolidine To a solution of 0.031 g (0.055 mmol) of 1-(1-(2-carboxamidoethyl)-7-indolecarbonyl)-3-(R)-4-(4-fluorophenyl)piperidinylmethyl)-4-(R)-(3-thienyl)pyrrolidine in 4 mL of toluene was added 0.0027 g (0.066 mmol) of NaH (60%) and the reaction mixture was stirred 1 h at rt. To the reaction mixture at rt was added 0.089 mL (0.11 mmol) of methanesulfonyl chloride and the reaction mixture was heated at reflux 12 h. The reaction mixture was concentrated and the residue was purified by chromatography (silica, $CH_2Cl_2$:EtOAc:$NH_3$ (2M in $CH_3OH$), 100:100:20) to give the title compound. Mass Spectrum (CI) m/e 637 (M+1).

EXAMPLE 321

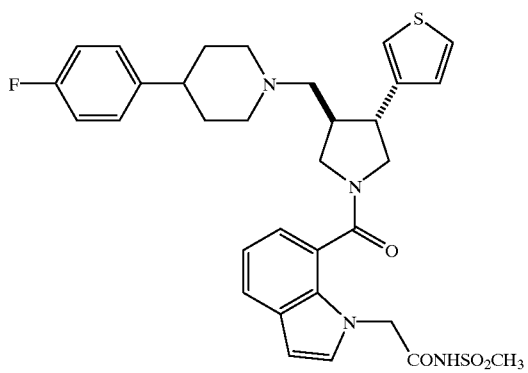

1-(1-(2-Methylsulfonamidocarbonylmethyl)-7-indolecarbonyl)-3-(R)-4-(4-fluorophenyl)piperidinylmethyl)-4-(R)-(3-thienyl)pyrrolidine The title compound was prepared from 1-(1-(carboxamidomethyl)-7-indolecarbonyl)-3-(R)-4-(4-fluorophenyl)piperidinylmethyl)-4-(R)-(3-thienyl)pyrrolidine (Example 256) according to procedures described in Example 321. Mass Spectrum (CI) m/e 623 (M+1).

EXAMPLE 322

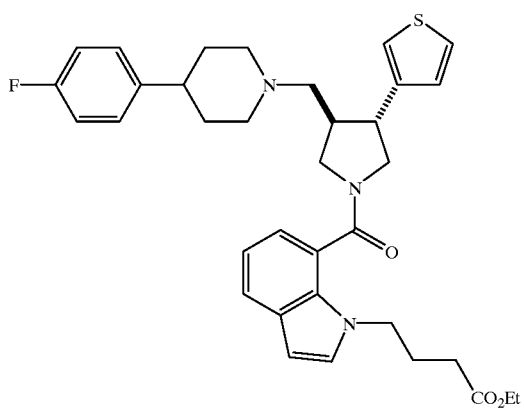

1-(1-(3-Ethoxycarbonylpropyl)-7-indolecarbonyl)-3-(R)-4-(4-fluorophenyl)piperidinylmethyl)-4-(R)-(3-thienyl)pyrrolidine A mixture of 0.138 g (0.283 mmol) of 1-(7-indolecarbonyl)-3-(R)-4-(4-fluorophenyl)piperidinylmethyl)-4-(R)-(3-thienyl)pyrrolidine (Example 248), 0.049 mL (0.34 mmol) of ethyl-4-bromobutyrate and 0.079 g (1.45 mmol) of KOH in 3 mL of DMSO was stifled at rt for 24 h. The reaction mixture was diluted with 30 mL of ether and 5 mL of water. The organic fraction was concentrated and the residue was purified by chromatography (silica, hexanes:acetone, 4:1) to give the title compound. Mass Spectrum (CI) m/e 602 (M+1).

EXAMPLE 323

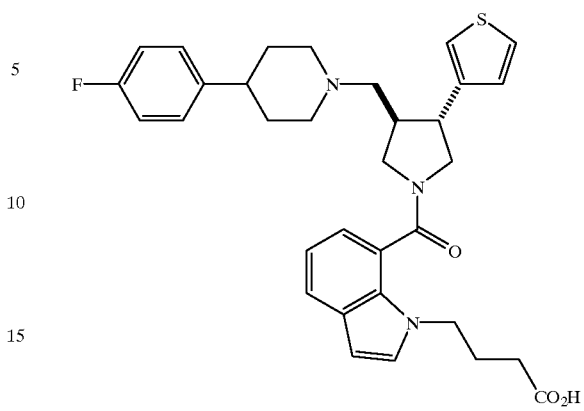

1-(1-(3-carboxypropyl)-7-indolecarbonyl)-3-(R)-4-(4-fluorophenyl)piperidinylmethyl)-4-(R)-(3-thienyl)pyrrolidine The water layer from Example 322 was allowed to sit overnight at rt, whereupon the title compound crystallized out and was isolated by filtration. Mass Spectrum (CI) m/e 574 (M+1).

EXAMPLE 324

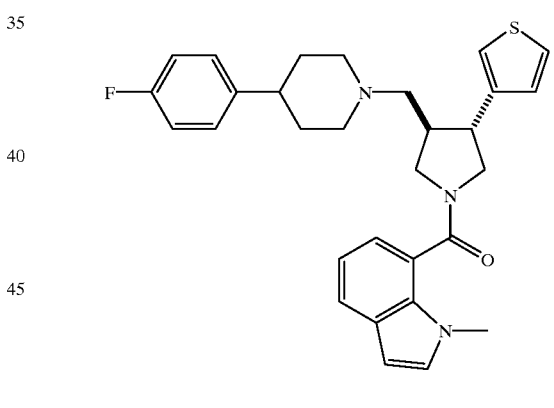

1-(1-Methyl-7-indolemethyl)-3-(R)-4-(4-fluorophenyl)piperidinylmethyl)-4-(R)-(3-thienyl)pyrrolidine To a solution of 0.1 g (0.2 mmol) of 1-(1-methyl-7-indolecarbonyl)-3-(R)-4-(4-fluorophenyl)piperidinylmethyl)-4-(R)-(3-thienyl)pyrrolidine (Example 252) in 3 mL of THF at rt was added 0.3 mL (0.3 mmol) of a 1M solution of $LiAlH_4$ in ether and the reaction mixture was stirred 2 h at rt. To the reaction mixture at 0° C. was added 1 mL of a 1N aqueous solution of NaOH. The raction mixture was filtered through a thin layer of $Na_2CO_3$, concentrated and the residue was purified by chromatography (silica, hexanes:EtOAc, 5:1) to give the title compound. Mass Spectrum (CI) m/e 488 (M+1).

EXAMPLE 325

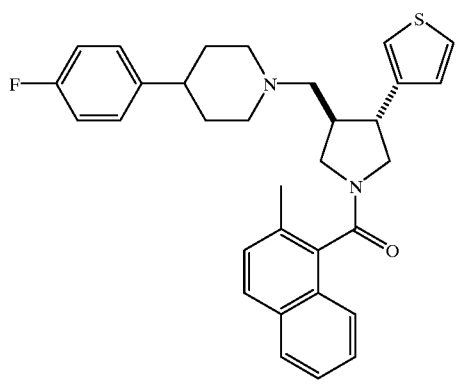

1-(2-Methyl-1-Naphthoyl)-3-(R)-4-(4-fluorophenyl)
piperidinylmethyl)-4-(R)-(3-thienyl)pyrrolidine A mixture of 0.06 g (0.117 mmol) of 3-(S)-(4-(4-fluorophenyl)piperidinylmethyl)-4-(R)-(3-thienyl) pyrrolidine, 0.04 g (0.212 mmol) of 2-methyl-1-naphthoic acid, 0.07 g (0.354 mmol) of 1-[3-(dimethylamino)propyl]-3-ethylcarbodilmide hydrochloride and 0.04 g (0.35 mmol) of dimethylaminopyridine in 5 mL of $CH_2Cl_2$ was stirred at rt for 24 h. The reaction mixture was concentrated and the residue was purified by chromatography (silica, hexanes:EtOAc, 4:1) to give the title compound. Mass Spectrum (CI) m/e 513 (M+1).

EXAMPLE 326

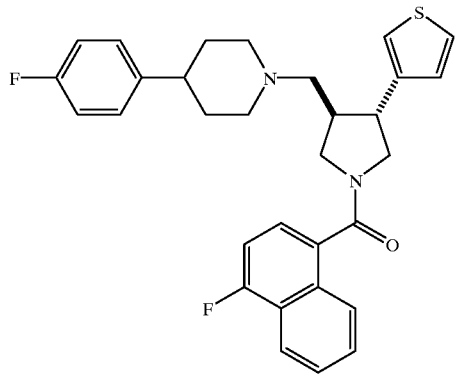

1-(4-Fluoro-1-naphthoyl)-3-(R)-4-(4-fluorophenyl)
piperidinylmethyl)-4-(R)-(3-thienyl)pyrrolidine (R,R isomer of Example 21)

The title compound was prepared from 3-(S)-(4-(4-fluorophenyl)piperidinylmethyl)-4-(R)-(3-thienyl) pyrrolidine and 4-fluoro-1-naphthoic acid according to procedures described in Example 325. Mass Spectrum (CI) m/e 517 (M+1).

EXAMPLE 327

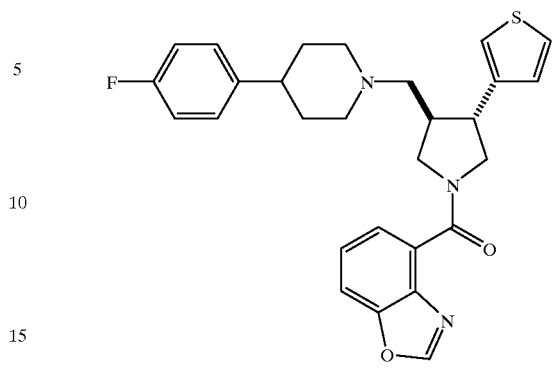

1-(7-Benzoxazolecarbonyl)-3-(R)-4-(4-fluorophenyl)
piperidinylmethyl)-4-(R)-(3-thienyl)pyrrolidine The title compound was prepared from 3-(S)-(4-(4-fluorophenyl)piperidinylmethyl)-4-(R)-(3-thienyl) pyrrolidine and 7-benzoxazolecarboxylic acid according to procedures described in Example 325. Mass Spectrum (CI) m/e 490 (M+1).

Preparation of 7-benzoxazole carboxylic acid
Step 1

Methyl-2-amino-3-hydroxybenzoate

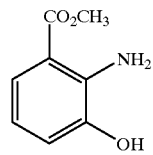

To a solution of 2 g (13.1 mmol) of 2-amino-3-hydroxybenzoic acid in 60 mL of $CH_3OH$ at 0° C. was bubbled HCl gas until the solution was saturated. The reaction was heated at reflux for 12 h. The reaction mixture was concentrated and dissolved in 30 mL of water. The solution was neutralized with sat'd $NaHCO_3$ solution and extracted with EtOAc. The organic fractions were dried over $MgSO_4$, filtered and the filtrate was concentrated to give 1.8 g of the title compound as a brown solid.
Step 2

Methyl-7-benzoxazole carboxylate

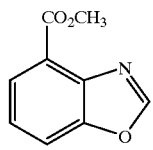

A solution of 0.22 g (1.32 mmol) of methyl-2-amino-3-hydroxybenzoate, 0.77 mL (4.6 mmol) of triethylorthoformate and 0.066 g (0.26 mmol) of pyridinium p-toluene sulfonate in 15 mL of xylene was heated at reflux for 18 h. The reaction mixture was concentrated and purified by chromatograph (silica, hexanes:EtOAc, 6:1) to give 0.22 g of the title compound.

Step 7-benzoxazole carboxylic acid

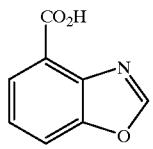

To a solution of 0.21 g (1.18 mmol) of methyl-7-benzoxazole carboxylate in 6 mL of $CH_3OH$ at 0° C. was added 2.9 mL of a 1N solution of KOH in water and the reaction mixture was stirred at rt for 1 h. The reaction mixture was partitioned between water and $CH_2Cl_2$. The aqueous fraction was made acidic with 1N HCl solution and extracted with $CH_2Cl_2$. The organic fraction was dried over $Na_2SO_4$, filtered and the filtrate was concentrated to give 0.17 g of the title compound as a yellow solid.

EXAMPLE 328

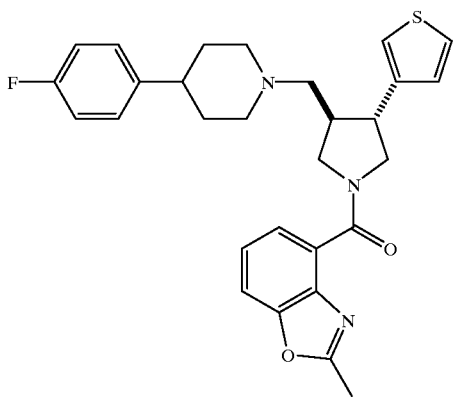

1-(2-Methyl-7-benzoxazolecarbonyl)-3-(R)-4-(4-fluorophenyl)piperidinylmethyl)-4-(R)-(3-thienyl)pyrrolidine The title compound was prepared from 3-(S)-(4-(4-fluorophenyl)piperidinylmethyl)-4-(R)-(3-thienyl)pyrrolidine and 2-methyl-7-benzoxazolecarboxylic acid according to procedures described in Example 325. Mass Spectrum (CI) m/e 504 (M+1).

1-methyl-7-benzoxazole carboxylic acid was prepared as described in Example 327 with the exception that in Step 2, acetyl chloride replaces triethylorthoformate.

EXAMPLE 329

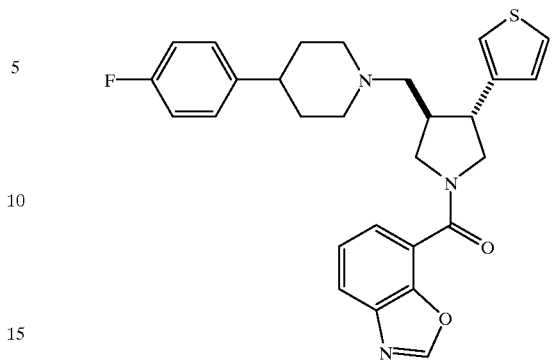

1-(4-Benzoxazolecarbonyl)-3-(R)-4-(4-fluorophenyl)piperidinylmethyl)-4-(R)-(3-thienyl)pyrrolidine The title compound was prepared from 3-(S)-(4-(4-fluorophenyl)piperidinylmethyl)-4-(R)-(3-thienyl)pyrrolidine and 4-benzoxazolecarboxylic acid according to procedures described in Example 325. Mass Spectrum (CI) m/e 490 (M+1).

4-benzoxazole carboxylic acid was prepared as described in Example 327 with the exception that 3-amino-2-hydroxybenzoic acid is used in place of 2-amino-3-hydroxybenzoic acid in Step 1.

EXAMPLE 330

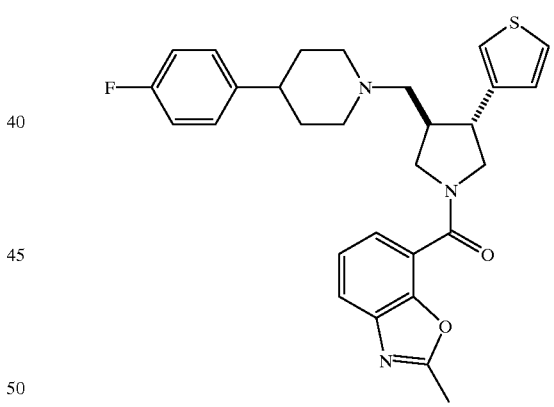

1-(2-Methyl-4-benzoxazolecarbonyl)-3-(R)-4-(4-fluorophenyl)piperidinylmethyl)-4-(R)-(3-thienyl)pyrrolidine The title compound was prepared from 3-(S)-(4-(4-fluorophenyl)piperidinylmethyl)-4-(R)-(3-thienyl)pyrrolidine and 2-methyl-4-benzoxazolecarboxylic acid according to procedures described in Example 325. Mass Spectrum (CI) m/e 504 (M+1).

2-methyl-4-benzoxazole carboxylic acid was prepared as described in Example 327 with the exception that methyl-3-amino-2-hydroxybenzoic acid is reacted with acetyl chloride.

EXAMPLE 331

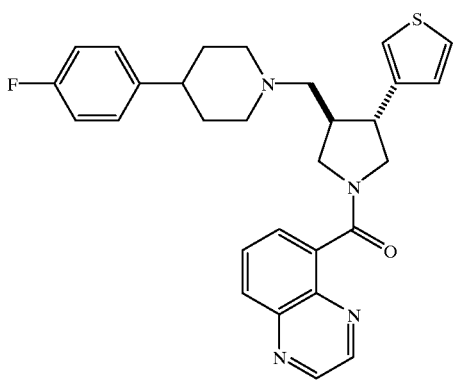

1-(1,4-benzpyrazine-4-carbonyl)-3-(R)-4-(4-fluorophenyl)piperidinylmethyl)-4-(R)-(3-thienyl)pyrrolidine The title compound was prepared from 3-(S)-(4-(4-fluorophenyl)piperidinylmethyl)-4-(R)-(3-thienyl)pyrrolidine and 1,4-benzpyrazine-8-carboxylic acid according to procedures described in Example 325. Mass Spectrum (CI) m/e 501 (M+1).

EXAMPLE 332

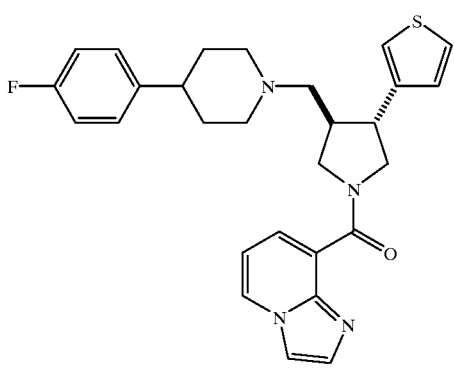

1-(Imidazo[1,2-a]pyridine-7-carbonyl)-3-(R)-4-(4-fluorophenyl)piperidinylmethyl)-4-(R)-(3-thienyl)pyrrolidine The title compound was prepared from 3-(S)-(4-(4-fluorophenyl)piperidinylmethyl)-4-(R)-(3-thienyl)pyrrolidine and Imidazo[1,2-a]pyridine-7-carboxylic carboxylic acid according to procedures described in Example 325. Mass Spectrum (CI) m/e 489 (M+1).

Preparation of Imidazo[1,2-a]pyridine-7-carboxylic acid
Step 1

Benzyl-imidazo[1,2-a]pyridine-7-carboxylate

A solution of 0.2 g (0.876 mmol) of 3-benzyloxcarbonyl-2-aminopyridine, 0.21 mL (1.3 ml) of chloroacetaldehyde and 0.147 g (1.75 mmol) of NaHCO$_3$ in 2 mL of water and 10 mL of EtOH was heated at reflux for 12 h. The reaction mixture was concentrated and the residue was purified by chromatography (silica, CH$_2$Cl$_2$:EtOAc:NH$_3$ (2M in CH$_3$OH), 100:50:5) ot give 0.165 g of the title compound.

Step 2

Imidazo[1,2-a]pyridine-7-carboxylic acid

A solution of 0.16 g (0.634 mmol) of benzyl-imidazo[1,2-a]pyridine-7-carboxylate and 1.5 mL of a 1M aqueous solution of KOH (1.6 mmol) in 4 mL of CH$_3$OH was stirred at rt for 2 h. The reaction mixture was made acidic with 1N HCl and partitioned between water and CH$_2$Cl$_2$. The organic fraction was dried over MgSO$_4$ filtered and the filtrate was concentrated to give 0.1 g of the title compound.

EXAMPLE 333

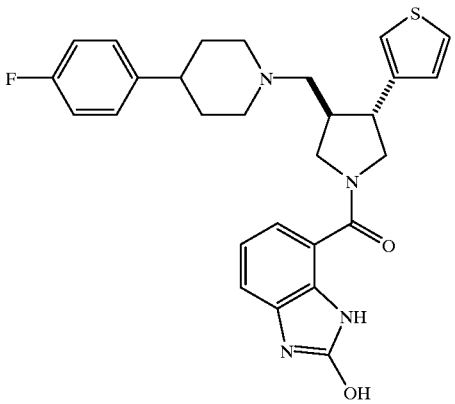

1-(2-Hydroxybenzimidazole-7-carbonyl)-3-(R)-4-(4-fluorophenyl)piperidinylmethyl)-4-(R)-(3-thienyl)pyrrolidine The title compound was prepared from 3-(S)-(4-(4-fluorophenyl)piperidinylmethyl)-4-(R)-(3-thienyl)pyrrolidine and 2-hydroxybenbenzimidazole-7-carboxylic acid according to procedures described in Example 325. Mass Spectrum (CI) m/e 505 (M+1).

Preparation of 2-hydroxybenzimidazole-7-carboxylic acid

A solution of 0.16 g (0.85 mmol) of 2,3-diaminobenzolic acid 0.14 g (0.85 mmol) of carbonyldiimidazole, 0.36 mL (2.55 mmol) of triethylamine in 10 mL of CH2Cl2 was stirred for 12 h at rt. The reaction mixture was concentrated and the residue was triturated three times with a:1 mixture of ether:hexanes. The residue was dried to give 0.15 g of the title compound.

EXAMPLE 334

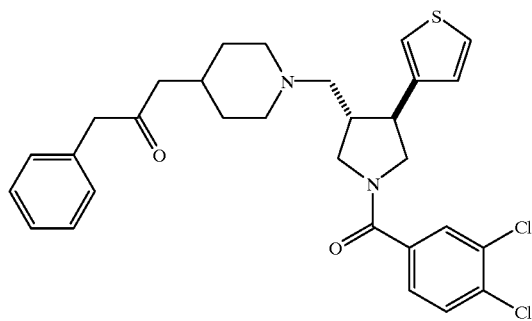

1-(3,4-Dichlorobenzoyl)-3-(RS)-(4-(4-(3-phenyl-2-oxopropyl)piperidinylmethyl)-4-(SR)-(3-thienyl)pyrrolidine The title compound was prepared from 1-(3,4-Dichlorobenzoyl)-3-(RS)-(4-(4-(3-phenyl-2- hydroxypropyl)piperidinylmethyl)-4-(SR)-(3-thienyl) pyrrolidine (Example 228) according to procedures described in Example 233, Step 3. Mass Spectrum (ESI) m/e=555 (M+1 $^{35}$Cl, $^{35}$Cl), 557 (M+1 $^{35}$Cl, $^{37}$Cl), and 559 (M+1 $^{37}$Cl, $^{37}$Cl), $^{13}$C-NMR (CDCl$_3$, 125 MHz): 207.6, 207.5, 167.3, 167.0.

EXAMPLE 335

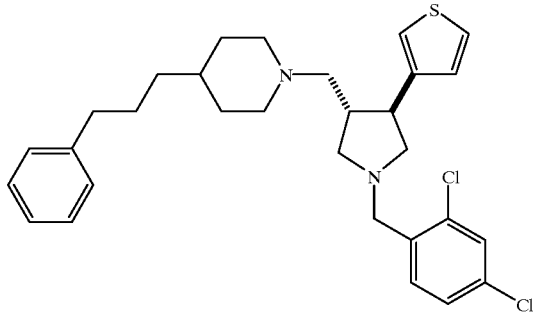

1-(2,4-Dichlorobenzyl)-3-(RS)-(4-(4-(3-phenylpropyl)piperidinylmethyl)-4-(SR)-(3-thienyl) pyrrolidine The title compound was prepared from 1-benzyl-3-(RS)-(4-(4-(3-phenylpropyl)piperidinylmethyl)-4-(SR)-(3-thienyl)pyrrolidine (Example 190) according to procedures described in Examples 2 and 3. Mass Spectrum (ESI) m/e=527 (M+1 $^{35}$Cl, $^{35}$Cl), 529 (M+1 $^{35}$Cl, $^{37}$Cl); and 531 (M+1 $^{37}$Cl, $^{37}$Cl).

EXAMPLE 336

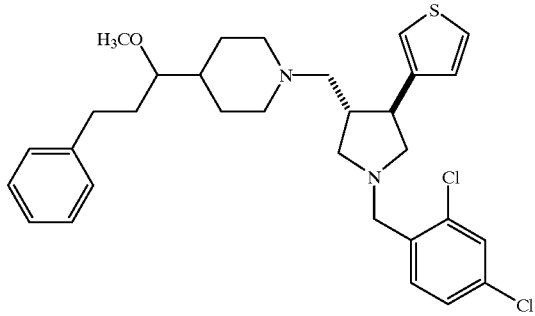

1-(2,4-Dichlorobenzyl)-3-(S)-(4-(4-(3-phenyl-1-(RS)-methoxypropyl)piperidinylmethyl)-4-(S)-(3-thienyl)pyrrolidine Mass Spectrum (ESI) m/e=557 (M+1 $^{35}$Cl, $^{35}$Cl), 559 (M+1 $^{35}$Cl, $^{37}$Cl), and 561 (M+1 $^{37}$Cl, $^{37}$Cl).

Step 1

1-Allyl-3-(R)-hydroxymethyl-4-(S)-(3-thienyl) pyrrolidine

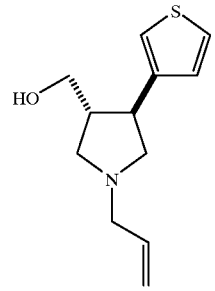

The title compound was prepared according to procedures described in Example 241, Steps 1, 2, and 3 with the change that N-methoxymethyl-N-trimethylsilylmethylallylamine replaces N-methoxymethyl-N-trimethylsilylmethylbenzylamine to prepare (S)-N-[(1-allyl)-4-(S)-(3-thienyl)-3-(R)pyrrolidinylcarbonyl)]-4-benzyl-2-oxazolidinone in Step 2.

Step 2

3-(R)-Hydroxymethyl-4-(S)-(3-thienyl)pyrrolidine

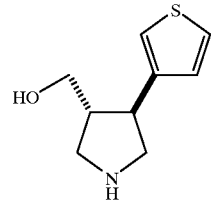

The title compound was prepared from 1-allyl-3-(R)-hydroxymethyl-4-(S)-(3-thienyl)pyrrolidine according to procedures described in Example 291.

Step 3

1-(2,4-Dichlorobenzyl)-3-(R)-hydroxymethyl-4-(S)-(3-thienyl)pyrrolidine

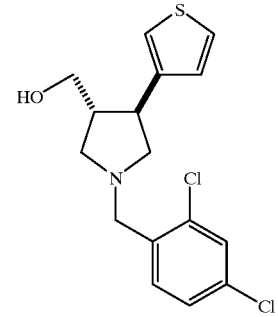

The title compound was prepared from 3-(R)-hydroxymethyl-4-(S)-(3-thienyl)pyrrolidine according to procedures described in Example 3.

Step 4

1-(2,4-Dichlorobenzyl)-3-(R)-formyl-4-(S)-(3-thienyl)pyrrolidine

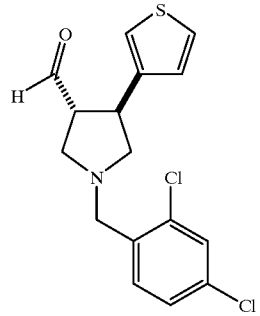

The title compound was prepared from 1-(2,4-dichlorobenzyl)-3-(R)-hydroxymethyl-4-(S)-(3-thienyl)pyrrolidine according to procedures described in Example 233, Step 3.

Step 5

4-(3-phenyl-1-(RS)-methoxypropyl)piperidine

To a solution of 0.218 g (0.68 mmol) of 1-t-butoxy carbonyl-4-(3-phenyl-1-hydroxypropyl)piperidine (Example 239) and 0.3 mL of methyl iodide in 2 mL of DMF was added 0.066 g (1.5 mmol)of NaH (60% dispersion in mineral oil) and the mixture was stirred for 16 h at rt. To the reaction was added 5 mL of water and the mixture was extracted with ethyl acetate. The combined organic fractions were washed with sat'd NaCl solution, dried over $MgSO_4$, filtered and the filtrate was concentrated. The residue was purified by chromatography (silica, hexanes:ethyl acetate, 4:1) to give 1-t-butoxy carbonyl-4-(3-phenyl-1-(RS)-methoxypropyl)piperidine. Removal of the BOC protecting group was achieved as described in Example 233, Step 6 to give the title compound.

Step 6

1-(2,4-Dichlorobenzyl)-3-(S)-(4-(4-(3-phenyl-1-(RS)-methoxypropyl)piperidinylmethyl)-4-(S)-(3-thienyl)pyrrolidine The title compound was prepared from 1-(2,4-dichlorobenzyl)-3-(R)-formyl-4-(S)-(3-thienyl)pyrrolidine and 4-(3-phenyl-1-(RS)-methoxypropyl)piperidine according to procedures described in Example 1, Step F.

The following Examples 337 to 35 were prepared from 1-(2,4-dichlorobenzyl)-3-(R)-formyl-4-(S)-(3-thienyl)pyrrolidine and the corresponding substituted piperidine according to procedures described in Example 336. When not commercially available, the preparation of the substituted piperidine is described.

EXAMPLE 337 AND 338

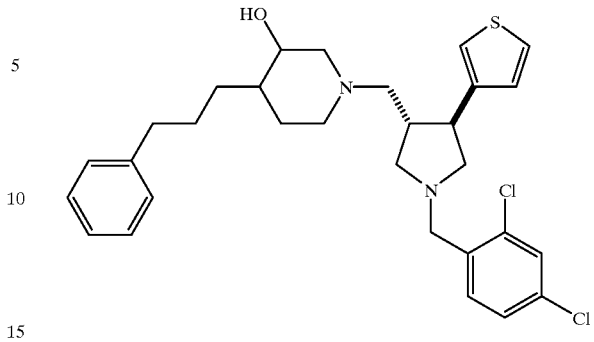

1-(2,4-Dichlorobenzyl)-3-(S)-(trans-(3-hydroxy-4-(3-phenylpropyl))piperidinylmethyl)-4-(S)-(3-thienyl)pyrrolidine (isomers #1 and #2)

Isomer #1
Mass Spectrum (ESI) m/e=543 (M+1 $^{35}Cl$, $^{35}Cl$), 545 (M+1 $^{35}Cl$, $^{37}Cl$), and 547 (M+1 $^{37}Cl$, $^{37}Cl$).

Isomr #2
Mass Spectrum (ESI) m/e=543 (M+1 $^{35}Cl$, $^{35}Cl$), 545 (M+1 $^{35}Cl$, $^{37}Cl$), and 547 (M+1 $^{37}Cl$, $^{37}Cl$).

Preparation of trans-3-Hydroxy-4-(3-phenylpropyl)piperidine

Step 1

4-(3-Phenylpropyl)pyridine

To a solution of 2.32 g (25.0 mmol) of 4-picoline in 40 mL of THF at −78° C. was slowly added 17.5 mL of a 1.6 M solution of n-butyllithium in hexanes (28.0 mmol). The reaction mixture was allowed to warm to rt and stirred for 1 h at rt. This reaction mixture was added via cannula to a solution of 6.8 mL (50.0 mmol) of (2-bromoethyl)benzene in 30 mL of THF at −50° C. The mixture was warmed to rt, quenched by the addition of 50 mL of H2O and extracted with ether. The combined organic fractions were extracted with 2N HCl. The combined aqueous fractions were brought to pH=12 with 5N NaOH and again extracted with ether. The combined ether layers were washed with sat'd NaCl solution, dried over $MgSO_4$, filtered and the filtrate was concentrated. The residue was purified by chromatography (silica, hexanes:ethyl acetate=3:1) to give the title compound.

Step 2

1Benzyl-4-(3-phenylpropyl)-1,2,3,6-tetrahydropyridine

A solution of 1.7 g (8.6 mmol) of 4-(3-phenylpropyl)pyridine and 1.5 mL of benzylbromide in 5 mL of ethanol was stirred at rt for 0.5 h. To the reaction mixture was added 10 mL of ethanol and the mixture was cooled to 0° C. To this mixture was added 0.5 g (13.2 mmol) of $NaBH_4$ small portions over a period of 1 h. To the reaction mixture was then added 5 mL of a 1N NaOH solution and the mixture was partitioned between 200 mL of ether and 50 mL of $H_2O$. The combined organic fractions were washed with sat'd NaCl solution, dried over $MgSO_4$, filtered and the filtrate was concentrated. The residue was purified by chromatography (silica, hexanes:ethyl acetate, 9:1) to give the title compound.

Step 3

(trans)-3-Hydroxy-4-(3-phenylpropyl)piperidine

A solution of 0.590 g (2.02 mmol) of 1-benzyl-4-(3-phenylpropyl)-1,2,3,6-tetrahydropyridine and 4.4 mL of a 1M solution of BH₃.THF in THF in 5 mL of THF was heated under reflux for 1 h. The mixture was cooled to rt, and 5 mL 1N NaOH and 5 mL 30% H₂O₂ were added and stirring was continued for 0.5 h. The mixture was partitioned between 75 mL of ether and 25 mL of H₂O. The combined organic fractions were washed with sat'd NaCl solution, dried over MgSO₄, filtered and the filtrate was concentrated. The residue and 2 mL of ethanolamine were combined in 2 mL of methanol and heated under reflux for 1 h. The mixture was cooled to rt and partititioned between 100 mL of ether and 50 mL of sat'd NaCl solution. The combined organic fractions were washed with sat'd NaCl solution, dried over MgSO₄, filtered and the filtrate was concentrated. The residue was purified by chromatography (silica, hexanes-:ethyl acetate, 2:1) to give 1-benzyl (trans)-3-hydroxy-4-(3-phenylpropyl)piperidine. Removal of the benzyl protecting group was achieved under standard conditions.

EXAMPLE 339

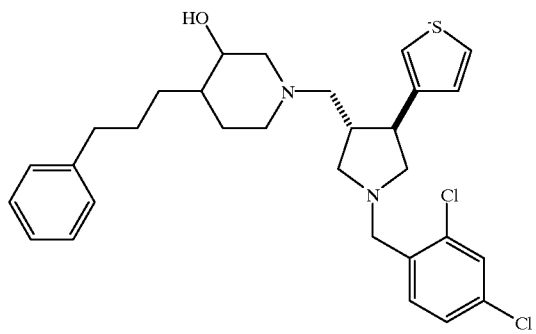

1-(2,4-Dichlorobenzyl)-3-(S)-(cis-(3-hydroxy-4-(3-phenylpropyl))piperidinylmethyl)-4-(S)-(3-thienyl)pyrrolidine Mass Spectrum (ESI) m/e=543 (M+1 ³⁵Cl, ³⁵Cl), 545 (M+1 ³⁵Cl, ³⁷Cl), and 547 (M+1 ³⁷Cl, ³⁷Cl).

Preparation of cis-3-Hydroxy-4-(3-phenylpropyl) piperidine

Step 1

1-Butyloxycarbonyl (trans)-3-hydroxy-4-(3-phenylpropyl)piperidine

A solution of 0.220 g (0.86 mmol) of (trans)-3-hydroxy-4-(3-phenylpropyl)piperidine (Example 337 and 338), 0.15 mL (1.1 mmol) of triethylamine, and 0.220 g (1.0 mmol) of di-t-butyl dicarbonate in 3 mL of methanol was stirred for 16 h. To this reaction mixtur was added 25 mL of H₂O and the mixture was extracted with ether. The combined organic fractions were washed with sat'd NaCl solution, dried over MgSO₄, filtered and the filtrate was concentrated. The residue was purified by chromatography (silica, hexanes-:ethyl acetate, 1:1) to give the title compound.

Step 2

1-Butyloxycarbonyl (cis)-3-(chloroacetoxy)-4-(3-phenylpropyl)piperidine

To a solution of 0.242 g (0.75 mmol) of 1-butyloxycarbonyl (trans)-3-hydroxy4-(3-phenylpropyl) piperidine, 0.189 g (1.5 mmol) of chloroacetic acid, and 0.524 g (1.5 mmol) of triphenylphosphine in 5 mL of THF at 0° C. was slowly added 0.348 g (1.5 mmol) of diethylazodicarboxylate (DEAD). The reaction mixture was allowed to warm to rt and was stirred for 16 h. To the reaction mixture was added 20 mL of ether and it was filtered through a thin pad of celite. The filtrate was washed with sat'd NaHCO3 solution and sat'd NaCl solution, dried over MgSO₄, filtered and the filtrate was concentrated. The residue was purified by chromatography (silica, hexanes-:ethyl acetate, 1:1) to give the title compound.

Step 3

1-Butyloxycarbonyl(cis)-3-hydroxy-4-(3-phenylpropyl) piperidine

A solution of 0.173 g (0.44 mmol) of 1-butyloxycarbonyl (cis)-3-(chloroacetoxy)-4-(3-phenylpropyl)piperidine and 0.30 g (2.2 mmol) of K₂CO₃ in 5 mL of methanol was stirred at rt for 24 h. To the reaction mixture was added 20 mL of sat'd NaCl solution and the mixture was extracted with ether. The combined organic fractions were dried over MgSO₄, filtered and the filtrate was concentrated. The residue was purified by chromatography (silica, hexanes-:ethyl acetate, 1:1) to give 1-butyloxycarbonyl (cis)-3-hydroxy-4-(3-phenylpropyl)piperidine. Removal of the BOC protecting group was achieved as described in Example 233, Step 6 to give the title compound.

EXAMPLE 339

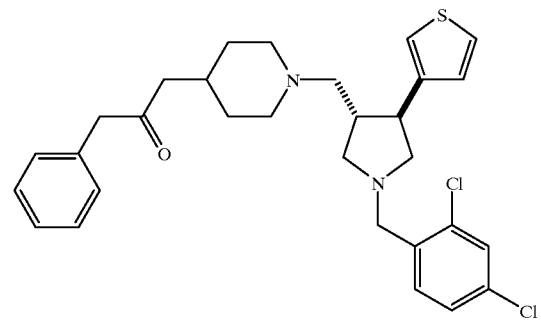

1-(2,4-Dichlorobenzyl)-3-(S)-(4-(3-phenyl-2-oxopropyl)piperidinylmethyl)-4-(S)-(3-thienyl)pyrrolidine The title compound was prepared from 1-(2,4-Dichlorobenzyl)-3-(S)-(4-(3-phenyl-2-hydroxyopropyl) piperidinylmethyl)-4-(S)-(3-thienyl)pyrrolidine (Example 229) according to procedures described in Example 233, Step 3.

Mass Spectrum (ESI) m/e=541 (M+1 ³⁵Cl, ³⁵Cl), 543 (M+1 ³⁵Cl, ³⁷Cl), and 545 (M+1 ³⁷Cl, ³⁷Cl). [α]$_D$=+11.7 (c=0.94, CHCl₃).

EXAMPLE 340

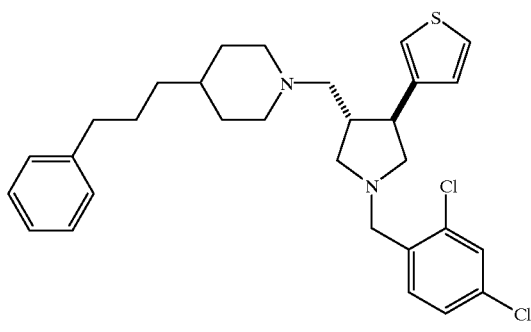

1-(2,4-Dichlorobenzyl)-3-(S)-(4-(3-phenylpropyl) piperidinylmethyl )-4-(S)-(3-thienyl)pyrrolidine (S,S stereoisomer of Example 335)

Mass Spectrum (ESI) m/e=527 (M+1 $^{35}$Cl, $^{35}$Cl), 529 (M+1 $^{35}$Cl, $^{37}$Cl), and 531 (M+1 $^{37}$Cl, $^{37}$Cl). $[\alpha]_D$=+12.4 (c=0.9, CHCl$_3$).

EXAMPLE 341

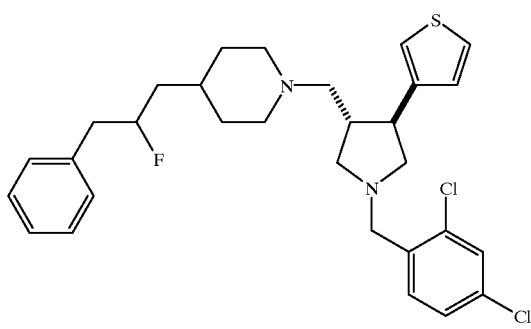

1-(2,4-Dichlorobenzyl)-3-(S)-(4-(3-phenyl-2-(R,S)-fluoropropyl)piperidinylmethyl)-4-(S)-(3-thienyl) pyrrolidine Mass Spectrum (ESI) m/e=545 (M+1 $^{35}$Cl, $^{35}$Cl), 547 (M+1 $^{35}$Cl, $^{37}$Cl), and 549 (M+1 $^{37}$Cl, $^{37}$Cl).

Preparation of 4-(3-Phenyl-2-fluoropropyl) piperidine

A solution of 0.27 mL (2.0 mmol) of (Diethylamino)sulfur trifluoride (DAST) in 2 mL of CH$_2$Cl$_2$ was cooled to −78° C. To this was added a solution of 1-benzyl-4-(3-Phenyl-2-hydroxypropyl)piperidine (Example 228, Step 2) in 2 mL of CH$_2$Cl$_2$. The mixture was stirred and warmed to rt. After 20 min, 10 mL of H2O were added and the mixture was extracted with CH$_2$Cl$_2$. The combined organic fractions were washed with sat'd NaHCO3 solution and sat'd NaCl solution, dried over MgSO$_4$, filtered and the filtrate was concentrated. The residue was purified by chromatography (silica, hexanes:ethyl acetate, 1:1) to give 1-benzyl-4-(3-phenyl-2-fluoropropyl)piperidine. Removal of the benzyl protecting group was achieved under standard conditions.

EXAMPLE 342

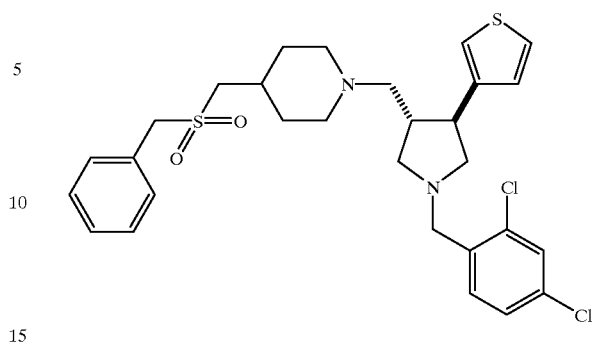

1-(2,4-Dichlorobenzyl)-3-(S)-(4-(benzylsulfonylmethyl)piperidinylmethyl)-4-(S)-(3-thienyl)pyrrolidine Mass Spectrum (ESI) m/e=577 (M+1 $^{35}$Cl, $^{35}$Cl), 579 (M+1 $^{35}$Cl, $^{37}$Cl), and 581 (M+1 $^{37}$Cl, $^{37}$Cl). $[\alpha]_D$=+9.3 (c=2.53, CHCl$_3$).

Preparation of 4-(benzylsulfonylmethyl)piperidine
Step 1

1-t-Butoxycarbonyl-4-(benzylmercaptomethyl) piperidine

To a solution of 500 mg (2.32 mmol) of 1-t-butoxycarbonyl-4-(hydroxymethyl)piperidine (Example 201) and 1 mL (4.5 mmol) of 2,6-di-t-butylpyridine in 10 mL of CH$_2$Cl$_2$ was added 0.4 mL (2.32 mmol) of triflouromethanesulfonic anhydride at −78° C. After stirring for 0.5 h, 0.5 mL (4.5 mmol) of benzylmercaptane were added. The mixture was warmed to 0° C. and allowed to stir for another 15 min. 10 mL of sat'd NaHCO3 solution were added and the mixture was extracted with CH$_2$Cl$_2$. The combined organic fractions were washed with sat'd NaHCO3 solution and sat'd NaCl solution, dried over MgSO$_4$, filtered and the filtrate was concentrated. The residue was purified by chromatography (silica, hexanes::ethyl acetate, 4:1) to give the title compound.

$^1$H NMR (CDCl3) δ7.31–7.33 (m, 5H), 4.08 (m, 2H), 3.70 (s, 2H), 2.65 (m, 2), 2.35 (d, J=7 Hz, 2H), 1.75 (m, 2H), 1.54 (m, 1H), 1.46 (s, 9H), 1.18 (m, 2H).
Step 2

1-t-Butoxycarbonyl-4-(benzylsulfonylmethyl) piperidine

To a solution of 0.147 g (0.46 mmol) of 1-t-butoxycarbonyl-4-(benzylmercaptomethyl)piperidine in 10 mL of THF was added a solution of 0.700 g (1.14 mmol) of potassium peroxymonosulfate in 3 mL of H$_2$O. After stirring vigorously for 1 h, the mixture was poured into 20 mL of H$_2$O and extracted with CH$_2$Cl$_2$. The combined organic fractions were washed with sat'd NaCl solution, dried over MgSO$_4$, filtered and the filtrate was concentrated to give the title compound.

$^1$H NMR (CDCl3) δ7.40 (m, 5H), 4.23 (s, 2H), 4.05 (m, 2H), 2.76 (d,J=7Hz, 2H), 2.70 (m, 2H), 2.15 (m, 1H), 1.85 (m, 2H), 1.43 (s, 9H), 1.21 (m, 2H).
Step 3

4-(Benzylsulfonylmethyl)piperidine

Removal of the BOC protecting group was achieved as described in Example 233, Step 6 to give the title compound.

EXAMPLE 343

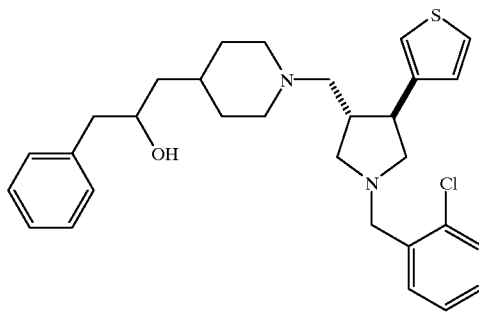

1-(2,4-Dichlorobenzyl )-3-(S)-(4-(3-phenyl-2-(R,S)-hydroxypropyl)piperidinylmethyl)-4-(S)-(3-thienyl) pyrrolidine Mass Spectrum (ESI) m/e=543 (M+1 $^{35}$Cl, $^{35}$Cl), 545 (M+1 $^{35}$Cl, $^{37}$Cl), and 547 (M+1 $^{37}$Cl, $^{37}$Cl).

1-Benzyl-4-(3-phenyl-2-hydroxypropyl)piperidine was obtained as described earlier. (Example 228, Step 2).

EXAMPLE 344

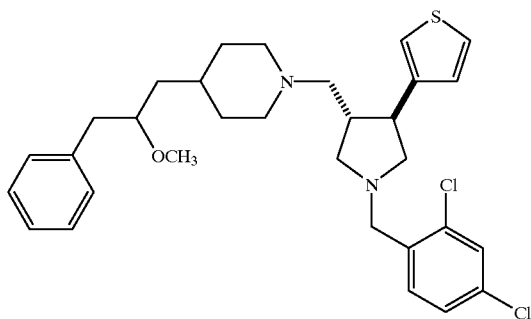

1-(2,4-Dichlorobenzyl)-3-(S)-(4-(3-phenyl-2-(R,S)-methoxypropyl)piperidinylmethyl)-4-(S)-(3-thienyl) pyrrolidine Mass Spectrum (ESI) m/e=557 (M+1 $^{35}$Cl, $^{35}$Cl), 559 (M+1 $^{35}$Cl, $^{37}$Cl), and 561 (M+1 $^{37}$Cl, $^{37}$Cl).

4-(3-Phenyl-2-(RS)-methoxypropyl)piperidine was prepared as described in Example 336.

EXAMPLES 345 AND 346

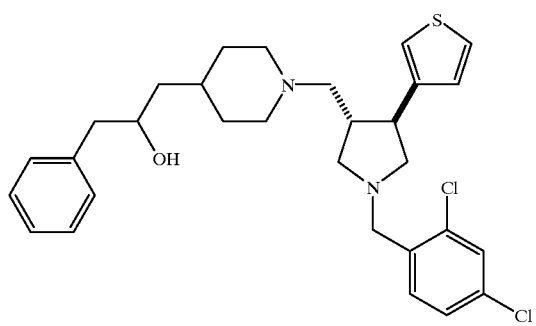

1-(2,4-Dichlorobenzyl)-3-(S)-(4-(3-phenyl-2-hydroxypropyl)piperidinylmethyl)-4-(S)-(3-thienyl) pyrrolidine (isomers 1 and 2) Resolution of Example 343

Step 1

1-(2,4-Dichlorobenzyl)-3-(S)-(4-(3-phenyl-2-((S)-2-phenylpropionyl)oxypropyl)piperidinylmethyl)-4-(S)-(3-thienyl)pyrrolidine (isomers 1 and 2)

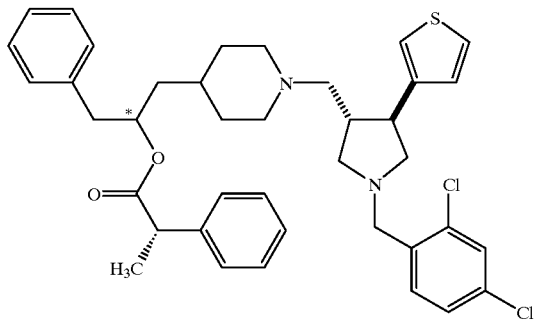

Step 1a

1-Benzyl-4-(3-phenyl-2-((S)-2-phenylpropionyl) oxypropyl)piperidine (Isomers 1a and 2a)

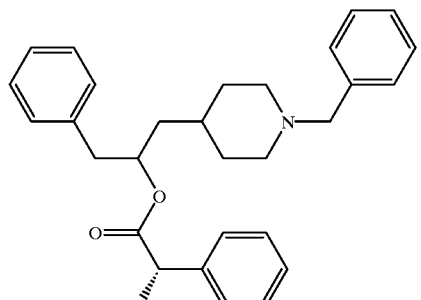

To a solution of 1 g (3.23 mmol) of 1-benzyl-4-(3-phenyl-2-hydroxypropyl)piperidine (Example 228, Step 2) and 0.775 g (5.16 mmol) of (S)-2-phenylpropionic acid in 10 mL of CH$_2$Cl$_2$ at 0° C. was added 1.32 g (6.9 mmol) of 1-[3-(dimethylamino)propyl]-3-ethylcarbodiimide hydrochloride and 0.1 g of 4-(dimethylamino)pyridine. The reaction was stirred for 5 h and let warm to rt. To the reaction mixture was added 80 mL of CH2Cl2 and the mixture was washed three times with 10% NaOH solution. The organic layer was washed with sat'd NaCl solution, dried over $MgSO_4$, filtered and the filtrate was concentrated. The residue was purified by chromatography (silica, hexanes:ethyl acetate, 4:1) to give isomer 1a of the the title compound. Mass Spectrum (ESI) m/e=442 (M+1). $[\alpha]_D$=−3.7 (c=2.44, $CHCl_3$).

Further elution afforded isomer 2a of the title compound. Mass Spectrum (ESI) m/e=442 (M+1). $[\alpha]^D$=+35.6 (c=2.18, $CHCl_3$).

Step 1b 4-(3-phenyl-2-((S)-2-phenylpropionyl)oxypropyl)piperidine (Isomers 1b and 2b)

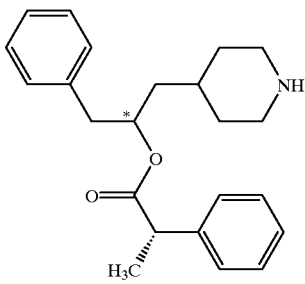

A solution of 0.310 g (0.7 mmol) of 1-benzyl-4-(3-phenyl-2-((S)-2-phenylpropionyl)oxypropyl)piperidine (Step 1a, isomer 1a), 0.8 g of ammonium formate, and 0.3 g of Pearlman's Catalyst ($Pd(OH)_2$, 20% Pd, moist, Degussa type) in 20 mL of methanol was heated at reflux for 1 h. The mixture was cooled to rt and filtered through a pad of celite and concentrated to afford isomer 1b of the title compound which was used without further purification.

Isomer 2b of the title compound was prepared in the same manner from 1-benzyl-4-(3-phenyl-2-((S)-2-phenylpropionyl)oxypropyl)piperidine (Step 1a, isomer 2a).

Step 1c 1-(2,4-Dichlorobenzyl)-3-(S)-(4-(3-phenyl-2-((S)-2-phenylpropionyl)oxypropyl)piperidinylmethyl)-4-(S)-(3-thienyl)pyrrolidine (isomer 1)

The title compound was prepared from 1-allyl-3-(R)-formyl-4-(S)-(3-thienyl)pyrrolidine (Example 292) and 4-(3-phenyl-2-((S)-2-phenylpropionyl)oxypropyl) piperidine (Isomer 1b) as described in Example 1, Step F. The allyl protecting group is removed as described in Example 291, and the pyrrolidine nitrogen is derivatized with 2,4-dichlorobenzaldehyde as described in Example 3.

Mass Spectrum (ESI) m/e=675 (M+1 $^{35}Cl$, $^{35}Cl$), 677 (M+1 $^{35}Cl$, $^{37}Cl$), and 679 (M+1 $^{37}Cl$, $^{37}Cl$). $[\alpha]_D$=+9.0 (c=1.36, $CHCl_3$).

Step 1d 1-(2,4-Dichlorobenzyl)-3-(S)-(4-(3-phenyl-2-((S)-2-phenylpropionyl)oxypropyl)piperidinylmethyl)-4-(S)-(3-thienyl)pyrrolidine (isomer 2)

The title compound was prepared from 1-allyl-3-(R)-formyl-4-(S)-(3-thienyl)pyrrolidine (Example 292) and 4-(3-phenyl-2-((S)-2-phenylpropionyl)oxypropyl) piperidine (Isomer 2b) as described in Example 1, Step F. The allyl protecting group is removed as described in Example 291, and the pyrrolidine nitrogen is derivatized with 2,4-dichlorobenzaldehyde as described in Example 3.

Mass Spectrum (ESI) m/e=675 (M+1 $^{35}Cl$, $^{35}Cl$), 677 (M+1 $^{35}Cl$, $^{37}Cl$), and 679 (M+1 $^{37}Cl$, $^{37}Cl$). $[\alpha]_D$=+34.0 (c=1.06, $CHCl_3$).

Step 2a 1-(2,4-Dichlorobenzyl)-3-(S)-(4-(3-phenyl-2-hydroxypropyl)piperidinylmethyl)-4-(S)-(3-thienyl) pyrrolidine (isomer 1)

To a solution of 0.1107 g (0.16 mmol) of 1-(2,4-dichlorobenzyl)-3-(S)-(4-(3-phenyl-2-((S)-2-phenylpropionyl)oxypropyl)piperidinylmethyl)-4-(S)-(3-thienyl)pyrrolidine (isomer 1) in 2 ml of THF at 0° C. was added 0.5 mL (0.5 mmol) of a 1 M solution of $LiAlH_4$ in THF. The solution was stirred at 0° C. for 1 h, then was quenched by addition of 0.5 mL of 5N NaOH solution. The mixture was diluted with ethyl acetate, dried over $MgSO_4$, filtered and the filtrate concentrated. The residue was purified by chromatography (silica, hexanes:acetone, 4:1) to give the title compound. Mass Spectrum (ESI) m/e=543 (M+1 $^{35}Cl$, $^{35}Cl$), 545 (M+1 $^{35}Cl$, $^{37}Cl$), and 547 (M+1 $^{37}Cl$, $^{37}Cl$). $[\alpha]_D$=+11.7 (c=1.54, $CHCl_3$).

Step 2b 1-(2,4-Dichlorobenzyl)-3-(S)-(4-(3-phenyl-2-hydroxypropyl)piperidinylmethyl)-4-(S)-(3-thienyl) pyrrolidine (isomer 2)

The title compound was prepared from 1-(2,4-dichlorobenzyl)-3-(S)-(4-(3-phenyl-2-((S)-2-phenylpropionyl)oxypropyl)piperidinylmethyl)-4-(S)-(3-thienyl)pyrrolidine (isomer 2) according to procedures described in Step 2a. Mass Spectrum (ESI) m/e=543 (M+1 $^{35}Cl$, $^{35}Cl$), 545 (M+1 $^{35}Cl$, $^{37}Cl$), and 547 (M+1 $^{37}Cl$, $^{37}Cl$). $[\alpha]_D$=+16.0 (c=2.0, $CHCl_3$).

EXAMPLE 347 AND 348

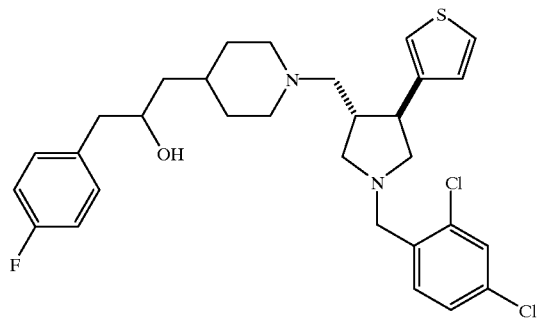

1-(2,4-Dichlorobenzyl)-3-(S)-(4-(3-(4-fluorophenyl)-2-hydroxypropyl)piperidinylmethyl)-4-(S)-(3-thienyl)pyrrolidine (isomers 1 and 2)

Isomer 1 of the title compound was prepared according to procedures described in Examples 345 and 346. Mass Spectrum (ESI) m/e=561 (M+1 $^{35}Cl$, $^{35}Cl$), 563 (M+1 $^{35}Cl$, $^{37}Cl$), and 565 (M+1 $^{37}Cl$, $^{37}Cl$). $[\alpha]_D$=+9.4(c=1.5, $CHCl_3$).

Isomer 2 of the title compound was prepared according to procedures describeb in Examples 345 and 346. Mass Spectrum (ESI) m/e=561 (M+1 $^{35}Cl$, $^{35}Cl$), 563 (M+1 $^{35}Cl$, $^{37}Cl$), and 565 (M+1 $^{37}Cl$, $^{37}Cl$). $[\alpha]_D$=+15.34 (c=1.6, $CHCl_3$).

The following Examples 349 to xxx were prepared from 1-allyl-3-(R)-formyl-4-(S)-(3-thienyl)pyrrolidine (Example 292). The piperidine groups were prepared according to procedures describd in Example 201 and were appended as described in Example 1, Step F. The allyl protecting group is removed as described in Example 291, and the pyrrolidine nitrogen is derivatized with 2,4-dichlorobenzaldehyde as described in Example 3.

EXAMPLE 349

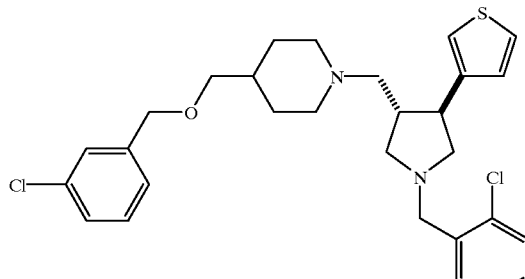

1-(2,4-Dichlorobenzyl)-3-(S)-(4-(3-chlorobenzyloxymethyl)piperidinylmethyl)-4-(S)-(3-thienyl)pyrrolidine Mass Spectrum (ESI) m/e=563 (M+1 $^{35}$Cl, $^{35}$Cl, $^{35}$Cl), 565 (M+1 $^{35}$Cl, $^{35}$Cl, $^{37}$Cl), 567 (M+1 $^{35}$Cl, $^{37}$Cl, $^{37}$Cl), and 569 (M+1 $^{37}$Cl, $^{37}$Cl, $^{37}$Cl).). [α]$_D$=+4.1 (c=0.8, CHCl$_3$).

EXAMPLE 350

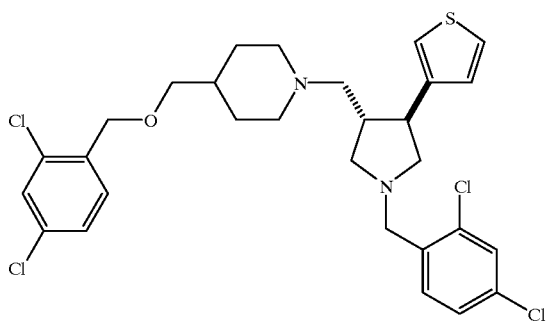

1-(2,4-Dichlorobenzyl)-3-(S)-(4-(2,4-dichlorobenzyloxymethyl)piperidinylmethyl)-4-(S)-(3-thienyl)pyrrolidine Mass Spectrum (ESI) m/e=597 (M+1 $^{35}$Cl, $^{35}$Cl, $^{35}$Cl, $^{35}$Cl), 599 (M+1 $^{35}$Cl, $^{35}$Cl, $^{35}$Cl, $^{37}$Cl), 601 (M+1 $^{35}$Cl, $^{35}$Cl, $^{37}$Cl, $^{37}$Cl), 603 (M+1 $^{35}$Cl, $^{37}$Cl, $^{37}$Cl, $^{37}$Cl), and 605 (M+1 $^{37}$Cl, $^{37}$Cl, $^{37}$Cl, $^{37}$Cl). ). [α]$_D$=+9.4 (c=1.6, CHCl$_3$).

EXAMPLE 351

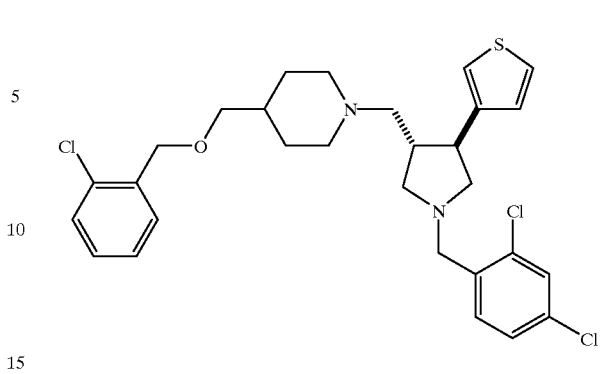

1-(2,4-Dichlorobenzyl)-3-(S)-(4-(2-chlorobenzyloxymethyl)piperdinylmethyl)-4-(S)-(3-thienyl)pyrrolidine Mass Spectrum (ESI) m/e=563 (M+1 $^{35}$Cl, $^{35}$Cl, $^{35}$Cl), 565 (M+1 $^{35}$Cl, $^{35}$Cl, $^{37}$Cl), 567 (M+1 $^{35}$Cl, $^{37}$Cl, $^{37}$Cl), and 569 (M+1 $^{37}$Cl, $^{37}$Cl, $^{37}$Cl).). [α]$_D$=+13.7 (c=3.1, CHCl$_3$).

EXAMPLE 352

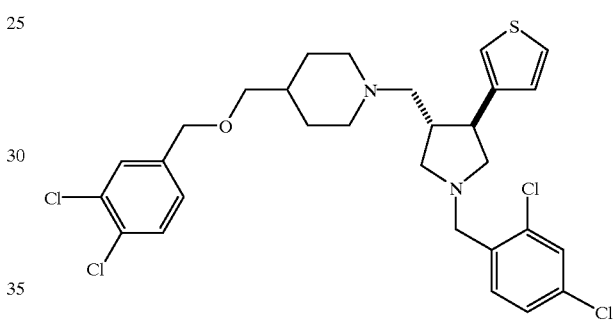

1-(2,4-Dichlorobenzyl)-3-(S)-(4-(3,4-dichlorobenzyloxymethyl)piperidinylmethyl)-4-(S)-(3-thienyl)pyrrolidine Mass Spectrum (ESI) m/e=597 (M+1 $^{35}$Cl, $^{35}$Cl, $^{35}$Cl, $^{35}$Cl), 599 (M+1 $^{35}$Cl, $^{35}$Cl, $^{35}$Cl, $^{37}$Cl), 601 (M+1 $^{35}$Cl, $^{35}$Cl, $^{37}$Cl, $^{37}$Cl), 603 (M+1 $^{35}$Cl, $^{37}$Cl, $^{37}$Cl, $^{37}$Cl), and 605 (M+1 $^{37}$Cl, $^{37}$Cl, $^{37}$Cl, $^{37}$Cl).). [α]$_D$=+9.7 (c+1.2, CHCl$_3$).

EXAMPLE 353

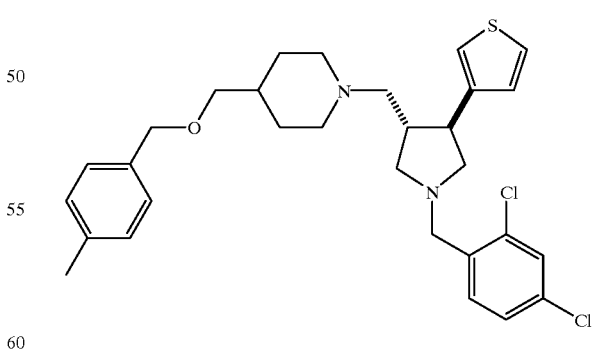

1-(2,4-Dichlorobenzyl)-3-(S )-(4-(4-methylbenzyloxymethyl)piperidinylmethyl)-4-(S)-(3-thienyl)pyrrolidine Mass Spectrum (ESI) m/e=543 (M+1 $^{35}$Cl, $^{35}$Cl), 545 (M+1 $^{35}$Cl, $^{37}$Cl), and 547 (M+1 $^{37}$Cl, $^{37}$Cl). [α]$_D$=+12.2 (c=1.5, CHCl$_3$).

EXAMPLE 354

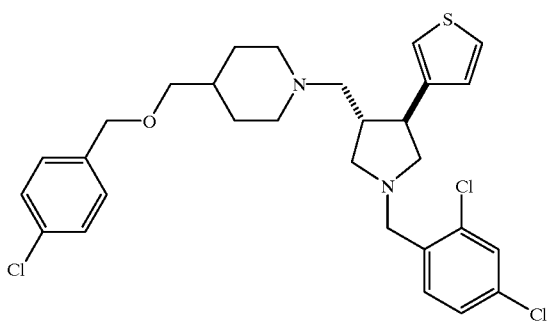

1-(2,4-Dichlorobenzy)-3-(S)-(4-(4-chlorobenzyloxymethyl)piperidinylmethyl)-4-(S)-(3-thienyl)pyrrolidine Mass Spectrum (ESI) m/e=563 (M+1 $^{35}$Cl, $^{35}$Cl, $^{35}$Cl), 565 (M+1 $^{35}$Cl, $^{35}$Cl, $^{37}$Cl), 567 (M+1 $^{35}$Cl, $^{37}$Cl, $^{37}$Cl), and 569 (M+1 $^{37}$Cl, $^{37}$Cl, $^{37}$Cl).). $[\alpha]_D$=+11.3 (c=1.4, CHCl$_3$).

EXAMPLE 355

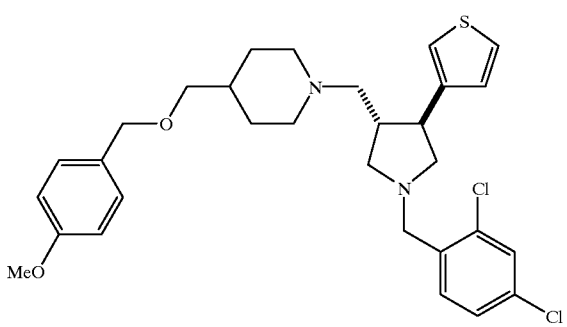

1-(2,4-Dichlorobenzyl)-3-(S)-(4-(methoxybenzyloxymethyl)piperdinylmethyl)-4-(S)-(3-thienyl)pyrrolidine Mass Spectrum (ESI) m/e=559 (M+1 $^{35}$Cl, $^{35}$Cl), 561 (M+1 $^{35}$Cl, $^{37}$Cl), and 563 (M+1 $^{37}$Cl, $^{37}$Cl). $[\alpha]_D$=+10.8 (c=1.2, CHCl$_3$).

Preparation of 4-(methoxybenzyloxymethyl)piperidine

Step 1

1-t-Butoxycarbonyl-4-(methoxybenzyloxymethyl)piperidine

The title compound was prepared as described in Example 201.

Step 2

4-(Methoxybenzyloxymethyl)piperidine 410 mg (1.2 mmol) of 1-t-butoxycarbonyl-4-(methoxybenzyloxymethyl)piperidine and 0.28 mL (2.4 mmol) of 2,6-lutidine were combined in 2.5 mL of CH$_2$Cl$_2$. 0.42 mL (1.8 mmol) of t-butyldimethylsilyl trifluoromethane sulfonate were added and the mixture was stirred for 1 h at rt. 10 mL of sat'd NH4Cl-solution were added and the mixture was extracted with CH$_2$Cl$_2$. The combined organic fractions were washed with sat'd NaCl solution, dried over MgSO$_4$, filtered and the filtrate was concentrated. The residue was redissolved in 3 mL of THF. 2 mL of a solution of tetrabutylammonium fluoride (1M in THF) were added and the mixture was stirred for 2 h at rt. 10 mL of sat'd NaHCO3-solution were added and the mixture was extracted with CH$_2$Cl$_2$. The combined organic fractions were washed with sat'd NaCl solution, dried over MgSO$_4$, filtered and the filtrate was concentrated to give the title compound which was used without further purification.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

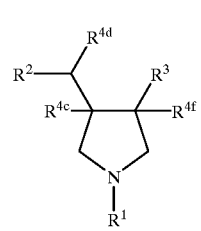

wherein:

$R^1$ is —X—$R^8$, wherein X is selected from the group consisting of:
(1) —CH$_2$—,
(2) —CO—,
(3) —CH$_2$CH$_2$—,
(4) —CH$_2$CH$_2$CH$_2$—, and
(5) —CH(C$_{1-6}$ alkyl)-,
and wherein $R^8$ is a selected from:
phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:
(a) C$_{1-6}$ alkyl, C$_{2-6}$ alkenyl, C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$, wherein R$^9$ and R$^{10}$ are independently selected from hydrogen, C$_{1-6}$ alkyl, C$_{2-6}$ alkenyl, and C$_{2-6}$ alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH($C_{1-6}$ alkyl), —N($C_{1-6}$ alkyl)($C_{1-6}$ alkyl), or trifluoromethyl,
(B) naphthyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH($C_{1-6}$ alkyl), —N($C_{1-6}$ alkyl)($C_{1-6}$ alkyl), or trifluoromethyl,
(C) heterocycle, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH($C_{1-6}$ alkyl), —N($C_{1-6}$ alkyl)($C_{1-6}$ alkyl), or trifluoromethyl,
(D) hydroxy,
(E) —O($C_{1-6}$ alkyl),
(F) —$CO_2(C_{1-6}$ alkyl),
(G) —$S(O)_n$—($C_{1-6}$ alkyl), wherein n is an integer selected from 0, 1 and 2,
(H) halogen,
(I) —$NH_2$,
(J) —NH($C_{1-6}$ alkyl), and
(K) —N($C_{1-6}$ alkyl)($C_{1-6}$ alkyl),
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9CO$—$NR^9R^{10}$,
(ix) —$S(O)_2$—$NR^9R^{10}$, wherein n is an integer selected from 0, 1 and 2,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvi) —O—$R^9$,
(xvii) —O($C_{1-6}$ alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(b) —O—$C_{1-6}$alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9CO$—$NR^9R^{10}$,
(ix) —$S(O)_2$—$NR^9R^{10}$,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvii) —O—$R^9$,
(xvii) —O($C_{1-6}$ alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(c) —$NO_2$,
(d) hydroxy,
(e) halogen,
(f) —$NR^9R^{10}$,
(g) —$NR^9$—$COR^{10}$,
(h) —$NR^9$—$CO_2R^{10}$,
(i) —CO—$NR^9R^{10}$,
(j) —OCO—$NR^9R^{10}$,
(k) —$NR^9CO$—$NR^9R^{10}$,
(l) —$S(O)_2$—$NR^9R^{10}$,
(m) —$NR^9S(O)_2$—$R^{10}$,
(n) —$NR^9S(O)_2$—$NR^9R^{10}$,
(o) —$S(O)_n$—$R^9$,
(p) —$CF_3$,
(q) —$CHF_2$,
(r) —$CH_2F$,
(s) —OCO—$R^9$,
(t) —$OCO_2$—$R^9$, and
(u) —CO—$R^9$;

$R^2$ is selected from the group consisting of:

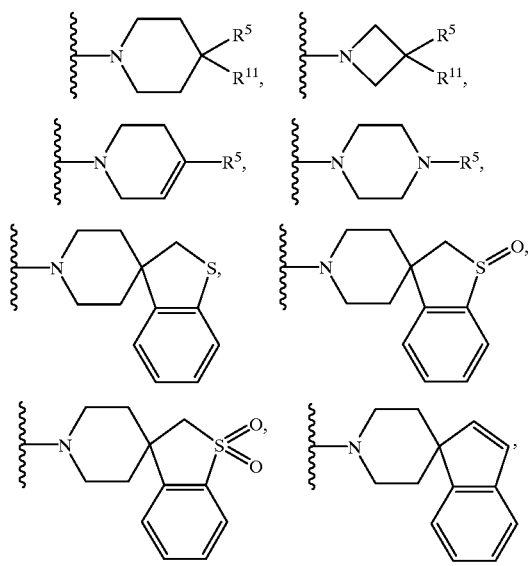

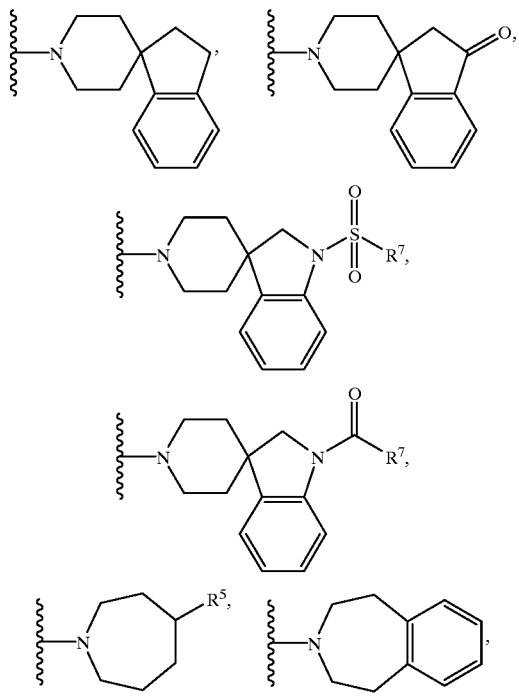

wherein R[5] is a selected from:
(1) —NR[6]CO—O—R[7], wherein R[6] is hydrogen, $C_{1-6}$ alkyl or $C_{1-6}$ alkyl-$C_{5-6}$ cycloalkyl, and R[7] is $C_{1-6}$ alkyl, $C_{5-6}$ cycloalkyl, benzyl or phenyl, wherein the alkyl, cycloalkyl, benzyl or phenyl is unsubstituted or substituted with halogen, $C_{1-3}$alkyl, $C_{1-3}$alkoxy or trifluoromethyl,
(2) phenyl, which is unsubstituted or substituted with halogen, hydroxy, $C_{1-6}$alkyl, $C_{1-6}$alkoxy, —$CO_2$($C_{1-6}$ alkyl), —$NH_2$, —NHR[9], —NR[9]R[10], or trifluoromethyl,
(3) -pyridyl,
(4) -thienyl,
(5) —$C_{1-6}$alkyl-phenyl, —$C_{1-6}$alkyl-naphthyl, —$C_{1-6}$alkyl-indenyl, —$C_{1-6}$alkyl-indanyl, and —$C_{1-6}$alkyl-heterocycle, wherein the phenyl, naphthyl, indenyl, indanyl, or heterocycle is unsubstituted or substituted with: halogen, hydroxy, $C_{1-6}$alkyl, $C_{1-6}$alkoxy, —$CO_2$($C_{1-6}$ alkyl), —$NH_2$, —NHR[9], —NR[9]R[10], or trifluoromethyl; and wherein the —$C_{1-6}$alkyl is optionally substituted with oxo, hydroxy, $C_{1-6}$alkoxy, acetoxy, or halogen,
(6) —O—$C_{1-6}$alkyl-phenyl, —O—$C_{1-6}$alkyl-naphthyl, —O—$C_{1-6}$alkyl-indenyl, —O—$C_{1-6}$alkyl-indanyl, and —O—$C_{1-6}$alkyl-heterocycle, wherein the phenyl, naphthyl, indenyl, indanyl, or heterocycle is unsubstituted or substituted with: halogen, hydroxy, $C_{1-6}$alkyl, $C_{1-6}$alkoxy, —$CO_2$($C_{1-6}$ alkyl), —$NH_2$, —NHR[9], —NR[9]R[10], or trifluoromethyl,
(7) —$C_{1-4}$alkyl-O—$C_{1-4}$alkyl-phenyl, wherein the phenyl is unsubstituted or substituted with halogen, hydroxy, $C_{1-6}$alkyl, $C_{1-6}$alkoxy, —$CO_2$($C_{1-6}$ alkyl), —$NH_2$, —NHR[9], —NR[9]R[10], or trifluoromethyl, and
(8) —$C_{1-4}$alkyl-S(O)$_n$—$C_{1-4}$alkyl-phenyl, wherein the phenyl is unsubstituted or substituted with halogen, hydroxy, $C_{1-6}$alkyl, $C_{1-6}$alkoxy, —$CO_2$($C_{1-6}$ alkyl), —$NH_2$, —NHR[9], —NR[9]R[10], or trifluoromethyl;
and wherein R[11] is a selected from:
(1) -hydrogen,
(2) —OH,
(3) —$C_{1-6}$alkyl, and
(4) -halogen;
R[3] is thienyl or furanyl, which may be unsubstituted or substituted, where the substituents are independently selected from:
(1) $C_{1-6}$ alkyl, which is unsubstituted or substituted, wherein the substituents are independently selected from:
(a) hydroxy,
(b) halogen,
(c) —NR[9]R[10],
(d) —NR[9]—COR[10],
(e) —NR[9]—$CO_2$R[10],
(f) —$CF_3$,
(g) —$CHF_2$,
(h) —$CH_2F$,
(i) —O—R[9], and
(j) phenyl,
(2) —O—$C_{1-6}$alkyl, unsubstituted or substituted with a substituent which is independently selected from:
(a) hydroxy,
(b) halogen,
(c) —NR[9]R[10],
(d) —NR[9]—COR[10],
(e) —NR[9]—$CO_2$R[10],
(f) —$CF_3$,
(g) —$CHF_2$,
(h) —$CH_2F$,
(i) —O—R[9], and
(j) phenyl,
(3) hydroxy,
(4) halogen,
(5) —$CF_3$,
(6) —$CHF_2$,
(7) —$CH_2F$,
(8) —O—R[9], and
(9) —O($C_{1-6}$ alkyl)-O—R[9];
R[4c], R[4d], and R[4f] are independently selected from the group consisting of:
(1) hydrogen, and
(2) $C_{1-6}$ alkyl;
and pharmaceutically acceptable salts thereof and individual diastereomers thereof.

2. A compound of the formula Ib:

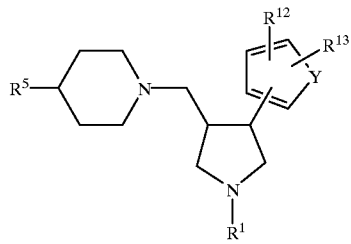

wherein:
R[1] is —X—R[8], wherein X is selected from the group consisting of:
(1) —$CH_2$—,
(2) —CO—, and
(3) —$CH_2CH_2$—, and wherein R$^8$ is a selected from:
  phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:
    (a) C$_{1-6}$ alkyl, C$_{2-6}$ alkenyl, C$_{2-6}$ alkynyl, wherein the alkyl, alkenyl, or alkynyl is unsubstituted or substituted, wherein the substituents are independently selected from:
      (i) hydroxy,
      (ii) halogen,
      (iii) —NR$^9$R$^{10}$, wherein R$^9$ and R$^{10}$ are independently selected from hydrogen, C$_{1-6}$ alkyl, C$_{2-6}$ alkenyl, and C$_{2-6}$ alkynyl, wherein the alkyl, alkenyl, or alkynyl is unsubstituted or substituted, wherein the substituents are independently selected from:
        (A) phenyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
        (B) naphthyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
        (C) heterocycle, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
        (D) hydroxy,
        (E) —O(C$_{1-6}$ alkyl),
        (F) —CO$_2$(C$_{1-6}$ alkyl),
        (G) —S(O)$_n$—(C$_{1-6}$ alkyl), wherein n is an integer selected from 0, 1 and 2,
        (H) halogen,
        (I) —NH$_2$,
        (J) —NH(C$_{1-6}$ alkyl), and
        (K) —N(C$_{1-6}$ alkyl)(C$_{1-6}$ alkyl),
      (iv) —NR$^9$—COR$^{10}$,
      (v) —NR$^9$—CO$_2$R$^{10}$,
      (vi) —CO—NR$^9$R$^{10}$,
      (vii) —OCO—NR$^9$R$^{10}$,
      (viii) —NR$^9$CO—NR$^9$R$^{10}$,
      (ix) —S(O)$_2$—NR$^9$R$^{10}$, wherein n is an integer selected from 0, 1 and 2,
      (x) —NR$^9$S(O)$_2$—R$^{10}$,
      (xi) —NR$^9$S(O)$_2$—NR$^9$R$^{10}$,
      (xii) —S(O)$_n$—R$^9$,
      (xiii) —CF$_3$,
      (xiv) —CHF$_2$,
      (xv) —CH$_2$F,
      (xvi) —O—R$^9$,
      (xvii) —O(C$_{1-6}$ alkyl)-O—R$^9$,
      (xviii) phenyl,
      (xix) naphthyl,
      (xx) indenyl,
      (xxi) indanyl,
      (xxii) heterocycle,
      (xxiii) —CO-phenyl,
      (xxiv) —CO-naphthyl,
      (xxv) —CO-indenyl,
      (xxvi) —CO-indanyl,
      (xxvii) —CO-heterocycle,
      (xxviii) —OCO—R$^9$,
      (xxix) —OCO$_2$—R$^9$, and
      (xxx) —CO—R$^9$,
    (b) —O—C$_{1-6}$alkyl, —O—C$_{2-6}$ alkenyl, —O—C$_{2-6}$ alkynyl, wherein the alkyl, alkenyl, or alkynyl is unsubstituted or substituted, wherein the substituents are independently selected from:
      (i) hydroxy,
      (ii) halogen,
      (iii) —NR$^9$R$^{10}$,
      (iv) —NR$^9$—COR$^{10}$,
      (v) —NR$^9$—CO$_2$R$^{10}$,
      (vi) —CO—NR$^9$R$^{10}$,
      (vii) —OCO—NR$^9$R$^{10}$,
      (viii) —NR$^9$CO—NR$^9$R$^{10}$,
      (ix) —S(O)$_2$—NR$^9$R$^{10}$,
      (x) —NR$^9$S(O)$_2$—R$^{10}$,
      (xi) —NR$^9$S(O)$_2$—NR$^9$R$^{10}$,
      (xii) —S(O)$_n$—R$^9$,
      (xiii) —CF$_3$,
      (xiv) —CHF$_2$,
      (xv) —CH$_2$F,
      (xvi) —O—R$^9$,
      (xvii) —O(C$_{1-6}$ alkyl)-O—R$^9$,
      (xviii) phenyl,
      (xix) naphthyl,
      (xx) indenyl,
      (xxi) indanyl,
      (xxii) heterocycle,
      (xxiii) —CO-phenyl,
      (xxiv) —CO-naphthyl,
      (xxv) —CO-indenyl,
      (xxvi) —CO-indanyl,
      (xxvii) —CO-heterocycle,
      (xxviii) —OCO—R$^9$,
      (xxix) —OCO$_2$—R$^9$, and
      (xxx) —CO—R$^9$,
    (c) —NO$_2$,
    (d) hydroxy,
    (e) halogen,
    (f) —NR$^9$R$^{10}$,
    (g) —NR$^9$—COR$^{10}$,
    (h) —NR$^9$—CO$_2$R$^{10}$,
    (i) —CO—NR$^9$R$^{10}$,
    (j) —OCO—NR$^9$R$^{10}$,
    (k) —NR$^9$CO—NR$^9$R$^{10}$,
    (l) —S(O)$_2$—NR$^9$R$^{10}$,
    (m) —NR$^9$S(O)$_2$—R$^{10}$,
    (n) —NR$^9$S(O)$_2$—NR$^9$R$^{10}$,
    (o) —S(O)$_n$—R$^9$,
    (p) —CF$_3$,
    (q) —CHF$_2$,
    (r) —CH$_2$F,
    (s) —OCO—R$^9$,
    (t) —OCO$_2$—R$^9$, and
    (u) —CO—R$^9$;
  R$^5$ is a selected from:
    (1) —NR$^6$CO—O—R$^7$, wherein R$^6$ is hydrogen, C$_{1-6}$ alkyl or C$_{1-6}$ alkyl-C$_{5-6}$ cycloalkyl, and R$^7$ is C$_{1-6}$ alkyl, C$_{5-6}$ cycloalkyl, benzyl or phenyl, wherein the alkyl, cycloalkyl, benzyl or phenyl is unsubstituted or substituted with halogen, C$_{1-3}$alkyl, C$_{1-3}$alkoxy or trifluoromethyl,
    (2) phenyl, which is unsubstituted or substituted with halogen, hydroxy, C$_{1-6}$alkyl, C$_{1-6}$alkoxy, —CO$_2$(C$_{1-6}$ alkyl), —NH₂, —NHR⁹, —NR⁹R¹⁰, or trifluoromethyl, (3) -pyridyl,
(4) -thienyl,
(5) —C₁₋₆alkyl-phenyl, —C₁₋₆alkyl-naphthyl, —C₁₋₆alkyl-indenyl, —C₁₋₆alkyl-indanyl, and —C₁₋₆alkyl-heterocycle, wherein the phenyl, naphthyl, indenyl, indanyl, or heterocycle is unsubsituted or substituted with: halogen, hydroxy, C₁₋₆alkyl, C₁₋₆alkoxy, —CO₂(C₁₋₆ alkyl), —NH₂, —NHR⁹, —NR⁹R¹⁰, or trifluoromethyl; and wherein the —C₁₋₆alkyl is optionally substituted with oxo, hydroxy, C₁₋₆alkoxy, acetoxy, or halogen,
(6) —O—C₁₋₆alkyl-phenyl, —O—C₁₋₆alkyl-naphthyl, —O—C₁₋₆alkyl-indenyl, —O—C₁₋₆alkyl-indanyl, and —O—C₁₋₆alkyl-heterocycle, wherein the phenyl, naphthyl, indenyl, indanyl, or heterocycle is unsubsituted or substituted with: halogen, hydroxy, C₁₋₆alkyl, C₁₋₆alkoxy, —CO₂(C₁₋₆ alkyl), —NH₂, —NHR⁹, —NR⁹R¹⁰, or trifluoromethyl,
(7) —C₁₋₄alkyl-O—C₁₋₄alkyl-phenyl, wherein the phenyl is unsubsituted or substituted with halogen, hydroxy, C₁₋₆alkyl, C₁₋₆alkoxy, —CO₂(C₁₋₆ alkyl), —NH₂, —NHR⁹, —NR⁹R¹⁰, or trifluoromethyl, and
(8) —C₁₋₄alkyl-S(O)ₙ—C₁₋₄alkyl-phenyl, wherein the phenyl is unsubsituted or substituted with halogen, hydroxy, C₁₋₆alkyl, C₁₋₆alkoxy, —CO₂(C₁₋₆ alkyl), —NH₂, —NHR⁹, —NR⁹R¹⁰, or trifluoromethyl;

R¹² and R¹³ are independently selected from:
(1) hydrogen,
(2) C₁₋₆ alkyl, which is unsubstituted or substituted, wherein the substituents are independently selected from:
  (a) hydroxy,
  (b) halogen,
  (c) —NR⁹R¹⁰,
  (d) —NR⁹—COR¹⁰,
  (e) —NR⁹—CO₂R¹⁰,
  (f) —CF₃,
  (g) —CHF₂,
  (h) —CH₂F,
  (i) —O—R⁹, and
  (j) phenyl,
(3) —O—C₁₋₆alkyl, unsubstituted or substituted with a substituent which is independently selected from:
  (a) hydroxy,
  (b) halogen,
  (c) —NR⁹R¹⁰,
  (d) —NR⁹—COR¹⁰,
  (e) —NR⁹—CO₂R¹⁰,
  (f) —CF₃,
  (g) —CHF₂,
  (h) —CH₂F,
  (i) —O—R⁹, and
  (j) phenyl,
(4) hydroxy,
(5) halogen,
(6) —CF₃,
(7) —CHF₂,
(8) —CH₂F,
(9) —O—R⁹, and
(10) —O(C₁₋₆ alkyl)-O—R⁹;

Y is —S— or —O—;
and pharmaceutically acceptable salts thereof and individual diastereomers thereof.

3. The compound of claim 2 of the formula Ic:

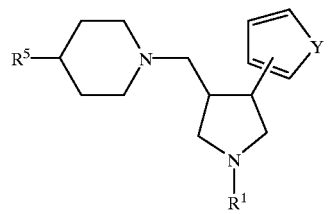

Ic wherein:
R¹, R⁵ and Y are as defined in claim 2;
and pharmaceutically acceptable salts and individual diastereomers thereof.

4. The compound of claim 3 of the formula Id:

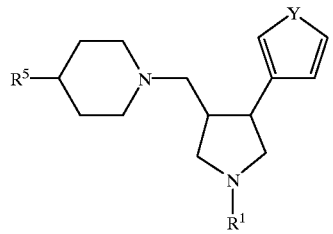

Id wherein:
R¹, R⁵ and Y are as defined in claim 2;
and pharmaceutically acceptable salts thereof and individual diastereomers thereof.

5. The compound of claim 4 wherein:
R¹ is —X—R⁸, wherein X is selected from the group consisting of:
(1) —CH₂—, and
(2) —CO—,
and wherein R⁸ is a selected from:
phenyl, naphthyl, indenyl, indanyl, indolyl, quinolyl, isoquinolyl, benzofuranyl, dihydrobenzofuranyl, methylenedioxybenzoyl, benzopyrazolyl, and benzotriazolyl, which may be unsubstituted or substituted, where the substituents are independently selected from:
(a) C₁₋₆ alkyl, C₂₋₆ alkenyl, C₂₋₆ alkynyl, wherein the alkyl, alkenyl, or alkynyl is unsubstituted or substituted, wherein the substituents are independently selected from:
  (i) hydroxy,
  (ii) halogen,
  (iii) —NR⁹R¹⁰, wherein R⁹ and R¹⁰ are independently selected from hydrogen, C₁₋₆ alkyl, C₂₋₆ alkenyl, and C₂₋₆ alkynyl, wherein the alkyl, alkenyl, or alkynyl is unsubstituted or substituted, wherein the substituents are independently selected from:
    (A) phenyl, unsubstituted or substituted, wherein the substituents are independently selected from: halogen, hydroxy, C₁₋₆alkyl, C₁₋₆alkoxy, —CO₂(C₁₋₆ alkyl), —NH₂, —NH(C₁₋₆ alkyl), —N(C₁₋₆ alkyl)(C₁₋₆ alkyl), or trifluoromethyl,
    (B) naphthyl, unsubstituted or substituted, wherein the substituents are independently selected from: halogen, hydroxy, C₁₋₆alkyl, C₁₋₆alkoxy, —CO₂(C₁₋₆ alkyl), —NH₂, —NH ($C_{1-6}$ alkyl), —N($C_{1-6}$ alkyl)($C_{1-6}$ alkyl), or trifluoromethyl, (C) heterocycle, unsubstituted or substituted, wherein the substituents are independently selected from: halogen, hydroxy, $C_{1-6}$alkyl, $C_{1-6}$alkoxy, —$CO_2$($C_{1-6}$ alkyl), —$NH_2$, —NH($C_{1-6}$ alkyl), —N($C_{1-6}$ alkyl)($C_{1-6}$ alkyl), or trifluoromethyl, (D) hydroxy,
(E) —O($C_{1-6}$ alkyl),
(F) —$CO_2$($C_{1-6}$ alkyl),
(G) —S(O)$_n$—($C_{1-6}$ alkyl), wherein n is an integer selected from 0, 1 and 2,
(H) halogen,
(I) —$NH_2$,
(J) —NH($C_{1-6}$ alkyl), and
(K) —N($C_{1-6}$ alkyl)($C_{1-6}$ alkyl), (iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9$CO—$NR^9R^{10}$,
(ix) —$S(O)_2$—$NR^9R^{10}$, wherein n is an integer selected from 0, 1 and 2,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvi) —O—$R^9$,
(xvii) —O($C_{1-6}$ alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$, (b) —O—$C_{1-6}$alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9$CO—$NR^9R^{10}$,
(ix) —$S(O)_2$—$NR^9R^{10}$,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvi) —O—$R^9$,
(xvii) —O($C_{1-6}$ alkyl)-O—$R^9$,
(xviii) phenyl, (xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$, (c) —$NO_2$,
(d) hydroxy,
(e) halogen,
(f) —$NR^9R^{10}$,
(g) —$NR^9$—$COR^{10}$,
(h) —$NR^9$—$CO_2R^{10}$,
(i) —CO—$NR^9R^{10}$,
(j) —OCO—$NR^9R^{10}$,
(k) —$NR^9$CO—$NR^9R^{10}$,
(l) —$S(O)_2$—$NR^9R^{10}$,
(m) —$NR^9S(O)_2$—$R^{10}$,
(n) —$NR^9S(O)_2$—$NR^9R^{10}$,
(o) —$S(O)_n$—$R^9$,
(p) —$CF_3$,
(q) —$CHF_2$,
(r) —$CH_2F$,
(s) —OCO—$R^9$,
(t) —$OCO_2$—$R^9$, and
(u) —CO—$R^9$;

wherein $R^5$ is a selected from:

(1) phenyl, which is unsubstituted or substituted with halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl, (2) —$C_{1-6}$alkyl-phenyl, —$C_{1-6}$alkyl-naphthyl, —$C_{1-6}$alkyl-indenyl, —$C_{1-6}$alkyl-indanyl, and —$C_{1-6}$alkyl-heterocycle, wherein the phenyl, naphthyl, indenyl, indanyl, or heterocycle is unsubstituted or substituted with: halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl; and wherein the —$C_{1-6}$alkyl is optionally substituted with oxo, hydroxy, $C_{1-6}$alkoxy, acetoxy, or halogen, (3) —O—$C_{1-6}$alkyl-phenyl, —O—$C_{1-6}$alkyl-naphthyl, —O—$C_{1-6}$alkyl-indenyl, —O—$C_{1-6}$alkyl-indanyl, and —O—$C_{1-6}$alkyl-heterocycle, wherein the phenyl, naphthyl, indenyl, indanyl, or heterocycle is unsubsituted or substituted with: halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl, (4) —$C_{1-4}$alkyl-O—$C_{1-4}$alkyl-phenyl, wherein the phenyl is unsubstituted or substituted with halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl, and (5) —$C_{1-4}$alkyl-$S(O)_n$—$C_{1-4}$alkyl-phenyl, wherein the phenyl is unsubstituted or substituted with halogen, hydroxy, $C_{1-6}$alkyl, $C_{1-6}$alkoxy, —$CO_2$($C_{1-6}$ alkyl), —$NH_2$, —$NHR^9$, —$NR^9R^{10}$, or trifluoromethyl;

Y is —S— or —O—;

and pharmaceutically acceptable salts and individual diastereomers thereof.

6. The compound of claim 1 wherein:
R[1] is selected from the group consisting of:
(1) —CH$_2$-phenyl,
(2) —CO-phenyl,
(3) —CH$_2$-(2,4-dichlorophenyl),
(4) —CO-(2,4-dichlorophenyl),
(5) —CH$_2$-(2-naphthyl),
(6) —CO-(1-naphthyl),
(7) —CH$_2$-indolyl, and
(8) —CO-indolyl.

7. The compound of claim 1 wherein:
R[1] is selected from the group consisting of:
(1) —CH$_2$-phenyl,
(2) —CO-phenyl,
(3) —CH$_2$-(2,4-dichlorophenyl),
(4) —CH$_2$-(7-indolyl), and
(5) —CO-(7-indolyl).

8. The compound of claim 1 wherein:
R[2] is:

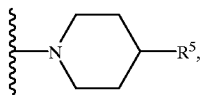

wherein R[5] is selected from:
(1) phenyl, which is unsubstituted or substituted with halogen, hydroxy, C$_{1-6}$alkyl, C$_{1-6}$alkoxy, or trifluoromethyl,
(2) —C$_{1-6}$alkyl-phenyl, wherein the phenyl is unsubsituted or substituted with: halogen, hydroxy, C$_{1-6}$alkyl, C$_{1-6}$alkoxy, or trifluoromethyl; and wherein the —C$_{1-6}$alkyl is optionally substituted with oxo, hydroxy, C$_{1-6}$alkoxy, acetoxy, or halogen,
(3) —O—C$_{1-6}$alkyl-phenyl, wherein the phenyl is unsubsituted or substituted with halogen, hydroxy, C$_{1-6}$alkyl, C$_{1-6}$alkoxy, or trifluoromethyl,
(4) —C$_{1-4}$alkyl-O—C$_{1-4}$alkyl-phenyl, wherein the phenyl is unsubsituted or substituted with halogen, hydroxy, C$_{1-6}$alkyl, C$_{1-6}$alkoxy, or trifluoromethyl, and
(5) —C$_{1-4}$alkyl-S(O)$_n$—C$_{1-4}$alkyl-phenyl, wherein n is an integer selected from 0, 1 and 2, and wherein the phenyl is unsubsituted or substituted with halogen, hydroxy, C$_{1-6}$alkyl, C$_{1-6}$alkoxy, or trifluoromethyl.

9. The compound of claim 1 wherein:
R[2] is:

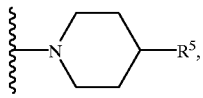

wherein R[5] is a selected from:
(1) phenyl, which is unsubstituted or substituted with halogen, hydroxy, C$_{1-6}$alkyl, C$_{1-6}$alkoxy, or trifluoromethyl,
(2) —C$_{2-4}$alkyl-phenyl, wherein the phenyl is unsubsituted or substituted with chloro, fluoro, trifluoromethyl, methyl or ethyl and wherein the —C$_{2-4}$alkyl is optionally substituted with oxo, hydroxy, halogen, or methoxy,
(3) —C$_{1-3}$alkyl-O—C$_{1-3}$alkyl-phenyl, wherein the phenyl is unsubsituted or substituted with chloro, fluoro, trifluoromethyl, methyl or ethyl, and
(4) —C$_{1-3}$alkyl-S(O)$_n$—C$_{1-3}$alkyl-phenyl, wherein the phenyl is unsubsituted or substituted with chloro, fluoro, trifluoromethyl, methyl or ethyl.

10. The compound of claim 1 wherein:
R[2] is:

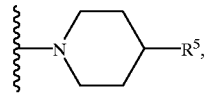

wherein R[5] is a selected from:
(1) phenyl, which is unsubstituted or substituted with halogen, hydroxy, C$_{1-6}$alkyl, C$_{1-6}$alkoxy, or trifluoromethyl,
(2) —C$_{3-4}$alkyl-phenyl, wherein the phenyl is unsubsituted or substituted with chloro, fluoro or methyl, and wherein the —C$_{3-4}$alkyl is optionally substituted with oxo, hydroxy, or methoxy,
(3) —C$_{1-3}$alkyl-O—C$_{1-3}$alkyl-phenyl, wherein the phenyl is unsubsituted or substituted with chloro, fluoro or methyl, and
(4) —C$_{1-3}$alkyl-S(O)$_n$—C$_{1-3}$alkyl-phenyl, wherein the phenyl is unsubsituted or substituted with chloro, fluoro or methyl.

11. The compound of claim 1 wherein:
R[2] is:

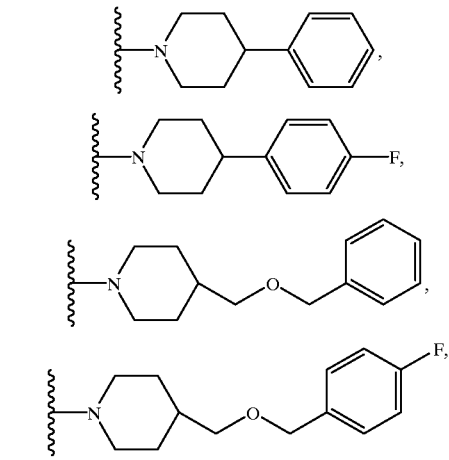

or

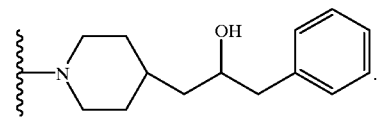

12. The compound of claim 1 wherein:
R[3] is thienyl or furanyl, which may be unsubstituted or substituted, where the substituents are independently selected from:
C$_{1-6}$ alkyl, which is unsubstituted or substituted, wherein the substituents are independently selected from:
(a) hydroxy,
(b) —O(C$_{1-6}$ alkyl), and
(c) —CO$_2$(C$_{1-6}$ alkyl).

13. The compound of claim 1 wherein:
R[3] is unsubstituted thienyl or furanyl.

14. The compound of claim 1 which is of the stereochemical configuration:

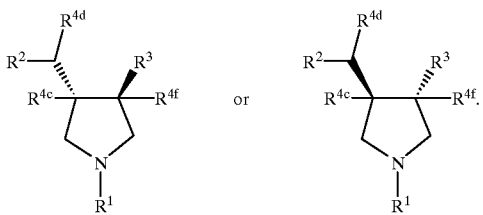

15. A compound which is selected from the group consisting of:

1-Benzyl-3-(RS)-(4-phenylpiperidinylmethyl)-4-(RS)-(3-thienyl)-pyrrolidine;
3-(SR)-(4-Phenylpiperidinylmethyl)-4-(RS)-(3-thienyl)pyrrolidine;
1-(1-Naphthylmethyl)-3-(RS)-(4-phenylpiperidinylmethyl)-4-(RS)-(3-thienyl)pyrrolidine;
1-(2-Naphthylmethyl)-3-(RS)-(4-phenylpiperidinylmethyl)-4-(RS)-(3-thienyl)pyrrolidine;
1-Benzyl-3-(RS)-(4-(4-fluorophenyl)piperdinylmethyl)-4-(RS)-(3-thienyl)pyrrolidine;
3-(SR)-(4-(4-Fluorophenyl)piperidinylmethyl)-4-(RS )-(3-thienyl)-pyrrolidine;
1-(2,3-Dichlorophenyl)methyl-3-(RS)-(4-(4-fluorophenyl)piperidinyl-methyl)-4-(RS)-(3-thienyl)pyrrolidine;
1-(1-Naphthylmethyl)-3-(RS)-(4-(4-fluorophenyl)piperidinylmethyl)-4-(RS)-(3-thienyl)pyrrolidine;
1-(2-Naphthylmethyl)-3-(RS)-(4-(4-fluorophenyl)piperidinylmethyl)-4-(RS)-(3-thienyl)pyrrolidine;
1-(4-Chlorobenzyl)-3-(RS)-(4-(4-fluorophenyl)piperidinylmethyl)-4-(RS)-(3-thienyl)pyrrolidine;
1-(3,4-Difluorobenzoyl)-3-(RS)-(4-phenylpiperidinylmethyl)-4-(RS)-(3-thienyl)pyrrolidine;
1-(7-Indolylcarbonyl)-3-(RS)-(4-phenylpiperidinylmethyl)-4-(RS)-(3-thienyl)pyrrolidine;
1-Benzoyl-3-(RS)-(4-phenylpiperidinylmethyl)-4-(RS)-(3-thienyl)pyrrolidine;
1-(1-Naphthoyl)-3-(RS)-(4-phenylpiperidinylmethyl)-4-(RS)-(3-thienyl)pyrrolidine;
1-(2,3-Dichlorobenzoyl)-3-(RS)-(4-phenylpiperidinylmethyl)-4-(RS)-(3-thienyl)pyrrolidine;
1-(3,4-Dichlorobenzoyl)-3-(RS)-(4-phenylpiperidinylmethyl)-4-(RS)-(3-thienyl)pyrrolidine;
1-(2,3-Dimethylbenzoyl)-3-(RS)-(4-phenylpiperidinylmethyl)-4-(RS)-(3-thienyl)pyrrolidine;
1-(6-Methoxy-1-naphthoyl)-3-(RS)-(4-phenylpiperldinylmethyl)-4-(RS)-(3-thienyl)pyrrolidine;
1-(4-Bromo-1-naphthoyl)-3-(RS)-(4-phenylpiperidinylmethyl)-4-(RS)-(3-thienyl)pyrrolidine;
1-(8-Bromo-1-naphthoyl)-3-(RS)-(4-phenylpiperidinylmethyl)-4-(RS)-(3-thienyl)pyrrolidine;
1-(4-Fluoro-1-naphthoyl)-3-(RS)-(4-phenylpiperidinylmethyl)-4-(RS)-(3-thienyl)pyrrolidine;
1-(8-Quinolinecarbonyl)-3-(RS)-(4-phenylpiperidinylmethyl)-4-(RS)-(3-thienyl)pyrrolidine;
1-(4-Quinolinylcarbonyl)-3-(RS)-(4-phenylpiperidinylmethyl)-4-(RS)-(3-thienyl)pyrrolidine;
1-(2,3-Difluorobenzoyl)-3-(RS)-(4-phenylpiperidinylmethyl)-4-(RS)-(3-thienyl) pyrrolidine;
1-(2,3,4-Trifluorobenzoyl)-3-(RS)-(4-phenylpiperidinylmethyl)-4-(RS)-(3-thienyl)pyrrolidine;
1-(2,3,4,5,6-Pentafluorobenzoyl)-3-(RS)-(4-phenylpiperidinylmethyl)-4-(RS)-(3-thienyl)pyrrolidine;
1-(3-Fluoro-4-trifluoromethylbenzoyl)-3-(RS)-(4-phenylpiperidinyl-methyl)4-(RS)-(3-thienyl)pyrrolidine;
1-(4-Chlorobenzoyl)-3-(RS)-(4-phenylpiperidinylmethyl)-4-(RS)-(3-thienyl)pyrrolidine;
1-(3-Chlorobenzoyl)-3-(RS)-(4-phenylpiperidinylmethyl)-4-(RS)-(3-thienyl)pyrrolidine;
1-(4-Methoxybenzoyl)-3-(RS)-(4-phenylpiperidinylmethyl)-4-(RS)-(3-thienyl)pyrrolidine;
1-(4-Methylbenzoyl)-3-(RS)-(4-phenylpiperidinylmethyl)-4-(RS)-(3-thienyl)pyrrolidine;
1-(2-Amino-3-methoxybenzoyl)-3-(RS)-(4-(4-fluorophenyl)piperidinyl-methyl)-4-(RS)-(3-thienyl)pyrrolidine;
1-(2-Acetoxy-3-methylbenzoyl)-3-(RS)-(4-(4-fluorophenyl)piperidinyl-methyl)-4-(RS)-(3-thienyl)pyrrolidine;
Acetyl-3-(RS)-(4-(4-fluorophenyl)piperidinylmethyl)-4-(RS)-(3-thienyl)pyrrolidine;
1-(2-Trifluoroacetylaminobenzoyl)-3-(RS)-(4-(4-fluorophenyl)-piperidinylmethyl)-4-(RS)-(3-thienyl)pyrrolidine;
1-(2-Difluoromethoxybenzoyl)-3-(RS)-(4-(4-fluorophenyl)piperidinyl-methyl)-4-(RS)-(3-thienyl)pyrrolidine;
1-(2-Amino-3-methylbenzoyl)-3-(RS)-(4-(4-fluorophenyl)piperidinyl-methyl)-4-(RS)-(3-thienyl)pyrrolidine;
1-(2-Methyl-3-fluorobenzoyl)-3-(RS)-(4-(4-fluorophenyl)piperidinyl-methyl)-4-(RS)-(3-thienyl)pyrrolidine;
1-(2-Methyl-3-aminobenzoyl)-3-(RS)-(4-(4-fluorophenyl)piperidinyl-methyl)-4-(RS)-(3-thienyl)pyrrolidine;
1-(2,3-Dihydroxybenzoyl)-3-(RS)-(4-(4-fluorophenyl)piperidinylmethyl)-4-(RS)-(3-thienyl)pyrrolidine;
1-(7-Indolecarbonyl)-3-(RS)-(4-(4-fluorophenyl)piperidinylmethyl)-4-(RS)-(3-thienyl)pyrrolidine;
1-(2-Chloro-3-pyridylcarbonyl)-3-(RS)-(4-(4-fluorophenyl)piperidinyl-methyl)-4-(RS)-(3-thienyl)pyrrolidine;
1-(2,3-Difluorobenzoyl)-3-(RS)-(4-(4-fluorophenyl)piperidinylmethyl)-4-(RS)-(3-thienyl)pyrrolidine;
1-(3,4-Difluorobenzoyl)-3-(RS)-(4-(4-fluorophenyl)piperidinylmethyl)-4-(RS)-(3-thienyl)pyrrolidine;
1-(2,4-Difluorobenzoyl)-3-(RS)-(4-(4-fluorophenyl)piperidinylmethyl)-4-(RS)-(3-thienyl)pyrrolidine;
1-(8-Quinolinylcarbonyl)-3-(RS)-(4-(4-fluorophenyl)piperidinylmethyl)-4-(RS)-(3-thienyl)pyrrolidine;
1-(4-Pyrazolylcarbonyl)-3-(RS)-(4-(4-fluorophenyl)piperidinylmethyl)-4-(RS)-(3-thienyl)pyrrolidine;
1-(5-Methyl-2-thienylcarbonyl)-3-(RS)-(4-(4-fluorophenyl)piperidinyl-methyl)-4-(RS)-(3-thienyl)pyrrolidine;
1-(3-Methyl-2-thienylcarbonyl)-3-(RS)-(4-(4-fluorophenyl)piperidinyl-methyl)-4-(RS)-(3-thienyl)pyrrolidine;
1-(4-Chlorobenzoyl)-3-(RS)-(4-(4-fluorophenyl)piperidinylmethyl)-4-(RS)-(3-thienyl)pyrrolidine;
1-Methoxycarbonyl-3-(RS)-(4-(4-fluorophenyl)piperidinylmethyl)-4-(RS)-(3-thienyl)pyrrolidine;
1-Isopropyloxycarbonyl-3-(RS)-(4-(4-fluorophenyl)piperidinylmethyl)-4-(RS)-(3-thienyl)pyrrolidine;
1-Benzoyl-3-(RS)-(4-(4-fluorophenyl)piperidinylmethyl)-4-(RS)-(3-thienyl)pyrrolidine;
1-(5-Chloro-2-thienylcarbonyl)-3-(RS)-(4-(4-fluorophenyl)piperidinyl-methyl)-4-(RS)-(3-thienyl)pyrrolidine;
1-(4-Methylbenzoyl)-3-(RS)-(4-(4-fluorophenyl)piperidinyl-methyl)-4-(RS)-(3-thienyl)pyrrolidine;
1-(4,5-Dichloro-3-thiazolylcarbonyl)-3-(RS)-(4-(4-fluorophenyl)piperidinylmethyl)-4-(RS)-(3-thienyl)pyrrolidine;
1-(4-Methyl-5-thiadizolylcarbonyl)-3-(RS)-(4-(4-fluorophenyl)piperidinylmethyl)-4-(RS)-(3-thienyl)pyrrolidine;
1-(4-Methyl-5-thiadizolylcarbonyl)-3-(RS)-(4-(4-fluorophenyl)piperidinylmethyl)-4-(RS)-(3-thienyl)pyrrolidine;

1-(3-Methyl-2-furanylcarbonyl)-3-(RS)-(4-(4-fluorophenyl) piperidinylmethyl)-4-(RS)-(3-thienyl)pyrrolidine;
1-(5-Methylthio-2-thienylcarbonyl)-3-(RS)-(4-(4-fluorophenyl)piperidinylmethyl)-4-(RS)-(3-thienyl) pyrrolidine;
1-(2,3-Dibromo-5-thienylcarbonyl)-3-(RS)-(4-(4-fluorophenyl)piperidinylmethyl)-4-(RS)-(3-thienyl) pyrrolidine;
1-(2,4-Dimethyl-5-thiazolylcarbonyl)-3-(RS)-(4-(4-fluorophenyl)pipelidinylmethyl)-4-(RS)-(3-thienyl) pyrrolidine;
1-(2-Bromo-3-methylbenzoyl)-3-(RS)-(4-(4-fluorophenyl) piperidinylmethyl)-4-(RS)-(3-thienyl)pyrrolidine;
1-(5-Isoxazolylcarbonyl)-3-(RS)-(4-(4-fluorophenyl) piperidinylmethyl)-4-(RS)-(3-thienyl)pyrrolidine;
1-(2-Thienylcarbonyl)-3-(RS)-(4-(4-fluorophenyl) piperidinylmethyl)-4-(RS)-(3-thienyl)pyrrolidine;
1-(3-Thienylcarbonyl)-3-(RS)-(4-(4-fluorophenyl) piperidinylmethyl)-4-(RS)-(3-thienyl)pyrrolidine;
1-(2-Nitro-4-thienylcarbonyl)-3-(RS)-(4-(4-fluorophenyl) pipenidinylmethyl)-4-(RS)-(3-thienyl)pyrrolidine;
1-(2-(2-pyridyl)-4-thienylcarbonyl)-3-(RS)-(4-(4-fluorophenyl)piperidinylmethyl)-4-(RS)-(3-thienyl) pyrrolidine;
1-(4-Methoxybenzoyl)-3-(RS)-(4-(4-fluorophenyl) piperidinylmethyl)-4-(RS)-(3-thienyl)pyrrolidine;
1-(3-Chlorobenzoyl)-3-(RS)-(4-(4-fluorophenyl) piperidinylmethyl)-4-(RS)-(3-thienyl)pyrrolidine;
1-(2,3-Dimethylbenzoyl)-3-(RS)-(4-(4-fluorophenyl) piperidinylmethyl)-4-(RS)-(3-thienyl)pyrrolidine;
1-(3,4-Dimethylbenzoyl)-3-(RS)-(4-(4-fluorophenyl) piperidinylmethyl)-4-(RS)-(3-thienyl)pyrrolidine;
1-(4-Nitrobenzoyl)-3-(RS)-(4-(4-fluorophenyl) piperidinylmethyl)-4-(RS)-(3-thienyl)pyrrolidine;
1-(2-Phenylbenzoyl)-3-(RS)-(4-(4-fluorophenyl) piperidinylmethyl)-4-(RS)-(3-thienyl)pyrrolidine;
1-(2,3-Dimethyl-7-indolylcarbonyl)-3-(RS)-(4-(4-fluorophenyl)piperidinylmethyl)-4-(RS)-(3-thienyl) pyrrolidine;
1-(7-Benzo-2,3-dihydrofuranylcarbonyl)-3-(RS)-(4-(4-fluorophenyl)-piperidinylmethyl)-4-(RS)-(3-thienyl) pyrrolidine;
1-(1-Naphthoyl)-3-(RS)-(4-(4-fluorophenyl) piperidinylmethyl)-4-(RS)-(3-thienyl)pyrrolidine;
1-(2-Benzoylbenzoyl)-3-(RS)-(4-(4-fluorophenyl) piperidinylmethyl)-4-(RS)-(3-thienyl)pyrrolidine;
1(1-Methyl-7-indolylcarbonyl)-3-(RS)-(4-(4-fluorophenyl) piperidinyl-methyl)-4-(RS)-(3-thienyl)pyrrolidine;
1-(1,2-Dimethyl-7-indolylcarbonyl)-3-(RS)-(4-(4-fluorophenyl)piperidinylmethyl)-4-(RS)-(3-thienyl) pyrrolidine;
1-(2,3-Methylenedioxybenzoyl)-3-(RS)-(4-(4-fluorophenyl)piperidinylmethyl)-4-(RS)-(3-thienyl) pyrrolidine;
1-(2,3-Difluoromethylenedioxybenzoyl)-3-(RS)-(4-(4-fluorophenyl)piperidinylmethyl)-4-(RS)-(3-thienyl) pyrrolidine;
1-(([1,2,3,4]Tetrazolo[1,5a]pyridinoyl)-3-(RS)-(4-(4-fluorophenyl)piperidinylmethyl)-4-(RS)-(3-thienyl) pyrrolidine;
1-(2-Indolecarbonyl)-3-(RS)-(4-(4-fluorophenyl) piperidinylmethyl)-4-(RS)-(3-thienyl)pyrrolidine;
1-(4-Indolecarbonyl)-3-(RS)-(4-(4-fluorophenyi) piperidinylmethyl)-4-(RS)-(3-thienyl)pyrrolidine;
1-(3-Indolecarbonyl)-3-(RS)-(4-(4-fluorophenyl) piperidinylmethyl)-4-(RS)-(3-thienyl)pyrrolidine;
1-(3-Indoleacteyl)-3-(RS)-(4-(4-fluorophenyl) piperidinylmethyl)-4-(RS)-(3-thienyl)pyrrolidine;
1-(1-Naphthoyl)-3-(SR)-formyl-4-(RS)-(3-thienyl) pyrrolidine;
1-(1-Naphthoyl)-3-(RS)-(4-(4-trifluoromethylphenyl) piperidinylmethyl)-4-(RS)-(3-thienyl)pyrrolidine;
1-(1-Naphthoyl)-3-(RS)-(4-(4-chlorophenyl) piperidinylmethyl)-4-(RS)-(3-thienyl)pyrrolidine;
1-(1-Naphthoyl)-3-(RS)-(4-(3,4-difluorophenyl) piperidinylmethyl)-4-(RS)-(3-thienyl)pyrrolidine;
1-(1-Naphthoyl)-3-(RS)-(4-(3,4,5-trifluorophenyl) piperidinylmethyl)-4-(RS)-(3-thienyl)pyrrolidine;
1-(1-Naphthoyl)-3-(RS)-(4-(4-methylphenyl) piperidinylmethyl)-4-(RS)-(3-thienyl)pyrrolidine;
1-(1-Naphthoyl)-3-(RS)-(4-(4-methoxyphenyl) piperidinylmethyl)-4-(RS)-(3-thienyl)pyrrolidine;
1-(1-Naphthoyl)-3-(RS)-(4-(2-methoxyphenyl) piperidinylmethyl)-4-(RS)-(3-thienyl)pyrrolidine;
1-(1-Naphthoyl)-3-(RS)-(4-(3-trifluoromethylphenyl) piperidinylmethyl)-4-(RS)-(3-thienyl)pyrrolidine;
1-(1-Naphthoyl)-3-(RS)-(4-((4-pyridyl)piperidinylmethyl)-4-(RS)-(3-thienyl)pyrrolidine.
1-(1-Naphthoyl)-3-(RS)-(4-(2-fluorophenyl) piperidinylmethyl)-4-(RS)-(3-thienyl)pyrrolidine;
1-(1-Naphthoyl)-3-(RS)-(4-(2-carbomethoxyphenyl) piperidinylmethyl)-4-(RS)-(3-thienyl)pyrrolidine;
1-(1-Naphthoyl)-3-(RS)-(4-(3-aminophenyl) piperidinylmethyl)-4-(RS)-(3-thienyl)pyrrolidine;
1-(1-Naphthoyl)-3-(RS)-(4-(3-chlorophenyl) piperidinylmethyl)-4-(RS)-(3-thienyl)pyrrolidine;
1-(1-Naphthoyl)-3-(RS)-(4-(2,4-difluorophenyl) piperidinylmethyl)-4-(RS)-(3-thienyl)pyrrolidine;
1-(1-Naphthoyl)-3-(RS)-(4-(3-fluorophenyl) piperidinylmethyl)-4-(RS)-(3-thienyl)pyrrolidine;
1-(1-Naphthoyl)-3-(RS)-(4-(3-thiophenyl) piperidinylmethyl)-4-(RS)-(3-thienyl)pyrrolidine;
1-(1-Naphthoyl)-3-(RS)-(4-(3-pyridyl)piperidinylmethyl)-4-(RS)-(3-thienyl)pyrrolidine;
1-(1-Naphthoyl)-3-(RS)-(spiro[indenyl-3,4'piperidin-1'-yl] methyl)-4-(RS)-(3-thienyl)pyrrolidine;
1-(1-Naphthoyl)-3-(RS)-(spiro[indanyl-3,4'piperidin-1'-yl] methyl)-4-(RS)-(3-thienyl)pyrrolidine;
1-(1-Naphthoyl)-3-(RS)-(spiro[indan-1-one-3,4'piperidin-1'-yl]methyl)-4-(RS)-(3-thienyl)pyrrolidine;
1-(1-Naphthoyl)-3-(RS)-(4-(4-bromophenyl)-piperidinylmethyl)-4-(RS)-(3-thienyl)pyrrolidine;
1-(1-Naphthoyl)-3-(RS)-(4-(4-hydroxyphenyl)-piperidinylmethyl)-4-(RS)-(3-thienyl)pyrrolidine;
1-(1-Naphthoyl)-3-(RS)-(4-(4-fluorophenyl)-tropanylmethyl)-4-(RS)-(3-thienyl)pyrrolidine;
1-(1-Naphthoyl)-3-(RS)-(4-(2-pyridyl)piperidinylmethyl)-4-(RS)-(3-thienyl )pyrrolidine;
1-(3,4-Dichlorobenzoyl)-3-(RS)-(spiro[indan-1-one-3,4'piperidin-1'-yl]methyl)-4-(RS)-(3-thienyl)pyrrolidine;
1-(2,3-Dichlorobenzoyl)-3-(RS)-(spiro[indan-1-one-3,4'piperidin-1'-yl]methyl)-4-(RS)-(3-thienyl)pyrrolidine;
1-(3,4-Dichlorobenzoyl)-3-(RS)-(spiro[indenyl-3,4'piperidin-1'-yl]methyl)-4-(RS)-(3-thienyl)pyrrolidine;
1-(2,3-Dichlorobenzoyl)-3-(RS)-(spiro[indenyl-3,4'piperidin-1'-yl]methyl)-4-(RS)-(3-thienyl)pyrrolidine;
1-(3,4-Dichlorobenzoyl)-3-(RS)-(spiro[indanyl-3,4'piperidin-1'-yl]methyl)-4-(RS)-(3-thienyl)pyrrolidine;
1-(2,3-Dichlorobenzoyl)-3-(RS)-(spiro[indanyl-3,4'piperidin-1'-yl]methyl)-4-(RS)-(3-thienyl)pyrrolidine;
1(1-Naphthoyl)-3-(RS)-(4-(4-fluorophenyl)-piperidinyl-1-ethyl)-4-(RS)-(3-thienyl)pyrrolidine;
1-Benzyl-3-(RS)-(4-hydroxy-4-(3-phenylpropyl) piperidinylmethyl)-4-(SR)-(3-thienyl)pyrrolidine;
1-Benzyl-3-(RS)-(4-hydroxy-4-(3-(4-fluorophenyl)propyl) piperidinylmethyl)-4-( SR)-(3-thienyl)pyrrolidine;

1-Benzyl-3-(RS)-(4-hydroxy-4-(3-(4-methoxyphenyl) propyl)piperidinylmethyl)-4-(SR)-(3-thienyl)pyrrolidine;
1-Benzyl-3-(RS)-(4-hydoxy-4-(3-(3-methoxyphenyl) propyl)piperidinylmethyl)-4-(SR)-(3-thienyl)pyrrolidine;
1-Benzyl-3-(RS)-(4-hydroxy-4-(3-(2-methylphenyl)propyl) piperidinylmethyl)-4-(SR)-(3-thienyl)pyrrolidine;
1-Benzyl-3-(RS)-(4-hydroxy-4-(3-(2-fluorophenyl)propyl) piperidinylmethyl)-4-(SR)-(3-thienyl)pyrrolidine;
1-Benzyl-3-(RS)-(4-hydroxy-4-(3-(3-fluorophenyl)propyl) piperidinylmethyl)-4-(SR)-(3-thienyl)pyrrolidine;
1-Benzyl-3-(RS)-(4-hydroxy-4-(3-(2-methoxyphenyl) propyl)piperidinylmethyl)-4-(SR)-(3-thienyl)pyrrolidine;
1-Benzyl-3-(RS)-(4-hydroxy-4-(3-(4-tetrazolylphenyl) propyl)piperidinylmethyl)-4-(SR)-(3-thienyl)pyrrolidine;
1-Benzyl-3-(RS)-(4-hydroxy-4-(3-phenylprop-2-enyl) piperidinylmethyl)-4-(SR)-(3-thienyl)pyrrolidine;
1-Benzyl-3-(RS)-(4-hydroxy-4-(2-methyl-3-phenylpropyl) piperidinyl-methyl)-4-(SR)-(3-thienyl)pyrrolidine;
1-Benzyl-3-(RS)-(4-hydroxy-4-(3-methyl-3-phenylpropyl) piperidinylmethyl)-4-(SR)-(3-thienyl)pyrrolidine;
1-(2-Phenethyl)-3-(RS)-(4-hydroxy-4-(3-phenylpropyl) piperidinylmethyl)-4-(SR)-(3-thienyl)pyrrolidine;
1-(3,4-Dimethylbenzyl)-3-(RS)-(4-hydroxy-4-(3-phenylpropyl)piperidinylmethyl)-4-(SR)-(3-thienyl) pyrrolidine;
1-(3,4-Dichlorobenzyl)-3-(RS)-(4-hydroxy-4-(3-phenylpropyl)piperidnylmethyl)-4-(SR)-(3-thienyl) pyrrolidine;
1-(2,3-Dichlorobenzyl)-3-(RS)-(4-hydroxy-4-(3-phenylpropyl)piperidinylmethyl)-4-(SR)-(3-thienyl) pyrrolidine;
1-(3,5-Dichlorobenzyl)-3-(RS)-(4-hydroxy-4-(3-phenylpropyl)piperidinylmethyl)-4-(SR)-(3-thienyl) pyrrolidine;
1-(4-Chlorobenzyl)-3-(RS)-(4-hydroxy-4-(3-phenylpropyl) piperidinylmethyl)-4-(SR)-(3-thienyl)pyrrolidine;
1-(4-Fluorobenzyl)-3-(RS)-(4-hydroxy-4-(3-phenylpropyl) piperidinylmethyl)-4-(SR)-(3-thienyl)pyrrolidine;
1-(4-Bromobenzyl)-3-(RS)-(4-hydroxy-4-(3-phenylpropyl) piperidinyl-methyl)-4-(SR)-(3-thienyl)pyrrolidine;
1-(2-Chlorobenzyl)-3-(RS)-(4-hydroxy-4-(3-phenylpropyl) piperidinylmethyl)-4-(SR)-(3-thienyl)pyrrolidine;
1-(2-Methylbenzyl)-3-(RS)-(4-hydroxy-4-(3-phenylpropyl) piperidinyl-methyl)-4-(SR)-(3-thienyl)pyrrolidine;
1-(3-Chlorobenzyl)-3-(RS)-(4-hydroxy-4-(3-phenylpropyl) piperidinyl-methyl)-4-(SR)-(3-thienyl)pyrrolidine;
1-(4-Nitrobenzyl)-3-(RS)-(4-hydroxy-4-(3-phenylpropyl) piperidinylmethyl)-4-(SR)-(3-thienyl)pyrrolidine;
1-(4-Methoxybenzyl)-3-(RS)-(4-hydroxy-4-(3-phenylpropyl)piperidinylmethyl)-4-(SR)-(3-thienyl) pyrrolidine;
1-(4-Methylbenzyl)-3-(RS)-(4-hydroxy-4-(3-phenylpropyl) piperidinyl-methyl)-4-(SR)-(3-thienyl)pyrrolidine;
1-(4-Trifluoromethylbenzyl)-3-(RS)-(4-hydroxy-4-(3-phenylpropyl)-piperidinylmethyl)-4-(SR)-(3-thienyl) pyrrolidine;
1-(3-Methylbenzyl)-3-(RS)-(4-hydroxy-4-(3-phenylpropyl) piperidinyl-methyl)-4-(SR)-(3-thienyl)pyrrolidine;
1-(2,4-Dichlorobenzyl)-3-(RS)-(4-hydroxy-4-(3-phenylpropyl)piperidinylmethyl)-4-(SR)-(3-thienyl) pyrrolidine;
1-Benzoyl-3-(RS)-(4-hydroxy-4-(3-phenylpropyl) piperidinylmethyl)-4-(SR)-(3-thienyl)pyrrolidine;
1-(4-Fluorobenzoyl)-3-(RS)-(4-hydroxy-4-(3-phenylpropyl)piperidinyl-methyl)-4-(SR)-(3-thienyl) pyrrolidine;
1-(4-Bromobenzoyl)-3-(RS)-(4-hydroxy-4-(3-phenylpropyl)piperidinyl-methyl)-4-(SR)-(3-thienyl) pyrrolidine;
1-(4-Nitrobenzoyl)-3-(RS)-(4-hydroxy-4-(3-phenylpropyl) piperidinyl-methyl)-4-(SR)-(3-thienyl)pyrrolidine;
1-(4-Methoxybenzoyl)-3-(RS)-(4-hydroxy-4-(3-phenylpropyl)piperidinylmethyl)-4-(SR)-(3-thienyl) pyrrolidine;
1-(2,4-Dichlorobenzoyl)-3-(RS)-(4-hydroxy-4-(3-phenylpropyl)piperidinylmethyl)-4-(SR)-(3-thienyl) pyrrolidine;
1-(3-Chlorobenzoyl)-3-(RS)-(4-hydroxy-4-(3-phenylpropyl)piperidiny-methyl)-4-(SR)-(3-thienyl) pyrrolidine;
1(4-Chlorobenzoyl)-3-(RS)-(4-hydroxy-4-(3-phenylpropyl) piperidinyl-methyl)-4-(SR)-(3-thienyl)pyrrolidine;
1-(2-Chlorobenzoyl)-3-(RS)-(4-hydroxy-4-(3-phenylpropyl)piperidinyl-methyl)-4-(SR)-(3-thienyl) pyrrolidine;
1-(2-Naphthoyl)-3-(RS)-(4-hydroxy-4-(3-phenylpropyl) piperidinylmethyl)-4-(SR)-(3-thienyl)pyrrolidine;
1-(1-Naphthoyl)-3-(RS)-(4-hydroxy-4-(3-phenylpropyl) piperidinylmethyl)-4-(SR)-(3-thienyl)pyrrolidine;
1-(3,4-Dichlorobenzoyl)-3-(RS)-(4-hydroxy-4-(3-phenylpropyl)piperidinylmethyl)-4-(SR)-(3-thienyl) pyrrolidine;
1-(2,3-Dichlorobenzoyl)-3-(RS)-(4-hydroxy-4-(3-phenylpropyl)piperidinylmethyl)-4-(SR)-(3-thienyl) pyrrolidine;
1-(4-Methylbenzoyl)-3-(RS)-(4-hydroxy-4-(3-phenylpropyl)piperidinylmethyl)-4-(SR)-(3-thienyl) pyrrolidine;
1-(4-Trifluoromethylbenzoyl)-3-(RS)-(4-hydroxy-4-(3-phenylpropyl)-piperidinylmethyl)-4-(SR)-(3-thienyl) pyrrolidine;
1-(4-Chloro-3-methylbenzoyl)-3-(RS)-(4-hydroxy-4-(3-phenylpropyl)-piperidinylmethyl)-4-(SR)-(3-thienyl) pyrrolidine;
1-(1-Naphthoyl)-3-(RS)-(4-hydroxy-4-(3-(4-fluorophenyl)-1-propyl)piperidinylmethyl)-4-(SR)-(3-thienyl) pyrrolidine;
1-(2,3-Dichlorobenzoyl)-3-(RS)-(4-hydroxy-4-(3-(4-fluorophenyl)-1-propyl)piperidinylmethyl)-4-(SR)-(3-thienyl)pyrrolidine;
1-(3,4-Dichlorobenzoyl)-3-(RS)-(4-hydroxy-4-(3-(4-fluorophenyl)-1-propyl)piperidinylmethyl)-4-(SR)-(3-thienyl)pyrrolidine;
1-(1-Naphthoyl)-3-(RS)-(4-hydroxy-4-(3(2-methylphenyl)-1-propyl)piperidinylmethyl)-4-(SR)-(3-thienyl) pyrrolidine;
1-(2,3-Dichlorobenzoyl)-3-(RS)-(4-hydroxy-4-(3-(2-methylphenyl)-1-propyl)piperidinylmethyl)-4-(SR)-(3-thienyl)pyrrolidine;
1-(3,4-Dichlorobenzoyl)-3-(RS)-(4-hydroxy-4-(3-(2-methylphenyl)-1-propyl)piperidinylmethyl)-4-(SR)-(3-thienyl)pyrrolidine;
1-(1-Naphthoyl)-3-(RS)-(4-hydroxy-4-(3-(2-fluorophenyl)-1-propyl)piperidinylmethyl)-4-(SR)-(3-thienyl) pyrrolidine;
1-(2,3-Dichlorobenzoyl)-3-(RS)-(4-hydroxy-4-(3-(2-fluorophenyl)-1-propyl)piperidinylmethyl)-4-(SR)-(3-thienyl)pyrrolidine;
1-(3,4-Dichlorobenzoyl)-3-(RS)-(4-hydroxy-4-(3-(2-fluorophenyl)-1-propyl)piperidinylmethyl)-4-(SR)-(3-thienyl)pyrrolidine;
1-(1-Naphthoyl)-3-(RS)-(4-hydroxy-4-(3-(3-fluorophenyl) propyl)piperidinylmethyl)-4-(SR)-(3-thienyl)pyrrolidine;
1-(2,3-Dichlorobenzoyl)-3-(RS)-(4-hydroxy-4-(3-(3-fluorophenyl)propyl)piperidinylmethyl)-4-(SR)-(3-thienyl)pyrrolidine;

1-(3,4-Dichlorobenzoyl)-3-(RS)-(4-hydroxy-4-(3-(3-fluorophenyl)-1-propyl)piperidinylmethyl)-4-(SR)-(3-thienyl)pyrrolidine;
1-(1-Naphthoyl)-3-(RS)-(4-hydroxy-4-(3-(4-methoxyphenyl)propyl)piperidinylmethyl)-4-(SR)-(3-thienyl)pyrrolidine;
1-(2,3-Dichlorobenzoyl)-3-(RS)-(4-hydroxy-4-(3-(4-methoxyphenyl)propyl)piperidinylmethyl)-4-(SR)-(3-thienyl)pyrrolidine;
1-(3,4-Dichlorobenzoyl)-3-(RS)-(4-hydroxy-4-(3-(4-methoxyphenyl)propyl)piperidinylmethyl)-4-(SR)-(3-thienyl)pyrrolidine;
1-(1-Naphthoyl)-3-(RS)-(4-hydroxy-4-(3-(3-methoxyphenyl)propyl)piperidinylmethyl)-4-(SR)-(3-thienyl)pyrrolidine;
1-(2,3-Dichlorobenzoyl)-3-(RS)-(4-hydroxy-4-(3-(3-methoxyphenyl)propyl)piperidinylmethyl)-4-(SR)-(3-thienyl)pyrrolidine;
1-(3,4-Dichlorobenzoyl)-3-(RS)-(4-hydroxy-4-(3-(3-methoxyphenyl)propyl)piperidinylmethyl)-4-(SR)-(3-thienyl)pyrrolidine;
1-(3,4-Dichlorobenzoyl)-3-(RS)-(4-hydroxy-4-(3-(2-methoxyphenyl)propyl)piperidinylmethyl)-4-(SR)-(3-thienyl)pyrrolidine;
1-(3,4-Dichlorobenzoyl)-3-(RS)-(4-hydroxy-4-(3-(4-tetrazolylphenyl)propyl)piperidinylmethyl)-4-(SR)-(3-thienyl)pyrrolidine;
1-(3,4-Dichlorobenzoyl)-3-(RS)-(4-hydroxy-4-(3-phenyl-2-propenyl)-piperidinylmethyl)-4-(SR)-(3-thienyl)pyrrolidine;
1-(3,4-Dichlorobenzoyl)-3-(RS)-(4-hydroxy-4-(2-methyl-3-phenylpropyl)-piperidinylmethyl)-4-(SR)-(3-thienyl)pyrrolidine;
1-(3,4-Dichlorobenzoyl)-3-(RS)-(4-hydroxy-4-(3-methyl-3-phenylpropyl)-piperidinylmethyl)-4-(SR)-(3-thienyl)pyrrolidine;
1-Benzyl-3-(RS)-(4-(3-phenylpropyl)piperidinylmethyl)-4-(SR)-(3-thienyl)pyrrolidine;
1-(3,4-Dichlorobenzoyl)-3-(RS)-(4-(3-phenylpropyl)piperidinylmethyl)-4-(SR)-(3-thienyl)pyrrolidine;
1-Benzyl-3-(RS)-(4-(2-(4-fluorophenoxy)ethyl)piperidinylmethyl)-4-(SR)-(3-thienyl)pyrrolidine;
1-(2,4-Dichlorobenzyl)-3-(RS)-(4-(2-(4-fluorophenoxy)ethyl)piperidinyl-methyl)-4-(SR)-(3-thienyl)pyrrolidine;
1-(3,4-Dichlorobenzoyl)-3-(RS)-(4-(2-(4-fluorophenoxy)ethyl)piperidinylmethyl)-4-(SR)-(3-thienyl)pyrrolidine;
1-Benzyl-3-(RS)-(4-(2-phenoxy)ethyl)piperidinylmethyl)-4-(SR)-(3-thienyl)pyrrolidine;
1-(2,4-Dichlorobenzyl)-3-(RS)-(4-(2-phenoxy)ethyl)piperidinylmethyl)-4-(SR)-(3-thienyl)pyrrolidine;
1-(3,4-Dichlorobenzoyl)-3-(RS)-(4-(2-(4-fluorophenoxy)ethyl)piperidinylmethyl)-4-(SR)-(3-thienyl)pyrrolidine;
1-Benzyl-3-(RS)-(4-(benzyloxymethyl)piperidinylmethyl)-4-(SR)-(3-thienyl)pyrrolidine;
1-(2,4-Dichlorobenzyl)-3-(RS)-(4-(benzyloxymethyl)piperidinylmethyl)-4-(SR)-(3-thienyl)pyrrolidine;
1-(3,4-Dichlorobenzoyl)-3-(RS)-(4-(benzyloxymethyl)piperidinylmethyl)-4-(SR)-(3-thienyl)pyrrolidine;
1-Benzyl-3-(RS)-(4-(4-fluorobenzyloxymethyl)piperidinylmethyl)-4-(SR)-(3-thienyl)pyrrolidine;
1-(2,4-Dichlorobenzyl)-3-(RS)-(4-(4-fluorobenzyloxymethyl)piperidinylmethyl)-4-(SR)-(3-thienyl)pyrrolidine;
1-(3,4-Dichlorobenzoyl)-3-(RS)-(4-(4-fluorobenzyloxymethyl)piperidinylmethyl)-4-(SR)-(3-thienyl)pyrrolidine;
1-(2-Chlorobenzyl)-3-(RS)-(4-(4-fluorobenzyloxymethyl)piperidinylmethyl)-4-(SR)-(3-thienyl)pyrrolidine;
1-(2-Methylbenzyl)-3-(RS)-(4-(4-fluorobenzyloxymethyl)piperidinylmethyl)-4-(SR)-(3-thienyl)pyrrolidine;
1-(3-Chlorobenzyl)-3-(RS)-(4-(4-fluorobenzyloxymethyl)piperidinylmethyl)-4-(SR)-(3-thienyl)pyrrolidine;
1-(3-Methylbenzyl)-3-(RS)-(4-(4-fluorobenzyloxymethyl)piperidinylmethyl)-4-(SR)-(3-thienyl)pyrrolidine;
1-(4-Chlorobenzyl)-3-(RS)-(4-(4-fluorobenzyloxymethyl)piperidinylmethyl)-4-(SR)-(3-thienyl)pyrrolidine;
1-(4-Methylbenzyl)-3-(RS)-(4-(4-fluorobenzyloxymethyl)piperidinylmethyl)-4-(SR)-(3-thienyl)pyrrolidine;
1-(4-Methoxybenzyl)-3-(RS)-(4-(4-fluorobenzyloxymethyl)piperidinylmethyl)-4-(SR)-(3-thienyl)pyrrolidine;
1-(4-Bromobenzyl)-3-(RS)-(4-(4-fluorobenzyloxymethyl)piperidinylmethyl)-4-(SR)-(3-thienyl)pyrrolidine;
1-(3,4-Dichlorobenzyl)-3-(RS)-(4-(4-fluorobenzyloxymethyl)piperidinylmethyl)-4-(SR)-(3-thienyl)pyrrolidine;
1-(3,5-Dichlorobenzyl)-3-(RS)-(4-(4-fluorobenzyloxymethyl)piperidinylmethyl)-4-(SR)-(3-thienyl)pyrrolidine;
1-(2,5-Dichlorobenzyl)-3-(RS)-(4-(4-fluorobenzyloxymethyl)piperidinylmethyl)-4-(SR)-(3-thienyl)pyrrolidine;
1-(2-Naphthyl)-3-(RS)-(4-(4-fluorobenzyloxymethyl)piperidinylmethyl)-4-(SR)-(3-thienyl)pyrrolidine;
1-(1-Naphthylmethyl)-3-(RS)-(4-(4-fluorobenzyloxymethyl)piperidinylmethyl)-4-(SR)-(3-thienyl)pyrrolidine;
1-(1-Naphthoyl)-3-(RS)-(4-(4-fluorobenzyloxymethyl)piperidinylmethyl)-4-(SR)-(3-thienyl)pyrrolidine;
1-Benzoyl-3-(RS)-(4-(4-fluorobenzyloxymethyl)piperidinylmethyl)-4-(SR)-(3-thienyl)pyrrolidine;
1-(4-Chlorobenzoyl)-3-(RS)-(4-(4-fluorobenzyloxymethyl)piperidinylmethyl)-4-(SR)-(3-thienyl)pyrrolidine;
1-(4-Methylbenzoyl)-3-(RS)-(4-(4-fluorobenzyloxymethyl)piperidinylmethyl)-4-(SR)-(3-thienyl)pyrrolidine;
1-(3-Chlorobenzoyl)-3-(RS)-(4-(4-fluorobenzyloxymethyl)piperidinylmethyl)-4-(SR)-(3-thienyl)pyrrolidine;
1-(2,6-Dichlorobenzoyl)-3-(RS)-(4-(4-fluorobenzyloxymethyl)piperidinylmethyl)-4-(SR)-(3-thienyl)pyrrolidine;
1-(2-Chlorobenzoyl)-3-(RS)-(4-(4-fluorobenzyloxymethyl)piperidinylmethyl)-4-(SR)-(3-thienyl)pyrrolidine;
1-(4-Nitrobenzoyl)-3-(RS)-(4-(4-fluorobenzyloxymethyl)piperidinylmethyl)-4-(SR)-(3-thienyl)pyrrolidine;
1-(3,4-Dichlorobenzoyl)-3-(RS)-(4-(2-(phenylmercapto)-1-ethyl)piperidinylmethyl)-4-(SR)-(3-thienyl)pyrrolidine;
1-(2,4-Dichlorobenzyl)-3-(RS)-(4-(2-(phenylmercapto)ethyl)piperidinylmethyl)-4-(SR)-(3-thienyl)pyrrolidine;
1-(3,4-Dichlorobenzoyl)-3-(RS)-(4-(3-phenyl-2-hydroxy-1-propyl)piperidinylmethyl)-4-(SR)-(3-thienyl)pyrrolidine;
1-(2,4-Dichylorobenzyl)-3-(RS)-(4-(3-phenyl-2-hydroxypropyl)piperidinylmethyl)-4-(SR)-(3-thienyl)pyrrolidine;
1-(2,4-Benzyl)-3-(RS)-(4-(3-phenyl-2-hydroxypropyl)piperidinylmethyl)-4-(SR)-(3-thienyl)pyrrolidine;
1-(3,4-Dichlorobenzoyl)-3-(RS)-(4-(3-phenyl-2-acetoxypropyl)piperidinylmethyl)-4-(SR)-(3-thienyl)pyrrolidine;
1-(2,4-Dichlorobenzyl)-3-(RS)-(4-(3-phenyl-2-acetoxypropyl)piperidinylmethyl)-4-(SR)-(3-thienyl)pyrrolidine;
1-(3,4-Dichlorobenzoyl)-3-(RS)-(4-(3-phenyl-3-hydroxypropyl)piperidinylmethyl)-4-(SR)-(3-thienyl)pyrrolidine;

1-(2,4-Dichlorobenzyl)-3-(RS)-(4-(3-phenyl-3-hydroxypropyl)piperidinylmethyl)-4-(SR)-(3-thienyl)pyrrolidine;
1-(3,4-Dichlorobenzoyl)-3-(RS)-(4-(4-(3-phenyl-3-acetoxypropyl)piperidinylmethyl)-4-(SR)-(3-thienyl)pyrrolidine;
1-(2,4-Dichlorobenzyl)-3-(RS)-(4-(3-phenyl-3-acetoxypropyl)piperidinylmethyl)-4-(SR)-(3-thienyl)pyrrolidine;
1-(2,4-Dichlorobenzyl)-3-(RS)-(4-(3-phenyl-3-oxopropyl)piperidinylmethyl)-4-(SR)-(3-thienyl)pyrrolidine;
1-(2,4-Dichlorobenzyl)-3-(RS)-(4-(4-(3-phenyl-3-oxopropyl)piperidinylmethyl)-4-(SR)-(3-thienyl)pyrrolidine;
1-(2,4-Dichlorobenzyl)-3-(RS)-(4-(3-phenyl-1-hydroxypropyl)piperidinylmethyl)-4-(SR)-(3-thienyl)pyrrolidine;
1-(2,4-Dichlorobenzyl)-3-(RS)-(4-(4-(3-phenyl-1-oxopropyl)piperidinylmethyl)-4-(SR)-(3-thienyl)pyrrolidine;
1-Benzyl-3-(R)-(4-(4-fluorophenyl)piperidinylmethyl)-4-(R)-(3-thienyl)-pyrrolidine;
3-(S)-(4-(4-fluorophenyl)piperidinylmethyl)-4-(R)-(3-thienyl)pyrrolidine;
1-(1-Naphthoyl)-3-(R)-(4-phenylpiperidinylmethyl)-4-(R)-(3-thienyl)pyrrolidine;
1-(Naphth-1-oyl)-3-(S)-(4-phenylpiperidinylmethyl)-4-(S)-(3-thienyl)pyrrolidine;
1-(1-Naphthoyl)-3-(R)-(4-(4-fluorophenyl)piperidinylmethyl)-4-(R)-(3-thienyl)pyrrolidine;
1-(3,4-Dichlorobenzoyl)-3-(R)-(4-(4-fluorophenyl)piperidinylmethyl)-4-(R)-(3-thienyl)pyrrolidine;
1-(2,3-Dichlorobenzoyl)-3-(R)-(4-(4-fluorophenyl)piperidinylmethyl)-4-(R)-(3-thienyl)pyrrolidine;
1-(7-Indolecarbonyl)-3-(R)-(4-(4-fluorophenyl)piperidinylmethyl)-4-(R)-(3-thienyl)pyrrolidine;
1-(2,3-Dimethylbenzoyl)-3-(R)-(4-(4-fluorophenyl)piperidinylmethyl)-4-(R)-(3-thienyl)pyrrolidine;
1-(7-2,3-Dihydrobenzofuranylcarbonyl)-3-(R)-(4-(4-fluorophenyl)piperidinylmethyl)-4-(R)-(3-thienyl)pyrrolidine;
1-(7-Benzofuranylcarbonyl)-3-(R)-(4-(4-fluorophenyl)piperidinylmethyl)-4-(R)-(3-thienyl)pyrrolidine;
1-(N-methyl-7-indolecarbonyl)-3-(R)-(4-(4-fluorophenyl)piperidinylmethyl)-4-(R)-(3-thienyl)pyrrolidine;
1-(1-Carbomethoxymethyl-7-indolecarbonyl)-3-(R)-(4-(4-fluorophenyl)piperidinylmethyl)-4-(R)-(3-thienyl)pyrrolidine;
1-(1-t-Butoxycarbonylmethyl-7-indolecarbonyl)-3-(R)-(4-(4-fluorophenyl)piperidinylmethyl)-4-(R)-(3-thienyl)pyrrolidine;
1-(1-Carboxymethyl-7-indolecarbonyl)-3-(R)-(4-(4-fluorophenyl)piperidinylmethyl)-4-(R)-(3-thienyl)pyrrolidine;
1-(1-Carboxamidomethyl-7-indolecarbonyl)-3-(R)-(4-(4-fluorophenyl)piperidinylmethyl)-4-(R)-(3-thienyl)pyrrolidine;
1-(1-(2-Hydroxyethyl)-7-indolecarbonyl)-3-(R)-(4-(4-fluorophenyl)piperidinylmethyl)-4-(R)-(3-thienyl)pyrrolidine;
1-(1-Ethyl-7-indolecarbonyl)-3-(R)-(4-(4-fluorophenyl)piperidinylmethyl)-4-(R)-(3-thienyl)pyrrolidine;
1-(1-Acetyl-7-indolecarbonyl)-3-(R)-(4-(4-fluorophenyl)piperidinylmethyl)-4-(R)-(3-thienyl)pyrrolidine;
1-(1-Methoxycarbonyl-7-indolecarbonyl)-3-(R)-(4-(4-fluorophenyl)piperidinylmethyl)-4-(R)-(3-thienyl)pyrrolidine;
1-(1-Allyl-7-indolecarbonyl)-3-(R)-(4-(4-fluorophenyl)piperidinylmethyl)-4-(R)-(3-thienyl)pyrrolidine;
1-(3-Methylbenzoyl)-3-(R)-(4-(4-fluorophenyl)piperidinylmethyl)-4-(R)-(3-thienyl)pyrrolidine;
1-(3-Methyl-2-phenylbenzoyl)-3-(R)-(4-(4-fluorophenyl)piperidinylmethyl)-4-(R)-(3-thienyl)pyrrolidine;
1-(2-Vinyl-3-methylbenzoyl)-3-(R)-(4-(4-fluorophenyl)piperidinylmethyl)-4-(R)-(3-thienyl)pyrrolidine;
1-(2-Ethyl-3-methylbenzoyl)-3-(R)-(4-(4-fluorophenyl)piperidinylmethyl)-4-(R)-(3-thienyl)pyrrolidine;
1-(7-Benzimidazolecarbonyl)-3-(R)-(4-(4-fluorophenyl)piperidinylmethyl)-4-(R)-(3-thienyl)pyrrolidine;
1-(1-Methyl-4-benzimidazolecarbonyl)-3-(R)-(4-(4-fluorophenyl)piperidinylmethyl)-4-(R)-(3-thienyl)pyrrolidine;
1-(1-Methyl-7-benzimidazolecarbonyl)-3-(R)-(4-(4-fluorophenyl)piperidinylmethyl)-4-(R)-(3-thienyl)pyrrolidine;
1-(1-(Methoxycarbonylmethyl)-4-benzimidazolecarbonyl)-3-(R)-(4-(4-fluorophenyl)piperidinylmethyl)-4-(R)-(3-thienyl)pyrrolidine;
1-(1-(Methoxycarbonylmethyl)-7-benzimidazolecarbonyl)-3-(R)-(4-(4-fluorophenyl)piperidinylmethyl)-4-(R)-(3-thienyl)pyrrolidine;
1-(1-(t-Butoxycarbonylmethyl)-4-benzimidazolecarbonyl)-3-(R)-(4-(4-fluorophenyl)piperidinylmethyl)-4-(R)-(3-thienyl)pyrrolidine;
1-(1-(t-Butoxycarbonylmethyl)-7-benzimidazolecarbonyl)-3-(R)-(4-(4-fluorophenyl)piperidinylmethyl)-4-(R)-(3-thienyl)pyrrolidine;
1-(1-(Carboxymethyl)-4-benzimidazolecarbonyl)-3-(R)-(4-(4-fluorophenyl)piperidinylmethyl)-4-(R)-(3-thienyl)pyrrolidine;
1-(1-(Carboxymethyl)-7-benzimidazolecarbonyl)-3-(R)-(4-(4-fluorophenyl)piperidinylmethyl)-4-(R)-(3-thienyl)pyrrolidine;
1-(1-(2-Hydroxyethyl)-7-benzimidazolecarbonyl)-3-(R)-(4-(4-fluorophenyl)piperidinylmethyl)-4-(R)-(3-thienyl)pyrrolidine;
1-(1-(2-Hydroxyethyl)-4-benzimidazolecarbonyl)-3-(R)-(4-(4-fluorophenyl)piperidinylmethyl)-4-(R)-(3-thienyl)pyrrolidine;
1-(1-Naphthoyl)-3-(RS)-(4-phenylpiperidinylmethyl)-4-(RS)-(3-furanyl)pyrrolidine;
1-(3,4-Dichlorobenzoyl)-3-(RS)-(4-phenylpiperidinylmethyl)-4-(RS)-(3-furanyl)pyrrolidine;
1-(2,3-Dichlorobenzoyl)-3-(RS)-(4-phenylpiperidinylmethyl)-4-(RS)-(3-furanyl)pyrrolidine;
1-(1-Naphthoyl)-3-(RS)-(4-(4-fluorophenyl)piperidinylmethyl)-4-(RS)-(3-furanyl)pyrrolidine;
1-(3,4-Dichlorobenzoyl)-3-(RS)-(4-(4-fluorophenyl)piperidinylmethyl)-4-(RS)-(3-furanyl)pyrrolidine;
1-(2,3-Dichlorobenzoyl)-3-(SR)-(4-(4-fluorophenyl)piperidinylmethyl)-4-(RS)-(3-furanyl)pyrrolidine;
1-(2,3-Difluorobenzoyl)-3-(RS)-(4-(4-fluorophenyl)piperidinylmethyl)-4-(RS)-(3-furanyl)pyrrolidine;
1-(2,3,4-Trifluorobenzoyl)-3-(RS)-(4-(4-fluorophenyl)piperidinylmethyl)-4-(RS)-(3-furanyl)pyrrolidine;
1-(2,3,4,5,6-Pentafluorobenzoyl)-3-(RS)-(4-(4-fluorophenyl)piperidinylmethyl)-4-(RS)-(3-furanyl)pyrrolidine;
1-(1-Naphthoyl)-3-(R)-(4-(4-fluorophenyl)piperidinylmethyl)-4-(R)-(3-furanyl)pyrrolidine;
1-(2,4-Dichlorobenzyl)-3-(S)-(4-hydroxy-4-(3-phenylpropyl)piperidinylmethyl)-4-(S)-(3-thienyl)pyrrolidine;
1-(2,4-Dichlorobenzyl)-3-(S)-(4-(4-fluorobenzyloxymethyl)piperidinyl-methyl)-4-(S)-(3-thienyl)pyrrolidine;

1-(2,3-Dichlorobenzyl)-3-(S)-(4-(4-fluorophenyl)piperidinylmethyl)-4-(S)-(3-thienyl)pyrrolidine;

1-(2,4-Dichlorobenzyl)-3-(S)-4-(4-fluorophenyl)piperidinylmethyl)-4-(S)-(3-thienyl)pyrrolidine;

1-(2-Chlorobenzyl)-3-(S)-(4-(4-fluorophenyl)piperidinylmethyl)-4-(S)-(3-thienyl)pyrrolidine;

1-(3-Chlorobenzyl)-3-(S)-(4-(4-fluorophenyl)piperidinylmethyl)-4-(S)-(3-thienyl)pyrrolidine;

1-(4-Chlorobenzyl)-3-(S)-(4-(4-fluorophenyl)piperidinylmethyl)-4-(S)-(3-thienyl)pyrrolidine;

1-(4-Methylbenzyl)-3-(S)-(4-(4-fluorophenyl)piperidinylmethyl)-4-(S)-(3-thienyl)pyrrolidine;

1-(4-Nitrobenzyl)-3-(S)-(4-(4-fluorophenyl)piperidinylmethyl)-4-(S)-(3-thienyl)pyrrolidine;

1-(4-Trifluoromethylbenzyl)-3-(S)-(4-(4-fluorophenyl)piperidinylmethyl)-4-(S)-(3-thienyl)pyrrolidine;

1-(3,4-Dichlorobenzyl)-3-(S)-(4-(4-fluorophenyl)piperidinylmethyl)-4-(S)-(3-thienyl)pyrrolidine;

1-(2,3-Dimethylbenzyl)-3-(S)-(4-(4-fluorophenyl)piperidinylmethyl)-4-(S)-(3-thienyl)pyrrolidine;

1-(3-Trifluoromethyl-4-chlorobenzyl)-3-(S)-(4-(4-fluorophenyl)piperidinylmethyl)-4-(S)-(3-thienyl)pyrrolidine;

1-(1-Naphthylmethyl)-3-(R)-(4-(4-fluorophenyl)piperidinylmethyl)-4-(R)-(3-thienyl)pyrrolidine;

1-(4-Nitrobenzyl)-3-(R)-(4-(4-fluorophenyl)piperidinylmethyl)-4-(R)-(3-thienyl)pyrrolidine;

1-(4-Methylbenzyl)-(R)-(4-(4-fluorophenyl)piperidinylmethyl)-4-(R)-(3-thienyl)pyrrolidine;

1-(1-n-propyl-7-indolecarbonyl)-3-(R)-4-(4-fluorophenyl)piperidinylmethyl)-4-(R)-(3-thienyl)pyrrolidine;

1-(1-(N,N-dimethylaminoethyl)-7-indolecarbonyl)-3-(R)-4-(4-fluorophenyl)-piperidinylmethyl)-4-(R)-(3-thienyl)pyrrolidine;

1-(1-Cyanomethyl-7-indolecarbonyl)-3-(R)-4-(4-fluorophenyl)piperidinylmethyl)-4-(R)-(3-thienyl)pyrrolidine;

1-(1-(2-Acetoxyethyl)-7-indolecarbonyl)-3-(R)-4-(4-fluorophenyl)piperidinylmethyl)-4-(R)-(3-thienyl)pyrrolidine;

1-(1-(2-Methoxyethyl)-7-indolecarbonyl)-3-(R)-4-(4-fluorophenyl)piperidinylmethyl)-4-(R)-(3-thienyl)pyrrolidine;

1-(1-(2-Phthalimidoethyl)-7-indolecarbonyl)-3-(R)-4-(4-fluorophenyl)-piperidinylmethyl)-4-(R)-(3-thienyl)pyrrolidine;

1-(1-(2-Aminoethyl)-7-indolecarbonyl)-3-(R)-4-(4-fluorophenyl)piperidinylmethyl)-4-(R)-(3-thienyl)pyrrolidine;

1-(1-(2-Methylsulfonylaminoethyl)-7-indolecarbonyl)-3-(R)-4-(4-fluorophenyl)-piperidinylmethyl)-4-(R)-(3-thienyl)pyrrolidine;

1-(1-(2-Acetylaminoethyl)-7-indolecarbonyl)-3-(R)-4-(4-fluorophenyl)-piperidinylmethyl)-4-(R)-(3-thienyl)pyrrolidine;

1-(1-(2-Methoxycarbonylaminoethyl)-7-indolecarbonyl)-3-(R)-4-(4-fluorophenyl)piperidinylmethyl)-4-(R)-(3-thienyl)pyrrolidine;

1-(1-(2-Carboxyethyl)-7-indolecarbonyl)-3-(R)-4-(4-fluorophenyl)piperidinylmethyl)-4-(R)-(3-thienyl)pyrrolidine;

1-(1-(2-Carboxamidoethyl)-7-indolecarbonyl)-3-(R)-4-(4-fluorophenyl)-piperidinylmethyl)-4-(R)-(3-thienyl)pyrrolidine;

1-(1-(2-Methylsulfonamidocarbonylethyl)-7-indolecarbonyl)-3-(R)-4-(4-fluorophenyl)piperidinylmethyl)-4-(R)-(3-thienyl)pyrrolidine;

1-(1-(2-Methylsulfonamidocarbonylmethyl)-7-indolecarbonyl)-3-(R)-4-(4-fluorophenyl)piperidinylmethyl)-4-(R)-(3-thienyl)pyrrolidine;

1-(1-(3-Ethoxycarbonylpropyl)-7-indolecarbonyl)-3-(R)-4-(4-fluorophenyl)-piperidinylmethyl)-4-(R)-(3-thienyl)pyrrolidine;

1-(1-(3-Carboxypropyl)-7-indolecarbonyl)-3-(R)-4-(4-fluorophenyl)-piperidinylmethyl)-4-(R)-(3-thienyl)pyrrolidine;

1-(1-Methyl-7-indolemethyl)-3-(R)-4-(4-fluorophenyl)piperidinylmethyl)-4-(R)-(3-thienyl)pyrrolidine;

1-(2-Methyl-1-Naphthoyl)-3-(R)-4-(4-fluorophenyl)piperidinylmethyl)-4-(R)-(3-thienyl)pyrrolidine;

1-(4-Fluoro-1-naphthoyl)-3-(R)-4-(4-fluorophenyl)piperidinylmethyl)-4-(R)-(3-thienyl)pyrrolidine;

1-(7-Benzoxazolecarbonyl)-3-(R)-4-(4-fluorophenyl)piperidinylmethyl)-4-(R)-(3-thienyl)pyrrolidine;

1-(2-Methyl-7-benzoxazolecarbonyl)-3-(R)-4-(4-fluorophenyl)piperidinylmethyl)-4-(R)-(3-thienyl)pyrrolidine;

1-(4-Benzoxazolecarbonyl)-3-(R)-4-(4-fluorophenyl)piperidinylmethyl)-4-(R)-(3-thienyl)pyrrolidine;

1-(2-Methyl-4-benzoxazolecarbonyl)-3-(R)-4-(4-fluorophenyl)piperidinylmethyl)-4-(R)-(3-thienyl)pyrrolidine;

1-(1,4-benzpyrazine-4-carbonyl)-3-(R)-4-(4-fluorophenyl)piperidinylmethyl)-4-(R)-(3-thienyl)pyrrolidine;

1-(Imidazo[1,2-a]pyridine-7-carbonyl)-3-(R)-4-(4-fluorophenyl)piperidinylmethyl)-4-(R)-(3-thienyl)pyrrolidine;

1-(2-Hydroxybenzimidazole-7-carbonyl)-3-(R)-4-(4-fluorophenyl)piperidinylmethyl)-4-(R)-(3-thienyl)pyrrolidine;

1-(3,4-Dichlorobenzoyl)-3-(RS)-(4-(4-(3-phenyl-2-oxopropyl)piperidinylmethyl)-4-(SR)-(3-thienyl)pyrrolidine;

1-(2,4-Dichlorobenzyl)-3-(RS)-(4-(4-(3-phenylpropyl)piperidinymethyl)-4-(SR)-(3-thienyl)pyrrolidine;

1-(2,4-Dichlorobenzyl)-3-(S)-(4-(4-(3-phenyl-1-(RS)-methoxypropyl)piperidinylmethyl)-4-(S)-(3-thienyl)pyrrolidine;

1-(2,4-Dichlorobenzyl)-3-(S)-(trans-(3-hydroxy-4-(3-phenylpropyl))piperidinylmethyl)-4-(S)-(3-thienyl)pyrrolidine;

1-(2,4-Dichlorobenzyl)-3-(S)-(cis-(3-hydroxy-4-(3-phenylpropyl))piperidinylmethyl)-4-(S)-(3-thienyl)pyrrolidine;

1-(2,4-Dichlorobenzyl)-3-(S)-(4-(3-phenyl-2-oxopropyl)piperidinylmethyl)-4-(S)-(3-thienyl)pyrrolidine;

1-(2,4-Dichlorobenzyl)-3-(S)-(4-(3-phenylpropyl)piperidinylmethyl)-4-(S)-(3-thienyl)pyrrolidine;

1-(2,4-Dichlorobenzyl)-3-(S)-(4-(3-phenyl-2-(R,S)-fluoropropyl)piperidinylmethyl)-4-(S)-(3-thienyl)pyrrolidine;

1-(2,4-Dichlorobenzyl)-3-(S)-(4-(benzylsulfonylmethyl)piperdinylmethyl)-4-(S)-(3-thienyl)pyrrolidine;

1-(2,4-Dichlorobenzyl)-3-(S)-(4-(3-phenyl-2-(R,S)-hydroxypropyl)piperidinylmethyl)-4-(S)-(3-thienyl)pyrrolidine;

1-(2,4-Dichlorobenzyl)-3-(S)-(4-(3-phenyl-2-(R,S)-methoxypropyl)piperidinylmethyl)-4-(S)-(3-thienyl)pyrrolidine;

1-(2,4-Dichlorobenzyl)-3-(S)-(4-(3-phenyl-2-hydroxypropyl)piperidinylmethyl)-4-(S)-(3-thienyl)pyrrolidine;

1-(2,4-Dichlorobenzyl)-3-(S)-(4-(3-(4-fluorophenyl)-2-hydroxypropyl)piperidinylmethyl)-4-(S)-(3-thienyl)pyrrolidine;

1-(2,4-Dichlorobenzyl)-3-(S)-(4-(3-chlorobenzyloxymethyl)piperidinylmethyl)-4-(S)-(3-thienyl)pyrrolidine;

1-(2,4-Dichlorobenzyl)-3-(S)-(4-(2,4-dichlorobenzyloxymethyl)piperidinylmethyl)-4-(S)-(3-thienyl)pyrrolidine;

1-(2,4-Dichlorobenzyl)-3-(S)-(4-(2-chlorobenzyloxymethyl)piperidinylmethyl)-4-(S)-(3-thienyl)pyrrolidine;

1-(2,4-Dichlorobenzyl)-3-(S)-(4-(3,4-dichlorobenzyloxymethyl)piperidinylmethyl)-4-(S)-(3-thienyl)pyrrolidine;

1-(2,4-Dichlorobenzyl)-3-(S)-(4-(4-methylbenzyloxymethyl)piperidinylmethyl)-4-(S)-(3-thienyl)pyrrolidine;

1-(2,4-Dichlorobenzyl)-3-(S)-(4-(4-chlorobenzyloxymethyl)piperidinylmethyl)-4-(S)-(3-thienyl)pyrrolidine;

1-(2,4-Dichlorobenzyl)-3-(S)-(4-(methoxybenzyloxymethyl)piperidinylmethyl)-4-(S)-(3-thienyl)pyrrolidine;

and pharmaceutically acceptable salts thereof and individual diastereomers thereof.

16. A pharmaceutical composition which comprises an inert carrier and a compound of claim 1.

17. A method for modulation of chemokine receptor activity in a mammal which comprises the administration of an effective amount of the compound of claim 1.

18. A method for treating infection by HIV, delaying of the onset of AIDS, or treating AIDS comprising the administration to a patient of an effective amount of the compound of claim 1.

19. A method for the treatment of an inflammatory and immunoregulatory disorder or disease which comprises the administration to a patient of an effective amount of the compound of claim 1.

20. A method for treatment of asthma, allergic rhinitis, dermatitis, conjunctivitis, atherosclerosis or rheumatoid arthritis which comprises the administration to a patient of an effective amount of the compound of claim 1.

* * * * *